US009593340B2

(12) United States Patent
Frazer et al.

(10) Patent No.: US 9,593,340 B2
(45) Date of Patent: Mar. 14, 2017

(54) EXPRESSION SYSTEM FOR MODULATING AN IMMUNE RESPONSE

(75) Inventors: Ian Hector Frazer, St. Lucia (AU); Julie Louise Dutton, Yeronga (AU)

(73) Assignee: Admedus Vaccines Pty Ltd., Woolloongabba (AU)

( * ) Notice: Subject to any disclaimer, the term of this patent is extended or adjusted under 35 U.S.C. 154(b) by 18 days.

(21) Appl. No.: 12/738,284

(22) PCT Filed: Oct. 2, 2008

(86) PCT No.: PCT/AU2008/001463

§ 371 (c)(1), (2), (4) Date: Oct. 14, 2010

(87) PCT Pub. No.: WO2009/049350

PCT Pub. Date: Apr. 23, 2009

(65) Prior Publication Data

US 2011/0020374 A1 Jan. 27, 2011

Related U.S. Application Data

(60) Provisional application No. 60/980,145, filed on Oct. 15, 2007.

(51) Int. Cl.

*C12N 15/79* (2006.01)
*A61K 39/145* (2006.01)
(Continued)

(52) U.S. Cl.

CPC .............. *C12N 15/79* (2013.01); *A61K 39/12* (2013.01); *A61K 39/145* (2013.01); (Continued)

(58) Field of Classification Search

CPC .................... C12N 15/79; C12N 15/67; C12N 2710/16222; C12N 2710/16234;
(Continued)

(56) References Cited

U.S. PATENT DOCUMENTS

| | | |
|---|---|---|
| 4,184,917 A | 1/1980 | Dorner et al. |
| 4,293,652 A | 10/1981 | Cohen |

(Continued)

FOREIGN PATENT DOCUMENTS

| | | |
|---|---|---|
| EP | 0 500 799 B1 | 1/1998 |
| EP | 1 092 444 B1 | 5/2006 |

(Continued)

OTHER PUBLICATIONS

Ramakrishna et al., Codon Optimization of the Tat Antigen of Human Immunodeficiency Virus Type 1 Generates Strong Immune Responses in Mice following Genetic Immunization, Journal of Virology, Sep. 2004, p. 9174-9189.*

(Continued)

*Primary Examiner* — Reza Ghafoorian
(74) *Attorney, Agent, or Firm* — Cooley LLP

(57) ABSTRACT

The present invention discloses methods and compositions for modulating the quality of an immune response to a target antigen in a mammal, which response results from the expression of a polynucleotide that encodes at least a portion of the target antigen, wherein the quality is modulated by replacing at least one codon of the polynucleotide with a synonymous codon that has a higher or lower preference of usage by the mammal to confer the immune response than the codon it replaces.

15 Claims, 20 Drawing Sheets

(51) Int. Cl.

| | |
|---|---|
| ***A61K 39/245*** | (2006.01) |
| ***A61K 39/29*** | (2006.01) |
| ***C07K 14/005*** | (2006.01) |
| ***C12N 15/67*** | (2006.01) |
| ***C40B 40/08*** | (2006.01) |
| ***C40B 50/04*** | (2006.01) |
| ***A61K 39/12*** | (2006.01) |
| *A61K 39/00* | (2006.01) |

(52) U.S. Cl.

CPC ............ *A61K 39/245* (2013.01); *A61K 39/29* (2013.01); *C07K 14/005* (2013.01); *C12N 15/67* (2013.01); *C40B 40/08* (2013.01); *C40B 50/04* (2013.01); *A61K 2039/53* (2013.01); *A61K 2039/54* (2013.01); *C12N 2710/16222* (2013.01); *C12N 2710/16234* (2013.01); *C12N 2710/16622* (2013.01); *C12N 2710/16634* (2013.01); *C12N 2710/20022* (2013.01); *C12N 2710/20034* (2013.01); *C12N 2760/16122* (2013.01); *C12N 2760/16134* (2013.01); *C12N 2770/24222* (2013.01); *C12N 2770/24234* (2013.01)

(58) Field of Classification Search

CPC ........... C12N 2710/16622; C12N 2710/16634; C12N 2710/20022; C12N 2760/16122; C12N 2760/16135; C12N 2770/24234; A61K 39/145; A61K 39/245; A61K 39/29; A61K 39/12; A61K 2039/53; A61K 2039/54; C07K 14/05; C40B 40/08; C40B 50/04

See application file for complete search history.

(56) References Cited

U.S. PATENT DOCUMENTS

| | | | | |
|---|---|---|---|---|
| 4,321,365 | A | 3/1982 | Wu et al. | |
| 4,351,901 | A | 9/1982 | Bahl | |
| 4,663,161 | A | 5/1987 | Mannino et al. | |
| 4,790,824 | A | 12/1988 | Morrow et al. | |
| 4,871,488 | A | 10/1989 | Mannino et al. | |
| 4,945,050 | A | 7/1990 | Sanford et al. | |
| 5,036,006 | A | 7/1991 | Sanford et al. | |
| 5,064,413 | A | 11/1991 | McKinnon et al. | |
| 5,093,242 | A | 3/1992 | Bachmair et al. | |
| 5,100,792 | A | 3/1992 | Sanford et al. | |
| 5,122,463 | A | 6/1992 | Varshavsky et al. | |
| 5,179,022 | A | 1/1993 | Sanford et al. | |
| 5,312,335 | A | 5/1994 | McKinnon et al. | |
| 5,371,015 | A | 12/1994 | Sanford et al. | |
| 5,383,851 | A | 1/1995 | McKinnon, Jr. et al. | |
| 5,399,163 | A | 3/1995 | Peterson et al. | |
| 5,478,744 | A | 12/1995 | Sanford et al. | |
| 5,501,979 | A | 3/1996 | Geller et al. | |
| 5,520,639 | A | 5/1996 | Peterson et al. | |
| 5,561,063 | A | 10/1996 | Hock et al. | |
| 5,584,807 | A | 12/1996 | McCabe | |
| 5,604,090 | A | 2/1997 | Alexander et al. | |
| 5,624,820 | A | 4/1997 | Cooper | |
| 5,674,703 | A | 10/1997 | Woo et al. | |
| 5,693,508 | A | 12/1997 | Chang | |
| 5,700,470 | A | 12/1997 | Saito et al. | |
| 5,719,054 | A | 2/1998 | Boursnell et al. | |
| 5,731,172 | A | 3/1998 | Saito et al. | |
| 5,786,340 | A | 7/1998 | Henning et al. | |
| 5,786,464 | A | 7/1998 | Seed | |
| 5,789,245 | A | 8/1998 | Dubensky, Jr. et al. | |
| 5,795,737 | A | 8/1998 | Seed et al. | |
| 5,821,235 | A | 10/1998 | Henning et al. | |
| 5,831,005 | A | 11/1998 | Zuckerman et al. | |
| 5,833,993 | A | 11/1998 | Wardley et al. | |
| 5,843,723 | A | 12/1998 | Dubensky, Jr. et al. | |
| 5,846,796 | A | 12/1998 | Cerami et al. | |
| 5,865,796 | A | 2/1999 | McCabe | |
| 5,952,221 | A | 9/1999 | Kurtzman et al. | |
| 5,985,641 | A | 11/1999 | Haynes et al. | |
| 5,993,412 | A | 11/1999 | Deily et al. | |
| 6,004,799 | A | 12/1999 | Luciw et al. | |
| 6,010,478 | A | 1/2000 | Bellhouse et al. | |
| 6,013,516 | A | 1/2000 | Verma et al. | |
| 6,033,905 | A | 3/2000 | Eiden et al. | |
| 6,120,764 | A | 9/2000 | Graham et al. | |
| 6,132,731 | A | 10/2000 | Kingsman | |
| 6,133,028 | A | 10/2000 | Imler et al. | |
| 6,136,594 | A | 10/2000 | Dalemans et al. | |
| 6,140,087 | A | 10/2000 | Graham et al. | |
| 6,143,548 | A | 11/2000 | O'Riordan et al. | |
| 6,156,303 | A | 12/2000 | Russell et al. | |
| 6,287,569 | B1 * | 9/2001 | Kipps et al. | 424/199.1 |
| 6,494,865 | B1 | 12/2002 | Alchas | |
| 6,818,222 | B1 * | 11/2004 | Barchfeld et al. | 424/236.1 |
| 2011/0287039 | A1 | 11/2011 | Frazer et al. | |

FOREIGN PATENT DOCUMENTS

| | | | |
|---|---|---|---|
| WO | 89/03429 | A1 | 4/1989 |
| WO | 90/11092 | A1 | 10/1990 |
| WO | 91/12882 | A1 | 9/1991 |
| WO | 92/03545 | A1 | 3/1992 |
| WO | 92/05266 | A2 | 4/1992 |
| WO | 92/14829 | A1 | 9/1992 |
| WO | 95/07995 | A2 | 3/1995 |
| WO | 96/17072 | A2 | 6/1996 |
| WO | 98/51810 | A1 | 11/1998 |
| WO | 99/02694 | A1 | 1/1999 |
| WO | 99/15641 | A1 | 4/1999 |
| WO | 99/24465 | A1 | 5/1999 |
| WO | 99/30742 | A1 | 6/1999 |
| WO | 99/31251 | A1 | 6/1999 |
| WO | 99/51754 | A1 | 10/1999 |
| WO | 00/00600 | A2 | 1/2000 |
| WO | 00/42190 | A1 | 7/2000 |
| WO | 00/61772 | A2 | 10/2000 |
| WO | 00/66759 | A1 | 10/2000 |
| WO | 01/81609 | A2 | 11/2001 |
| WO | 02/080982 | A2 | 10/2002 |
| WO | 02/099035 | A2 | 12/2002 |
| WO | 2004/024915 | A1 | 3/2004 |
| WO | WO 2004/042059 | A1 | 5/2004 |
| WO | 2009/049350 | A1 | 4/2009 |

OTHER PUBLICATIONS

Arregui et al., A Synthetic E7 Gene of Human Papillomavirus Type 16 That Yields Enhanced Expression of the Protein in Mammalian Cells and Is Useful for DNA Immunization Studies, Journal of Virology, Apr. 2003, p. 4928-4937.*

Uchijima et al., Optimization of Codon Usage of Plasmid DNA Vaccine Is Required for the Effective MHC Class I-Restricted T Cell Responses Against an Intracellular Bacterium, The Journal of Immunology, 1998, 161: 5594-5599.*

Cladel et al., CRPV Genomes with Synonymous Codon Optimizations in the CRPV E7 Gene Show Phenotypic Differences in Growth and Altered Immunity upon E7 Vaccination, PLoS ONE 3(8): e2947, Aug. 13, 2008.*

Gu et al., "tRNA$^{ser}$(CGA) differentially regulates expression of wild-type and codon-modified papillomavirus L1 genes," *Nucleic Acids Research* 32(15):4448-4461, 2004.

Liu et al., "Codon Modified Human Papillomavirus Type 16 E7 DNA Vaccine Enhances Cytotoxic T-Lymphocyte Induction and Anti-tumour Activity," *Virology* 301:43-52, 2002.

Nagata et al., "Codon Optimization Effect on Translational Efficiency of DNA Vaccine in Mammalian Cells: Analysis of Plasmid DNA Encoding a CTL Epitope Derived from Microorganisms," *Biochemical and Biophysical Research Communications* 261:445-451, 1999.

Zheng et al., "Codon usage bias in *Chlamydia trachomatis* and the effect of codon modification in the MOMP gene on immune responses to vaccination," *Biochem. Cell Biol.* 85:218-226, 2007.

(56) References Cited

OTHER PUBLICATIONS

Ausubel et al. (ed.), *Current Protocols in Molecular Biology*(Table of Contents), John Wiley & Sons Inc, 1994-1998 (Ed. name and years not on copy).
Altschul et al., "Gapped BLAST and PSI-BLAST: a new generation of protein database search programs," *Nucleic Acids Research* 25(17):3389-3402, 1997.
Boshart et al., "A Very Strong Enhancer is Located Upstream of an Immediate Early Gene of Human Cytomegalovirus," *Cell* 41:521-530, Jun. 1985.
Croyle et al., "Beta Cyclodextrins Enhance Adenoviral-Mediated Gene Delivery to the Intestine," *Pharmaceutical Research* 15(9), 1998, pp. 1348-1355.
Croyle et al., "In vitro and in vivo assessment of adenovirus 41 as a vector for gene delivery to the intestine," *Gene Therapy* 5:645-654, 1998.
Croyle et al., "Role of Integrin Expression in Adenovirus-Mediated Gene Delivery to the Intestinal Epithelium," *Human Gene Therapy* 9:561-573, Mar. 1, 1998.
Dayhoff et al., "A Model of Evolutionary Change in Proteins," *Atlas of Protein Sequence and Structure*, pp. 345-352, 1978.
Deamer et al., "Large Volume Liposomes by an Ether Vaporization Method," *Biochimica et Biophysica Acta* 443:629-634, 1976.
Debs et al., "Regulation of Gene Expression in Vivo by Liposome-mediated Delivery of a Purified Transcription Factor," *Journal of Biological Chemistry* 265(18):10189-10192, Jun. 25, 1990.
Devereux et al., "A comprehensive set of sequence analysis programs for the VAX," *Nucleic Acids Research* 12(1), 1984, pp. 387-395.
Dijkema et al., "Cloning and expression of the chromosomal immune interferon gene of the rat," *The EMBO Journal* 4(3):761-767, 1985.
Doe et al., "Induction of HIV-1 envelope (gp120)-specific cytotoxic T lymphocyte responses in mice by recombinant CHO cell-derived gp120 is enhanced by enzymatic removal of N-linked glycans," *Eur. J. Immunol.* 24:2369-2376, 1994.
Dreyer et al., "Primary Isolate Neutralization by HIV Type 1-Infected Patient Sera in the Era of Highly Active Antiretroviral Therapy," *AIDS Research and Human Retroviruses* 15(17):1563-1571, 1999.
Dubensky Jr. et al., Sindbis virus DNA-based expression vectors: utility for in vitro and in vivo gene transfer, *Journal of Virology* 70(1):508-519, 1996, 13 pages total.
Edmonds et al., "A point mutational analysis of human papillomavirus type 16 E7 protein," *Journal of Virology* 63(6):2650-2656, 1989, 8 pages total.
Enoch et al., "Formation and properties of 1000-Å-diameter, single-bilayer phospholipid vesicles," *Proc. Natl. Acad. Sci. USA* 76(1):145-149, Jan. 1979.
Erickson et al., "Hepatitis C Virus-Specific CTL Responses in the Liver of Chimpanzees with Acute and Chronic Hepatitis C," *Journal of Immunology* 151(8):4189-4199, Oct. 15, 1993.
Felgner et al., "Lipofection: A highly efficient, lipid-mediated DNA-transfection procedure," *Proc. Natl. Acad. Sci. USA* 84:7413-7417, Nov. 1987.
Felgner, "Particulate systems and polymers for in vitro and in vivo delivery of polynucleotides," *Advanced Drug Delivery Reviews* 5:163-187, 1990.
Foreman et al., "Adenovirus-Mediated Transduction of Intestinal Cells In Vivo," *Human Gene Therapy* 9:1313-1321, Jun. 10, 1998.
Fraley et al., "Entrapment of a bacterial plasmid in phospholipid vesicles: Potential for gene transfer," *Proc. Natl. Acad. Sci. USA* 76(7):3348-3352, Jul. 1979.
Fraley et al., "Introduction of Liposome-encapsulated SV40 DNA into Cells," *The Journal of Biological Chemistry* 255(21):10431-10435, Nov. 10, 1980.
Frazer, "Expression System for Modulating an Immune Response," Sequence Listing, PCT/AU2008/001463, Oct. 2, 2008,73 pages.
Frazer et al., "Immunological Responses in Human Papillomavirus 16 E6/E7-transgenic Mice to E7 protein Correlate with the Presence of Skin Disease," *Cancer Research* 55:2635-2639, 1995.
Gluzman (ed.), *Eukaryotic Viral Vectors*, Cold Spring Harbor Laboratory, 1982,Table of Contents, 5 pages total.
Gonnet et al., "Exhaustive Matching of the Entire Protein Sequence Database," *Science* 256(5062):1443-1445, Jun. 5, 1992, 4 pages total.
Gorman et al., "The Rous sarcoma virus long terminal repeat is a strong promoter when introduced into a variety of eukaryotic cells by DNA-mediated transfection," *Proc. Natl. Acad. Sci. USA* 79:6777-6781, Nov. 1982.
Heck et al., "Efficiency of binding the retinoblastoma protein correlates with the transforming capacity of the E7 oncoproteins of the human papillomaviruses," *Proc. Natl. Acad. Sci. USA* 89:4442-4446, May 1992.
Hug et al., "Liposomes for the transformation of eukaryotic cells," *Biochimica et Biophysica Acta* 1097:1-17, 1991.
Jeffery et al., "The Preparation and Characterization of Poly(lactide-co-glycolide) Microparticles. II. The Entrapment of a Model Protein Using a (Water-in-Oil)-in-Water Emulsion Solvent Evaporation technique," *Pharmaceutical Research* 10(3):362-368, 1993.
Lalvani et al., "Rapid Effector Function in $CD8^+$ Memory T Cells," *J. Exp. Med.* 186(6):859-865, Sep. 15, 1997.
Lois et al., "Germline Transmission and Tissue-Specific Expression of Transgenes Delivered by Lentiviral Vectors," *Science* 295:868-372, 2002, 6 pages total.
Malone et al., "Cationic liposome-mediated RNA transfection," *Proc. Natl. Acad. Sci. USA* 86:6077-6081, Aug. 1989.
McGee et al., "The encapsulation of a model protein in poly (D, L lactide-co-glycolide) microparticles of various sizes: an evaluation of process reproducibility," *J. Microencapsulation* 14(2):197-210, 1997.
McHeyzer-Williams et al., "Enumeration and Characterization of Memory Cells in the $T_H$ Compartment," *Immunological Reviews* (150):5-21, 1996.
McMichael et al., "A New Look at T Cells," *J. Exp. Med.* 187(9):1367-1371, May 4, 1998.
Michael et al., "Binding-incompetent Adenovirus Facilitates Molecular Conjugate-mediated Gene Transfer by the Receptor-mediated Endocytosis Pathway," *The Journal of Biological Chemistry* 268(10):6866-6869, Apr. 5, 1993.
Montefiori et al., "Evaluation of antiviral drugs and neutralizing antibodies to human immunodeficiency virus by a rapid and sensitive micotiter infection assay," *Journal of Clinical Microbiology* 26(2):231-235, 1988, 6 pages total.
Muller et al., "Herpes simplex virus type 2 tegument proteins contain subdominant T-cell epitopes detectable in BALB/c mice after DNA immunization and infection," *Journal of General Virology* 90:1153-1163, 2009.
Muzyczka, "Adeno-associated Virus (AAV) Vectors: Will They Work?," *J. Clin. Invest.* 94:1351, Oct. 1994.
Nakamura et al., "Condon usage tabulated from the international DNA sequence databases (abstract)," *Nucleic Acids Research* 24(1):214, 1996.
O'Hagan et al., "Biodegradable microparticles for oral immunization," *Vaccine* 11(2):149-154, 1993.
Okada et al., "Gene therapy against an experimental glioma using adeno-associated virus vectors," *Gene Therapy* 3:957-964, 1996.
Ostro et al., "Incorporation of High Molecular Weight RNA into Large Artificial Lipid Vesicles," *Biochemical and Biophysical research Communications* 76(3):836-842, 1977.
Papahadjopoulos et al., "Cochleate Lipid Cylinders: Formation by Fusion of Unilamellar Lipid Vesicles," *Biochimica et Biophysica Acta* 394:483-491, 1975.
Perri et al., "An Alphavirus Replicon Particle Chimera Derived from Venezuelan Equine Encephalitis and Sindbis Viruses is a Potent Gene-Based Vaccine Delivery Vector," *Journal of Virology* 77(19):10394-10403, 2003, 11 pages total.
Rogers et al., "Amino Acid Sequences Common to Rapidly Degraded Proteins: The PEST Hypothesis," *Science* 234(4774):364-368, Oct. 17, 1986, 6 pages total.

(56) References Cited

OTHER PUBLICATIONS

Sambrook et al (ed.), *Molecular Cloning: a Laboratory Manual*, Cold Spring Harbor Laboratory Press, New York, 2001, Table of Contents and Preface.

Sarver et al., "Bovine Papilloma Virus Deoxyribonucleic Acid: a Novel Eucaryotic Cloning Vector," *Molecular and Cellular Biology* 1(6):486-496, Jun. 1981.

Schaefer-Ridder et al., "Liposomes as Gene Carriers: Efficient Transformation of Mouse L Cells by Thymidine Kinase Gene," *Science* 215(4529):166-168, Jan. 8, 1982, 4 pages total.

Smith et al., "Generating a synthetic genome by whole genome assembly: øX174 bacteriophage from synthetic oligonucleotides," *PNAS* 100(26), 15440-15445, Dec. 23, 2003.

Straubinger et al., "Liposomes as Carriers for Intracellular Delivery of Nucleic Acids," *Methods in Enzymology* 101:512-527, 1983.

Szoka, Jr. et al., "Procedure for preparation of liposomes with large internal aqueous space and high capture by reverse-phase evaporation," *Proc. Natl. Acad. Sci. USA* 75(9):4194-4198, Sep. 1978.

Wagner et al., "Coupling of adenovirus to transferrin-polylysine/DNA complexes greatly enhances receptor-mediated gene delivery and expression of transfected genes," *Proc. Natl. Acad. Sci. USA* 89:6099-6103, Jul. 1992.

Wilson et al., "The Introduction of Poliovirus RNA into Cells via Lipid Vesicles (Liposomes)," *Cell* 17:77-84, May 1979.

Wirtz et al., "Efficient gene delivery to the inflamed colon by local administration of recombinant adenoviruses with normal or modified fibre structure," *Gut* 44:800-807, 1999.

Wolfsberg et al., "Sequence Similarity Searching Using the BLAST Family of Programs," *Current Protocols*, May 2001, 18 pages total.

* cited by examiner

```
          1         11        21        31        41        51
IgkC1     GGTACCGCCGCCACCATGGAGACAGACACACTCCTGCTATGGGTACTGCTGCTCTGGGTT
IgkS1-1   GGTACCGCCGCCACCATGGAGACAGACACACTCCTGCTATGGGTACTGCTGCTCTGGGTT
IgkS1-2   GGTACCGCCGCCACCATGGAGACAGACACACTCCTGCTATGGGTACTGCTGCTCTGGGTT
IgkS1-3   GGTACCGCCGCCACCATGGAGACAGACACACTCCTGCTATGGGTACTGCTGCTCTGGGTT
IgkS1-4   GGTACCGCCGCCACCATGGAGACAGACACACTCCTGCTATGGGTACTGCTGCTCTGGGTT
IgkC2     GGTACCGCCGCCACCATGGAGACCGACACCCTCCTGCTGTGGGTGCTGCTGCTCTGGGTG

          61        71        81        91        101       111
IgkC1     CCAGGTTCCACTGGTGACGGATCCATGCATGGAGATACACCTACATTGCATGAATATATG
IgkS1-1   CCAGGTTCCACTGGTGACGGATCCATGCATGGAGATACACCTACATTGCATGAATATATG
IgkS1-2   CCAGGTTCCACTGGTGACGGATCCATGCATGGAGATACACCTACATTGCATGAATATATG
IgkS1-3   CCAGGTTCCACTGGTGACGGATCCATGCATGGAGATACACCTACATTGCATGAATATATG
IgkS1-4   CCAGGTTCCACTGGTGACGGATCCATGCATGGAGATACACCTACATTGCATGAATATATG
IgkC2     CCCGGCTCCACCGGCGACGGATCCATGCACGGCGACACCCCCACCCTGCACGAGTACATG

          121       131       141       151       161       171
IgkC1     TTAGATTTGCAACCAGAGACAACTGGTCTCTACGGTTATGGGCAATTAAATGACAGCTCA
IgkS1-1   TTAGATTTGCAACCAGAGACAACTGGTCTCTACGGTTATGGGCAATTAAATGACAGCTCA
IgkS1-2   TTAGATTTGCAACCAGAGACAACTGGTCTCTACGGTTATGGGCAATTAAATGACAGCTCA
IgkS1-3   TTAGATTTGCAACCAGAGACAACTGGTCTCTACGGTTATGGGCAATTAAATGACAGCTCA
IgkS1-4   TTAGATTTGCAACCAGAGACAACTGGTCTCTACGGTTATGGGCAATTAAATGACAGCTCA
IgkC2     CTGGACCTGCAGCCCGAGACCACCGGCCTGTACGGCTACGGCCAGCTCAACGACAGCAGC

          181       191       201       211       221       231
IgkC1     GAGGAGGAGGATGAAATAGATGGTCCAGCTGGACAAGCAGAACCGGACAGAGCCCATTAC
IgkS1-1   GAGGAGGAGGATGAAATAGATGGTCCAGCGGGACAAGCGGAACCGGACAGAGCGCATTAC
IgkS1-2   GAGGAGGAGGATGAAATAGATGGTCCAGCAGGACAAGCAGAACCGGACAGAGCACATTAC
IgkS1-3   GAGGAGGAGGATGAAATAGATGGTCCAGCTGGACAAGCTGAACCGGACAGAGCTCATTAC
IgkS1-4   GAGGAGGAGGATGAAATAGATGGTCCAGCCGGACAAGCCGAACCGGACAGAGCCCATTAC
IgkC2     GAGGAGGAGGACGAGATCGACGGCCCCGCCGGCCAGGCCGAGCCCGACCGCGCCCACTAC

          241       251       261       271       281       291
IgkC1     AATATTGTAACCTTTTGTTGCAAGTGTGACTCTACGCTTCGGTTGTGCGTACAAAGCACA
IgkS1-1   AATATTGTAACCTTTTGTTGCAAGTGTGACTCTACGCTTCGGTTGTGCGTACAAAGCACA
IgkS1-2   AATATTGTAACCTTTTGTTGCAAGTGTGACTCTACGCTTCGGTTGTGCGTACAAAGCACA
IgkS1-3   AATATTGTAACCTTTTGTTGCAAGTGTGACTCTACGCTTCGGTTGTGCGTACAAAGCACA
IgkS1-4   AATATTGTAACCTTTTGTTGCAAGTGTGACTCTACGCTTCGGTTGTGCGTACAAAGCACA
IgkC2     AACATCGTGACCTTCTGCTGCAAGTGCGACAGCACCCTGCGCCTCTGCGTGCAGAGCACC

          301       311       321       331       341       351
IgkC1     CACGTAGACATTCGTACTTTGGAAGACCTGTTAATGGGCACACTAGGAATTGTGTGCCCC
IgkS1-1   CACGTAGACATTCGTACTTTGGAAGACCTGTTAATGGGCACACTAGGAATTGTGTGCCCC
IgkS1-2   CACGTAGACATTCGTACTTTGGAAGACCTGTTAATGGGCACACTAGGAATTGTGTGCCCC
IgkS1-3   CACGTAGACATTCGTACTTTGGAAGACCTGTTAATGGGCACACTAGGAATTGTGTGCCCC
IgkS1-4   CACGTAGACATTCGTACTTTGGAAGACCTGTTAATGGGCACACTAGGAATTGTGTGCCCC
IgkC2     CACGTGGACATCCGCACCCTGGAGGACCTGCTGATGGGCACCCTGGGCATCGTGTGCCCC

          361       371       381
IgkC1     ATCTGCTCTCAGAAGCCCTAAGAATTC
IgkS1-1   ATCTGCTCTCAGAAGCCCTAAGAATTC
IgkS1-2   ATCTGCTCTCAGAAGCCCTAAGAATTC
IgkS1-3   ATCTGCTCTCAGAAGCCCTAAGAATTC
IgkS1-4   ATCTGCTCTCAGAAGCCCTAAGAATTC
IgkC2     ATCTGCTCCCAGAAGCCCTAAGAATTC
```

FIGURE 1

```
           1         11        21        31        41        51
IgkS1-5    GGTACCGCCGCCACCATGGAGACAGACACACTCCTGCTATGGGTACTGCTGCTCTGGGTT
IgkS1-6    GGTACCGCCGCCACCATGGAGACAGACACACTCCTGCTATGGGTACTGCTGCTCTGGGTT
IgkS1-7    GGTACCGCCGCCACCATGGAGACAGACACACTCCTGCTATGGGTACTGCTGCTCTGGGTT
IgkS1-8    GGTACCGCCGCCACCATGGAGACAGACACACTCCTGCTATGGGTACTGCTGCTCTGGGTT
IgkS1-9    GGTACCGCCGCCACCATGGAGACAGACACACTCCTGCTATGGGTACTGCTGCTCTGGGTT
IgkS1-10   GGTACCGCCGCCACCATGGAGACAGACACACTCCTGCTATGGGTACTGCTGCTCTGGGTT
IgkC1      GGTACCGCCGCCACCATGGAGACAGACACACTCCTGCTATGGGTACTGCTGCTCTGGGTT
IgkC2      GGTACCGCCGCCACCATGGAGACCGACACCCTCCTGCTGTGGGTGCTGCTGCTCTGGGTG

           61        71        81        91        101       111
IgkS1-5    CCAGGTTCCACTGGTGACGGATCCATGCATGGAGATACACCTACATTGCATGAATATATG
IgkS1-6    CCAGGTTCCACTGGTGACGGATCCATGCATGGAGATACACCTACATTGCATGAATATATG
IgkS1-7    CCAGGTTCCACTGGTGACGGATCCATGCATGGAGATACACCTACATTGCATGAATATATG
IgkS1-8    CCAGGTTCCACTGGTGACGGATCCATGCATGGAGATACACCTACATTGCATGAATATATG
IgkS1-9    CCAGGTTCCACTGGTGACGGATCCATGCATGGAGATACACCTACATTGCATGAATATATG
IgkS1-10   CCAGGTTCCACTGGTGACGGATCCATGCATGGAGATACACCTACATTGCATGAATATATG
IgkC1      CCAGGTTCCACTGGTGACGGATCCATGCATGGAGATACACCTACATTGCATGAATATATG
IgkC2      CCCGGCTCCACCGGCGACGGATCCATGCACGGCGACACCCCCACCCTGCACGAGTACATG

           121       131       141       151       161       171
IgkS1-5    TTAGATTTGCAACCAGAGACAACTGGTCTCTACGGTTATGGGCAATTAAATGACAGCTCA
IgkS1-6    TTAGATTTGCAACCAGAGACAACTGGTCTCTACGGTTATGGGCAATTAAATGACAGCTCA
IgkS1-7    TTAGATTTGCAACCAGAGACAACTGGTCTCTACGGTTATGGGCAATTAAATGACAGCTCA
IgkS1-8    TTAGATTTGCAACCAGAGACAACTGGTCTCTACGGTTATGGGCAATTAAATGACAGCTCA
IgkS1-9    TTAGATTTGCAACCAGAGACAACTGGTCTCTACGGTTATGGGCAATTAAATGACAGCTCA
IgkS1-10   TTAGATTTGCAACCAGAGACAACTGGTCTCTACGGTTATGGGCAATTAAATGACAGCTCA
IgkC1      TTAGATTTGCAACCAGAGACAACTGGTCTCTACGGTTATGGGCAATTAAATGACAGCTCA
IgkC2      CTGGACCTGCAGCCCGAGACCACCGGCCTGTACGGCTACGGCCAGCTCAACGACAGCAGC

           181       191       201       211       221       231
IgkS1-5    GAGGAGGAGGATGAAATAGATGGTCCAGCTGGACAAGCAGAACCGGACAGGGCCCATTAC
IgkS1-6    GAGGAGGAGGATGAAATAGATGGTCCAGCTGGACAAGCAGAACCGGACAGAGCCCATTAC
IgkS1-7    GAGGAGGAGGATGAAATAGATGGTCCAGCTGGACAAGCAGAACCGGACCGGGCCCATTAC
IgkS1-8    GAGGAGGAGGATGAAATAGATGGTCCAGCTGGACAAGCAGAACCGGACCGAGCCCATTAC
IgkS1-9    GAGGAGGAGGATGAAATAGATGGTCCAGCTGGACAAGCAGAACCGGACCGTGCCCATTAC
IgkS1-10   GAGGAGGAGGATGAAATAGATGGTCCAGCTGGACAAGCAGAACCGGACCGCGCCCATTAC
IgkC1      GAGGAGGAGGATGAAATAGATGGTCCAGCTGGACAAGCAGAACCGGACAGAGCCCATTAC
IgkC2      GAGGAGGAGGACGAGATCGACGGCCCCGCCGGCCAGGCCGAGCCCGACCGCGCCCACTAC

           241       251       261       271       281       291
IgkS1-5    AATATTGTAACCTTTTGTTGCAAGTGTGACTCTACGCTTAGGTTGTGCGTACAAAGCACA
IgkS1-6    AATATTGTAACCTTTTGTTGCAAGTGTGACTCTACGCTTAGATTGTGCGTACAAAGCACA
IgkS1-7    AATATTGTAACCTTTTGTTGCAAGTGTGACTCTACGCTTCGGTTGTGCGTACAAAGCACA
IgkS1-8    AATATTGTAACCTTTTGTTGCAAGTGTGACTCTACGCTTCGATTGTGCGTACAAAGCACA
IgkS1-9    AATATTGTAACCTTTTGTTGCAAGTGTGACTCTACGCTTCGTTTGTGCGTACAAAGCACA
IgkS1-10   AATATTGTAACCTTTTGTTGCAAGTGTGACTCTACGCTTCGCTTGTGCGTACAAAGCACA
IgkC1      AATATTGTAACCTTTTGTTGCAAGTGTGACTCTACGCTTCGGTTGTGCGTACAAAGCACA
IgkC2      AACATCGTGACCTTCTGCTGCAAGTGCGACAGCACCCTGCGCCTCTGCGTGCAGAGCACC

           301       311       321       331       341       351
IgkS1-5    CACGTAGACATTAGGACTTTGGAAGACCTGTTAATGGGCACACTAGGAATTGTGTGCCCC
IgkS1-6    CACGTAGACATTAGAACTTTGGAAGACCTGTTAATGGGCACACTAGGAATTGTGTGCCCC
IgkS1-7    CACGTAGACATTCGGACTTTGGAAGACCTGTTAATGGGCACACTAGGAATTGTGTGCCCC
IgkS1-8    CACGTAGACATTCGAACTTTGGAAGACCTGTTAATGGGCACACTAGGAATTGTGTGCCCC
IgkS1-9    CACGTAGACATTCGTACTTTGGAAGACCTGTTAATGGGCACACTAGGAATTGTGTGCCCC
IgkS1-10   CACGTAGACATTCGCACTTTGGAAGACCTGTTAATGGGCACACTAGGAATTGTGTGCCCC
IgkC1      CACGTAGACATTCGTACTTTGGAAGACCTGTTAATGGGCACACTAGGAATTGTGTGCCCC
IgkC2      CACGTGGACATCCGCACCCTGGAGGACCTGCTGATGGGCACCCTGGGCATCGTGTGCCCC

           361       371       381
IgkS1-5    ATCTGCTCTCAGAAGCCCTAAGAATTC
IgkS1-6    ATCTGCTCTCAGAAGCCCTAAGAATTC
IgkS1-7    ATCTGCTCTCAGAAGCCCTAAGAATTC
IgkS1-8    ATCTGCTCTCAGAAGCCCTAAGAATTC
IgkS1-9    ATCTGCTCTCAGAAGCCCTAAGAATTC
IgkS1-10   ATCTGCTCTCAGAAGCCCTAAGAATTC
IgkC1      ATCTGCTCTCAGAAGCCCTAAGAATTC
IgkC2      ATCTGCTCCCAGAAGCCCTAAGAATTC
```

FIGURE 2

```
            1         11        21        31        41        51
IgkC1       GGTACCGCCGCCACCATGGAGACAGACACACTCCTGCTATGGGTACTGCTGCTCTGGGTT
IgkS1-12    GGTACCGCCGCCACCATGGAGACAGACACACTCCTGCTATGGGTACTGCTGCTCTGGGTT
IgkS1-31    GGTACCGCCGCCACCATGGAGACAGACACACTCCTGCTATGGGTACTGCTGCTCTGGGTT
IgkC2       GGTACCGCCGCCACCATGGAGACCGACACCCTCCTGCTGTGGGTGCTGCTGCTCTGGGTG

            61        71        81        91        101       111
IgkC1       CCAGGTTCCACTGGTGACGGATCCATGCATGGAGATACACCTACATTGCATGAATATATG
IgkS1-12    CCAGGTTCCACTGGTGACGGATCCATGCATGGAGATACACCTACATTGCATGAATATATG
IgkS1-31    CCAGGTTCCACTGGTGACGGATCCATGCATGGAGATACACCTACATTGCATGAATATATG
IgkC2       CCCGGCTCCACCGGCGACGGATCCATGCACGGCGACACCCCCACCCTGCACGAGTACATG

            121       131       141       151       161       171
IgkC1       TTAGATTTGCAACCAGAGACAACTGGTCTCTACGGTTATGGGCAATTAAATGACAGCTCA
IgkS1-12    TTAGATTTGCAACCAGAGACAACTGGTCTCTACGGTTATGGGCAATTAAACGACAGCTCA
IgkS1-31    TTAGATTTGCAACCAGAGACAACTGGTCTCTACGGTTATGGGCAATTAAATGACAGCTCA
IgkC2       CTGGACCTGCAGCCCGAGACCACCGGCCTGTACGGCTACGGCCAGCTCAACGACAGCAGC

            181       191       201       211       221       231
IgkC1       GAGGAGGAGGATGAAATAGATGGTCCAGCTGGACAAGCAGAACCGGACAGAGCCCATTAC
IgkS1-12    GAGGAGGAGGATGAAATAGATGGTCCAGCTGGACAAGCAGAACCGGACAGAGCCCATTAC
IgkS1-31    GAGGAGGAGGATGAAATAGATGGTCCAGCTGGACAAGCAGAACCGGACAGAGCCCATTAC
IgkC2       GAGGAGGAGGACGAGATCGACGGCCCCGCCGGCCAGGCCGAGCCCGACCGCGCCCACTAC

            241       251       261       271       281       291
IgkC1       AATATTGTAACCTTTTGTTGCAAGTGTGACTCTACGCTTCGGTTGTGCGTACAAAGCACA
IgkS1-12    AACATTGTAACCTTTTGTTGCAAGTGTGACTCTACGCTTCGGTTGTGCGTACAAAGCACA
IgkS1-31    AATATTGTAACCTTTTGTTGCAAATGTGACTCTACGCTTCGGTTGTGCGTACAAAGCACA
IgkC2       AACATCGTGACCTTCTGCTGCAAGTGCGACAGCACCCTGCGCCTCTGCGTGCAGAGCACC

            301       311       321       331       341       351
IgkC1       CACGTAGACATTCGTACTTTGGAAGACCTGTTAATGGGCACACTAGGAATTGTGTGCCCC
IgkS1-12    CACGTAGACATTCGTACTTTGGAAGACCTGTTAATGGGCACACTAGGAATTGTGTGCCCC
IgkS1-31    CACGTAGACATTCGTACTTTGGAAGACCTGTTAATGGGCACACTAGGAATTGTGTGCCCC
IgkC2       CACGTGGACATCCGCACCCTGGAGGACCTGCTGATGGGCACCCTGGGCATCGTGTGCCCC

            361       371       381
IgkC1       ATCTGCTCTCAGAAGCCCTAAGAATTC
IgkS1-12    ATCTGCTCTCAGAAGCCCTAAGAATTC
IgkS1-31    ATCTGCTCTCAGAAACCCTAAGAATTC
IgkC2       ATCTGCTCCCAGAAGCCCTAAGAATTC
```

FIGURE 3

```
            1         11        21        31        41        51
IgkC1       GGTACCGCCGCCACCATGGAGACAGACACACTCCTGCTATGGGTACTGCTGCTCTGGGTT
IgkS1-13    GGTACCGCCGCCACCATGGAGACAGATACACTCCTGCTATGGGTACTGCTGCTCTGGGTT
IgkS1-14    GGTACCGCCGCCACCATGGAGACAGACACACTCCTGCTATGGGTACTGCTGCTCTGGGTT
IgkC2       GGTACCGCCGCCACCATGGAGACCGACACCCTCCTGCTGTGGGTGCTGCTGCTCTGGGTG

            61        71        81        91        101       111
IgkC1       CCAGGTTCCACTGGTGACGGATCCATGCATGCAGATACACCTACATTGCATGAATATATG
IgkS1-13    CCAGGTTCCACTGGTGATGGATCCATGCATGGAGATACACCTACATTGCATGAATATATG
IgkS1-14    CCAGGTTCCACTGGTGACGGATCCATGCATGGAGACACACCTACATTGCATGAATATATG
IgkC2       CCCGGCTCCACCGGCGACGGATCCATGCACGGCGACACCCCCACCCTGCACGAGTACATG

            121       131       141       151       161       171
IgkC1       TTAGATTTGCAACCAGAGACAACTGGTCTCTACGGTTATGGGCAATTAAATGACAGCTCA
IgkS1-13    TTAGATTTGCAACCAGAGACAACTGGTCTCTACGGTTATGGGCAATTAAATGATAGCTCA
IgkS1-14    TTAGACTTGCAACCAGAGACAACTGGTCTCTACGGTTATGGGCAATTAAATGACAGCTCA
IgkC2       CTGGACCTGCAGCCCGAGACCACCGCCCTGTACGGCTACGGCCAGCTCAACGACAGCAGC

            181       191       201       211       221       231
IgkC1       GAGGAGGAGGATGAAATAGATGGTCCAGCTGGACAAGCAGAACCGGACAGAGCCCATTAC
IgkS1-13    GAGGAGGAGGATGAAATAGATGGTCCAGCTGGACAAGCAGAACCGGATAGAGCCCATTAC
IgkS1-14    GAGGAGGAGGACGAAATAGACGGTCCAGCTGGACAAGCAGAACCGGACAGAGCCCATTAC
IgkC2       GAGGAGGAGGACGAGATCGACGGCCCCGCCGGCCAGGCCGAGCCCGACCGCGCCCACTAC

            241       251       261       271       281       291
IgkC1       AATATTGTAACCTTTTGTTGCAAGTGTGACTCTACGCTTCGGTTGTGCGTACAAAGCACA
IgkS1-13    AATATTGTAACCTTTTGTTGCAAGTGTGATTCTACGCTTCGGTTGTGCGTACAAAGCACA
IgkS1-14    AATATTGTAACCTTTTGTTGCAAGTGTGACTCTACGCTTCGGTTGTGCGTACAAAGCACA
IgkC2       AACATCGTGACCTTCTGCTGCAAGTGCGACAGCACCCTGCGCCTCTGCGTGCAGAGCACC

            301       311       321       331       341       351
IgkC1       CACGTAGACATTCGTACTTTGGAAGACCTGTTAATGGGCACACTAGGAATTGTGTGCCCC
IgkS1-13    CACGTAGATATTCGTACTTTGGAAGATCTGTTAATGGGCACACTAGGAATTGTGTGCCCC
IgkS1-14    CACGTAGACATTCGTACTTTGGAAGACCTGTTAATGGGCACACTAGGAATTGTGTGCCCC
IgkC2       CACGTGGACATCCGCACCCTGGAGGACCTGCTGATGGGCACCCTGGGCATCGTGTGCCCC

            361       371       381
IgkC1       ATCTGCTCTCAGAAGCCCTAAGAATTC
IgkS1-13    ATCTGCTCTCAGAAGCCCTAAGAATTC
IgkS1-14    ATCTGCTCTCAGAAGCCCTAAGAATTC
IgkC2       ATCTGCTCCCAGAAGCCCTAAGAATTC
```

FIGURE 4

```
           1         11        21        31        41        51
IgkC1      GGTACCGCCGCCACCATGGAGACAGACACACTCCTGCTATGGGTACTGCTGCTCTGGGTT
IgkS1-15   GGTACCGCCGCCACCATGGAGACAGACACACTCCTGCTATGGGTACTGCTGCTCTGGGTT
IgkS1-16   GGTACCGCCGCCACCATGGAGACAGACACACTCCTGCTATGGGTACTGCTGCTCTGGGTT
IgkC2      GGTACCGCCGCCACCATGGAGACCGACACCCTCCTGCTGTGGGTGCTGCTGCTCTGGGTG

           61        71        81        91        101       111
IgkC1      CCAGGTTCCACTGGTGACGGATCCATGCATGGAGATACACCTACATTGCATGAATATATG
IgkS1-15   CCAGGTTCCACTGGTGACGGATCCATGCATGGAGATACACCTACATTGCATGAATATATG
IgkS1-16   CCAGGTTCCACTGGTGACGGATCCATGCATGGAGATACACCTACATTGCATGAATATATG
IgkC2      CCCGGCTCCACCGGCGACGGATCCATGCACGGCGACACCCCCACCCTGCACGAGTACATG

           121       131       141       151       161       171
IgkC1      TTAGATTTGCAACCAGAGACAACTGGTCTCTACGGTTATGGGCAATTAAATGACAGCTCA
IgkS1-15   TTAGATTTGCAACCAGAGACAACTGGTCTCTACGGTTATGGGCAATTAAATGACAGCTCA
IgkS1-16   TTAGATTTGCAACCAGAGACAACTGGTCTCTACGGTTATGGGCAATTAAATGACAGCTCA
IgkC2      CTGGACCTGCAGCCCGAGACCACCGGCCTGTACGGCTACGGCCAGCTCAACGACAGCAGC

           181       191       201       211       221       231
IgkC1      GAGGAGGAGGATGAAATAGATGGTCCAGCTGGACAAGCAGAACCGGACAGAGCCCATTAC
IgkS1-15   GAGGAGGAGGATGAAATAGATGGTCCAGCTGGACAAGCAGAACCGGACAGAGCCCATTAC
IgkS1-16   GAGGAGGAGGATGAAATAGATGGTCCAGCTGGACAAGCAGAACCGGACAGAGCCCATTAC
IgkC2      GAGGAGGAGGACGAGATCGACGGCCCCGCCGGCCAGGCCGAGCCCGACCGCGCCCACTAC

           241       251       261       271       281       291
IgkC1      AATATTGTAACCTTTTGTTGCAAGTGTGACTCTACGCTTCGGTTGTGCGTACAAAGCACA
IgkS1-15   AATATTGTAACCTTTTGTTGTAAGTGTGACTCTACGCTTCGGTTGTGTGTACAAAGCACA
IgkS1-16   AATATTGTAACCTTTTGCTGCAAGTGCGACTCTACGCTTCGGTTGTGCGTACAAAGCACA
IgkC2      AACATCGTGACCTTCTGCTGCAAGTGCGACAGCACCCTGCGCCTCTGCGTGCAGAGCACC

           301       311       321       331       341       351
IgkC1      CACGTAGACATTCGTACTTTGGAAGACCTGTTAATGGGCACACTAGGAATTGTGTGCCCC
IgkS1-15   CACGTAGACATTCGTACTTTGGAAGACCTGTTAATGGGCACACTAGGAATTGTGTGTCCC
IgkS1-16   CACGTAGACATTCGTACTTTGGAAGACCTGTTAATGGGCACACTAGGAATTGTGTGCCCC
IgkC2      CACGTGGACATCCGCACCCTGGAGGACCTGCTGATGGGCACCCTGGGCATCGTGTGCCCC

           361       371       381
IgkC1      ATCTGCTCTCAGAAGCCCTAAGAATTC
IgkS1-15   ATCTGTTCTCAGAAGCCCTAAGAATTC
IgkS1-16   ATCTGCTCTCAGAAGCCCTAAGAATTC
IgkC2      ATCTGCTCCCAGAAGCCCTAAGAATTC
```

FIGURE 5

```
           1         11        21        31        41        51
IgkS1-17   GGTACCGCCGCCACCATGGAGACAGACACACTCCTGCTATGGGTACTGCTGCTCTGGGTT
IgkS1-18   GGTACCGCCGCCACCATGGAAACAGACACACTCCTGCTATGGGTACTGCTGCTCTGGGTT
IgkC2      GGTACCGCCGCCACCATGGAGACCGACACCCTCCTGCTGTGGGTGCTGCTGCTCTGGGTG
IgkC1      GGTACCGCCGCCACCATGGAGACAGACACACTCCTGCTATGGGTACTGCTGCTCTGGGTT

           61        71        81        91        101       111
IgkS1-17   CCAGGTTCCACTGGTGACGGATCCATGCATGGAGATACACCTACATTGCATGAGTATATG
IgkS1-18   CCAGGTTCCACTGGTGACGGATCCATGCATGGAGATACACCTACATTGCATGAATATATG
IgkC2      CCCGGCTCCACCGGCGACGGATCCATGCACGGCGACACCCCCACCCTGCACGAGTACATG
IgkC1      CCAGGTTCCACTGGTGACGGATCCATGCATGGAGATACACCTACATTGCATGAATATATG

           121       131       141       151       161       171
IgkS1-17   TTAGATTTGCAACCAGAGACAACTGGTCTCTACGGTTATGGGCAATTAAATGACAGCTCA
IgkS1-18   TTAGATTTGCAACCAGAAACAACTGGTCTCTACGGTTATGGGCAATTAAATGACAGCTCA
IgkC2      CTGGACCTGCAGCCCGAGACCACCGGCCTGTACGGCTACGGCCAGCTCAACGACAGCAGC
IgkC1      TTAGATTTGCAACCAGAGACAACTGGTCTCTACGGTTATGGGCAATTAAATGACAGCTCA

           181       191       201       211       221       231
IgkS1-17   GAGGAGGAGGATGAGATAGATGGTCCAGCTGGACAAGCAGAGCCGGACAGAGCCCATTAC
IgkS1-18   GAAGAAGAAGATGAAATAGATGGTCCAGCTGGACAAGCAGAACCGGACAGAGCCCATTAC
IgkC2      GAGGAGGAGGACGAGATCGACGGCCCCGCCGGCCAGGCCGAGCCCGACCGCGCCCACTAC
IgkC1      GAGGAGGAGGATGAAATAGATGGTCCAGCTGGACAAGCAGAACCGGACAGAGCCCATTAC

           241       251       261       271       281       291
IgkS1-17   AATATTGTAACCTTTTGTTGCAAGTGTGACTCTACGCTTCGGTTGTGCGTACAAAGCACA
IgkS1-18   AATATTGTAACCTTTTGTTGCAAGTGTGACTCTACGCTTCGGTTGTGCGTACAAAGCACA
IgkC2      AACATCGTGACCTTCTGCTGCAAGTGCGACAGCACCCTGCGCCTCTGCGTGCAGAGCACC
IgkC1      AATATTGTAACCTTTTGTTGCAAGTGTGACTCTACGCTTCGGTTGTGCGTACAAAGCACA

           301       311       321       331       341       351
IgkS1-17   CACGTAGACATTCGTACTTTGGAGGACCTGTTAATGGGCACACTAGGAATTGTGTGCCCC
IgkS1-18   CACGTAGACATTCGTACTTTGGAAGACCTGTTAATGGGCACACTAGGAATTGTGTGCCCC
IgkC2      CACGTGGACATCCGCACCCTGGAGGACCTGCTGATGGGCACCCTGGGCATCGTGTGCCCC
IgkC1      CACGTAGACATTCGTACTTTGGAAGACCTGTTAATGGGCACACTAGGAATTGTGTGCCCC

           361       371       381
IgkS1-17   ATCTGCTCTCAGAAGCCCTAAGAATTC
IgkS1-18   ATCTGCTCTCAGAAGCCCTAAGAATTC
IgkC2      ATCTGCTCCCAGAAGCCCTAAGAATTC
IgkC1      ATCTGCTCTCAGAAGCCCTAAGAATTC
```

FIGURE 6

```
             1         11        21        31        41        51
IgkC1        GGTACCGCCGCCACCATGGAGACAGACACACTCCTGCTATGGGTACTGCTGCTCTGGGTT
IgkS1-19     GGTACCGCCGCCACCATGGAGACAGACACACTCCTGCTATGGGTACTGCTGCTCTGGGTT
IgkS1-20     GGTACCGCCGCCACCATGGAGACAGACACACTCCTGCTATGGGTACTGCTGCTCTGGGTT
IgkC2        GGTACCGCCGCCACCATGGAGACCGACACCCTCCTGCTGTGGGTGCTGCTGCTCTGGGTG

             61        71 .      81        91        101       111
IgkC1        CCAGGTTCCACTGGTGACGGATCCATGCATGGAGATACACCTACATTGCATGAATATATG
IgkS1-19     CCAGGTTCCACTGGTGACGGATCCATGCATGGAGATACACCTACATTGCATGAATATATG
IgkS1-20     CCAGGTTCCACTGGTGACGGATCCATGCATGGAGATACACCTACATTGCATGAATATATG
IgkC2        CCCGGCTCCACCGGCGACGGATCCATGCACGGCGACACCCCCACCCTGCACGAGTACATG

             121       131       141       151       161       171
IgkC1        TTAGATTTGCAACCAGAGACAACTGGTCTCTACGGTTATGGGCAATTAAATGACAGCTCA
IgkS1-19     TTAGATTTGCAGCCAGAGACAACTGGTCTCTACGGTTATGGGCAGTTAAATGACAGCTCA
IgkS1-20     TTAGATTTGCAACCAGAGACAACTGGTCTCTACGGTTATGGGCAATTAAATGACAGCTCA
IgkC2        CTGGACCTGCAGCCCGAGACCACCGGCCTGTACGGCTACGGCCAGCTCAACGACAGCAGC

             181       191       201       211       221       231
IgkC1        GAGGAGGAGGATGAAATAGATGGTCCAGCTGGACAAGCAGAACCGGACAGAGCCCATTAC
IgkS1-19     GAGGAGGAGGATGAAATAGATGGTCCAGCTGGACAGGCAGAACCGGACAGAGCCCATTAC
IgkS1-20     GAGGAGGAGGATGAAATAGATGGTCCAGCTGGACAAGCAGAACCGGACAGAGCCCATTAC
IgkC2        GAGGAGGAGGACGAGATCGACGGCCCCGCCGGCCAGGCCGAGCCCGACCGCGCCCACTAC

             241       251       261       271       281       291
IgkC1        AATATTGTAACCTTTTGTTGCAAGTGTGACTCTACGCTTCGGTTGTGCGTACAAAGCACA
IgkS1-19     AATATTGTAACCTTTTGTTGCAAGTGTGACTCTACGCTTCGGTTGTGCGTACAGAGCACA
IgkS1-20     AATATTGTAACCTTTTGTTGCAAGTGTGACTCTACGCTTCGGTTGTGCGTACAAAGCACA
IgkC2        AACATCGTGACCTTCTGCTGCAAGTGCGACAGCACCCTGCGCCTCTGCGTGCAGAGCACC

             301       311       321       331       341       351
IgkC1        CACGTAGACATTCGTACTTTGGAAGACCTGTTAATGGGCACACTAGGAATTGTGTGCCCC
IgkS1-19     CACGTAGACATTCGTACTTTGGAAGACCTGTTAATGGGCACACTAGGAATTGTGTGCCCC
IgkS1-20     CACGTAGACATTCGTACTTTGGAAGACCTGTTAATGGGCACACTAGGAATTGTGTGCCCC
IgkC2        CACGTGGACATCCGCACCCTGGAGGACCTGCTGATGGGCACCCTGGGCATCGTGTGCCCC

             361       371       381
IgkC1        ATCTGCTCTCAGAAGCCCTAAGAATTC
IgkS1-19     ATCTGCTCTCAGAAGCCCTAAGAATTC
IgkS1-20     ATCTGCTCTCAAAAGCCCTAAGAATTC
IgkC2        ATCTGCTCCCAGAAGCCCTAAGAATTC
```

FIGURE 7

```
              1         11        21        31        41        51
IgkC1         GGTACCGCCGCCACCATGGAGACAGACACACTCCTGCTATGGGTACTGCTGCTCTGGGTT
IgkS1-21      GGTACCGCCGCCACCATGGAGACAGACACACTCCTGCTATGGGTACTGCTGCTCTGGGTT
IgkS1-22      GGTACCGCCGCCACCATGGAGACAGACACACTCCTGCTATGGGTACTGCTGCTCTGGGTT
IgkS1-23      GGTACCGCCGCCACCATGGAGACAGACACACTCCTGCTATGGGTACTGCTGCTCTGGGTT
IgkS1-24      GGTACCGCCGCCACCATGGAGACAGACACACTCCTGCTATGGGTACTGCTGCTCTGGGTT
IgkC2         GGTACCGCCGCCACCATGGAGACCGACACCCTCCTGCTGTGGGTGCTGCTGCTCTGGGTG

              61        71        81        91        101       111
IgkC1         CCAGGTTCCACTGGTGACGGATCCATGCATGGAGATACACCTACATTGCATGAATATATG
IgkS1-21      CCAGGGTCCACTGGGGACGGATCCATGCATGGGGATACACCTACATTGCATGAATATATG
IgkS1-22      CCAGGATCCACTGGAGACGGATCCATGCATGCAGATACACCTACATTGCATGAATATATG
IgkS1-23      CCAGGTTCCACTGGTGACGGATCCATGCATGGTGATACACCTACATTGCATGAATATATC
IgkS1-24      CCAGGCTCCACTGGCGACGGATCCATGCATGGCGATACACCTACATTGCATGAATATATG
IgkC2         CCCGGCTCCACCGGCGACGGATCCATGCACGGCGACACCCCCACCCTGCACGAGTACATG

              121       131       141       151       161       171
IgkC1         TTAGATTTGCAACCAGAGACAACTGGTCTCTACGGTTATGGGCAATTAAATGACAGCTCA
IgkS1-21      TTAGATTTGCAACCAGAGACAACTGGGCTCTACGGGTATGGGCAATTAAATGACAGCTCA
IgkS1-22      TTAGATTTGCAACCAGAGACAACTGGACTCTACGGATATGGACAATTAAATGACAGCTCA
IgkS1-23      TTAGATTTGCAACCAGAGACAACTGCTCTCTACGGTTATGGTCAATTAAATGACAGCTCA
IgkS1-24      TTAGATTTGCAACCAGAGACAACTGGCCTCTACGGCTATGGCCAATTAAATGACAGCTCA
IgkC2         CTGGACCTGCAGCCCGAGACCACCGGCCTGTACGGCTACGGCCAGCTCAACGACAGCAGC

              181       191       201       211       221       231
IgkC1         GAGGAGGAGGATGAAATAGATGGTCCAGCTGGACAAGCAGAACCGGACAGAGCCCATTAC
IgkS1-21      GAGGAGGAGGATGAAATAGATGGGCCAGCTGGGCAAGCAGAACCGGACAGAGCCCATTAC
IgkS1-22      GAGGAGGAGGATGAAATAGATGGACCAGCTGGACAAGCAGAACCGGACAGAGCCCATTAC
IgkS1-23      GAGGAGGAGGATGAAATAGATGGTCCAGCTGGTCAAGCAGAACCGGACAGAGCCCATTAC
IgkS1-24      GAGGAGGAGGATGAAATAGATGGCCCAGCTGGCCAAGCAGAACCGGACAGAGCCCATTAC
IgkC2         GAGGAGGAGGACGAGATCGACGGCCCCGCCGGCCAGGCCGAGCCCGACCGCGCCCACTAC

              241       251       261       271       281       291
IgkC1         AATATTGTAACCTTTTGTTGCAAGTGTGACTCTACGCTTCGGTTGTGCGTACAAAGCACA
IgkS1-21      AATATTGTAACCTTTTGTTGCAAGTGTGACTCTACGCTTCGGTTGTGCGTACAAAGCACA
IgkS1-22      AATATTGTAACCTTTTGTTGCAAGTGTGACTCTACGCTTCGGTTGTGCGTACAAAGCACA
IgkS1-23      AATATTGTAACCTTTTGTTGCAAGTGTGACTCTACGCTTCGGTTGTGCGTACAAAGCACA
IgkS1-24      AATATTGTAACCTTTTGTTGCAAGTGTGACTCTACGCTTCGGTTGTGCGTACAAAGCACA
IgkC2         AACATCGTGACCTTCTGCTGCAAGTGCGACAGCACCCTGCGCCTCTGCGTGCAGAGCACC

              301       311       321       331       341       351
IgkC1         CACGTAGACATTCGTACTTTGGAAGACCTGTTAATGGGCACACTAGGAATTGTGTGCCCC
IgkS1-21      CACGTAGACATTCGTACTTTGGAAGACCTGTTAATGGGGACACTAGGGATTGTGTGCCCC
IgkS1-22      CACGTAGACATTCGTACTTTGGAAGACCTGTTAATGGGAACACTAGGAATTGTGTGCCCC
IgkS1-23      CACGTAGACATTCGTACTTTGGAAGACCTGTTAATGGGTACACTAGGTATTGTGTGCCCC
IgkS1-24      CACGTAGACATTCGTACTTTGGAAGACCTGTTAATGGGCACACTAGGCATTGTGTGCCCC
IgkC2         CACGTGGACATCCGCACCCTGGAGGACCTGCTGATGGGCACCCTGGGCATCGTGTGCCCC

              361       371       381
IgkC1         ATCTGCTCTCAGAAGCCCTAAGAATTC
IgkS1-21      ATCTGCTCTCAGAAGCCCTAAGAATTC
IgkS1-22      ATCTGCTCTCAGAAGCCCTAAGAATTC
IgkS1-23      ATCTGCTCTCAGAAGCCCTAAGAATTC
IgkS1-24      ATCTGCTCTCAGAAGCCCTAAGAATTC
IgkC2         ATCTGCTCCCAGAAGCCCTAAGAATTC
```

FIGURE 8

```
          1         11        21        31        41        51
IgkC1     GGTACCGCCGCCACCATGGAGACAGACACACTCCTGCTATGGGTACTGCTGCTCTGGGTT
IgkS1-25  GGTACCGCCGCCACCATGGAGACAGACACACTCCTGCTATGGGTACTGCTGCTCTGGGTT
IgkS1-26  GGTACCGCCGCCACCATGGAGACAGACACACTCCTGCTATGGGTACTGCTGCTCTGGGTT
IgkC2     GGTACCGCCGCCACCATGGAGACCGACACCCTCCTGCTGTGGGTGCTGCTGCTCTGGGTG

          61        71        81        91        101       111
IgkC1     CCAGGTTCCACTGGTGACGGATCCATGCATGGAGATACACCTACATTGCATGAATATATG
IgkS1-25  CCAGGTTCCACTGGTGACGGATCCATGCATGGAGATACACCTACATTGCATGAATATATG
IgkS1-26  CCAGGTTCCACTGGTGACGGATCCATGCACGGAGATACACCTACATTGCACGAATATATG
IgkC2     CCCGGCTCCACCGGCGACGGATCCATGCACGGCGACACCCCCACCCTGCACGAGTACATG

          121       131       141       151       161       171
IgkC1     TTAGATTTGCAACCAGAGACAACTGGTCTCTACGGTTATGGGCAATTAAATGACAGCTCA
IgkS1-25  TTAGATTTGCAACCAGAGACAACTGGTCTCTACGGTTATGGGCAATTAAATGACAGCTCA
IgkS1-26  TTAGATTTGCAACCAGAGACAACTGGTCTCTACGGTTATGGGCAATTAAATGACAGCTCA
IgkC2     CTGGACCTGCAGCCCGAGACCACCGGCCTGTACGGCTACGGCCAGCTCAACGACAGCAGC

          181       191       201       211       221       231
IgkC1     GAGGAGGAGGATGAAATAGATGGTCCAGCTGGACAAGCAGAACCGGACAGAGCCCATTAC
IgkS1-25  GAGGAGGAGGATGAAATAGATGGTCCAGCTGGACAAGCAGAACCGGACAGAGCCCATTAC
IgkS1-26  GAGGAGGAGGATGAAATAGATGGTCCAGCTGGACAAGCAGAACCGGACAGAGCCCACTAC
IgkC2     GAGGAGGAGGACGAGATCGACGGCCCCGCCGGCCAGGCCGAGCCCGACCGCGCCCACTAC

          241       251       261       271       281       291
IgkC1     AATATTGTAACCTTTTGTTGCAAGTGTGACTCTACGCTTCGGTTGTGCGTACAAAGCACA
IgkS1-25  AATATTGTAACCTTTTGTTGCAAGTGTGACTCTACGCTTCGGTTGTGCGTACAAAGCACA
IgkS1-26  AATATTGTAACCTTTTGTTGCAAGTGTGACTCTACGCTTCGGTTGTGCGTACAAAGCACA
IgkC2     AACATCGTGACCTTCTGCTGCAAGTGCGACAGCACCCTGCGCCTCTGCGTGCAGAGCACC

          301       311       321       331       341       351
IgkC1     CACGTAGACATTCGTACTTTGGAAGACCTGTTAATGGGCACACTAGGAATTGTGTGCCCC
IgkS1-25  CATGTAGACATTCGTACTTTGGAAGACCTGTTAATGGGCACACTAGGAATTGTGTGCCCC
IgkS1-26  CACGTAGACATTCGTACTTTGGAAGACCTGTTAATGGGCACACTAGGAATTGTGTGCCCC
IgkC2     CACGTGGACATCCGCACCCTGGAGGACCTGCTGATGGGCACCCTGGGCATCGTGTGCCCC

          361       371       381
IgkC1     ATCTGCTCTCAGAAGCCCTAAGAATTC
IgkS1-25  ATCTGCTCTCAGAAGCCCTAAGAATTC
IgkS1-26  ATCTGCTCTCAGAAGCCCTAAGAATTC
IgkC2     ATCTGCTCCCAGAAGCCCTAAGAATTC
```

FIGURE 9

```
             1         11        21        31        41        51
IgkC1        GGTACCGCCGCCACCATGGAGACAGACACACTCCTGCTATGGGTACTGCTGCTCTGGGTT
IgkS1-27     GGTACCGCCGCCACCATGGAGACAGACACACTCCTGCTATGGGTACTGCTGCTCTGGGTT
IgkS1-28     GGTACCGCCGCCACCATGGAGACAGACACACTCCTGCTATGGGTACTGCTGCTCTGGGTT
IgkS1-29     GGTACCGCCGCCACCATGGAGACAGACACACTCCTGCTATGGGTACTGCTGCTCTGGGTT
IgkC2        GGTACCGCCGCCACCATGGAGACCGACACCCTCCTGCTGTGGGTGCTGCTGCTCTGGGTG

             61        71        81        91        101       111
IgkC1        CCAGGTTCCACTGGTGACGGATCCATGCATGGAGATACACCTACATTGCATGAATATATG
IgkS1-27     CCAGGTTCCACTGGTGACGGATCCATGCATGGAGATACACCTACATTGCATGAATATATG
IgkS1-28     CCAGGTTCCACTGGTGACGGATCCATGCATGGAGATACACCTACATTGCATGAATATATG
IgkS1-29     CCAGGTTCCACTGGTGACGGATCCATGCATGGAGATACACCTACATTGCATGAATATATG
IgkC2        CCCGGCTCCACCGGCGACGGATCCATGCACGGCGACACCCCCACCCTGCACGAGTACATG

             121       131       141       151       161       171
IgkC1        TTAGATTTGCAACCAGAGACAACTGGTCTCTACGGTTATGGGCAATTAAATGACAGCTCA
IgkS1-27     TTAGATTTGCAACCAGAGACAACTGGTCTCTACGGTTATGGGCAATTAAATGACAGCTCA
IgkS1-28     TTAGATTTGCAACCAGAGACAACTGGTCTCTACGGTTATGGGCAATTAAATGACAGCTCA
IgkS1-29     TTAGATTTGCAACCAGAGACAACTGGTCTCTACGGTTATGGGCAATTAAATGACAGCTCA
IgkC2        CTGGACCTGCAGCCCGAGACCACCGGCCTGTACGGCTACGGCCAGCTCAACGACAGCAGC

             181       191       201       211       221       231
IgkC1        GAGGAGGAGGATGAAATAGATGGTCCAGCTGGACAAGCAGAACCGGACAGAGCCCATTAC
IgkS1-27     GAGGAGGAGGATGAAATAGATGGTCCAGCTGGACAAGCAGAACCGGACAGAGCCCATTAC
IgkS1-28     GAGGAGGAGGATGAAATTGATGGTCCAGCTGGACAAGCAGAACCGGACAGAGCCCATTAC
IgkS1-29     GAGGAGGAGGATGAAATCGATGGTCCAGCTGGACAAGCAGAACCGGACAGAGCCCATTAC
IgkC2        GAGGAGGAGGACGAGATCGACGGCCCCGCCGGCCAGGCCGAGCCCGACCGCGCCCACTAC

             241       251       261       271       281       291
IgkC1        AATATTGTAACCTTTTGTTGCAAGTGTGACTCTACGCTTCGGTTGTGCGTACAAAGCACA
IgkS1-27     AATATAGTAACCTTTTGTTGCAAGTGTGACTCTACGCTTCGGTTGTGCGTACAAAGCACA
IgkS1-28     AATATTGTAACCTTTTGTTGCAAGTGTGACTCTACGCTTCGGTTGTGCGTACAAAGCACA
IgkS1-29     AATATCGTAACCTTTTGTTGCAAGTGTGACTCTACGCTTCGGTTGTGCGTACAAAGCACA
IgkC2        AACATCGTGACCTTCTGCTGCAAGTGCGACAGCACCCTGCGCCTCTGCGTGCAGAGCACC

             301       311       321       331       341       351
IgkC1        CACGTAGACATTCGTACTTTGGAAGACCTGTTAATGGGCACACTAGGAATTGTGTGCCCC
IgkS1-27     CACGTAGACATACGTACTTTGGAAGACCTGTTAATGGGCACACTAGGAATAGTGTGCCCC
IgkS1-28     CACGTAGACATTCGTACTTTGGAAGACCTGTTAATGGGCACACTAGGAATTGTGTGCCCC
IgkS1-29     CACGTAGACATCCGTACTTTGGAAGACCTGTTAATGGGCACACTAGGAATCGTGTGCCCC
IgkC2        CACGTGGACATCCGCACCCTGGAGGACCTGCTGATGGGCACCCTGGGCATCGTGTGCCCC

             361       371       381
IgkC1        ATCTGCTCTCAGAAGCCCTAAGAATTC
IgkS1-27     ATATGCTCTCAGAAGCCCTAAGAATTC
IgkS1-28     ATTTGCTCTCAGAAGCCCTAAGAATTC
IgkS1-29     ATCTGCTCTCAGAAGCCCTAAGAATTC
IgkC2        ATCTGCTCCCAGAAGCCCTAAGAATTC
```

FIGURE 10

```
          1         11        21        31        41        51
IgkS1-50  GGTACCGCCGCCACCATGGAAACTGACACTCTGCTGCTGTGGGTACTGCTGCTGTGGGTT
IgkS1-51  GGTACCGCCGCCACCATGGAAACTGACACTCTACTACTATGGGTACTACTACTATGGGTT
IgkS1-52  GGTACCGCCGCCACCATGGAAACTGACACTCTTCTTCTTTGGGTACTTCTTCTTTGGGTT
IgkS1-53  GGTACCGCCGCCACCATGGAAACTGACACTCTCCTCCTCTGGGTACTCCTCCTCTGGGTT
IgkS1-54  GGTACCGCCGCCACCATGGAAACTGACACTTTGTTGTTGTGGGTATTGTTGTTGTGGGTT
IgkS1-55  GGTACCGCCGCCACCATGGAAACTGACACTTTATTATTATGGGTATTATTATTATGGGTT
IgkC3     GGTACCGCCGCCACCATGGAGACAGACACACTCCTGCTATGGGTACTGCTGCTCTGGGTT
IgkC4     GGTACCGCCGCCACCATGGAGACCGACACCCTCCTGCTGTGGGTGCTGCTGCTCTGGGTG

          61        71        81        91        101       111
IgkS1-50  CCAGGATCGACTGGAGACGGATCCATGCATGGAGACACTCCAACTCTGCATGAATATATG
IgkS1-51  CCAGGATCGACTGGAGACGGATCCATGCATGGAGACACTCCAACTCTACATGAATATATG
IgkS1-52  CCAGGATCGACTGGAGACGGATCCATGCATGGAGACACTCCAACTCTTCATGAATATATG
IgkS1-53  CCAGGATCGACTGGAGACGGATCCATGCATGGAGACACTCCAACTCTCCATGAATATATG
IgkS1-54  CCAGGATCGACTGGAGACGGATCCATGCATGGAGACACTCCAACTTTGCATGAATATATG
IgkS1-55  CCAGGATCGACTGGAGACGGATCCATGCATGGAGACACTCCAACTTTACATGAATATATG
IgkC3     CCAGGTTCCACTGGTGACGGATCCATGCATGGAGATACACCTACATTGCATGAATATATG
IgkC4     CCCGGCTCCACCGGCGACGGATCCATGCACGGCGACACCCCCACCCTGCACGAGTACATG

          121       131       141       151       161       171
IgkS1-50  CTGGACCTGCAACCGCAAACTACTGACCTGTACTGCTATGAACAACTGAATGACAGCTCG
IgkS1-51  CTAGACCTACAACCGGAAACTACTGACCTATACTGCTATGAACAACTAAATGACAGCTCG
IgkS1-52  CTTGACCTTCAACCGGAAACTACTGACCTTTACTGCTATGAACAACTTAATGACAGCTCG
IgkS1-53  CTCGACCTCCAACCGGAAACTACTGACCTCTACTGCTATGAACAACTCAATGACAGCTCG
IgkS1-54  TTGGACTTGCAACCGGAAACTACTGACTTGTACTGCTATGAACAATTGAATGACAGCTCG
IgkS1-55  TTAGACTTACAACCGGAAACTACTGACTTATACTGCTATGAACAATTAAATGACAGCTCG
IgkC3     TTAGATTTGCAACCAGAGACAACTGATCTCTACTGTTATGAGCAATTAAATGACAGCTCA
IgkC4     CTGGACCTGCAGCCCGAGACCACCGACCTGTACTGCTACGAGCAGCTCAACGACAGCAGC

          181       191       201       211       221       231
IgkS1-50  GAAGAAGAAGACGAAATAGACGGACCTGCAGGACAAGCAGAACCAGACCGCGCACATTAC
IgkS1-51  GAAGAAGAAGACGAAATAGACGGACCTGCAGGACAAGCAGAACCAGACCGCGCACATTAC
IgkS1-52  GAAGAAGAAGACGAAATAGACGGACCTGCAGGACAAGCAGAACCAGACCGCGCACATTAC
IgkS1-53  GAAGAAGAAGACGAAATAGACGGACCTGCAGGACAAGCAGAACCAGACCGCGCACATTAC
IgkS1-54  GAAGAAGAAGACGAAATAGACGGACCTGCAGGACAAGCAGAACCAGACCGCGCACATTAC
IgkS1-55  GAAGAAGAAGACGAAATAGACGGACCTGCAGGACAAGCAGAACCAGACCGCGCACATTAC
IgkC3     GAGGAGGAGGATGAAATAGATGGTCCAGCTGGACAAGCAGAACCGGACAGAGCCCATTAC
IgkC4     GAGGAGGAGGACGAGATCGACGGCCCCGCCGGCCAGGCCGAGCCCGACCGCGCCCACTAC

          241       251       261       271       281       291

IgkS1-50  AATATTGTAACTTTTTGCTGCAAGTGCGACAGTACTCTGCGCCTGTGCGTACAAAGCACT
IgkS1-51  AATATTGTAACTTTTTGCTGCAAGTGCGACAGTACTCTACGCCTATGCGTACAAAGCACT
IgkS1-52  AATATTGTAACTTTTTGCTGCAAGTGCGACAGTACTCTTCGCCTTTGCGTACAAAGCACT
IgkS1-53  AATATTGTAACTTTTTGCTGCAAGTGCGACAGTACTCTCCGCCTCTGCGTACAAAGCACT
IgkS1-54  AATATTGTAACTTTTTGCTGCAAGTGCGACAGTACTTTGCGCTTGTGCGTACAAAGCACT
IgkS1-55  AATATTGTAACTTTTTGCTGCAAGTGCGACAGTACTTTACGCTTATGCGTACAAAGCACT
IgkC3     AATATTGTAACCTTTTGTTGCAAGTGTGACTCTACGCTTCGGTTGTGCGTACAAAGCACA
IgkC4     AACATCGTGACCTTCTGCTGCAAGTGCGACAGCACCCTGCGCCTCTGCGTGCAGAGCACC

          301       311       321       331       341       351
IgkS1-50  CATGTAGACATTCGCACTCTGGAAGACCTGCTGATGGGAACTCTGGGAATTGTTTGCCCG
IgkS1-51  CATGTAGACATTCGCACTCTAGAAGACCTACTAATGGGAACTCTAGGAATTGTTTGCCCG
IgkS1-52  CATGTAGACATTCGCACTCTTGAAGACCTTCTTATGGGAACTCTTGGAATTGTTTGCCCG
IgkS1-53  CATGTAGACATTCGCACTCTCGAAGACCTCCTCATGGGAACTCTCGGAATTGTTTGCCCG
IgkS1-54  CATGTAGACATTCGCACTTTGGAAGACTTGTTGATGGGAACTTTGGGAATTGTTTGCCCG
IgkS1-55  CATGTAGACATTCGCACTTTAGAAGACTTATTAATGGGAACTTTAGGAATTGTTTGCCCG
IgkC3     CACGTAGACATTCGTACTTTGGAAGACCTGTTAATGGGCACACTAGGAATTGTGTGCCCC
IgkC4     CACGTGGACATCCGCACCCTGGAGGACCTGCTGATGGGCACCCTGGGCATCGTGTGCCCC

          361       371       381
IgkS1-51  ATCTGCTCGCAAAAGCCTTAAGAATTC
IgkS1-53  ATCTGCTCGCAAAAGCCTTAAGAATTC
IgkS1-50  ATCTGCTCGCAAAAGCCTTAAGAATTC
IgkS1-52  ATCTGCTCGCAAAAGCCTTAAGAATTC
IgkS1-55  ATCTGCTCGCAAAAGCCTTAAGAATTC
IgkS1-54  ATCTGCTCGCAAAAGCCTTAAGAATTC
IgkC3     ATCTGCTCTCAGAAGCCCTAAGAATTC
IgkC4     ATCTGCTCCCAGAAGCCCTAAGAATTC
```

FIGURE 11

```
          1         11        21        31        41        51
IgkS1-32  GGTACCGCCGCCACCATGGAGACAGACACACTCCTGCTATGGGTACTGCTGCTCTGGGTT
IgkS1-33  GGTACCGCCGCCACCATGGAGACAGACACACTCCTGCTATGGGTACTGCTGCTCTGGGTT
IgkC1     GGTACCGCCGCCACCATGGAGACAGACACACTCCTGCTATGGGTACTGCTGCTCTGGGTT
IgkC2     GGTACCGCCGCCACCATGGAGACCGACACCCTCCTGCTGTGGGTGCTGCTGCTCTGGGTG

          61        71        81        91        101       111
IgkS1-32  CCAGGTTCCACTGGTGACGGATCCATGCATGGAGATACACCTACATTGCATGAATATATG
IgkS1-33  CCAGGTTCCACTGGTGACGGATCCATGCATGGAGATACACCTACATTGCATGAATATATG
IgkC1     CCAGGTTCCACTGGTGACGGATCCATGCATGGAGATACACCTACATTGCATGAATATATG
IgkC2     CCCGGCTCCACCGGCGACGGATCCATGCACGGCGACACCCCCACCCTGCACGAGTACATG

          121       131       141       151       161       171
IgkS1-32  TTAGATTTTCAACCAGAGACAACTGGTTTTTACGGTTATGGGCAATTAAATGACAGCTCA
IgkS1-33  TTAGATTTCCAACCAGAGACAACTGGTTTCTACGGTTATGGGCAATTAAATGACAGCTCA
IgkC1     TTAGATTTGCAACCAGAGACAACTGGTCTCTACGGTTATGGGCAATTAAATGACAGCTCA
IgkC2     CTGGACCTGCAGCCCGAGACCACCGGCCTGTACGGCTACGGCCAGCTCAACGACAGCAGC

          181       191       201       211       221       231
IgkS1-32  GAGGAGGAGGATGAAATAGATGGTCCAGCTGGACAAGCAGAACCGGACAGAGCCCATTAC
IgkS1-33  GAGGAGGAGGATGAAATAGATGGTCCAGCTGGACAAGCAGAACCGGACAGAGCCCATTAC
IgkC1     GAGGAGGAGGATGAAATAGATGGTCCAGCTGGACAAGCAGAACCGGACAGAGCCCATTAC
IgkC2     GAGGAGGAGGACGAGATCGACGGCCCCGCCGGCCAGGCCGAGCCCGACCGCGCCCACTAC

          241       251       261       271       281       291
IgkS1-32  AATATTGTAACCTTTTGTTGCAAGTGTGACTCTACGCTTCGGTTGTGCGTACAAAGCACA
IgkS1-33  AATATTGTAACCTTCTGTTGCAAGTGTGACTCTACGCTTCGGTTGTGCGTACAAAGCACA
IgkC1     AATATTGTAACCTTTTGTTGCAAGTGTGACTCTACGCTTCGGTTGTGCGTACAAAGCACA
IgkC2     AACATCGTGACCTTCTGCTGCAAGTGCGACAGCACCCTGCGCCTCTGCGTGCAGAGCACC

          301       311       321       331       341       351
IgkS1-32  CACGTAGACATTCGTACTTTGGAAGACCTGTTAATGGGCACACTAGGAATTGTGTGCCCC
IgkS1-33  CACGTAGACATTCGTACTTTGGAAGACCTGTTAATGGGCACACTAGGAATTGTGTGCCCC
IgkC1     CACGTAGACATTCGTACTTTGGAAGACCTGTTAATGGGCACACTAGGAATTGTGTGCCCC
IgkC2     CACGTGGACATCCGCACCCTGGAGGACCTGCTGATGGGCACCCTGGGCATCGTGTGCCCC

          361       371       381
IgkS1-32  ATCTGCTCTCAGAAGCCCTAAGAATTC
IgkS1-33  ATCTGCTCTCAGAAGCCCTAAGAATTC
IgkC1     ATCTGCTCTCAGAAGCCCTAAGAATTC
IgkC2     ATCTGCTCCCAGAAGCCCTAAGAATTC
```

FIGURE 12

```
           1         11        21        31        41        51
IgkS1-56   GGTACCGCCGCCACCATGGAAACTGACACTCTCCTGCTATGGGTACTGCTGCTCTGGGTT
IgkS1-57   GGTACCGCCGCCACCATGGAAACTGACACTCTCCTGCTATGGGTACTGCTGCTCTGGGTT
IgkS1-58   GGTACCGCCGCCACCATGGAAACTGACACTCTCCTGCTATGGGTACTGCTGCTCTGGGTT
IgkS1-59   GGTACCGCCGCCACCATGGAAACTGACACTCTCCTGCTATGGGTACTGCTGCTCTGGGTT
IgkC3      GGTACCGCCGCCACCATGGAGACAGACACACTCCTGCTATGGGTACTGCTGCTCTGGGTT
IgkC4      GGTACCGCCGCCACCATGGAGACCGACACCCTCCTGCTGTGGGTGCTGCTGCTCTGGGTG

           61        71        81        91        101       111
IgkS1-56   CCGGGATCGACTGGAGACGGATCCATGCATGGAGACACTCCGACTTTGCATGAATATATG
IgkS1-57   CCAGGATCGACTGGAGACGGATCCATGCATGGAGACACTCCAACTTTGCATGAATATATG
IgkS1-58   CCTGGATCGACTGGAGACGGATCCATGCATGGAGACACTCCTACTTTGCATGAATATATG
IgkS1-59   CCCGGATCGACTGGAGACGGATCCATGCATGGAGACACTCCCACTTTGCATGAATATATG
IgkC3      CCAGGTTCCACTGGTGACGGATCCATGCATGGAGATACACCTACATTGCATGAATATATG
IgkC4      CCCGGCTCCACCGGCGACGGATCCATGCACGGCGACACCCCCACCCTGCACGAGTACATG

           121       131       141       151       161       171
IgkS1-56   CTCGACTTGCAACCGGAAACTACTGACCTCTACTGCTATGAACAATTGAATGACAGCTCG
IgkS1-57   CTCGACTTGCAACCAGAAACTACTGACCTCTACTGCTATGAACAATTGAATGACAGCTCG
IgkS1-58   CTCGACTTGCAACCTGAAACTACTGACCTCTACTGCTATGAACAATTGAATGACAGCTCG
IgkS1-59   CTCGACTTGCAACCCGAAACTACTGACCTCTACTGCTATGAACAATTGAATGACAGCTCG
IgkC3      TTAGATTTGCAACCAGAGACAACTGATCTCTACTGTTATGAGCAATTAAATGACAGCTCA
IgkC4      CTGGACCTGCAGCCCGAGACCACCGACCTGTACTGCTACGAGCAGCTCAACGACAGCAGC

           181       191       201       211       221       231
IgkS1-56   GAAGAAGAAGACGAAATAGACGGACCGGCAGGACAAGCAGAACCGGACCGCGCACATTAC
IgkS1-57   GAAGAAGAAGACGAAATAGACGGACCAGCAGGACAAGCAGAACCAGACCGCGCACATTAC
IgkS1-58   GAAGAAGAAGACGAAATAGACGGACCTGCAGGACAAGCAGAACCTGACCGCGCACATTAC
IgkS1-59   GAAGAAGAAGACGAAATAGACGGACCCGCAGGACAAGCAGAACCCGACCGCGCACATTAC
IgkC3      GAGGAGGAGGATGAAATAGATGGTCCAGCTGGACAAGCAGAACCGGACAGAGCCCATTAC
IgkC4      GAGGAGGAGGACGAGATCGACGGCCCCGCCGGCCAGGCCGAGCCCGACCGCGCCCACTAC

           241       251       261       271       281       291
IgkS1-56   AATATTGTAACTTTTTGCTGCAAGTGCGACAGTACTCTCCGCTTGTGCGTACAAAGCACT
IgkS1-57   AATATTGTAACTTTTTGCTGCAAGTGCGACAGTACTCTCCGCTTGTGCGTACAAAGCACT
IgkS1-58   AATATTGTAACTTTTTGCTGCAAGTGCGACAGTACTCTCCGCTTGTGCGTACAAAGCACT
IgkS1-59   AATATTGTAACTTTTTGCTGCAAGTGCGACAGTACTCTCCGCTTGTGCGTACAAAGCACT
IgkC3      AATATTGTAACCTTTTGTTGCAAGTGTGACTCTACGCTTCGGTTGTGCGTACAAAGCACA
IgkC4      AACATCGTGACCTTCTGCTGCAAGTGCGACAGCACCCTGCGCCTCTGCGTGCAGAGCACC

           301       311       321       331       341       351
IgkS1-56   CATGTAGACATTCGCACTTTGGAAGACCTCCTCATGGGAACTTTGGGAATTGTTTGCCCG
IgkS1-57   CATGTAGACATTCGCACTTTGGAAGACCTCCTCATGGGAACTTTGGGAATTGTTTGCCCA
IgkS1-58   CATGTAGACATTCGCACTTTGGAAGACCTCCTCATGGGAACTTTGGGAATTGTTTGCCCT
IgkS1-59   CATGTAGACATTCGCACTTTGGAAGACCTCCTCATGGGAACTTTGGGAATTGTTTGCCCC
IgkC3      CACGTAGACATTCGTACTTTGGAAGACCTGTTAATGGGCACACTAGGAATTGTGTGCCCC
IgkC4      CACGTGGACATCCGCACCCTGGAGGACCTGCTGATGGGCACCCTGGGCATCGTGTGCCCC

           361       371       381
IgkS1-56   ATCTGCTCGCAAAAGCCGTAAGAATTC
IgkS1-57   ATCTGCTCGCAAAAGCCATAAGAATTC
IgkS1-58   ATCTGCTCGCAAAAGCCTTAAGAATTC
IgkS1-59   ATCTGCTCGCAAAAGCCCTAAGAATTC
IgkC3      ATCTGCTCTCAGAAGCCCTAAGAATTC
IgkC4      ATCTGCTCCCAGAAGCCCTAAGAATTC
```

FIGURE 13

```
          1         11        21        31        41        51
IgkS1-34  GGTACCGCCGCCACCATGGAGACAGACACACTCCTGCTATGGGTACTGCTGCTCTGGGTT
IgkS1-35  GGTACCGCCGCCACCATGGAGACAGACACACTCCTGCTATGGGTACTGCTGCTCTGGGTT
IgkS1-36  GGTACCGCCGCCACCATGGAGACAGACACACTCCTGCTATGGGTACTGCTGCTCTGGGTT
IgkS1-37  GGTACCGCCGCCACCATGGAGACAGACACACTCCTGCTATGGGTACTGCTGCTCTGGGTT
IgkS1-38  GGTACCGCCGCCACCATGGAGACAGACACACTCCTGCTATGGGTACTGCTGCTCTGGGTT
IgkS1-39  GGTACCGCCGCCACCATGGAGACAGACACACTCCTGCTATGGGTACTGCTGCTCTGGGTT
IgkC1     GGTACCGCCGCCACCATGGAGACAGACACACTCCTGCTATGGGTACTGCTGCTCTGGGTT
IgkC2     GGTACCGCCGCCACCATGGAGACCGACACCCTCCTGCTGTGGGTGCTGCTGCTCTGGGTG

          61        71        81        91        101       111
IgkS1-34  CCAGGTAGTACTGGTGACGGAAGTATGCATGGAGATACACCTACATTGCATGAATATATG
IgkS1-35  CCAGGTAGCACTGGTGACGGAAGCATGCATGGAGATACACCTACATTGCATGAATATATG
IgkS1-36  CCAGGTTCGACTGGTGACGGATCGATGCATGGAGATACACCTACATTGCATGAATATATG
IgkS1-37  CCAGGTTCAACTGGTGACGGATCAATGCATGGAGATACACCTACATTGCATGAATATATG
IgkS1-38  CCAGGTTCTACTGGTGACGGATCTATGCATGGAGATACACCTACATTGCATGAATATATG
IgkS1-39  CCAGGTTCCACTGGTGACGGATCCATGCATGGAGATACACCTACATTGCATGAATATATG
IgkC1     CCAGGTTCCACTGGTGACGGATCCATGCATGGAGATACACCTACATTGCATGAATATATG
IgkC2     CCCGGCTCCACCGGCGACGGATCCATGCACGGCGACACCCCCACCCTGCACGAGTACATG

          121       131       141       151       161       171
IgkS1-34  TTAGATTTGCAACCAGAGACAACTGGTCTCTACGGTTATGGGCAATTAAATGACAGTAGT
IgkS1-35  TTAGATTTGCAACCAGAGACAACTGGTCTCTACGGTTATGGGCAATTAAATGACAGCAGC
IgkS1-36  TTAGATTTGCAACCAGAGACAACTGGTCTCTACGGTTATGGGCAATTAAATGACTCGTCG
IgkS1-37  TTAGATTTGCAACCAGAGACAACTGGTCTCTACGGTTATGGGCAATTAAATGACTCATCA
IgkS1-38  TTAGATTTGCAACCAGAGACAACTGGTCTCTACGGTTATGGGCAATTAAATGACTCTTCT
IgkS1-39  TTAGATTTGCAACCAGAGACAACTGGTCTCTACGGTTATGGGCAATTAAATGACTCCTCC
IgkC1     TTAGATTTGCAACCAGAGACAACTGGTCTCTACGGTTATGGGCAATTAAATGACAGCTCA
IgkC2     CTGGACCTGCAGCCCGAGACCACCGGCCTGTACGGCTACGGCCAGCTCAACGACAGCAGC

          181       191       201       211       221       231
IgkS1-34  GAGGAGGAGGATGAAATAGATGGTCCAGCTGGACAAGCAGAACCGGACAGAGCCCATTAC
IgkS1-35  GAGGAGGAGGATGAAATAGATGGTCCAGCTGGACAAGCAGAACCGGACAGAGCCCATTAC
IgkS1-36  GAGGAGGAGGATGAAATAGATGGTCCAGCTGGACAAGCAGAACCGGACAGAGCCCATTAC
IgkS1-37  GAGGAGGAGGATGAAATAGATGGTCCAGCTGGACAAGCAGAACCGGACAGAGCCCATTAC
IgkS1-38  GAGGAGGAGGATGAAATAGATGGTCCAGCTGGACAAGCAGAACCGGACAGAGCCCATTAC
IgkS1-39  GAGGAGGAGGATGAAATAGATGGTCCAGCTGGACAAGCAGAACCGGACAGAGCCCATTAC
IgkC1     GAGGAGGAGGATGAAATAGATGGTCCAGCTGGACAAGCAGAACCGGACAGAGCCCATTAC
IgkC2     GAGGAGGAGGACGAGATCGACGGCCCCGCCGGCCAGGCCGAGCCCGACCGCGCCCACTAC

          241       251       261       271       281       291
IgkS1-34  AATATTGTAACCTTTTGTTGCAAGTGTGACAGTACGCTTCGGTTGTGCGTACAAAGTACA
IgkS1-35  AATATTGTAACCTTTTGTTGCAAGTGTGACAGCACGCTTCGGTTGTGCGTACAAAGCACA
IgkS1-36  AATATTGTAACCTTTTGTTGCAAGTGTGACTCGACGCTTCGGTTGTGCGTACAATCGACA
IgkS1-37  AATATTGTAACCTTTTGTTGCAAGTGTGACTCAACGCTTCGGTTGTGCGTACAATCAACA
IgkS1-38  AATATTGTAACCTTTTGTTGCAAGTGTGACTCTACGCTTCGGTTGTGCGTACAATCTACA
IgkS1-39  AATATTGTAACCTTTTGTTGCAAGTGTGACTCCACGCTTCGGTTGTGCGTACAATCCACA
IgkC1     AATATTGTAACCTTTTGTTGCAAGTGTGACTCTACGCTTCGGTTGTGCGTACAAAGCACA
IgkC2     AACATCGTGACCTTCTGCTGCAAGTGCGACAGCACCCTGCGCCTCTGCGTGCAGAGCACC

          301       311       321       331       341       351
IgkS1-34  CACGTAGACATTCGTACTTTGGAAGACCTGTTAATGGGCACACTAGGAATTGTGTGCCCC
IgkS1-35  CACGTAGACATTCGTACTTTGGAAGACCTGTTAATGGGCACACTAGGAATTGTGTGCCCC
IgkS1-36  CACGTAGACATTCGTACTTTGGAAGACCTGTTAATGGGCACACTAGGAATTGTGTGCCCC
IgkS1-37  CACGTAGACATTCGTACTTTGGAAGACCTGTTAATGGGCACACTAGGAATTGTGTGCCCC
IgkS1-38  CACGTAGACATTCGTACTTTGGAAGACCTGTTAATGGGCACACTAGGAATTGTGTGCCCC
IgkS1-39  CACGTACACATTCGTACTTTGGAAGACCTGTTAATGGGCACACTAGGAATTGTGTGCCCC
IgkC1     CACGTAGACATTCGTACTTTGGAAGACCTGTTAATGGGCACACTAGGAATTGTGTGCCCC
IgkC2     CACGTGGACATCCGCACCCTGGAGGACCTGCTGATGGGCACCCTGGGCATCGTGTGCCCC

          361       371       381
IgkS1-34  ATCTGCAGTCAGAAGCCCTAAGAATTC
IgkS1-35  ATCTGCAGCCAGAAGCCCTAAGAATTC
IgkS1-36  ATCTGCTCGCAGAAGCCCTAAGAATTC
IgkS1-37  ATCTGCTCACAGAAGCCCTAAGAATTC
IgkS1-38  ATCTGCTCTCAGAAGCCCTAAGAATTC
IgkS1-39  ATCTGCTCCCAGAAGCCCTAAGAATTC
IgkC1     ATCTGCTCTCAGAAGCCCTAAGAATTC
IgkC2     ATCTGCTCCCAGAAGCCCTAAGAATTC
```

FIGURE 14

```
           1         11        21        31        41        51
IgkC1      GGTACCGCCGCCACCATGGAGACAGACACACTCCTGCTATGGGTACTGCTGCTCTGGGTT
IgkS1-40   GGTACCGCCGCCACCATGGAGACGGACACGCTCCTGCTATGGGTACTGCTGCTCTGGGTT
IgkS1-41   GGTACCGCCGCCACCATGGAGACAGACACACTCCTGCTATGGGTACTGCTGCTCTGGGTT
IgkS1-42   GGTACCGCCGCCACCATGGAGACTGACACTCTCCTGCTATGGGTACTGCTGCTCTGGGTT
IgkS1-43   GGTACCGCCGCCACCATGGAGACCGACACCCTCCTGCTATGGGTACTGCTGCTCTGGGTT
IgkC2      GGTACCGCCGCCACCATGGAGACCGACACCCTCCTGCTGTGGGTGCTGCTGCTCTGGGTG

           61        71        81        91        101       111
IgkC1      CCAGGTTCCACTGGTGACGGATCCATGCATGGAGATACACCTACATTGCATGAATATATG
IgkS1-40   CCAGGTTCCACGGGTGACGGATCCATGCATGGAGATACGCCTACGTTGCATGAATATATG
IgkS1-41   CCAGGTTCCACAGGTGACGGATCCATGCATGGAGATACACCTACATTGCATGAATATATG
IgkS1-42   CCAGGTTCCACTGGTGACGGATCCATGCATGGAGATACTCCTACTTTGCATGAATATATG
IgkS1-43   CCAGGTTCCACCGGTGACGGATCCATGCATGGAGATACCCCTACCTTGCATGAATATATG
IgkC2      CCCGGCTCCACCGGCGACGGATCCATGCACGGCGACACCCCCACCCTGCACGAGTACATG

           121       131       141       151       161       171
IgkC1      TTAGATTTGCAACCAGAGACAACTGGTCTCTACGGTTATGGGCAATTAAATGACAGCTCA
IgkS1-40   TTAGATTTGCAACCAGAGACGACGGGTCTCTACGGTTATGGGCAATTAAATGACAGCTCA
IgkS1-41   TTAGATTTGCAACCAGAGACAACAGGTCTCTACGGTTATGGGCAATTAAATGACAGCTCA
IgkS1-42   TTAGATTTGCAACCAGAGACTACTGGTCTCTACGGTTATGGGCAATTAAATGACAGCTCA
IgkS1-43   TTAGATTTGCAACCAGAGACCACCGGTCTCTACGGTTATGGGCAATTAAATGACAGCTCA
IgkC2      CTGGACCTGCAGCCCGAGACCACCGGCCTGTACGGCTACGGCCAGCTCAACGACAGCAGC

           181       191       201       211       221       231
IgkC1      GAGGAGGAGGATGAAATAGATGGTCCAGCTGGACAAGCAGAACCGGACAGAGCCCATTAC
IgkS1-40   GAGGAGGAGGATGAAATAGATGGTCCAGCTGGACAAGCAGAACCGGACAGAGCCCATTAC
IgkS1-41   GAGGAGGAGGATGAAATAGATGGTCCAGCTGGACAAGCAGAACCGGACAGAGCCCATTAC
IgkS1-42   GAGGAGGAGGATGAAATAGATGGTCCAGCTGGACAAGCAGAACCGGACAGAGCCCATTAC
IgkS1-43   GAGGAGGAGGATGAAATAGATGGTCCAGCTGGACAAGCAGAACCGGACAGAGCCCATTAC
IgkC2      GAGGAGGAGGACGAGATCGACGGCCCCGCCGGCCAGGCCGAGCCCGACCGCGCCCACTAC

           241       251       261       271       281       291
IgkC1      AATATTGTAACCTTTTGTTGCAAGTGTGACTCTACGCTTCGGTTGTGCGTACAAAGCACA
IgkS1-40   AATATTGTAACGTTTTGTTGCAAGTGTGACTCTACGCTTCGGTTGTGCGTACAAAGCACG
IgkS1-41   AATATTGTAACATTTTGTTGCAAGTGTGACTCTACACTTCGGTTGTGCGTACAAAGCACA
IgkS1-42   AATATTGTAACTTTTTGTTGCAAGTGTGACTCTACTCTTCGGTTGTGCGTACAAAGCACT
IgkS1-43   AATATTGTAACCTTTTGTTGCAAGTGTGACTCTACCCTTCGGTTGTGCGTACAAAGCACC
IgkC2      AACATCGTGACCTTCTGCTGCAAGTGCGACAGCACCCTGCGCCTCTGCGTGCAGAGCACC

           301       311       321       331       341       351
IgkC1      CACGTAGACATTCGTACTTTGGAAGACCTGTTAATGGGCACACTAGGAATTGTGTGCCCC
IgkS1-40   CACGTAGACATTCGTACGTTGGAAGACCTGTTAATGGGCACGCTAGGAATTGTGTGCCCC
IgkS1-41   CACGTAGACATTCGTACATTGGAAGACCTGTTAATGGGCACACTAGGAATTGTGTGCCCC
IgkS1-42   CACGTAGACATTCGTACTTTGGAAGACCTGTTAATGGGCACTCTAGGAATTGTGTGCCCC
IgkS1-43   CACGTAGACATTCGTACCTTGGAAGACCTGTTAATGGGCACCCTAGGAATTGTGTGCCCC
IgkC2      CACGTGGACATCCGCACCCTGGAGGACCTGCTGATGGGCACCCTGGGCATCGTGTGCCCC

           361       371       381
IgkC1      ATCTGCTCTCAGAAGCCCTAAGAATTC
IgkS1-40   ATCTGCTCTCAGAAGCCCTAAGAATTC
IgkS1-41   ATCTGCTCTCAGAAGCCCTAAGAATTC
IgkS1-42   ATCTGCTCTCAGAAGCCCTAAGAATTC
IgkS1-43   ATCTGCTCTCAGAAGCCCTAAGAATTC
IgkC2      ATCTGCTCCCAGAAGCCCTAAGAATTC
```

FIGURE 15

```
           1         11        21        31        41        51
IgkC1      GGTACCGCCGCCACCATGGAGACAGACACACTCCTGCTATGGGTACTGCTGCTCTGGGTT
IgkS1-44   GGTACCGCCGCCACCATGGAGACAGACACACTCCTGCTATGGGTACTGCTGCTCTGGGTT
IgkS1-45   GGTACCGCCGCCACCATGGAGACAGACACACTCCTGCTATGGGTACTGCTGCTCTGGGTT
IgkC2      GGTACCGCCGCCACCATGGAGACCGACACCCTCCTGCTGTGGGTGCTGCTGCTCTGGGTG

           61        71        81        91        101       111
IgkC1      CCAGGTTCCACTGGTGACGGATCCATGCATGGAGATACACCTACATTGCATGAATATATG
IgkS1-44   CCAGGTTCCACTGGTGACGGATCCATGCATGGAGATACACCTACATTGCATGAATATATG
IgkS1-45   CCAGGTTCCACTGGTGACGGATCCATGCATGGAGATACACCTACATTGCATGAATACATG
IgkC2      CCCGGCTCCACCGGCGACGGATCCATGCACGGCGACACCCCCACCCTGCACGAGTACATG

           121       131       141       151       161       171
IgkC1      TTAGATTTGCAACCAGAGACAACTGGTCTCTACGGTTATGGGCAATTAAATGACAGCTCA
IgkS1-44   TTAGATTTGCAACCAGAGACAACTGGTCTCTATGGTTATGGGCAATTAAATGACAGCTCA
IgkS1-45   TTAGATTTGCAACCAGAGACAACTGGTCTCTACGGTTACGGGCAATTAAATGACAGCTCA
IgkC2      CTGGACCTGCAGCCCGAGACCACCGGCCTGTACGGCTACGGCCAGCTCAACGACAGCAGC

           181       191       201       211       221       231
IgkC1      GAGGAGGAGGATGAAATAGATGGTCCAGCTGGACAAGCAGAACCGGACAGAGCCCATTAC
IgkS1-44   GAGGAGGAGGATGAAATAGATGGTCCAGCTGGACAAGCAGAACCGGACAGAGCCCATTAT
IgkS1-45   GAGGAGGAGGATGAAATAGATGGTCCAGCTGGACAAGCAGAACCGGACAGAGCCCATTAC
IgkC2      GAGGAGGAGGACGAGATCGACGGCCCCGCCGGCCAGGCCGAGCCCGACCGCGCCCACTAC

           241       251       261       271       281       291·
IgkC1      AATATTGTAACCTTTTGTTGCAAGTGTGACTCTACGCTTCGGTTGTGCGTACAAAGCACA
IgkS1-44   AATATTGTAACCTTTTGTTGCAAGTGTGACTCTACGCTTCGGTTGTGCGTACAAAGCACA
IgkS1-45   AATATTGTAACCTTTTGTTGCAAGTGTGACTCTACGCTTCGGTTGTGCGTACAAAGCACA
IgkC2      AACATCGTGACCTTCTGCTGCAAGTGCGACAGCACCCTGCGCCTCTGCGTGCAGAGCACC

           301       311       321       331       341       351
IgkC1      CACGTAGACATTCGTACTTTGGAAGACCTGTTAATGGGCACACTAGGAATTGTGTGCCCC
IgkS1-44   CACGTAGACATTCGTACTTTGGAAGACCTGTTAATGGGCACACTAGGAATTGTGTGCCCC
IgkS1-45   CACGTAGACATTCGTACTTTGGAAGACCTGTTAATGGGCACACTAGGAATTGTGTGCCCC
IgkC2      CACGTGGACATCCGCACCCTGGAGGACCTGCTGATGGGCACCCTGGGCATCGTGTGCCCC

           361       371       381
IgkC1      ATCTGCTCTCAGAAGCCCTAAGAATTC
IgkS1-44   ATCTGCTCTCAGAAGCCCTAAGAATTC
IgkS1-45   ATCTGCTCTCAGAAGCCCTAAGAATTC
IgkC2      ATCTGCTCCCAGAAGCCCTAAGAATTC
```

FIGURE 16

```
            1         11        21        31        41        51
IgkC1       GGTACCGCCGCCACCATGGAGACAGACACACTCCTGCTATGGGTACTGCTGCTCTGGGTT
IgkS1-46    GGTACCGCCGCCACCATGGAGACAGACACACTCCTGCTATGGGTGCTGCTGCTCTGGGTG
IgkS1-47    GGTACCGCCGCCACCATGGAGACAGACACACTCCTGCTATGGGTACTGCTGCTCTGGGTA
IgkS1-48    GGTACCGCCGCCACCATGGAGACAGACACACTCCTGCTATGGGTTCTGCTGCTCTGGGTT
IgkS1-49    GGTACCGCCGCCACCATGGAGACAGACACACTCCTGCTATGGGTCCTGCTGCTCTGGGTC
IgkC2       GGTACCGCCGCCACCATGGAGACCGACACCCTCCTGCTGTGGGTGCTGCTGCTCTGGGTG

            61        71        81        91        101       111
IgkC1       CCAGGTTCCACTGGTGACGGATCCATGCATGGAGATACACCTACATTGCATGAATATATG
IgkS1-46    CCAGGTTCCACTGGTGACGGATCCATGCATGGAGATACACCTACATTGCATGAATATATG
IgkS1-47    CCAGGTTCCACTGGTGACGGATCCATGCATGGAGATACACCTACATTGCATGAATATATG
IgkS1-48    CCAGGTTCCACTGGTGACGGATCCATGCATGGAGATACACCTACATTGCATGAATATATG
IgkS1-49    CCAGGTTCCACTGGTGACGGATCCATGCATGGAGATACACCTACATTGCATGAATATATG
IgkC2       CCCGGCTCCACCGGCGACGGATCCATGCACGGCGACACCCCCACCCTGCACGAGTACATG

            121       131       141       151       161       171
IgkC1       TTAGATTTGCAACCAGAGACAACTGGTCTCTACGGTTATGGGCAATTAAATGACAGCTCA
IgkS1-46    TTAGATTTGCAACCAGAGACAACTGGTCTCTACGGTTATGGGCAATTAAATGACAGCTCA
IgkS1-47    TTAGATTTGCAACCAGAGACAACTGGTCTCTACGGTTATGGGCAATTAAATGACAGCTCA
IgkS1-48    TTAGATTTGCAACCAGAGACAACTGGTCTCTACGGTTATGGGCAATTAAATGACAGCTCA
IgkS1-49    TTAGATTTGCAACCAGAGACAACTGGTCTCTACGGTTATGGGCAATTAAATGACAGCTCA
IgkC2       CTGGACCTGCAGCCCGAGACCACCGGCCTGTACGGCTACGGCCAGCTCAACGACAGCAGC

            181       191       201       211       221       231
IgkC1       GAGGAGGAGGATGAAATAGATGGTCCAGCTGGACAAGCAGAACCGGACAGAGCCCATTAC
IgkS1-46    GAGGAGGAGGATGAAATAGATGGTCCAGCTGGACAAGCAGAACCGGACAGAGCCCATTAC
IgkS1-47    GAGGAGGAGGATGAAATAGATGGTCCAGCTGGACAAGCAGAACCGGACAGAGCCCATTAC
IgkS1-48    GAGGAGGAGGATGAAATAGATGGTCCAGCTGGACAAGCAGAACCGGACAGAGCCCATTAC
IgkS1-49    GAGGAGGAGGATGAAATAGATGGTCCAGCTGGACAAGCAGAACCGGACAGAGCCCATTAC
IgkC2       GAGGAGGAGGACGAGATCGACGGCCCCGCCGGCCAGGCCGAGCCCGACCGCGCCCACTAC

            241       251       261       271       281       291
IgkC1       AATATTGTAACCTTTTGTTGCAAGTGTGACTCTACGCTTCGGTTGTGCGTACAAAGCACA
IgkS1-46    AATATTGTGACCTTTTGTTGCAAGTGTGACTCTACGCTTCGGTTGTGCGTGCAAAGCACA
IgkS1-47    AATATTGTAACCTTTTGTTGCAAGTGTGACTCTACGCTTCGGTTGTGCGTACAAAGCACA
IgkS1-48    AATATTGTTACCTTTTGTTGCAAGTGTGACTCTACGCTTCGGTTGTGCGTTCAAAGCACA
IgkS1-49    AATATTGTCACCTTTTGTTGCAAGTGTGACTCTACGCTTCGGTTGTGCGTCCAAAGCACA
IgkC2       AACATCGTGACCTTCTGCTGCAAGTGCGACAGCACCCTGCGCCTCTGCGTGCAGAGCACC

            301       311       321       331       341       351
IgkC1       CACGTAGACATTCGTACTTTGGAAGACCTGTTAATGGGCACACTAGGAATTGTGTGCCCC
IgkS1-46    CACGTGGACATTCGTACTTTGGAAGACCTGTTAATGGGCACACTAGGAATTGTGTGCCCC
IgkS1-47    CACGTAGACATTCGTACTTTGGAAGACCTGTTAATGGGCACACTAGGAATTGTATGCCCC
IgkS1-48    CACGTTGACATTCGTACTTTGGAAGACCTGTTAATGGGCACACTAGGAATTGTTTGCCCC
IgkS1-49    CACGTCGACATTCGTACTTTGGAAGACCTGTTAATGGGCACACTAGGAATTGTCTGCCCC
IgkC2       CACGTGGACATCCGCACCCTGGAGGACCTGCTGATGGGCACCCTGGGCATCGTGTGCCCC

            361       371       381
IgkC1       ATCTGCTCTCAGAAGCCCTAAGAATTC
IgkS1-46    ATCTGCTCTCAGAAGCCCTAAGAATTC
IgkS1-47    ATCTGCTCTCAGAAGCCCTAAGAATTC
IgkS1-48    ATCTGCTCTCAGAAGCCCTAAGAATTC
IgkS1-49    ATCTGCTCTCAGAAGCCCTAAGAATTC
IgkC2       ATCTGCTCCCAGAAGCCCTAAGAATTC
```

FIGURE 17

EXPRESSION SYSTEM FOR MODULATING AN IMMUNE RESPONSE

CROSS-REFERENCE TO RELATED APPLICATIONS

This application is a U.S. national stage application filed under 35 U.S.C. §371 of International Patent Application No. PCT/AU2008/001463, accorded an international filing date of Oct. 2, 2008, which claims the benefit of U.S. Provisional Application No. 60/980,145 filed Oct. 15, 2007, all of which applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing 900145_410USPC_SEQUENCE_LISTING.txt. The text file is about 178 KB, was created on Nov. 7, 2013, and is being submitted electronically via EFS-Web.

FIELD OF THE INVENTION

The present invention relates generally to gene expression. More particularly, the present invention relates to methods for modulating the quality of an immune response to a target antigen in a mammal, which response results from the expression of a polynucleotide that encodes at least a portion of the target antigen, wherein the quality is modulated by replacing at least one codon of the polynucleotide with a synonymous codon that has a higher or lower preference of usage by the mammal to confer the immune response than the codon it replaces. Even more particularly, the present invention relates to the use of a protein-encoding polynucleotide whose codon composition has been modified for modulating the quality of an immune response to an antigen in a mammal.

BACKGROUND OF THE INVENTION

The expression of foreign heterologous genes in transformed cells is now commonplace. A large number of mammalian genes, including, for example, murine and human genes, have been successfully expressed in various host cells, including bacterial, yeast, insect, plant and mammalian host cells. Nevertheless, despite the burgeoning knowledge of expression systems and recombinant DNA technology, significant obstacles remain when one attempts to express a foreign or synthetic gene in a selected host cell. For example, translation of a synthetic gene, even when coupled with a strong promoter, often proceeds much more slowly than would be expected. The same is frequently true of exogenous genes that are foreign to the host cell. This lower than expected translation efficiency is often due to the protein coding regions of the gene having a codon usage pattern that does not resemble those of highly expressed genes in the host cell. It is known in this regard that codon utilization is highly biased and varies considerably in different organisms and that biases in codon usage can alter peptide elongation rates. It is also known that codon usage patterns are related to the relative abundance of tRNA isoacceptors, and that genes encoding proteins of high versus low abundance show differences in their codon preferences.

The implications of codon preference phenomena on gene expression are manifest in that these phenomena can affect the translational efficiency of messenger RNA (mRNA). It is widely known in this regard that translation of "rare codons", for which the corresponding iso-tRNA is in low abundance relative to other iso-tRNAs, may cause a ribosome to pause during translation which can lead to a failure to complete a nascent polypeptide chain and an uncoupling of transcription and translation. Thus, the expression of an exogenous gene may be impeded severely if a particular host cell of an organism or the organism itself has a low abundance of iso-tRNAs corresponding to one or more codons of the exogenous gene. Accordingly, a major aim of investigators in this field is to first ascertain the codon preference for particular cells in which an exogenous gene is to be expressed, and to subsequently alter the codon composition of that gene for optimized expression in those cells.

Codon-optimization techniques are known for improving the translational kinetics of translationally inefficient protein coding regions. Traditionally, these techniques have been based on the replacement of codons that are rarely or infrequently used in the host cell with those that are host-preferred. Codon frequencies can be derived from literature sources for the highly expressed genes of many organisms (see, for example, Nakamura et al., 1996, Nucleic Acids Res 24: 214-215). These frequencies are generally expressed on an 'organism-wide average basis' as the percentage of occasions that a synonymous codon is used to encode a corresponding amino acid across a collection of protein-encoding genes of that organism, which are preferably highly expressed.

Typically, codons are classified as: (a) "common" codons (or "preferred" codons) if their frequency of usage is above about 4/3×the frequency of usage that would be expected in the absence of any bias in codon usage; (b) "rare" codons (or "non-preferred" codons) if their frequency of usage is below about 2/3×the frequency of usage that would be expected in the absence of any bias in codon usage; and (c) "intermediate" codons (or "less preferred" codons) if their frequency of usage is in-between the frequency of usage of "common" codons and of "rare" codons. Since an amino acid can be encoded by 2, 3, 4 or 6 codons, the frequency of usage of any selected codon, which would be expected in the absence of any bias in codon usage, will be dependent upon the number of synonymous codons which code for the same amino acid as the selected codon. Accordingly, for a particular amino acid, the frequency thresholds for classifying codons in the "common", "intermediate" and "rare" categories will be dependent upon the number of synonymous codons for that amino acid. Consequently, for amino acids having 6 choices of synonymous codon, the frequency of codon usage that would be expected in the absence of any bias in codon usage is 16% and thus the "common", "intermediate" and "rare" codons are defined as those codons that have a frequency of usage above 20%, between 10 and 20% and below 10%, respectively. For amino acids having 4 choices of synonymous codon, the frequency of codon usage that would be expected in the absence of codon usage bias is 25% and thus the "common", "intermediate" and "rare" codons are defined as those codons that have a frequency of usage above 33%, between 16 and 33% and below 16%, respectively. For isoleucine, which is the only amino acid having 3 choices of synonymous codon, the frequency of codon usage that would be expected in the absence of any bias in codon usage is 33% and thus the "common", "intermediate" and "rare" codons for isoleucine are defined as those codons that have a frequency of usage above 45%, between 20 and 45% and below 20%, respectively. For amino acids having 2 choices of synonymous codon, the frequency of codon usage that would be expected in the absence of codon usage bias is 50% and thus the "common", "intermediate" and "rare" codons are defined as those codons that have a frequency of usage above 60%, between 30 and 60% and below 30%, respectively. Thus, the categorization of codons into the "common", "intermediate" and "rare" classes (or "preferred", "less preferred" or "non preferred", respectively) has been based conventionally on a compilation of codon usage for an organism in general (e.g., 'human-wide') or for a class of organisms in general (e.g., 'mammal-wide'). For example, reference may be made to Seed (see U.S. Pat. Nos. 5,786,464 and 5,795,737) who discloses preferred, less preferred and non-preferred codons for mammalian cells in general. However, the present inventor revealed in WO 99/02694 and in WO 00/42190 that there are substantial differences in the relative abundance of particular iso-tRNAs in different cells or tissues of a single multicellular organism (e.g., a mammal or a plant) and that this plays a pivotal role in protein translation from a coding sequence with a given codon usage or composition.

Thus, in contrast to the art-recognized presumption that different cells of a multicellular organism have the same bias in codon usage, it was revealed for the first time that one cell type of a multicellular organism uses codons in a manner distinct from another cell type of the same organism. In other words, it was discovered that different cells of an organism can exhibit different translational efficiencies for the same codon and that it was not possible to predict which codons would be preferred, less preferred or non preferred in a selected cell type. Accordingly, it was proposed that differences in codon translational efficiency between cell types could be exploited, together with codon composition of a gene, to regulate the production of a protein in, or to direct that production to, a chosen cell type.

Therefore, in order to optimize the expression of a protein-encoding polynucleotide in a particular cell type, WO 99/02694 and in WO 00/42190 teach that it is necessary to first determine the translational efficiency for each codon in that cell type, rather than to rely on codon frequencies calculated on an organism-wide average basis, and then to codon modify the polynucleotide based on that determination.

The present inventor further disclosed in WO 2004/042059 a strategy for enhancing or reducing the quality of a selected phenotype that is displayed, or proposed to be displayed, by an organism of interest. The strategy involves codon modification of a polynucleotide that encodes a phenotype-associated polypeptide that either by itself, or in association with other molecules, in the organism of interest imparts or confers the selected phenotype upon the organism. Unlike previous methods, however, this strategy does not rely on data that provide a ranking of synonymous codons according to their preference of usage in an organism or class of organisms. Nor does it rely on data that provide a ranking of synonymous codons according to their translational efficiencies in one or more cells of the organism or class of organisms. Instead, it relies on ranking individual synonymous codons that code for an amino acid in the phenotype-associated polypeptide according to their preference of usage by the organism or class of organisms, or by a part thereof, for producing the selected phenotype.

SUMMARY OF THE INVENTION

The present invention is predicated in part on the experimental determination of a ranking of individual synonymous codons according to their preference for producing an immune response, including a humoral immune response, to an antigen in a mammal. Significantly, this ranking is not coterminous with a ranking of codon frequency values derivable from an analysis of the frequency with which codons are used to encode their corresponding amino acids across a collection of highly expressed mammalian protein-encoding genes, as for example disclosed by Seed (supra). Nor is it coterminous with a ranking of translational efficiency values obtained from an analysis of the translational efficiencies of codons in specific cell types, as disclosed for example in WO 99/02694 for COS-1 cells and epithelial cells and in WO 2004/024915 for CHO cells. Indeed, the present inventors have determined that codon modification of wild-type antigen-encoding polynucleotides to replace codons found in the wild-type sequence with codons having a higher preference for producing an immune response than the codons they replaced significantly enhances the immune response to the encoded antigen, as compared to the immune response obtained with the wild-type sequence. As a result, the present invention enables for the first time the construction of antigen-encoding polynucleotides, which are codon-optimized for efficient production of immune responses in a mammal.

Thus, in one aspect of the present invention, methods are provided for constructing a synthetic polynucleotide from which a polypeptide is producible to confer an immune response to a target antigen in a mammal in a different quality than that conferred by a parent polynucleotide that encodes the same polypeptide, wherein the polypeptide corresponds to at least a portion of the target antigen. These methods generally comprise: (a) selecting a first codon of the parent polynucleotide for replacement with a synonymous codon, wherein the synonymous codon is selected on the basis that it exhibits a different preference for conferring an immune response ("an immune response preference") than the first codon in a comparison of immune response preferences; and (b) replacing the first codon with the synonymous codon to construct the synthetic polynucleotide, wherein the comparison of immune response preferences of the codons is represented by TABLE 1:

TABLE 1

| Amino Acid | Ranking of Immune Response Preferences for Synonymous Codons |
|---|---|
| Ala | $Ala^{GCT} > Ala^{GCC} > (Ala^{GCA}, Ala^{GCG})$ |
| Arg | $(Arg^{CGA}, Arg^{CGC}, Arg^{CGT}, Arg^{AGA}) > (Arg^{AGG}, Arg^{CGG})$ |
| Asn | $Asn^{AAC} > Asn^{AAT}$ |
| Asp | $Asp^{GAC} > Asp^{GAT}$ |
| Cys | $Cys^{TGC} > Cys^{TGT}$ |
| Glu | $Glu^{GAA} > Glu^{GAG}$ |
| Gln | $Gln^{CAA} = Gln^{CAG}$ |
| Gly | $Gly^{GGA} > (Gly^{GGG}, Gly^{GGT}, Gly^{GGC})$ |
| His | $His^{CAC} = His^{CAT}$ |
| Ile | $Ile^{ATC} >> Ile^{ATT} > Ile^{ATA}$ |
| Leu | $(Leu^{CTG}, Leu^{CTC}) > (Leu^{CTA}, Leu^{CTT}) >> Leu^{TTG} > Leu^{TTA}$ |
| Lys | $Lys^{AAG} = Lys^{AAA}$ |
| Phe | $Phe^{TTT} > Phe^{TTC}$ |
| Pro | $Pro^{CCC} > Pro^{CCT} >> (Pro^{CCA}, Pro^{CCG})$ |
| Ser | $Ser^{TCG} >> (Ser^{TCT}, Ser^{TCA}, Ser^{TCC}) >> (Ser^{AGC}, Ser^{AGT})$ |
| Thr | $Thr^{ACG} > Thr^{ACC} >> Thr^{ACA} > Thr^{ACT}$ |

TABLE 1-continued

| Amino Acid | Ranking of Immune Response Preferences for Synonymous Codons |
|---|---|
| Tyr | Tyr$^{TAC}$ > Tyr$^{TAT}$ |
| Val | (Val$^{GTG}$, Val$^{GTC}$) > Val$^{GTT}$ > Val$^{GTA}$ |

Thus, a stronger or enhanced immune response to the target antigen (e.g., an immune response that is at least about 110%, 150%, 200%, 300%, 400%, 500%, 600%, 700%, 800%, 900%, 1000% and all integer percentages in between, of that produced from the parent polynucleotide under identical conditions) can be achieved by selecting a synonymous codon that has a higher immune response preference than the first codon it replaces. In specific embodiments, the synonymous codon is selected such that it has a higher immune response preference that is at least about 10% (and at least about 11% to at least about 1000% and all integer percentages in between) higher than the immune response preference of the codon it replaces. In illustrative examples of this type, the first and synonymous codons are selected from TABLE 2:

TABLE 2

| First Codon | Synonymous Codon |
|---|---|
| Ala$^{GCG}$ | Ala$^{GCT}$ |
| Ala$^{GCG}$ | Ala$^{GCC}$ |
| Ala$^{GCA}$ | Ala$^{GCT}$ |
| Ala$^{GCA}$ | Ala$^{GCC}$ |
| Ala$^{GCC}$ | Ala$^{GCT}$ |
| Arg$^{CGG}$ | Arg$^{CGA}$ |
| Arg$^{CGG}$ | Arg$^{CGC}$ |
| Arg$^{CGG}$ | Arg$^{CGT}$ |
| Arg$^{CGG}$ | Arg$^{AGA}$ |
| Arg$^{AGG}$ | Arg$^{CGA}$ |
| Arg$^{AGG}$ | Arg$^{CGC}$ |
| Arg$^{AGG}$ | Arg$^{CGT}$ |
| Arg$^{AGG}$ | Arg$^{AGA}$ |
| Asn$^{AAT}$ | Asn$^{AAC}$ |
| Asp$^{GAT}$ | Asp$^{GAC}$ |
| Cys$^{TGT}$ | Cys$^{TGC}$ |
| Glu$^{GAG}$ | Glu$^{GAA}$ |
| Gly$^{GGC}$ | Gly$^{GGA}$ |
| Gly$^{GGT}$ | Gly$^{GGA}$ |
| Gly$^{GGG}$ | Gly$^{GGA}$ |
| Ile$^{ATA}$ | Ile$^{ATC}$ |
| Ile$^{ATA}$ | Ile$^{ATT}$ |
| Ile$^{ATT}$ | Ile$^{ATC}$ |
| Leu$^{TTA}$ | Leu$^{CTG}$ |
| Leu$^{TTA}$ | Leu$^{CTC}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTG}$ |
| Leu$^{TTG}$ | Leu$^{CTC}$ |
| Leu$^{TTG}$ | Leu$^{CTA}$ |
| Leu$^{TTG}$ | Leu$^{CTT}$ |
| Leu$^{CTT}$ | Leu$^{CTG}$ |
| Leu$^{CTT}$ | Leu$^{CTC}$ |
| Leu$^{CTA}$ | Leu$^{CTG}$ |
| Leu$^{CTA}$ | Leu$^{CTC}$ |
| Phe$^{TTC}$ | Phe$^{TTT}$ |
| Pro$^{CCG}$ | Pro$^{CCC}$ |
| Pro$^{CCG}$ | Pro$^{CCT}$ |
| Pro$^{CCA}$ | Pro$^{CCC}$ |
| Pro$^{CCA}$ | Pro$^{CCT}$ |
| Pro$^{CCT}$ | Pro$^{CCC}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGT}$ | Ser$^{TCC}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACC}$ |
| Thr$^{ACT}$ | Thr$^{ACA}$ |
| Thr$^{ACA}$ | Thr$^{ACG}$ |
| Thr$^{ACA}$ | Thr$^{ACC}$ |
| Thr$^{ACC}$ | Thr$^{ACG}$ |
| Tyr$^{TAT}$ | Tyr$^{TAC}$ |
| Val$^{GTA}$ | Val$^{GTG}$ |
| Val$^{GTA}$ | Val$^{GTC}$ |
| Val$^{GTA}$ | Val$^{GTT}$ |
| Val$^{GTT}$ | Val$^{GTG}$ |
| Val$^{GTT}$ | Val$^{GTC}$ |

In other illustrative examples of this type, the first and synonymous codons are selected from TABLE 3:

TABLE 3

| First Codon | Synonymous Codon |
|---|---|
| Ala$^{GCG}$ | Ala$^{GCT}$ |
| Ala$^{GCA}$ | Ala$^{GCT}$ |
| Ala$^{GCC}$ | Ala$^{GCT}$ |
| Arg$^{CGG}$ | Arg$^{CGA}$ |
| Arg$^{CGG}$ | Arg$^{CGT}$ |
| Arg$^{CGG}$ | Arg$^{AGA}$ |
| Arg$^{AGG}$ | Arg$^{CGA}$ |
| Arg$^{AGG}$ | Arg$^{CGT}$ |
| Arg$^{AGG}$ | Arg$^{AGA}$ |
| Glu$^{GAG}$ | Glu$^{GAA}$ |
| Gly$^{GGC}$ | Gly$^{GGA}$ |
| Gly$^{GGT}$ | Gly$^{GGA}$ |
| Gly$^{GGG}$ | Gly$^{GGA}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTA}$ |
| Leu$^{TTG}$ | Leu$^{CTT}$ |
| Phe$^{TTC}$ | Phe$^{TTT}$ |
| Pro$^{CCG}$ | Pro$^{CCT}$ |
| Pro$^{CCA}$ | Pro$^{CCT}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACA}$ |
| Thr$^{ACA}$ | Thr$^{ACG}$ |
| Thr$^{ACC}$ | Thr$^{ACG}$ |
| Val$^{GTA}$ | Val$^{GTT}$ |

Suitably, in some of the illustrative examples noted above, the method further comprises selecting a second codon of the parent polynucleotide for replacement with a synonymous codon, wherein the synonymous codon is selected on the basis that it exhibits a higher immune response preference than the second codon in a comparison of immune response preferences; and (b) replacing the second codon with the synonymous codon, wherein the comparison of immune response preferences of the codons is represented by TABLE 4:

TABLE 4

| Second Codon | Synonymous Codon |
|---|---|
| $Ala^{GCG}$ | $Ala^{GCT}$ |
| $Ala^{GCG}$ | $Ala^{GCC}$ |
| $Ala^{GCA}$ | $Ala^{GCT}$ |
| $Ala^{GCA}$ | $Ala^{GCC}$ |
| $Ala^{GCC}$ | $Ala^{GCT}$ |
| $Arg^{CGG}$ | $Arg^{CGA}$ |
| $Arg^{CGG}$ | $Arg^{CGC}$ |
| $Arg^{CGG}$ | $Arg^{CGT}$ |
| $Arg^{CGG}$ | $Arg^{AGA}$ |
| $Arg^{AGG}$ | $Arg^{CGA}$ |
| $Arg^{AGG}$ | $Arg^{CGC}$ |
| $Arg^{AGG}$ | $Arg^{CGT}$ |
| $Arg^{AGG}$ | $Arg^{AGA}$ |
| $Asn^{AAT}$ | $Asn^{AAC}$ |
| $Asp^{GAT}$ | $Asp^{GAC}$ |
| $Cys^{TGT}$ | $Cys^{TGC}$ |
| $Glu^{GAG}$ | $Glu^{GAA}$ |
| $Gly^{GGC}$ | $Gly^{GGA}$ |
| $Gly^{GGT}$ | $Gly^{GGA}$ |
| $Gly^{GGG}$ | $Gly^{GGA}$ |
| $Ile^{ATA}$ | $Ile^{ATC}$ |
| $Ile^{ATA}$ | $Ile^{ATT}$ |
| $Ile^{ATT}$ | $Ile^{ATC}$ |
| $Leu^{TTA}$ | $Leu^{CTG}$ |
| $Leu^{TTA}$ | $Leu^{CTC}$ |
| $Leu^{TTA}$ | $Leu^{CTA}$ |
| $Leu^{TTA}$ | $Leu^{CTT}$ |
| $Leu^{TTA}$ | $Leu^{TTG}$ |
| $Leu^{TTG}$ | $Leu^{CTG}$ |
| $Leu^{TTG}$ | $Leu^{CTC}$ |
| $Leu^{TTG}$ | $Leu^{CTA}$ |
| $Leu^{TTG}$ | $Leu^{CTT}$ |
| $Leu^{CTT}$ | $Leu^{CTG}$ |
| $Leu^{CTT}$ | $Leu^{CTC}$ |
| $Leu^{CTA}$ | $Leu^{CTG}$ |
| $Leu^{CTA}$ | $Leu^{CTC}$ |
| $Phe^{TTC}$ | $Phe^{TTT}$ |
| $Pro^{CCG}$ | $Pro^{CCC}$ |
| $Pro^{CCG}$ | $Pro^{CCT}$ |
| $Pro^{CCA}$ | $Pro^{CCC}$ |
| $Pro^{CCA}$ | $Pro^{CCT}$ |
| $Pro^{CCT}$ | $Pro^{CCC}$ |
| $Ser^{AGT}$ | $Ser^{TCG}$ |
| $Ser^{AGT}$ | $Ser^{TCT}$ |
| $Ser^{AGT}$ | $Ser^{TCA}$ |
| $Ser^{AGT}$ | $Ser^{TCC}$ |
| $Ser^{AGC}$ | $Ser^{TCG}$ |
| $Ser^{AGC}$ | $Ser^{TCT}$ |
| $Ser^{AGC}$ | $Ser^{TCA}$ |
| $Ser^{AGC}$ | $Ser^{TCC}$ |
| $Ser^{TCC}$ | $Ser^{TCG}$ |
| $Ser^{TCA}$ | $Ser^{TCG}$ |
| $Ser^{TCT}$ | $Ser^{TCG}$ |
| $Thr^{ACT}$ | $Thr^{ACG}$ |
| $Thr^{ACT}$ | $Thr^{ACC}$ |
| $Thr^{ACT}$ | $Thr^{ACA}$ |
| $Thr^{ACA}$ | $Thr^{ACG}$ |
| $Thr^{ACA}$ | $Thr^{ACC}$ |
| $Thr^{ACC}$ | $Thr^{ACG}$ |
| $Tyr^{TAT}$ | $Tyr^{TAC}$ |
| $Val^{GTA}$ | $Val^{GTG}$ |
| $Val^{GTA}$ | $Val^{GTC}$ |
| $Val^{GTA}$ | $Val^{GTT}$ |
| $Val^{GTT}$ | $Val^{GTG}$ |
| $Val^{GTT}$ | $Val^{GTC}$ |

Conversely, a weaker or reduced immune response to the target antigen (e.g., an immune response that is at less than about 90%, 80%, 70%, 60%, 50%, 40%, 30%, 20%, 10%, 1% and all integer percentages in between, of that produced from the parent polynucleotide under identical conditions) can be achieved by selecting a synonymous codon that has a lower immune response preference than the first codon it replaces. In specific embodiments of this type, the synonymous codon is selected such that it has an immune response preference that is less than about 90% of the immune response preference of the codon it replaces. In illustrative examples, the first and synonymous codons are selected from the TABLE 5:

TABLE 5

| First Codon | Synonymous Codon |
|---|---|
| $Ala^{GCT}$ | $Ala^{GCG}$ |
| $Ala^{GCT}$ | $Ala^{GCA}$ |
| $Ala^{GCT}$ | $Ala^{GCC}$ |
| $Ala^{GCC}$ | $Ala^{GCG}$ |
| $Ala^{GCC}$ | $Ala^{GCA}$ |
| $Arg^{CGA}$ | $Arg^{AGG}$ |
| $Arg^{CGA}$ | $Arg^{CGG}$ |
| $Arg^{CGC}$ | $Arg^{AGG}$ |
| $Arg^{CGC}$ | $Arg^{CGG}$ |
| $Arg^{CGT}$ | $Arg^{AGG}$ |
| $Arg^{CGT}$ | $Arg^{CGG}$ |
| $Arg^{AGA}$ | $Arg^{AGG}$ |
| $Arg^{AGA}$ | $Arg^{CGG}$ |
| $Asn^{AAC}$ | $Asn^{AAT}$ |
| $Asp^{GAC}$ | $Asp^{GAT}$ |
| $Cys^{TGC}$ | $Cys^{TGT}$ |
| $Glu^{GAA}$ | $Glu^{GAG}$ |
| $Gly^{GGA}$ | $Gly^{GGC}$ |
| $Gly^{GGA}$ | $Gly^{GGT}$ |
| $Gly^{GGA}$ | $Gly^{GGG}$ |
| $Ile^{ATC}$ | $Ile^{ATA}$ |
| $Ile^{ATC}$ | $Ile^{ATT}$ |
| $Ile^{ATT}$ | $Ile^{ATA}$ |
| $Leu^{CTG}$ | $Leu^{CTA}$ |
| $Leu^{CTG}$ | $Leu^{CTT}$ |
| $Leu^{CTG}$ | $Leu^{TTG}$ |
| $Leu^{CTG}$ | $Leu^{TTA}$ |
| $Leu^{CTC}$ | $Leu^{CTA}$ |
| $Leu^{CTC}$ | $Leu^{CTT}$ |
| $Leu^{CTC}$ | $Leu^{TTG}$ |
| $Leu^{CTC}$ | $Leu^{TTA}$ |
| $Leu^{CTA}$ | $Leu^{TTG}$ |
| $Leu^{CTA}$ | $Leu^{TTA}$ |
| $Leu^{CTT}$ | $Leu^{TTG}$ |
| $Leu^{CTT}$ | $Leu^{TTA}$ |
| $Leu^{TTG}$ | $Leu^{TTA}$ |
| $Phe^{TTT}$ | $Phe^{TTC}$ |
| $Pro^{CCC}$ | $Pro^{CCT}$ |
| $Pro^{CCC}$ | $Pro^{CCA}$ |
| $Pro^{CCC}$ | $Pro^{CCG}$ |
| $Pro^{CCT}$ | $Pro^{CCA}$ |
| $Pro^{CCT}$ | $Pro^{CCG}$ |
| $Ser^{TCG}$ | $Ser^{TCT}$ |
| $Ser^{TCG}$ | $Ser^{TCA}$ |
| $Ser^{TCG}$ | $Ser^{TCC}$ |
| $Ser^{TCG}$ | $Ser^{AGC}$ |
| $Ser^{TCG}$ | $Ser^{AGT}$ |
| $Ser^{TCT}$ | $Ser^{AGC}$ |
| $Ser^{TCT}$ | $Ser^{AGT}$ |
| $Ser^{TCA}$ | $Ser^{AGC}$ |
| $Ser^{TCA}$ | $Ser^{AGT}$ |
| $Ser^{TCC}$ | $Ser^{AGC}$ |
| $Ser^{TCC}$ | $Ser^{AGT}$ |
| $Thr^{ACG}$ | $Thr^{ACC}$ |
| $Thr^{ACG}$ | $Thr^{ACA}$ |
| $Thr^{ACG}$ | $Thr^{ACT}$ |
| $Thr^{ACC}$ | $Thr^{ACA}$ |
| $Thr^{ACC}$ | $Thr^{ACT}$ |
| $Thr^{ACA}$ | $Thr^{ACT}$ |
| $Tyr^{TAC}$ | $Tyr^{TAT}$ |
| $Val^{GTG}$ | $Val^{GTT}$ |
| $Val^{GTG}$ | $Val^{GTA}$ |
| $Val^{GTC}$ | $Val^{GTT}$ |
| $Val^{GTC}$ | $Val^{GTA}$ |
| $Val^{GTT}$ | $Val^{GTA}$ |

In other illustrative examples, the first and synonymous codons are selected from TABLE 6:

TABLE 6

| First Codon | Synonymous Codon |
|---|---|
| Ala$^{GCT}$ | Ala$^{GCG}$ |
| Ala$^{GCT}$ | Ala$^{GCA}$ |
| Ala$^{GCT}$ | Ala$^{GCC}$ |
| Arg$^{CGA}$ | Arg$^{AGG}$ |
| Arg$^{CGA}$ | Arg$^{CGG}$ |
| Arg$^{CGT}$ | Arg$^{AGG}$ |
| Arg$^{CGT}$ | Arg$^{CGG}$ |
| Arg$^{AGA}$ | Arg$^{AGG}$ |
| Arg$^{AGA}$ | Arg$^{CGG}$ |
| Glu$^{GAA}$ | Glu$^{GAG}$ |
| Gly$^{GGA}$ | Gly$^{GGC}$ |
| Gly$^{GGA}$ | Gly$^{GGT}$ |
| Gly$^{GGA}$ | Gly$^{GGG}$ |
| Leu$^{CTA}$ | Leu$^{TTG}$ |
| Leu$^{CTA}$ | Leu$^{TTA}$ |
| Leu$^{CTT}$ | Leu$^{TTG}$ |
| Leu$^{CTT}$ | Leu$^{TTA}$ |
| Leu$^{TTG}$ | Leu$^{TTA}$ |
| Phe$^{TTT}$ | Phe$^{TTC}$ |
| Pro$^{CCT}$ | Pro$^{CCA}$ |
| Pro$^{CCT}$ | Pro$^{CCG}$ |
| Ser$^{TCG}$ | Ser$^{TCT}$ |
| Ser$^{TCG}$ | Ser$^{TCA}$ |
| Ser$^{TCG}$ | Ser$^{TCC}$ |
| Ser$^{TCG}$ | Ser$^{AGC}$ |
| Ser$^{TCG}$ | Ser$^{AGT}$ |
| Ser$^{TCT}$ | Ser$^{AGC}$ |
| Ser$^{TCT}$ | Ser$^{AGT}$ |
| Ser$^{TCA}$ | Ser$^{AGC}$ |
| Ser$^{TCA}$ | Ser$^{AGT}$ |
| Ser$^{TCC}$ | Ser$^{AGC}$ |
| Thr$^{ACG}$ | Thr$^{ACC}$ |
| Thr$^{ACG}$ | Thr$^{ACA}$ |
| Thr$^{ACG}$ | Thr$^{ACT}$ |
| Thr$^{ACA}$ | Thr$^{ACT}$ |
| Val$^{GTT}$ | Val$^{GTA}$ |

Suitably, in some of the illustrative examples noted above, the method further comprises selecting a second codon of the parent polynucleotide for replacement with a synonymous codon, wherein the synonymous codon is selected on the basis that it exhibits a lower immune response preference than the second codon in a comparison of immune response preferences; and; (b) replacing the second codon with the synonymous codon, wherein the comparison of immune response preferences of the codons is represented by TABLE 7:

TABLE 7

| Second Codon | Synonymous Codon |
|---|---|
| Ala$^{GCT}$ | Ala$^{GCG}$ |
| Ala$^{GCT}$ | Ala$^{GCA}$ |
| Ala$^{GCT}$ | Ala$^{GCC}$ |
| Ala$^{GCC}$ | Ala$^{GCG}$ |
| Ala$^{GCC}$ | Ala$^{GCA}$ |
| Arg$^{CGA}$ | Arg$^{AGG}$ |
| Arg$^{CGA}$ | Arg$^{CGG}$ |
| Arg$^{CGC}$ | Arg$^{AGG}$ |
| Arg$^{CGC}$ | Arg$^{CGG}$ |
| Arg$^{CGT}$ | Arg$^{AGG}$ |
| Arg$^{CGT}$ | Arg$^{CGG}$ |
| Arg$^{AGA}$ | Arg$^{AGG}$ |
| Arg$^{AGA}$ | Arg$^{CGG}$ |
| Asn$^{AAC}$ | Asn$^{AAT}$ |
| Asp$^{GAC}$ | Asp$^{GAT}$ |
| Cys$^{TGC}$ | Cys$^{TGT}$ |
| Glu$^{GAA}$ | Glu$^{GAG}$ |
| Gly$^{GGA}$ | Gly$^{GGC}$ |
| Gly$^{GGA}$ | Gly$^{GGT}$ |
| Gly$^{GGA}$ | Gly$^{GGG}$ |
| Ile$^{ATC}$ | Ile$^{ATA}$ |
| Ile$^{ATC}$ | Ile$^{ATT}$ |
| Ile$^{ATT}$ | Ile$^{ATA}$ |
| Leu$^{CTG}$ | Leu$^{CTA}$ |
| Leu$^{CTG}$ | Leu$^{CTT}$ |
| Leu$^{CTG}$ | Leu$^{TTG}$ |
| Leu$^{CTG}$ | Leu$^{TTA}$ |
| Leu$^{CTC}$ | Leu$^{CTA}$ |
| Leu$^{CTC}$ | Leu$^{CTT}$ |
| Leu$^{CTC}$ | Leu$^{TTG}$ |
| Leu$^{CTC}$ | Leu$^{TTA}$ |
| Leu$^{CTA}$ | Leu$^{TTG}$ |
| Leu$^{CTA}$ | Leu$^{TTA}$ |
| Leu$^{CTT}$ | Leu$^{TTG}$ |
| Leu$^{CTT}$ | Leu$^{TTA}$ |
| Leu$^{TTG}$ | Leu$^{TTA}$ |
| Pro$^{CCC}$ | Pro$^{CCT}$ |
| Pro$^{CCC}$ | Pro$^{CCA}$ |
| Pro$^{CCC}$ | Pro$^{CCG}$ |
| Pro$^{CCT}$ | Pro$^{CCA}$ |
| Pro$^{CCT}$ | Pro$^{CCG}$ |
| Ser$^{TCG}$ | Ser$^{TCT}$ |
| Ser$^{TCG}$ | Ser$^{TCA}$ |
| Ser$^{TCG}$ | Ser$^{TCC}$ |
| Ser$^{TCG}$ | Ser$^{AGC}$ |
| Ser$^{TCG}$ | Ser$^{AGT}$ |
| Ser$^{TCT}$ | Ser$^{AGC}$ |
| Ser$^{TCT}$ | Ser$^{AGT}$ |
| Ser$^{TCA}$ | Ser$^{AGC}$ |
| Ser$^{TCA}$ | Ser$^{AGT}$ |
| Ser$^{TCC}$ | Ser$^{AGC}$ |
| Ser$^{TCC}$ | Ser$^{AGT}$ |
| Thr$^{ACG}$ | Thr$^{ACC}$ |
| Thr$^{ACG}$ | Thr$^{ACA}$ |
| Thr$^{ACG}$ | Thr$^{ACT}$ |
| Thr$^{ACC}$ | Thr$^{ACA}$ |
| Thr$^{ACC}$ | Thr$^{ACT}$ |
| Thr$^{ACA}$ | Thr$^{ACT}$ |
| Tyr$^{TAC}$ | Tyr$^{TAT}$ |
| Val$^{GTG}$ | Val$^{GTT}$ |
| Val$^{GTG}$ | Val$^{GTA}$ |
| Val$^{GTC}$ | Val$^{GTT}$ |
| Val$^{GTC}$ | Val$^{GTA}$ |
| Val$^{GTT}$ | Val$^{GTA}$ |

In another aspect, the invention provides a synthetic polynucleotide constructed according to any one of the above methods.

In accordance with the present invention, synthetic polynucleotides that are constructed by methods described herein are useful for expression in a mammal to elicit an immune response to a target antigen. Accordingly, in yet another aspect, the present invention provides chimeric constructs that comprise a synthetic polynucleotide of the invention, which is operably connected to a regulatory polynucleotide.

In some embodiments, the chimeric construct is in the form of a pharmaceutical composition that optionally comprises a pharmaceutically acceptable excipient and/or carrier. Accordingly, in another aspect, the invention provides pharmaceutical compositions that are useful for modulating an immune response to a target antigen in a mammal, which response is conferred by the expression of a parent polynucleotide that encodes a polypeptide corresponding to at least a portion of the target antigen. These compositions generally comprise a chimeric construct and a pharmaceutically acceptable excipient and/or carrier, wherein the chimeric construct comprises a synthetic polynucleotide that is operably connected to a regulatory polynucleotide and that is distinguished from the parent polynucleotide by the replacement of a first codon in the parent polynucleotide with a synonymous codon that has a different immune response preference than the first codon and wherein the first and synonymous codons are selected according to any one of TABLES 2, 3, 5 and 6. In some embodiments, the compositions further comprise an adjuvant that enhances the effectiveness of the immune response. In some embodiments, the composition is formulated for transcutaneous or dermal administration, e.g., by biolistic or microneedle delivery or by intradermal injection. Suitably, in embodiments in which a stronger or enhanced immune response to the target antigen is desired, the first and synonymous codons are selected according to TABLES 2 or 3. Conversely, in embodiments in which a weaker or reduced immune response to the target antigen is desired, the first and synonymous codons are selected according to TABLES 5 or 6.

In yet another aspect, the invention embraces methods of modulating the quality of an immune response to a target antigen in a mammal, which response is conferred by the expression of a parent polynucleotide that encodes a polypeptide corresponding to at least a portion of the target antigen. These methods generally comprise: introducing into the mammal a synthetic polynucleotide that is operably connected to a regulatory polynucleotide and that is distinguished from the parent polynucleotide by the replacement of a first codon in the parent polynucleotide with a synonymous codon that has a different immune response preference than the first codon and wherein the first and synonymous codons are selected according to any one of TABLES 2, 3, 5 and 6. In these methods, expression of the synthetic polynucleotide results in a different quality (e.g., stronger or weaker) of immune response than the one obtained through expression of the parent polynucleotide under the same conditions. Suitably, the chimeric construct is introduced into the mammal by delivering the construct to antigen-presenting cells (e.g., dendritic cells, macrophages, Langerhans cells or their precursors) of the mammal. In some embodiments, the chimeric construct is introduced into the dermis and/or epidermis of the mammal (e.g., by transcutaneous or intradermal administration) and in this regard any suitable administration site is envisaged including the abdomen. Generally, the immune response is selected from a cell-mediated response and a humoral immune response. In some embodiments, the immune response is a humoral immune response. In other embodiments, the immune response is a cellular immune response. In still other embodiments, the immune response is a humoral immune response and a cellular immune response.

In a related aspect, the invention encompasses methods of enhancing the quality of an immune response to a target antigen in a mammal, which response is conferred by the expression of a parent polynucleotide that encodes a polypeptide corresponding to at least a portion of the target antigen. These methods generally comprise: introducing into the mammal a chimeric construct comprising a synthetic polynucleotide that is operably connected to a regulatory polynucleotide and that is distinguished from the parent polynucleotide by the replacement of a first codon in the parent polynucleotide with a synonymous codon that has a higher immune response preference than the first codon, wherein the first and synonymous codons are selected according to TABLES 2 or 3. In these methods, expression of the synthetic polynucleotide typically results in a stronger or enhanced immune response than the one obtained through expression of the parent polynucleotide under the same conditions.

In another related aspect, the invention extends to methods of reducing the quality of an immune response to a target antigen in a mammal, which response is conferred by the expression of a parent polynucleotide that encodes a polypeptide corresponding to at least a portion of the target antigen. These methods generally comprise: introducing into the mammal a chimeric construct comprising a synthetic polynucleotide that is operably connected to a regulatory polynucleotide and that is distinguished from the parent polynucleotide by the replacement of a first codon in the parent polynucleotide with a synonymous codon that has a lower immune response preference than the first codon, wherein the first and synonymous codons are selected according to TABLES 5 or 6. In these methods, expression of the synthetic polynucleotide typically results in a weaker or reduced immune response than the one obtained through expression of the parent polynucleotide under the same conditions.

Yet a further aspect of the present invention embraces methods of enhancing the quality of an immune response to a target antigen in a mammal, which response is conferred by the expression of a first polynucleotide that encodes a polypeptide corresponding to at least a portion of the target antigen. These methods generally comprise: co-introducing into the mammal a first nucleic acid construct comprising the first polynucleotide in operable connection with a regulatory polynucleotide; and a second nucleic acid construct comprising a second polynucleotide that is operably connected to a regulatory polynucleotide and that encodes an iso-tRNA corresponding to a codon of the first polynucleotide, wherein the codon has a low or intermediate immune response preference and is selected from the group consisting of $Ala^{GCA}$, $Ala^{GCG}$, $Ala^{GCC}$, $Arg^{AGG}$, $Arg^{CGG}$, $Asn^{AAT}$, $Asp^{GAT}$, $Cys^{TGT}$, $Glu^{GAG}$, $Gly^{GGG}$, $Gly^{GGT}$, $Gly^{GGC}$, $Ile^{ATA}$, $Ile^{ATT}$, $Leu^{TTG}$, $Leu^{TTA}$, $Leu^{CTA}$, $Leu^{CTT}$, $Phe^{TTC}$, $Pro^{CCA}$, $Pro^{CCG}$, $Pro^{CCT}$, $Ser^{AGC}$, $Ser^{AGT}$, $Ser^{TCT}$, $Ser^{TCA}$, $Ser^{TCC}$, $Thr^{ACA}$, $Thr^{ACT}$, $Tyr^{TAT}$, $Val^{GTA}$ and $Val^{GTT}$. In specific embodiments, the codon has a 'low' immune response preference, and is selected from the group consisting of $Ala^{GCA}$, $Ala^{GCG}$, $Arg^{AGG}$, $Arg^{CGG}$, $Asn^{AAT}$, $Asp^{GAT}$, $Cys^{TGT}$, $Glu^{GAG}$, $Gly^{GGG}$, $Gly^{GGT}$, $Gly^{GGC}$, $Ile^{ATA}$, $Leu^{TTG}$, $Leu^{TTA}$, $Phe^{TTC}$, $Pro^{CCA}$, $Pro^{CCG}$, $Ser^{AGC}$, $Ser^{AGT}$, $Thr^{ACT}$, $Tyr^{TAT}$ and $Val^{GTA}$.

BRIEF DESCRIPTION OF THE DRAWINGS

FIG. 1 is a diagrammatic representation depicting a nucleotide sequence alignment of secreted ALA E7 constructs and controls (IgkC1 (SEQ ID NO:93), IgkS1-1 (SEQ ID NO:94), IgkS1-2 (SEQ ID NO:95), IgkS1-3 (SEQ ID NO:96), IgkS1-4 (SEQ ID NO:97) and IgkC2 (SEQ ID NO:98)) as further defined in Example 1 and Table 12. The sequences are ligated into the KpnI and EcoRI sites of pCDNA3.

FIG. 2 is a diagrammatic representation depicting a nucleotide sequence alignment of secreted ARG E7 constructs and controls (IgkS1-5 (SEQ ID NO:99), IgkS1-6 (SEQ ID NO:100), IgkS1-7 (SEQ ID NO:101), IgkS1-8 (SEQ ID NO:102), IgkS1-9 (SEQ ID NO:103), IgkS1-10 (SEQ ID NO:104), IgkC1 (SEQ ID NO:93), and IgkC2 (SEQ ID NO:98)) as further defined in Example 1 and Table 12. The sequences are ligated into the KpnI and EcoRI sites of pCDNA3.

FIG. 3 is a diagrammatic representation depicting a nucleotide sequence alignment of secreted ASN and LYS E7 constructs and controls (IgkC1 (SEQ ID NO:93), IgkS1-12 (SEQ ID NO:105), IgkS1-31 (SEQ ID NO:106), and IgkC2

Figure 18:
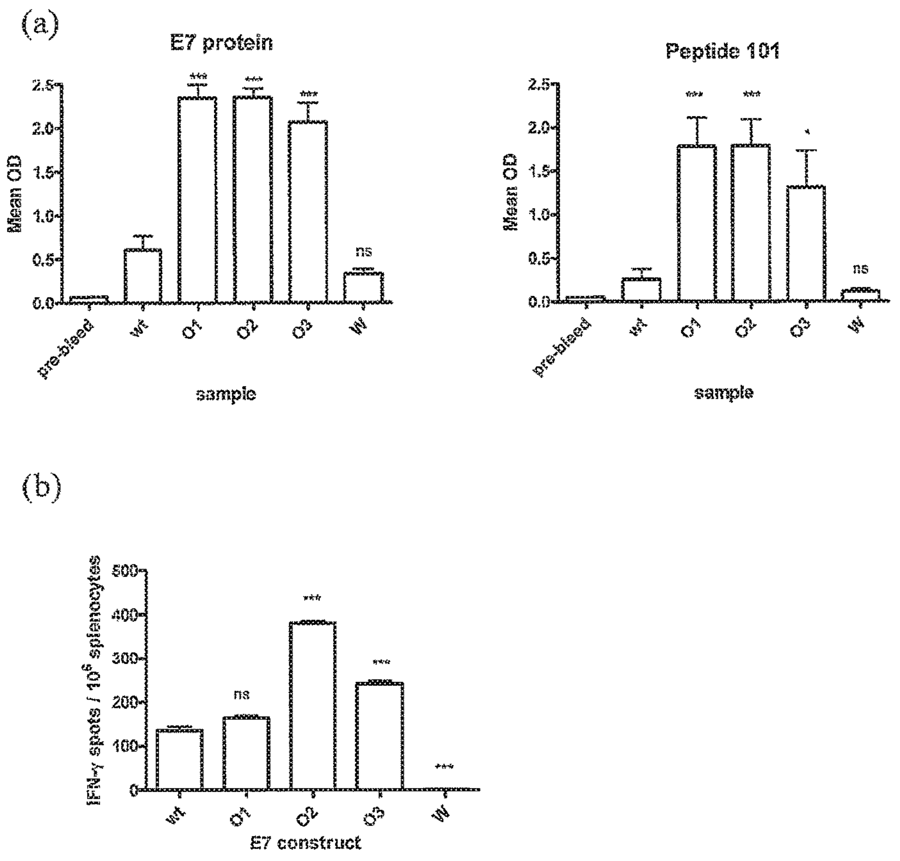

(SEQ ID NO:98)) as further defined in Example 1 and Table 12. The sequences are ligated into the KpnI and EcoRI sites of pCDNA3.

FIG. 4 is a diagrammatic representation depicting a nucleotide sequence alignment of secreted ASP E7 constructs and controls (IgkC1 (SEQ ID NO:93), IgkS1-13 (SEQ ID NO:107), IgkS1-14 (SEQ ID NO:108), and IgkC2 (SEQ ID NO:98)) as further defined in Example 1 and Table 12. The sequences are ligated into the KpnI and EcoRI sites of pCDNA3.

FIG. 5 is a diagrammatic representation depicting a nucleotide sequence alignment of secreted CYS E7 constructs and controls (IgkC1 (SEQ ID NO:93), IgkS1-15 (SEQ ID NO:109), IgkS1-16 (SEQ ID NO:110), and IgkC2 (SEQ ID NO:98)) as further defined in Example 1 and Table 12. The sequences are ligated into the KpnI and EcoRI sites of pCDNA3.

FIG. 6 is a diagrammatic representation depicting a nucleotide sequence alignment of secreted GLU E7 constructs and controls (IgkS1-17 (SEQ ID NO:111), IgkS1-18 (SEQ ID NO:112), IgkC2 (SEQ ID NO:98), and IgkC1 (SEQ ID NO:93)) as further defined in Example 1 and Table 12. The sequences are ligated into the KpnI and EcoRI sites of pCDNA3.

FIG. 7 is a diagrammatic representation depicting a nucleotide sequence alignment of secreted GLN E7 constructs and controls (IgkC1 (SEQ ID NO:93), IgkS1-19 (SEQ ID NO:113), IgkS1-20 (SEQ ID NO:114), and IgkC2 (SEQ ID NO:98)) as further defined in Example 1 and Table 12. The sequences are ligated into the KpnI and EcoRI sites of pCDNA3.

FIG. 8 is a diagrammatic representation depicting a nucleotide sequence alignment of secreted GLY E7 constructs and controls (IgkC1 (SEQ ID NO:93), IgkS1-21 (SEQ ID NO:115), IgkS1-22 (SEQ ID NO:116), IgkS1-23 (SEQ ID NO:117), IgkS1-24 (SEQ ID NO:118), and IgkC2 (SEQ ID NO:98)) as further defined in Example 1 and Table 12. The sequences are ligated into the KpnI and EcoRI sites of pCDNA3.

FIG. 9 is a diagrammatic representation depicting a nucleotide sequence alignment of secreted HIS E7 constructs and controls (IgkC1 (SEQ ID NO:93), IgkS1-25 (SEQ ID NO:119), IgkS1-26 (SEQ ID NO:120), and IgkC2 (SEQ ID NO:98)) as further defined in Example 1 and Table 12. The sequences are ligated into the KpnI and EcoRI sites of pCDNA3.

FIG. 10 is a diagrammatic representation depicting a nucleotide sequence alignment of secreted ILE E7 constructs and controls (IgkC1 (SEQ ID NO:93), IgkS1-27 (SEQ ID NO:121), IgkS1-28 (SEQ ID NO:122), IgkS1-29 (SEQ ID NO:123) and IgkC2 (SEQ ID NO:98)) as further defined in Example 1 and Table 12. The sequences are ligated into the KpnI and EcoRI sites of pCDNA3.

FIG. 11 is a diagrammatic representation depicting a nucleotide sequence alignment of secreted LEU E7 constructs and controls (IgkS1-50 (SEQ ID NO:124), IgkS1-51 (SEQ ID NO:125), IgkS1-52 (SEQ ID NO:126), IgkS1-53 (SEQ ID NO:127), IgkS1-54 (SEQ ID NO:128), IgkS1-55 (SEQ ID NO:129), IgkC3 (SEQ ID NO:130), and IgkC4 (SEQ ID NO:131)) as further defined in Example 1 and Table 12. The sequences are ligated into the KpnI and EcoRI sites of pCDNA3. The LEU E7 constructs are oncogenic (i.e., encode wild-type E7 protein).

FIG. 12 is a diagrammatic representation depicting a nucleotide sequence alignment of secreted PHE E7 constructs and controls (IgkS1-32 (SEQ ID NO:132), IgkS1-33 (SEQ ID NO:133), IgkC1 (SEQ ID NO:93), and IgkC2 (SEQ ID NO:98)) as further defined in Example 1 and Table 12. The sequences are ligated into the KpnI and EcoRI sites of pCDNA3. Two LEU residues were mutated to PHE in this sequence so that there are three instead of one PHE residue.

FIG. 13 is a diagrammatic representation depicting a nucleotide sequence alignment of secreted PRO E7 constructs and controls (IgkS1-56 (SEQ ID NO:134), IgkS1-57 (SEQ ID NO:135), IgkS1-58 (SEQ ID NO:136), IgkS1-59 (SEQ ID NO:137), IgkC3 (SEQ ID NO:130), and IgkC4 (SEQ ID NO:131)) as further defined in Example 1 and Table 12. The sequences are ligated into the KpnI and EcoRI sites of pCDNA3. The PRO E7 constructs are oncogenic (i.e., encode wild-type E7 protein).

FIG. 14 is a diagrammatic representation depicting a nucleotide sequence alignment of secreted SER E7 constructs and controls (IgkS1-34 (SEQ ID NO:138), IgkS1-35 (SEQ ID NO:139), IgkS1-36 (SEQ ID NO:140), IgkS1-37 (SEQ ID NO:141), IgkS1-38 (SEQ ID NO:142), IgkS1-39 (SEQ ID NO:143), IgkC1 (SEQ ID NO:93), and IgkC2 (SEQ ID NO:98)) as further defined in Example 1 and Table 12. The sequences are ligated into the KpnI and EcoRI sites of pCDNA3.

FIG. 15 is a diagrammatic representation depicting a nucleotide sequence alignment of secreted THR E7 constructs and controls (IgkC1 (SEQ ID NO:93), IgkS1-40 (SEQ ID NO:144), IgkS1-41 (SEQ ID NO:145), IgkS1-42 (SEQ ID NO:146), IgkS1-43 (SEQ ID NO:147), and IgkC2 (SEQ ID NO:98)) as further defined in Example 1 and Table 12. The sequences are ligated into the KpnI and EcoRI sites of pCDNA3.

FIG. 16 is a diagrammatic representation depicting a nucleotide sequence alignment of secreted TYR E7 constructs and controls (IgkC1 (SEQ ID NO:93), IgkS1-44 (SEQ ID NO:148), IgkS1-45 (SEQ ID NO:149) and IgkC2 (SEQ ID NO:98)) as further defined in Example 1 and Table 12. The sequences are ligated into the KpnI and EcoRI sites of pCDNA3.

FIG. 17 is a diagrammatic representation depicting a nucleotide sequence alignment of secreted VAL E7 constructs and controls (IgkC1 (SEQ ID NO:93), IgkS1-46 (SEQ ID NO:150), IgkS1-47 (SEQ ID NO:151), IgkS1-48 (SEQ ID NO:152), IgkS1-49 (SEQ ID NO:153), and IgkC2 (SEQ ID NO:98)) as further defined in Example 1 and Table 12. The sequences are ligated into the KpnI and EcoRI sites of pCDNA3.

FIG. 18 is a graphical representation showing the response to gene gun immunization with optimized and de-optimized E7 constructs measured by (a) ELISA, (b) Memory B cell ELISPOT, and (c) IFN-γ ELISPOT. For part (a) eight mice were immunized per group (4 immunizations, 3 weeks apart) and the sera taken three weeks after the final immunization; (left) E7 protein ELISA, (right) E7 peptide 101 ELISA. Wells were done in duplicate. For parts (b) and (c) mice were immunized twice, three weeks apart and the spleens collected three weeks after the second immunization. The spleens were pooled prior to analysis. The Memory B cell and IFN-γ ELISPOTs were conducted twice and three times, respectively, and the wells done in triplicate. Three mice were used per group per repeat. The results shown in parts (b) and (c) are from individual experiments and are representative of the complete data sets. The particular ELISPOT experimental data included here were gathered together with the corresponding data in FIG. 20 and therefore may be directly compared. Unpaired two-tailed t-tests were used to compare the modified constructs to wild-type. * $P<0.001$,  $0.001 \le P<0.01$, * $0.01 \le P \le 0.05$, ns=not significant ($P>0.05$). In (a) O1-O3 were not significantly different from MC as measured by unpaired two-tailed t-tests. wt=wild-type codon usage E7; O1-O3=codon-optimized E7 constructs 1 to 3; W=codon de-optimized E7; MC=mammalian consensus codon usage E7.

Figure 19:
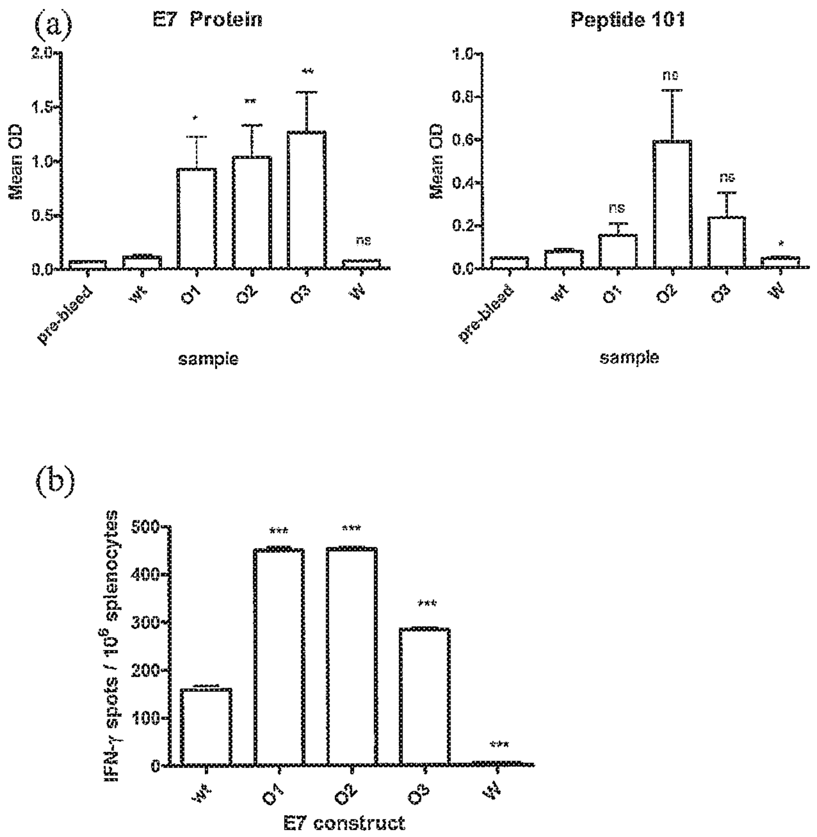

FIG. 19 is a graphical representation showing the response to immunization by intradermal injection with optimized and de-optimized constructs measured by (a) ELISA, (b) Memory B cell ELISPOT, and (c) IFN-γ ELISPOT. For part (a) eight mice were immunized per group (4 immunizations, 3 weeks apart) and the sera taken three weeks after the final immunization; (left) E7 protein ELISA, (right) E7 peptide 101 ELISA. Wells were done in duplicate. For parts (b) and (c) mice were immunized twice, three weeks apart and the spleens collected three weeks after the second immunization. The spleens were pooled prior to analysis. The Memory B cell and IFN-γ ELISPOTs were conducted twice and three times, respectively, and the wells done in triplicate. Three mice were used per group per repeat. The results shown in parts (b) and (c) are from individual experiments and are representative of the complete data sets. The particular ELISPOT experimental data included here were gathered together with the corresponding data in FIG. 20 and therefore may be directly compared. Unpaired two-tailed t-tests were used to compare the modified constructs to wild-type. * $P<0.001$, $0.001 \le P<0.01$, * $0.01 \le P \le 0.05$, ns=not significant ($P>0.05$). In (a) O1-O3 were not significantly different from MC as measured by unpaired two-tailed t-tests. wt=wild-type codon usage E7; O1-O3=codon-optimized E7 constructs 1 to 3; W=codon de-optimized E7; MC=mammalian consensus codon usage E7.

Figure 20:
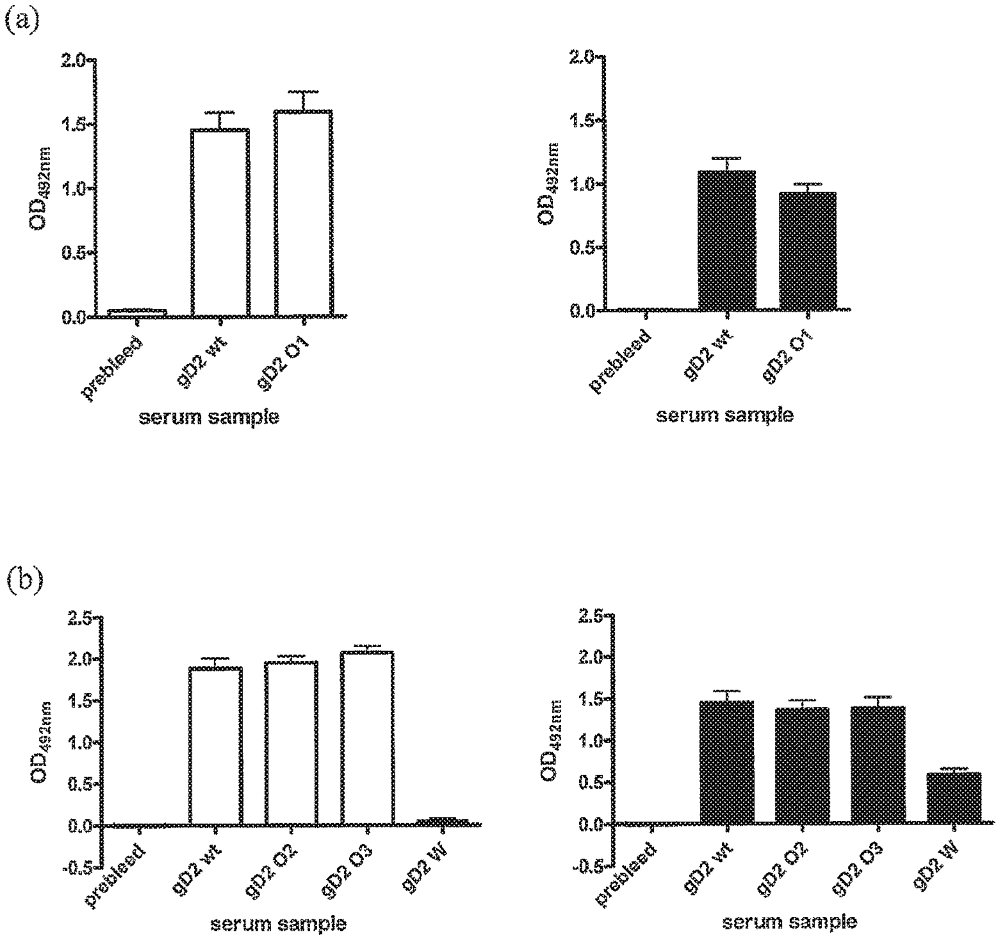

FIG. 20 is a graphical representation showing the results of an ELISA that measures binding of serum from mice immunized with various gD2 constructs by intradermal injection (white bars) or gene gun immunization (black bars), to C-terminally His-tagged gD2tr. Note that the His-tagged gD2tr protein was used in an unpurified state (in CHO cell supernatant) and that background readings of non-specific binding to control supernatant have been subtracted from the results.

TABLE 8

BRIEF DESCRIPTION OF THE SEQUENCES

| SEQUENCE ID NUMBER | SEQUENCE | LENGTH |
|---|---|---|
| SEQ ID NO: 1 | IgkS2-13 Asp GAT construct nucleotide sequence | 387 nts |
| SEQ ID NO: 2 | IgkS2-14 Asp GAC construct nucleotide sequence | 387 nts |
| SEQ ID NO: 3 | IgkS2-15 Cys TGT construct nucleotide sequence | 387 nts |
| SEQ ID NO: 4 | IgkS2-16 Cys TGC construct nucleotide sequence | 387 nts |
| SEQ ID NO: 5 | IgkS2-17 Glu GAG construct nucleotide sequence | 387 nts |
| SEQ ID NO: 6 | IgkS2-18 Glu GAA construct nucleotide sequence | 387 nts |
| SEQ ID NO: 7 | IgkS2-19 Gln CAG construct nucleotide sequence | 387 nts |
| SEQ ID NO: 8 | IgkS2-20 Gln CAA construct nucleotide sequence | 387 nts |
| SEQ ID NO: 9 | IgkS2-21 Gly GGG construct nucleotide sequence | 387 nts |
| SEQ ID NO: 10 | IgkS2-22 Gly GGA construct nucleotide sequence | 387 nts |
| SEQ ID NO: 11 | IgkS2-23 Gly GGT construct nucleotide sequence | 387 nts |
| SEQ ID NO: 12 | IgkS2-24 Gly GGC construct nucleotide sequence | 387 nts |
| SEQ ID NO: 13 | IgkS2-27 Ile ATA construct nucleotide sequence | 387 nts |
| SEQ ID NO: 14 | IgkS2-28 Ile ATT construct nucleotide sequence | 387 nts |
| SEQ ID NO: 15 | IgkS2-29 Ile ATC construct nucleotide sequence | 387 nts |
| SEQ ID NO: 16 | IgkS2-34 Ser AGT construct nucleotide sequence | 387 nts |
| SEQ ID NO: 17 | IgkS2-35 Ser AGC construct nucleotide sequence | 387 nts |
| SEQ ID NO: 18 | IgkS2-36 Ser TCG construct nucleotide sequence | 387 nts |
| SEQ ID NO: 19 | IgkS2-37 Ser TCA construct nucleotide sequence | 387 nts |
| SEQ ID NO: 20 | IgkS2-38 Ser TCT construct nucleotide sequence | 387 nts |
| SEQ ID NO: 21 | IgkS2-39 Ser TCC construct nucleotide sequence | 387 nts |
| SEQ ID NO: 22 | IgkS2-40 Thr ACG construct nucleotide sequence | 387 nts |
| SEQ ID NO: 23 | IgkS2-41 Thr ACA construct nucleotide sequence | 387 nts |
| SEQ ID NO: 24 | IgkS2-42 Thr ACT construct nucleotide sequence | 387 nts |
| SEQ ID NO: 25 | IgkS2-43 Thr ACC construct nucleotide sequence | 387 nts |
| SEQ ID NO: 26 | IgkS2-46 Val GTG construct nucleotide sequence | 387 nts |
| SEQ ID NO: 27 | IgkS2-47 Val GTA construct nucleotide sequence | 387 nts |
| SEQ ID NO: 28 | IgkS2-48 Val GTT construct nucleotide sequence | 387 nts |
| SEQ ID NO: 29 | IgkS2-49 Val GTG construct nucleotide sequence | 387 nts |
| SEQ ID NO: 30 | IgkS2-1 Ala GCG Linker nucleotide sequence | 408 nts |
| SEQ ID NO: 31 | IgkS2-2 Ala GCA Linker nucleotide sequence | 408 nts |
| SEQ ID NO: 32 | IgkS2-3 Ala GCT Linker nucleotide sequence | 408 nts |
| SEQ ID NO: 33 | IgkS2-4 Ala GCC Linker nucleotide sequence | 408 nts |
| SEQ ID NO: 34 | IgkS2-5 Arg AGG Linker nucleotide sequence | 408 nts |
| SEQ ID NO: 35 | IgkS2-6 Arg AGA Linker nucleotide sequence | 408 nts |
| SEQ ID NO: 36 | IgkS2-7 Arg CGG Linker nucleotide sequence | 408 nts |
| SEQ ID NO: 37 | IgkS2-8 Arg CGA Linker nucleotide sequence | 408 nts |
| SEQ ID NO: 38 | IgkS2-9 Arg CGT Linker nucleotide sequence | 408 nts |
| SEQ ID NO: 39 | IgkS2-10 Arg CGC Linker nucleotide sequence | 408 nts |
| SEQ ID NO: 40 | IgkS2-11 Asn AAT Linker nucleotide sequence | 408 nts |
| SEQ ID NO: 41 | IgkS2-12 Asn AAC Linker nucleotide sequence | 408 nts |
| SEQ ID NO: 42 | IgkS2-25 His CAT Linker nucleotide sequence | 408 nts |
| SEQ ID NO: 43 | IgkS2-26 His CAC Linker nucleotide sequence | 408 nts |
| SEQ ID NO: 44 | IgkS2-30 Lys AAG Linker nucleotide sequence | 408 nts |
| SEQ ID NO: 45 | IgkS2-31 Lys AAA Linker nucleotide sequence | 408 nts |
| SEQ ID NO: 46 | IgkS2-32 Phe TTT Linker nucleotide sequence | 408 nts |
| SEQ ID NO: 47 | IgkS2-33 Phe TTC Linker nucleotide sequence | 408 nts |
| SEQ ID NO: 48 | IgkS2-44 Tyr TAT Linker nucleotide sequence | 408 nts |
| SEQ ID NO: 49 | IgkS2-45 Tyr TAC Linker nucleotide sequence | 408 nts |

TABLE 8-continued

| BRIEF DESCRIPTION OF THE SEQUENCES | | |
|---|---|---|
| SEQUENCE ID NUMBER | SEQUENCE | LENGTH |
| SEQ ID NO: 50 | Influenza A Virus HA hemagglutinin (A/Hong Kong/213/03(H5N1)) BAE07201 wild-type | 1707 nts |
| SEQ ID NO: 51 | Influenza A Virus HA hemagglutinin (A/Hong Kong/213/03(H5N1)) BAE07201 wild-type | 568 aa |
| SEQ ID NO: 52 | Influenza A Virus HA hemagglutinin (A/Hong Kong/213/03(H5N1)) Codon modified | 1707 nts |
| SEQ ID NO: 53 | Influenza A Virus HA hemagglutinin (A/swine/Korea/PZ72-1/2006 (H3N1)) DQ923506 wild-type | 1701 nts |
| SEQ ID NO: 54 | Influenza A Virus HA hemagglutinin (A/swine/Korea/PZ72-1/2006 (H3N1)) DQ923506 wild-type | 566 aa |
| SEQ ID NO: 55 | Influenza A Virus HA hemagglutinin (A/swine/Korea/PZ72-1/2006 (H3N1)) Codon modified | 1701 nts |
| SEQ ID NO: 56 | Influenza A Virus NA neuraminidase (A/Hong Kong/213/03(H5N1)) AB212056 wild-type | 1410 nts |
| SEQ ID NO: 57 | Influenza A Virus NA neuraminidase (A/Hong Kong/213/03(H5N1)) AB212056 wild-type | 469 aa |
| SEQ ID NO: 58 | Influenza A Virus NA neuraminidase (A/Hong Kong/213/03(H5N1)) Codon modified | 1410 nts |
| SEQ ID NO: 59 | Influenza A Virus NA neuraminidase (A/swine/MI/PU243/04 (H3N1)) DQ150427 wild-type | 1410 nts |
| SEQ ID NO: 60 | Influenza A Virus NA neuraminidase (A/swine/MI/PU243/04 (H3N1)) DQ150427 wild-type | 469 aa |
| SEQ ID NO: 61 | Influenza A Virus NA neuraminidase (A/swine/MI/PU243/04 (H3N1)) Codon modified | 1410 nts |
| SEQ ID NO: 62 | Hepatitis C Virus E1 (Serotype 1A, isolate H77) AF009606 wild-type | 576 nts |
| SEQ ID NO: 63 | Hepatitis C Virus E1 (Serotype 1A, isolate H77) NP 751920 wild-type | 192 aa |
| SEQ ID NO: 64 | Hepatitis C Virus E1 (Serotype 1A, isolate H77) Codon modified | 576 nts |
| SEQ ID NO: 65 | Hepatitis C Virus E2 (Serotype 1A, isolate H77) AF009606 wild-type | 1089 nts |
| SEQ ID NO: 66 | Hepatitis C Virus E2 (Serotype 1A, isolate 1177) NP 751921 wild-type | 363 aa |
| SEQ ID NO: 67 | Hepatitis C Virus E2 (Serotype 1A, isolate H77) Codon modified | 1089 nts |
| SEQ ID NO: 68 | Epstein Barr Virus (Type 1, gp350 B95-8) NC 007605 wild-type | 2724 nts |
| SEQ ID NO: 69 | Epstein Barr Virus (Type 1, gp350 B95-8) CAD53417 wild-type | 907 aa |
| SEQ ID NO: 70 | Epstein Barr Virus (Type 1, gp350 B95-8) Codon modified | 2724 nts |
| SEQ ID NO: 71 | Epstein Barr Virus (Type 2, gp350 AG876) NC 009334 wild-type | 2661 nts |
| SEQ ID NO: 72 | Epstein Barr Virus (Type 2, gp350 AG876) YP 001129462 wild-type | 886 aa |
| SEQ ID NO: 73 | Epstein Barr Virus (Type 2, gp350 AG876) Codon Modified | 2661 nts |
| SEQ ID NO: 74 | Herpes Simplex Virus 2 (Glycoprotein B strain HG52) NC 001798 wild-type | 2715 nts |
| SEQ ID NO: 75 | Herpes Simplex Virus 2 (Glycoprotein B strain HG52) CAB06752 wild-type | 904 aa |
| SEQ ID NO: 76 | Herpes Simplex Virus 2 (Glycoprotein B strain HG52) Codon modified | 2715 nts |
| SEQ ID NO: 77 | Herpes Simplex Virus (Glycoprotein D strain HG52) NC 001798 wild-type | 1182 nts |
| SEQ ID NO: 78 | Herpes Simplex Virus (Glycoprotein D strain HG52) NP 0044536 wild-type | 393 aa |
| SEQ ID NO: 79 | Herpes Simplex Virus (Glycoprotein D strain HG52) Codon modified | 1182 nts |
| SEQ ID NO: 80 | HPV-16 E7 wild-type | 387 nts |
| SEQ ID NO: 81 | HPV-16 E7 O1 | 387 nts |
| SEQ ID NO: 82 | HPV-16 E7 O2 | 387 nts |
| SEQ ID NO: 83 | HPV-16 E7 O3 | 417 nts |
| SEQ ID NO: 84 | HPV-16 E7 W | 387 nts |
| SEQ ID NO: 85 | HSV-2 gD2 wild-type | 1182 nts |
| SEQ ID NO: 86 | HSV-2 gD2 O1 | 1182 nts |
| SEQ ID NO: 87 | HSV-2 gD2 O2 | 1182 nts |
| SEQ ID NO: 88 | HSV-2 gD2 O3 | 1182 nts |
| SEQ ID NO: 89 | HSV-2 gD2 W | 1182 nts |

TABLE 8-continued

| BRIEF DESCRIPTION OF THE SEQUENCES | | |
|---|---|---|
| SEQUENCE ID NUMBER | SEQUENCE | LENGTH |
| SEQ ID NO: 90 | Common forward primer | 41 nts |
| SEQ ID NO: 91 | ODN-7909 | 24 nts |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, frequency, percentage, dimension, size, or amount that varies by no more than 15%, and preferably by no more than 10%, 9%, 8%, 7%, 6%, 5%, 4%, 3%, 2%, 1% to a reference quantity, level, value, frequency, percentage, dimension, size, or amount.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

As used herein, the term "cis-acting sequence" or "cis-regulatory region" or similar term shall be taken to mean any sequence of nucleotides which is derived from an expressible genetic sequence wherein the expression of the genetic sequence is regulated, at least in part, by the sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Throughout this specification, unless the context requires otherwise, the words "comprise," "comprises" and "comprising" will be understood to imply the inclusion of a stated step or element or group of steps or elements but not the exclusion of any other step or element or group of steps or elements.

As used herein, a "chimeric construct" refers to a polynucleotide having heterologous nucleic acid elements. Chimeric constructs include "expression cassettes" or "expression constructs," which refer to an assembly that is capable of directing the expression of the sequence(s) or gene(s) of interest. An expression cassette generally includes control elements such as a promoter that is operably linked to (so as to direct transcription of) a synthetic polynucleotide of the invention, and often includes a polyadenylation sequence as well. Within certain embodiments of the invention, the chimeric construct may be contained within a vector. In addition to the components of the chimeric construct, the vector may include, one or more selectable markers, a signal which allows the vector to exist as single-stranded DNA (e.g., a M13 origin of replication), at least one multiple cloning site, and a "mammalian" origin of replication (e.g., a SV40 or adenovirus origin of replication).

As used herein, "conferred immune response," "immune response that is conferred" and the like refer to a temporary or permanent change in immune response to a target antigen, which occurs or would occur after the introduction of a polynucleotide to the mammal, and which would not occur in the absence of that introduction. Typically, such a temporary or permanent change occurs as a result of the transcription and/or translation of genetic information contained within that polynucleotide in a cell, or in at least one cell or cell type or class of cell within a mammal or within a class of mammals, and can be used to distinguish the mammal, or class of mammals to which the polynucleotide has been provided from a similar mammal, or class of mammals, to which the polynucleotide has not been provided.

By "corresponds to" or "corresponding to" is meant an antigen which encodes an amino acid sequence that displays substantial similarity to an amino acid sequence in a target antigen. In general the antigen will display at least about 30, 40, 50, 55, 60, 65, 70, 75, 80, 85, 90, 91, 92, 93, 94, 95, 96, 97, 98, 99% similarity or identity to at least a portion of the target antigen (e.g., at least 10%, 20%, 30%, 40%, 50%, 60%, 70%, 80%, 90% or 95% of the amino acid sequence of the target antigen).

By "effective amount," in the context of modulating an immune response or treating or preventing a disease or condition, is meant the administration of that amount of composition to an individual in need thereof, either in a single dose or as part of a series, that is effective for achieving that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The terms "enhancing an immune response," "producing a stronger immune response" and the like refer to increasing an animal's capacity to respond to a target antigen (e.g., a foreign or disease-specific antigen or a self antigen), which can be determined for example by detecting an increase in the number, activity, and ability of the animal's cells that are primed to attack such antigens or an increase in the titer or activity of antibodies in the animal, which are immuno-interactive with the target antigen. Strength of immune response can be measured by standard immunoassays including: direct measurement of antibody titers or peripheral blood lymphocytes; cytolytic T lymphocyte assays; assays of natural killer cell cytotoxicity; cell proliferation assays including lymphoproliferation (lymphocyte activation) assays; immunoassays of immune cell subsets; assays of T-lymphocytes specific for the antigen in a sensitized subject; skin tests for cell-mediated immunity; etc. Such assays are well known in the art. See, e.g., Erickson et al., 1993, J. Immunol. 151:4189-4199; Doe et al., 1994, Eur. J. Immunol. 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., 1998, J. Exp. Med. 187(9)1367-1371; Mcheyzer-Williams, M. G., et al., 1996, Immunol. Rev. 150:5-21; Lalvani, A., et al., 1997, J. Exp. Med. 186:859-865). Any statistically significant increase in strength of immune response as measured for example by immunoassay is considered an "enhanced immune response" or "immunoenhancement" as used herein. Enhanced immune response is also indicated by physical manifestations such as fever and inflammation, as well as healing of systemic and local infections, and reduction of symptoms in disease, i.e., decrease in tumor size, alleviation of symptoms of a disease or condition including, but not restricted to, leprosy, tuberculosis, malaria, naphthous ulcers, herpetic and papillomatous warts, gingivitis, arthrosclerosis, the concomitants of AIDS such as Kaposi's sarcoma, bronchial infections, and the like. Such physical manifestations also encompass "enhanced immune response" or "immunoenhancement" as used herein. By contrast, "reducing an immune response," "producing a weaker immune response" and the like refer to decreasing an animal's capacity to respond to a target antigen, which can be determined for example by conducting immunoassays or assessing physical manifestations, as described for example above.

The terms "expression" or "gene expression" refer to production of RNA message and/or translation of RNA message into proteins or polypeptides.

By "expression vector" is meant any autonomous genetic element capable of directing the synthesis of a protein encoded by the vector. Such expression vectors are known by practitioners in the art.

The term "gene" is used in its broadest context to include both a genomic DNA region corresponding to the gene as well as a cDNA sequence corresponding to exons or a recombinant molecule engineered to encode a functional form of a product.

As used herein the term "heterologous" refers to a combination of elements that are not naturally occurring or that are obtained from different sources.

"Immune response" or "immunological response" refers to the concerted action of lymphocytes, antigen-presenting cells, phagocytic cells, granulocytes, and soluble macromolecules produced by the above cells or the liver (including antibodies, cytokines, and complement) that results in selective damage to, destruction of, or elimination from the body of cancerous cells, metastatic tumor cells, metastatic breast cancer cells, invading pathogens, cells or tissues infected with pathogens, or, in cases of autoimmunity or pathological inflammation, normal human cells or tissues. In some embodiments, an "immune response" encompasses the development in an individual of a humoral and/or a cellular immune response to a polypeptide that is encoded by an introduced synthetic polynucleotide of the invention. As known in the art, the terms "humoral immune response" includes and encompasses an immune response mediated by antibody molecules, while a "cellular immune response" includes and encompasses an immune response mediated by T-lymphocytes and/or other white blood cells. Thus, an immune response that is stimulated by a synthetic polynucleotide of the invention may be one that stimulates the production of antibodies (e.g., neutralizing antibodies that block bacterial toxins and pathogens such as viruses entering cells and replicating by binding to toxins and pathogens, typically protecting cells from infection and destruction). The synthetic polynucleotide may also elicit production of cytolytic T lymphocytes (CTLs). Hence, an immunological response may include one or more of the following effects: the production of antibodies by B-cells; and/or the activation of suppressor T-cells and/or memory/effector T-cells directed specifically to an antigen or antigens present in the composition or vaccine of interest. In some embodiments, these responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al., 1988, J Clin Microbiol. 26:231-235; Dreyer et al., 1999, AIDS Res Hum Retroviruses 15(17):1563-1571). The innate immune system of mammals also recognizes and responds to molecular features of pathogenic organisms and cancer cells via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature dendritic cells of, for example, the monocyte and plamsacytoid lineage (MDC, PDC), as well as gamma, delta, alpha and beta T cells and B cells and the like. Thus, the present invention also contemplates an immune response wherein the immune response involves both an innate and adaptive response.

A composition is "immunogenic" if it is capable of either: a) generating an immune response against a target antigen (e.g., a viral or tumor antigen) in an individual; or b) reconstituting, boosting, or maintaining an immune response in an individual beyond what would occur if the agent or composition was not administered. An agent or composition is immunogenic if it is capable of attaining either of these criteria when administered in single or multiple doses.

"Immunomodulation," modulating an immune response" and the like refer to the modulation of the immune system in response to a stimulus and includes increasing or decreasing an immune response to a target antigen or changing an immune response from one that is predominantly a humoral immune response to one that is a more cell-mediated immune response and vice versa. For example, it is known in the art that decreasing the amount of antigen for immunization can change the bias of the immune system from a predominantly humoral immune response to a predominantly cellular immune response.

By "isoaccepting transfer RNA" or "iso-tRNA" is meant one or more transfer RNA molecules that differ in their anticodon nucleotide sequence but are specific for the same amino acid.

As used herein, the term "mammal" refers to any mammal including, without limitation, humans and other primates, including non-human primates such as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age. Thus, both adult and newborn individuals are intended to be covered.

By "modulating," "modulate" and the like is meant increasing or decreasing, either directly or indirectly, the quality of a selected phenotype (e.g., an immune response). In certain embodiments, "modulation" or "modulating" means that a desired/selected immune response is more efficient (e.g., at least 10%, 20%, 30%, 40%, 50%, 60% or more), more rapid (e.g., at least 10%, 20%, 30%, 40%, 50%, 60% or more), greater in magnitude (e.g., at least 10%, 20%, 30%, 40%, 50%, 60% or more), and/or more easily induced (e.g., at least 10%, 20%, 30%, 40%, 50%, 60% or more) than if the parent polynucleotide had been used under the same conditions as the synthetic polynucleotide. In other embodiments, "modulation" or "modulating" means changing an immune response from a predominantly antibody-mediated immune response as conferred by the parent polynucleotide, to a predominantly cellular immune response as conferred by the synthetic polynucleotide under the same conditions. In still other embodiments, "modulation" or "modulating" means changing an immune response from a predominantly cellular immune response as conferred by the parent polynucleotide, to a predominantly antibody-mediated immune response as conferred by the synthetic polynucleotide under the same conditions.

By "natural gene" is meant a gene that naturally encodes the protein. However, it is possible that the parent polynucleotide encodes a protein that is not naturally-occurring but has been engineered using recombinant techniques.

The term "5' non-coding region" is used herein in its broadest context to include all nucleotide sequences which are derived from the upstream region of an expressible gene, other than those sequences which encode amino acid residues which comprise the polypeptide product of the gene, wherein 5' non-coding region confers or activates or otherwise facilitates, at least in part, expression of the gene.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The terms "operably connected," "operably linked" and the like as used herein refer to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence. Terms such as "operably connected," therefore, include placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

By "pharmaceutically-acceptable carrier" is meant a solid or liquid filler, diluent or encapsulating substance that may be safely used in topical or systemic administration.

The term "phenotype" means any one or more detectable physical or functional characteristics, properties, attributes or traits of an organism, tissue, or cell, or class of organisms, tissues or cells, which generally result from the interaction between the genetic makeup (i.e., genotype) of the organism, tissue, or cell, or the class of organisms, tissues or cells and the environment.

By "phenotypic preference" is meant the preference with which an organism uses a codon to produce a selected phenotype. This preference can be evidenced, for example, by the quality of a selected phenotype that is producible by a polynucleotide that comprises the codon in an open reading frame which codes for a polypeptide that produces the selected phenotype. In certain embodiment, the preference of usage is independent of the route by which the polynucleotide is introduced into the organism. However, in other embodiments, the preference of usage is dependent on the route of introduction of the polynucleotide into the organism.

The term "polynucleotide" or "nucleic acid" as used herein designates mRNA, RNA, cRNA, cDNA or DNA. The term typically refers to oligonucleotides greater than 30 nucleotides in length.

"Polypeptide," "peptide" and "protein" are used interchangeably herein to refer to a polymer of amino acid residues and to variants and synthetic analogues of the same.

Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. As used herein, the terms "polypeptide," "peptide" and "protein" are not limited to a minimum length of the product. Thus, peptides, oligopeptides, dimers, multimers, and the like, are included within the definition. Both full-length proteins and fragments thereof are encompassed by the definition. The terms also include post expression modifications of a polypeptide, for example, glycosylation, acetylation, phosphorylation and the like. In some embodiments, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The terms "polypeptide variant," and "variant" refer to polypeptides that vary from a reference polypeptide by the addition, deletion or substitution (generally conservative in nature) of at least one amino acid residue. Typically, variants retain a desired activity of the reference polypeptide, such as antigenic activity in inducing an immune response against a target antigen. In general, variant polypeptides are "substantially similar" or substantially identical" to the reference polypeptide, e.g., amino acid sequence identity or similarity of more than 50%, generally more than 60%-70%, even more particularly 80%-85% or more, such as at least 90%-95% or more, when the two sequences are aligned. Often, the variants will include the same number of amino acids but will include substitutions, as explained herein.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but may alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridize and serve as a site for the initiation of synthesis. By "substantially complementary", it is meant that the primer is sufficiently complementary to hybridize with a target nucleotide sequence. Preferably, the primer contains no mismatches with the template to which it is designed to hybridize but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridize therewith and thereby form a template for synthesis of the extension product of the primer.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

The term "quality" is used herein in its broadest sense and includes a measure, strength, intensity, degree or grade of a phenotype, e.g., a superior or inferior immune response.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 10. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

The term "synthetic polynucleotide" as used herein refers to a polynucleotide that is formed by recombinant or synthetic techniques and typically includes polynucleotides that are not normally found in nature.

The term "synonymous codon" as used herein refers to a codon having a different nucleotide sequence than another codon but encoding the same amino acid as that other codon.

By "treatment," "treat," "treated" and the like is meant to include both therapeutic and prophylactic treatment.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Abbreviations

The following abbreviations are used throughout the application:

nt=nucleotide nts=nucleotides aa=amino acid(s)

kb=kilobase(s) or kilobase pair(s)

kDa=kilodalton(s)

d=day h=hour s=seconds

3. Immune Response Preference Ranking of Codons in Mammals

The present invention provides for the first time an immune response preference ranking of individual synonymous codons in mammals. This ranking was determined using a construct system that comprises a series of reporter constructs each comprising a different coding sequence for an antigenic polypeptide (e.g., a papillomavirus E7 polypeptide), wherein the coding sequence of individual constructs is distinguished from a parent coding sequence that encodes the antigenic polypeptide by the substitution of a single species of iso-accepting codon for each other species of iso-accepting codon that is present in the parent coding sequence. Accordingly, the coding sequence of individual synthetic constructs uses the same iso-accepting codon to encode most instances and preferably every instance of a particular amino acid residue (e.g., $Ala^{GCT}$ for all alanines) in the antigenic polypeptide and individual synthetic constructs differ in the species of iso-accepting codon used to encode a particular amino acid residue across the polypeptide sequence. As used herein, the species of iso-accepting codon that is used to encode a particular amino acid residue in the antigenic polypeptide is referred to as a "standardized codon". An illustrative synthetic construct system is described in Example 1, which covers the entire set of synonymous codons that code for amino acids.

Test mammals (e.g., mice) were immunized with the synthetic construct system in which individual mammals were immunized with a different synthetic construct and the host immune response (e.g., a humoral immune response or a cellular immune response) to the antigenic polypeptide was determined for each construct. In accordance with the present invention, the strength of immune response obtained from individual synthetic constructs provides a direct correlation to the immune preference of a corresponding standardized codon in a test mammal. Accordingly, the stronger the immune response produced from a given construct in a test mammal, the higher the immune preference will be of the corresponding standardized codon.

Comparison of the immune response preferences so determined with the translational efficiencies derived from codon usage frequency values for mammalian cells in general as determined by Seed (see U.S. Pat. Nos. 5,786,464 and 5,795,737) reveals several differences in the ranking of codons. For convenience, these differences are highlighted in TABLE 9, in which Seed 'preferred' codons are highlighted with a blue background, Seed 'less preferred' codons are highlighted with a green background, and Seed 'non preferred' codons are highlighted with a grey background.

TABLE 9

| aa | Preferential codon usage as predicted by Seed for mammalian cells in general | Experimentally determined codon immune response preferences in test mammals |
|---|---|---|
| Ala | GCC >> (GCG, GCT, GCA) | GCT > GCC > (GCA GCG) |
| Arg | CGC >> (CGA, CGT, AGA, AGG, CGG) | (CGA, CGC, CGT, AGA) > (AGG, CGG) |
| Asn | AAC >> AAT | AAC > AAT |
| Asp | GAC >> GAT | GAC > GAT |
| Cys | TGC >> TGT | TGC > TGT |
| Glu | (GAA, GAG) | GAA > GAG |
| Gln | CAG >> CAA | CAA = CAG |
| Gly | GGC > GGG > (GGT, GGA) | GGA > (GGG, GGT, GGC) |
| His | CAC >> CAT | CAC = CAT |
| Ile | ATC > ATT > ATA | ATC >> ATT > ATA |
| Leu | CTG > CTC > (TTA, CTA, CTT, TTG) | (CTG, CTC) > (CTA, CTT) >> TTG > TTA |
| Lys | AAG >> AAA | AAG = AAA |
| Phe | TTC >> TTT | TTT > TTC |
| Pro | CCC >> (CCG, CCA, CCT) | CCC > CCT >> (CCA, CCG) |
| Ser | AGC > TCC > (TCG, AGT, TCA, TCT) | TCG >> (TCT, TCA, TCC) >> (AGC, AGT) |
| Thr | ACC >> (ACG, ACA, ACT) | ACG > ACC >> ACA > ACT |
| Tyr | TAC >> TAT | TAC > TAT |
| Val | GTG > GTC > (GTA, GTT) | (GTG, GTC) > GTT > GTA |

As will be apparent from the above table:

(i) several codons deemed by Seed to have a higher codon usage ranking in mammalian cells than at least one other synonymous codon have in fact a lower immune response preference ranking than the or each other synonymous codon (e.g., $Ala^{GCC}$ has a higher codon usage ranking but lower immune response preference ranking than $Ala^{GCT}$; $Gly^{GGC}$ has a higher codon usage ranking but lower immune response preference ranking than $Gly^{GGA}$; $Phe^{TTC}$ has a higher codon usage ranking but lower immune response preference ranking than $Phe^{TTT}$; $Ser^{AGC}$ has a higher codon usage ranking but lower immune response preference ranking than any one of $Ser^{TCG}$, $Ser^{TCT}$, $Ser^{TCG}$, $Ser^{TCA}$ and $Ser^{TCC}$; and $Thr^{ACC}$ has a higher codon usage ranking but lower immune response preference ranking than $Thr^{ACG}$);

(ii) several codons deemed by Seed to have a lower codon usage ranking in mammalian cells than at least one other synonymous codon have in fact a higher immune response preference ranking than the or each other synonymous codon (e.g., $Ala^{GCT}$ has a lower codon usage ranking but higher immune response preference ranking than $Ala^{GCC}$; $Gly^{GGA}$ has a lower codon usage ranking but higher immune response preference ranking than $Gly^{GGC}$ or $Gly^{GGG}$; $Phe^{TTT}$ has a lower codon usage ranking but higher immune response preference ranking than $Phe^{TTC}$; $Ser^{TCG}$ has a lower codon usage ranking but higher immune response preference ranking than $Ser^{AGC}$ or $Ser^{TCC}$; $Ser^{TCT}$ and $Ser^{TCA}$ have a lower codon usage ranking but higher immune response preference ranking than $Ser^{AGC}$; and $Thr^{AGC}$ has a lower codon usage ranking but higher immune response preference ranking than $Thr^{ACC}$);

(iii) several codons deemed by Seed to have a higher codon usage ranking in mammalian cells than another synonymous codon have in fact the same immune response preference ranking as the other synonymous codon (e.g., $Gln^{CAG}$ has a higher codon usage ranking than, but the same immune response preference ranking as, $Gln^{CAA}$; $His^{CAC}$ has a higher codon usage ranking than, but the same immune response preference ranking as, $His^{CAT}$; $Leu^{CTG}$ has a higher codon usage ranking than, but the same immune response preference ranking as $Leu^{CTC}$; $Lys^{AAG}$ has a higher codon usage ranking than, but the same immune response preference ranking as, $Lys^{AAA}$; $Val^{GTG}$ has a higher codon usage ranking than, but the same immune response preference ranking as, $Val^{GTC}$); and (iv) several codons deemed by Seed to have the same codon usage ranking in mammalian cells as at least one other synonymous codon have in fact a different immune response preference ranking than the or each other synonymous codon (e.g., $Ala^{GCT}$ has the same codon usage ranking as, but a higher immune response preference ranking than, $Ala^{GCA}$ and $Ala^{GCG}$; $Arg^{CGA}$, $Arg^{CGT}$ and $Arg^{AGA}$ have the same codon usage ranking as, but a higher immune response preference ranking than, $Arg^{AGG}$ and $Arg^{CGG}$; $Glu^{GAA}$ has the same codon usage ranking as, but a higher immune response preference ranking than, $Glu^{GAG}$; $Gly^{GGA}$ has the same codon usage ranking as, but a higher immune response preference ranking than, $Gly^{GGT}$; $Leu^{CTA}$ and $Leu^{CTT}$ have the same codon usage ranking as, but a higher immune response preference ranking than, $Leu^{TTG}$ and $Leu^{TTA}$; $Pro^{CCT}$ has the same codon usage ranking as, but a higher immune response preference ranking than, $Pro^{CCA}$ or $Pro^{CCG}$; $Ser^{TCG}$ has the same codon usage ranking as, but a higher immune response preference ranking than, any one of $Ser^{TCT}$, $Ser^{TCA}$ and $Ser^{AGT}$; $Ser^{TCT}$ and $Ser^{TCA}$ have the same codon usage ranking as, but a higher immune response preference ranking than, $Ser^{AGT}$; $Thr^{ACG}$ has the same codon usage ranking as, but a higher immune response preference ranking than, any one of $Thr^{ACA}$ and $Thr^{ACT}$; $Thr^{ACG}$ has the same codon usage ranking as, but a higher immune response preference ranking than, $Thr^{ACT}$; $Val^{GTT}$ has the same codon usage ranking as, but a higher immune response preference ranking than, $Val^{GTA}$).

Accordingly, the present invention enables for the first time the modulation of an immune response to a target antigen in a mammal from a polynucleotide that encodes a polypeptide that corresponds to at least a portion of the target antigen by replacing at least one codon of the polynucleotide with a synonymous codon that has a higher or lower preference for producing an immune response than the codon it replaces. In some embodiments, therefore, the present invention embraces methods of constructing a synthetic polynucleotide from which a polypeptide is producible to confer an enhanced or stronger immune response than one conferred by a parent polynucleotide that encodes the same polypeptide. These methods generally comprise selecting from TABLE 1 a codon (often referred to herein arbitrarily as a "first codon") of the parent polynucleotide for replacement with a synonymous codon, wherein the synonymous codon is selected on the basis that it exhibits a higher immune response preference than the first codon and replacing the first codon with the synonymous codon to construct the synthetic polynucleotide. Illustrative selections of the first and synonymous codons are made according to TABLE 2.

In some embodiments, the selection of the first and synonymous codons is made according to TABLE 3, which is the same as TABLE 2 with the exception that it excludes selections based on codon usage rankings as disclosed by Seed. In illustrative examples of this type, the selection of a second codon (and subsequent codons if desired) for replacement with a synonymous codon is made according to TABLE 4.

Where synonymous codons are classified into three ranks ('high', 'intermediate' and 'low' ranks) based on their immune response preference ranking (e.g., the synonymous codons for Ala, Ile, Leu, Pro, Ser, Thr and Val), it is preferred that the synonymous codon that is selected is a high rank codon when the first codon is a low rank codon. However, this is not essential and the synonymous codon can be selected from intermediate rank codons. In the case of two or more synonymous codons having similar immune response preferences, it will be appreciated that any one of these codons can be used to replace the first codon.

In other embodiments, the invention provides methods of constructing a synthetic polynucleotide from which a polypeptide is producible to confer a reduced or weaker immune response than one conferred by a parent polynucleotide that encodes the same polypeptide. These methods generally comprise selecting from TABLE 1 a first codon of the parent polynucleotide for replacement with a synonymous codon, wherein the synonymous codon is selected on the basis that it exhibits a lower immune response preference than the first codon and replacing the first codon with the synonymous codon to construct the synthetic polynucleotide. Illustrative selections of the first and synonymous codons are made according to TABLE 5.

In some embodiments, the selection of the first and synonymous codons is made according to TABLE 6, which is the same as TABLE 5 with the exception that it excludes selections based on codon usage rankings as disclosed by Seed. In illustrative examples of this type, the selection of a second codon (and subsequent codons if desired) for replacement with a synonymous codon is made according to TABLE 7.

Where synonymous codons are classified into the three ranks noted above, it is preferred that the synonymous codon that is selected is a low rank codon when the first codon is a high rank codon but this is not essential and thus the synonymous codon can be selected from intermediate rank codons if desired.

Generally, the difference in strength of the immune response produced in the mammal from the synthetic polynucleotide as compared to that produced from the parent polynucleotide depends on the number of first/second codons that are replaced by synonymous codons, and on the difference in immune response preference ranking between the first/second codons and the synonymous codons. Put another way, the fewer such replacements, and/or the smaller the difference in immune response preference ranking between the synonymous and first/codons codons, the smaller the difference will be in the immune response produced by the synthetic polynucleotide and the one produced by the parent polynucleotide. Conversely, the more such replacements, and/or the greater the difference in immune response preference ranking between the synonymous and first/second codons, the greater the difference will be in the immune response produced by the synthetic polynucleotide and the one produced by the parent polynucleotide.

It is preferable but not necessary to replace all the codons of the parent polynucleotide with synonymous codons having different (e.g., higher or lower) immune response preference rankings than the first/second codons. Changes in the conferred immune response can be accomplished even with partial replacement. Generally, the replacement step affects at least about 5%, 10%, 15%, 20%, 25%, 30%, usually at least about 35%, 40%, 50%, and typically at least about 60%, 70%, 80%, 90%, 95%, 96%, 97%, 98%, 99% or more of the first/second codons of the parent polynucleotide. In embodiments in which a stronger or enhanced immune response is required, it is generally desirable to replace some, preferably most and more preferably all, low rank codons in a parent polynucleotide with synonymous codons that are intermediate, or preferably high rank codons. Typically, replacement of low with intermediate or high rank codons will result in an increase in the strength of immune response from the synthetic polynucleotide so constructed, as compared to the one produced from the parent polynucleotide under the same conditions. However, it is often desirable to replace some, preferably most and more preferably all, intermediate rank codons in the parent polynucleotide with high rank codons, if stronger or more enhanced immune responses are desired.

By contrast, in some embodiments in which a weaker or reduced immune response is required, it is generally desirable to replace some, preferably most and more preferably all, high rank codons in a parent polynucleotide with synonymous codons that are intermediate, or preferably low rank codons. Typically, replacement of high with intermediate or low rank codons will result in a substantial decrease in the strength of immune response from the synthetic polynucleotide so constructed, as compared to the one produced from the parent polynucleotide under the same condition. In specific embodiments in which it is desired to confer a weaker or more reduced immune response, it is generally desirable to replace some, preferably most and more preferably all, intermediate rank codons in the parent polynucleotide with low rank codons.

In illustrative examples requiring a stronger or enhanced immune response, the number of, and difference in immune response preference ranking between, the first/second codons and the synonymous codons are selected such that the immune response conferred by the synthetic polynucleotide is at least about 110%, 150%, 200%, 250%, 300%, 350%, 400%, 450%, 500%, 600%, 700%, 800%, 900%, 1000%, or more, of the immune response conferred by the parent polynucleotide under the same conditions. Conversely, in some embodiments requiring a lower or weaker immune response, the number of, and difference in phenotypic preference ranking between, the first/second codons and the synonymous codons are selected such that the immune response conferred by the synthetic polynucleotide is no more than about 90%, 80%, 70%, 60%, 50%, 40%, 30%, 20%, 10%, 5%, or less of the immune response conferred by the parent polynucleotide under the same conditions.

4. Modulating Immune Responses in Mammals by Expression of Isoaccepting Transfer RNA-Encoding Polynucleotides It is possible to take advantage of the immune response preference rankings of codons discussed in Section 3 to modulate an immune response to a target antigen by changing the level of iso-tRNAs in the cell population which is the target of the immunization. Accordingly, the invention also features methods of enhancing the quality of an immune response to a target antigen in a mammal, wherein the response is conferred by the expression of a first polynucleotide that encodes a polypeptide corresponding to at least a portion of the target antigen. These methods generally comprise: introducing into the mammal a first nucleic acid construct comprising the first polynucleotide in operable connection with a regulatory polynucleotide. A second nucleic acid construct is then introduced into the mammal, which comprises a second polynucleotide that is operably connected to a regulatory polynucleotide and that encodes an iso-tRNA corresponding to a low immune preference codon of the first polynucleotide.

In practice, therefore, an iso-tRNA is introduced into the mammal by the second nucleic acid construct when the iso-tRNA corresponds to a low immune response preference codon in the first polynucleotide, which are suitably selected from the group consisting of $Ala^{GCA}$, $Ala^{GCG}$, $Ala^{GCC}$, $Arg^{AGG}$, $Arg^{CGG}$, $Asn^{AAT}$, $Asp^{GAT}$, $Cys^{TGT}$, $Glu^{GAG}$, $Gly^{GGG}$, $Gly^{GGT}$, $Gly^{GGC}$, $Ile^{ATA}$, $Ile^{ATT}$, $Leu^{TTG}$, $Leu^{TTA}$, $Leu^{CTA}$, $Leu^{CTT}$, $Phe^{TTC}$, $Pro^{CCA}$, $Pro^{CCG}$, $Pro^{CCT}$, $Ser^{AGC}$, $Ser^{AGT}$, $Ser^{TCA}$, $Ser^{TCC}$, $Thr^{ACA}$, $Thr^{ACT}$, $Tyr^{TAT}$, $Val^{GTA}$ and $Val^{GTT}$. In specific embodiments, the supplied iso-tRNAs are specific for codons that have 'low' immune response preference codons, which may be selected from the group consisting of $Ala^{GCA}$, $Ala^{GCG}$, $Arg^{AGG}$, $Arg^{CGG}$, $Asn^{AAT}$, $Asp^{GAT}$, $Cys^{TGT}$, $Glu^{GAG}$, $Gly^{GGG}$, $Gly^{GGT}$, $Gly^{GGC}$, $Ile^{ATA}$, $Leu^{TTG}$, $Leu^{TTA}$, $Phe^{TTC}$, $Pro^{CCA}$, $Pro^{CCG}$, $Ser^{AGC}$, $Ser^{AGT}$, $Thr^{ACT}$, $Tyr^{TAT}$, and $Val^{GTA}$. The first construct (i.e., antigen-expressing construct) and the second construct (i.e., the iso-tRNA-expressing construct) may be introduced simultaneously or sequentially (in either order) and may be introduced at the same or different sites. In some embodiments, the first and second constructs are contained in separate vectors. In other embodiments, they are contained in a single vector. If desired, two or more second constructs may be introduced each expressing a different iso-tRNA corresponding to a low preference codon of the first polynucleotide. The first and second nucleic acid constructs may be constructed and administered concurrently or contemporaneously to a mammal according to any suitable method, illustrative examples of which are discussed below for the chimeric constructs of the invention.

In some embodiments, a plurality of different iso-tRNA-expressing constructs (e.g., 2, 3, 4, 5, 6, 7, 8 9, 10, 11, 12, 13, 14, 15, 16, 17, 18, 19, 20 or more) are administered concurrently or contemporaneously with the antigen-expressing construct, wherein individual iso-tRNA-expressing constructs express a different iso-tRNA than other iso-tRNA-expressing constructs.

5. Antigens

Target antigens useful in the present invention are typically proteinaceous molecules, representative examples of which include polypeptides and peptides. Target antigens may be selected from endogenous antigens produced by a host or exogenous antigens that are foreign to the host. Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhans cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/- ureter), trophoblastic cancer, urethral cancer, urinary system cancer, uroplakins, uterine sarcoma, uterus cancer, vaginal cancer, vulva cancer, Waldenstroms macroglobulinemia, Wilms' tumor. In certain embodiments, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign or exogenous antigens are suitably selected from antigens of pathogenic organisms. Exemplary pathogenic organisms include, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, orthomyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuraminidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis, Candida* spp., *Cladophialophora carrionii, Coccidioides immitis, Conidiobolus* spp., *Cryptococcus* spp., *Curvularia* spp., *Epidermophyton* spp., *Exophiala jeanselmei, Exserohilum* spp., *Fonsecaea compacta, Fonsecaea pedrosoi, Fusarium oxysporum, Fusarium solani, Geotrichum candidum, Histoplasma capsulatum* var. *capsulatum, Histoplasma capsulatum* var. *duboisii, Hortaea werneckii, Lacazia loboi, Lasiodiplodia theobromae, Leptosphaeria senegalensis, Madurella grisea, Madurella mycetomatis, Malassezia furfur, Microsporum* spp., *Neotestudina rosatii, Onychocola canadensis, Paracoccidioides brasiliensis, Phialophora verrucosa, Piedraia hortae, Piedra iahortae, Pityriasis versicolor, Pseudallescheria boydii, Pyrenochaeta romeroi, Rhizopus arrhizus, Scopulariopsis brevicaulis, Scytalidium dimidiatum, Sporothrix schenckii, Trichophyton* spp., *Trichosporon* spp., *Zygomycete fungi, Absidia corymbifera, Rhizomucor pusillus* and *Rhizopus arrhizus*. Thus, representative fungal antigens that can be used in the compositions and methods of the present invention include, but are not limited to, candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidioides* fungal antigens such as spherule antigens and other *coccidioides* fungal antigen components; and *tinea* fungal antigens such as trichophytin and other *coccidioides* fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli, Clostridium*

*perfringens, Pseudomonas aeruginosa, Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the kDa major secreted protein, antigen 85A and other mycobacterial antigen components; *Helicobacter pylori* bacterial antigen components, pneumococcal bacterial antigens such as pneumolysin, pneumococcal capsular polysaccharides and other pneumococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other *toxoplasma* antigen components; *schistosoma* antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

The present invention also contemplates toxin components as antigens, illustrative examples of which include staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, mycobacterium, and herpes viruses.

6. Construction of Synthetic Polynucleotides

Replacement of one codon for another can be achieved using standard methods known in the art. For example codon modification of a parent polynucleotide can be effected using several known mutagenesis techniques including, for example, oligonucleotide-directed mutagenesis, mutagenesis with degenerate oligonucleotides, and region-specific mutagenesis. Exemplary in vitro mutagenesis techniques are described for example in U.S. Pat. Nos. 4,184,917, 4,321,365 and 4,351,901 or in the relevant sections of Ausubel, et al. (CURRENT PROTOCOLS IN MOLECULAR BIOLOGY, John Wiley & Sons, Inc. 1997) and of Sambrook, et al., (MOLECULAR CLONING. A LABORATORY MANUAL, Cold Spring Harbor Press, 1989). Instead of in vitro mutagenesis, the synthetic polynucleotide can be synthesized de novo using readily available machinery as described, for example, in U.S. Pat. No. 4,293,652. However, it should be noted that the present invention is not dependent on, and not directed to, any one particular technique for constructing the synthetic polynucleotide.

The parent polynucleotide is suitably a natural gene. However, it is possible that the parent polynucleotide is not naturally-occurring but has been engineered using recombinant techniques. Parent polynucleotides can be obtained from any suitable source, such as from eukaryotic or prokaryotic organisms, including but not limited to mammals or other animals, and pathogenic organisms such as yeasts, bacteria, protozoa and viruses.

The invention also contemplates synthetic polynucleotides encoding one or more desired portions of a target antigen. In some embodiments, the synthetic polynucleotide encodes at least about 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000, or even at least about 2000, 3000, 4000 or 5000 contiguous amino acid residues, or almost up to the total number of amino acids present in a full-length target antigen. In some embodiments, the synthetic polynucleotide encodes a plurality of portions of the target antigen, wherein the portions are the same or different. In illustrative examples of this type, the synthetic polynucleotide encodes a multi-epitope fusion protein. A number of factors can influence the choice of portion size. For example, the size of individual portions encoded by the synthetic polynucleotide can be chosen such that it includes, or corresponds to the size of, T cell epitopes and/or B cell epitopes, and their processing requirements. Practitioners in the art will recognize that class I-restricted T cell epitopes are typically between 8 and 10 amino acid residues in length and if placed next to unnatural flanking residues, such epitopes can generally require 2 to 3 natural flanking amino acid residues to ensure that they are efficiently processed and presented. Class II-restricted T cell epitopes usually range between 12 and 25 amino acid residues in length and may not require natural flanking residues for efficient proteolytic processing although it is believed that natural flanking residues may play a role. Another important feature of class II-restricted epitopes is that they generally contain a core of 9-10 amino acid residues in the middle which bind specifically to class II MHC molecules with flanking sequences either side of this core stabilizing binding by associating with conserved structures on either side of class II MHC antigens in a sequence independent manner. Thus the functional region of class II-restricted epitopes is typically less than about 15 amino acid residues long. The size of linear B cell epitopes and the factors effecting their processing, like class II-restricted epitopes, are quite variable although such epitopes are frequently smaller in size than 15 amino acid residues. From the foregoing, it is advantageous, but not essential, that the size of individual portions of the target antigen is at least 6, 7, 8, 9, 10, 11, 12, 13, 14, 15, 20, 25, 30 amino acid residues. Suitably, the size of individual portions is no more than about 500, 200, 100, 80, 60, 50, 40 amino acid residues. In certain advantageous embodiments, the size of individual portions is sufficient for presentation by an antigen-presenting cell of a T cell and/or a B cell epitope contained within the peptide.

As will be appreciated by those of skill in the art, it is generally not necessary to immunize with a polypeptide that shares exactly the same amino acid sequence with the target antigen to produce an immune response to that antigen. In some embodiments, therefore, the polypeptide encoded by the synthetic polynucleotide is desirably a variant of at least a portion of the target antigen. "Variant" polypeptides include proteins derived from the target antigen by deletion (so-called truncation) or addition of one or more amino acids to the N-terminal and/or C-terminal end of the target antigen; deletion or addition of one or more amino acids at one or more sites in the target antigen; or substitution of one or more amino acids at one or more sites in the target antigen. Variant polypeptides encompassed by the present invention will have at least 40%, 50%, 60%, 70%, generally at least 75%, 80%, 85%, typically at least about 90% to 95% or more, and more typically at least about 96%, 97%, 98%, 99% or more sequence similarity or identity with the amino acid sequence of the target antigen or portion thereof as determined by sequence alignment programs described elsewhere herein using default parameters. A variant of a target antigen may differ from that antigen generally by as much 1000, 500, 400, 300, 200, 100, 50 or 20 amino acid residues or suitably by as few as 1-15 amino acid residues, as few as 1-10, such as 6-10, as few as 5, as few as 4, 3, 2, or even 1 amino acid residue.

Variant polypeptides corresponding to at least a portion of a target antigen may contain conservative amino acid substitutions at various locations along their sequence, as compared to the target antigen amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., 1992, *Science* 256(5062): 144301445), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. Dependent on their structural properties, amino acid residues may fall in two or more classes. For the naturally-occurring protein amino acids, sub-classification according to the this scheme is presented in the Table 10.

TABLE 10

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |

TABLE 10-continued

| Original Residue | Exemplary Substitutions |
|---|---|
| Phe | Met, Leu, Tyr |
| Ser | Thr |
| Thr | Ser |
| Trp | Tyr |
| Tyr | Trp, Phe |
| Val | Ile, Leu |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Conservative substitutions are shown in Table 11 below under the heading of exemplary substitutions. More preferred substitutions are shown under the heading of preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 11

EXEMPLARY AND PREFERRED AMINO ACID SUBSTITUTIONS

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

The invention further contemplates a chimeric construct comprising a synthetic polynucleotide of the invention, which is operably linked to a regulatory polynucleotide. The regulatory polynucleotide suitably comprises transcriptional and/or translational control sequences, which will be compatible for expression in the organism of interest or in cells of that organism. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the organism of interest or may be derived from an alternative source, where the region is functional in the chosen organism. The choice of promoter will differ depending on the intended host or cell or tissue type. For example, promoters which could be used for expression in mammals include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, the mouse mammary tumor virus LTR promoter, the adenovirus major late promoter (Ad MLP), the herpes simplex virus promoter, and a HPV promoter, particularly the HPV upstream regulatory region (URR), among others. All these promoters are well described and readily available in the art.

Enhancer elements may also be used herein to increase expression levels of the mammalian constructs. Examples include the SV40 early gene enhancer, as described for example in Dijkema et al. (1985, EMBO J. 4:761), the enhancer/promoter derived from the long terminal repeat (LTR) of the Rous Sarcoma Virus, as described for example in Gorman et al., (1982, Proc. Natl. Acad. Sci. USA 79:6777) and elements derived from human CMV, as described for example in Boshart et al. (1985, Cell 41:521), such as elements included in the CMV intron A sequence.

The chimeric construct may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5'AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

In some embodiments, the chimeric construct further contains a selectable marker gene to permit selection of cells containing the construct. Selection genes are well known in the art and will be compatible for expression in the cell of interest.

It will be understood, however, that expression of protein-encoding polynucleotides in heterologous systems is now well known, and the present invention is not directed to or dependent on any particular vector, transcriptional control sequence or technique for expression of the polynucleotides. Rather, synthetic polynucleotides prepared according to the methods set forth herein may be introduced into a mammal in any suitable manner in the form of any suitable construct or vector, and the synthetic polynucleotides may be expressed with known transcription regulatory elements in any conventional manner.

In addition, chimeric constructs can be constructed that include sequences coding for adjuvants. Particularly suitable are detoxified mutants of bacterial ADP-ribosylating toxins, for example, diphtheria toxin, pertussis toxin (PT), cholera toxin (CT), *Escherichia coli* heat-labile toxins (LT1 and LT2), *Pseudomonas* endotoxin A, *Clostridium botulinum* C2 and C3 toxins, as well as toxins from *C. perfringens, C. spiriforma* and *C. difficile*. In some embodiments, the chimeric constructs include coding sequences for detoxified mutants of *E. coli* heat-labile toxins, such as the LT-K63 and LT-R72 detoxified mutants, described in U.S. Pat. No. 6,818,222. In some embodiments, the adjuvant is a protein-destabilising element, which increases processing and presentation of the polypeptide that corresponds to at least a portion of the target antigen through the class I MHC pathway, thereby leading to enhanced cell-mediated immunity against the polypeptide. Illustrative protein-destabilising elements include intracellular protein degradation signals or degrons which may be selected without limitation from a destabilising amino acid at the amino-terminus of a polypeptide of interest, a PEST region or a ubiquitin. For example, the coding sequence for the polypeptide can be modified to include a destabilising amino acid at its amino-terminus so that the protein so modified is subject to the N-end rule pathway as disclosed, for example, by Bachmair et al. in U.S. Pat. No. 5,093,242 and by Varshaysky et al. in U.S. Pat. No. 5,122,463. In some embodiments, the destabilising amino acid is selected from isoleucine and glutamic acid, especially from histidine tyrosine and glutamine, and more especially from aspartic acid, asparagine, phenylalanine, leucine, tryptophan and lysine. In certain embodiments, the destabilising amino acid is arginine. In some proteins, the amino-terminal end is obscured as a result of the protein's conformation (i.e., its tertiary or quaternary structure). In these cases, more extensive alteration of the amino-terminus may be necessary to make the protein subject to the N-end rule pathway. For example, where simple addition or replacement of the single amino-terminal residue is insufficient because of an inaccessible amino-terminus, several amino acids (including lysine, the site of ubiquitin joining to substrate proteins) may be added to the original amino-terminus to increase the accessibility and/or segmental mobility of the engineered amino terminus. In some embodiments, a nucleic acid sequence encoding the amino-terminal region of the polypeptide can be modified to introduce a lysine residue in an appropriate context. This can be achieved most conveniently by employing DNA constructs encoding "universal destabilising segments". A universal destabilising segment comprises a nucleic acid construct which encodes a polypeptide structure, preferably segmentally mobile, containing one or more lysine residues, the codons for lysine residues being positioned within the construct such that when the construct is inserted into the coding sequence of the protein-encoding synthetic polynucleotide, the lysine residues are sufficiently spatially proximate to the amino-terminus of the encoded protein to serve as the second determinant of the complete amino-terminal degradation signal. The insertion of such constructs into the 5' portion of a polypeptide-encoding synthetic polynucleotide would provide the encoded polypeptide with a lysine residue (or residues) in an appropriate context for destabilization. In other embodiments, the polypeptide is modified to contain a PEST region, which is rich in an amino acid selected from proline, glutamic acid, serine and threonine, which region is optionally flanked by amino acids comprising electropositive side chains. In this regard, it is known that amino acid sequences of proteins with intracellular half-lives less than about 2 hours contain one or more regions rich in proline (P), glutamic acid (E), serine (S), and threonine (T) as for example shown by Rogers et al. (1986, Science 234 (4774): 364-368). In still other embodiments, the polypeptide is conjugated to a ubiquitin or a biologically active fragment thereof, to produce a modified polypeptide whose rate of intracellular proteolytic degradation is increased, enhanced or otherwise elevated relative to the unmodified polypeptide.

One or more adjuvant polypeptides may be co-expressed with an 'antigenic' polypeptide that corresponds to at least a portion of the target antigen. In certain embodiments, adjuvant and antigenic polypeptides may be co-expressed in the form of a fusion protein comprising one or more adjuvant polypeptides and one or more antigenic polypeptides. Alternatively, adjuvant and antigenic polypeptides may be co-expressed as separate proteins.

Furthermore, chimeric constructs can be constructed that include chimeric antigen-coding gene sequences, encoding, e.g., multiple antigens/epitopes of interest, for example derived from a single or from more than one target antigen. In certain embodiments, multi-cistronic cassettes (e.g., bi-cistronic cassettes) can be constructed allowing expression of multiple adjuvants and/or antigenic polypeptides from a single mRNA using, for example, the EMCV IRES, or the like. In other embodiments, adjuvants and/or antigenic polypeptides can be encoded on separate coding sequences that are operably connected to independent transcription regulatory elements.

In some embodiments, the chimeric constructs of the invention are in the form of expression vectors which are suitably selected from self-replicating extrachromosomal vectors (e.g., plasmids) and vectors that integrate into a host genome. In illustrative examples of this type, the expression vectors are viral vectors, such as simian virus 40 (SV40) or bovine papilloma virus (BPV), which has the ability to replicate as extrachromosomal elements (Eukaryotic Viral Vectors, Cold Spring Harbor Laboratory, Gluzman ed., 1982; Sarver et al., 1981, Mol. Cell. Biol. 1:486). Viral vectors include retroviral (lentivirus), adeno-associated virus (see, e.g., Okada, 1996, Gene Ther. 3:957-964; Muzyczka, 1994, J. Clin. Invst. 94:1351; U.S. Pat. Nos. 6,156,303; 6,143,548 5,952,221, describing AAV vectors; see also U.S. Pat. Nos. 6,004,799; 5,833,993), adenovirus (see, e.g., U.S. Pat. Nos. 6,140,087; 6,136,594; 6,133,028; 6,120,764), reovirus, herpesvirus, rotavirus genomes etc., modified for introducing and directing expression of a polynucleotide or transgene in cells. Retroviral vectors can include those based upon murine leukemia virus (see, e.g., U.S. Pat. No. 6,132,731), gibbon ape leukemia virus (see, e.g., U.S. Pat. No. 6,033,905), simian immuno-deficiency virus, human immuno-deficiency virus (see, e.g., U.S. Pat. No. 5,985,641), and combinations thereof.

Vectors also include those that efficiently deliver genes to animal cells in vivo (e.g., stem cells) (see, e.g., U.S. Pat. Nos. 5,821,235 and 5,786,340; Croyle et al., 1998, Gene Ther. 5:645; Croyle et al., 1998, Pharm. Res. 15:1348; Croyle et al., 1998, Hum. Gene Ther. 9:561; Foreman et al., 1998, Hum. Gene Ther. 9:1313; Wirtz et al., 1999, Gut 44:800). Adenoviral and adeno-associated viral vectors suitable for in vivo delivery are described, for example, in U.S. Pat. Nos. 5,700,470, 5,731,172 and 5,604,090. Additional vectors suitable for in vivo delivery include herpes simplex virus vectors (see, e.g., U.S. Pat. No. 5,501,979), retroviral vectors (see, e.g., U.S. Pat. Nos. 5,624,820, 5,693,508 and 5,674,703; and WO92/05266 and WO92/14829), bovine papilloma virus (BPV) vectors (see, e.g., U.S. Pat. No. 5,719,054), CMV-based vectors (see, e.g., U.S. Pat. No. 5,561,063) and parvovirus, rotavirus and Norwalk virus vectors. Lentiviral vectors are useful for infecting dividing as well as non-dividing cells (see, e.g., U.S. Pat. No. 6,013,516).

Additional viral vectors which will find use for delivering the nucleic acid molecules encoding the antigens of interest include those derived from the pox family of viruses, including vaccinia virus and avian poxvirus. By way of example, vaccinia virus recombinants expressing the chimeric constructs can be constructed as follows. The antigen coding sequence is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with. respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the chimeric constructs of the present invention. For a description of Sindbis-virus derived vectors useful for the practice of the instant methods, see, Dubensky et al. (1996, J. Virol. 70:508-519; and International Publication Nos. WO 95/07995, WO 96/17072); as well as, Dubensky, Jr., T. W., et al., U.S. Pat. No. 5,843,723, and Dubensky, Jr., T. W., U.S. Pat. No. 5,789,245. Exemplary vectors of this type are chimeric alphavirus vectors comprised of sequences derived from Sindbis virus and Venezuelan equine encephalitis virus. See, e.g., Perri et al. (2003, J. Virol. 77: 10394-10403) and International Publication Nos. WO 02/099035, WO 02/080982, WO 01/81609, and WO 00/61772.

In other illustrative embodiments, lentiviral vectors are employed to deliver a chimeric construct of the invention into selected cells or tissues. Typically, these vectors comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). A wide variety of lentiviruses may be utilized within the context of the present invention, including for example, lentiviruses selected from the group consisting of HIV, HIV-1, HIV-2, FIV, BIV, EIAV, MVV, CAEV, and SIV. Illustrative examples of lentiviral vectors are described in PCT Publication Nos. WO 00/66759, WO 00/00600, WO 99/24465, WO 98/51810, WO 99/51754, WO 99/31251, WO 99/30742, and WO 99/15641. Desirably, a third generation SIN lentivirus is used. Commercial suppliers of third generation SIN (self-inactivating) lentiviruses include INVITROGEN (ViraPower Lentiviral Expression System). Detailed methods for construction, transfection, harvesting, and use of lentiviral vectors are given, for example, in the INVITROGEN technical manual "ViraPower Lentiviral Expression System version B 050102 25-0501", available at the web site, invitrogen.com/Content/Tech-Online/molecular biology/manuals_p-ps/virapower_lentiviral_system-_man.pdf. Lentiviral vectors have emerged as an efficient method for gene transfer. Improvements in biosafety characteristics have made these vectors suitable for use at biosafety level 2 (BL2). A number of safety features are incorporated into third generation SIN (self-inactivating) vectors. Deletion of the viral 3' LTR U3 region results in a provirus that is unable to transcribe a full length viral RNA. In addition, a number of essential genes are provided in trans, yielding a viral stock that is capable of but a single round of infection and integration. Lentiviral vectors have several advantages, including: 1) pseudotyping of the vector using amphotropic envelope proteins allows them to infect virtually any cell type; 2) gene delivery to quiescent, post mitotic, differentiated cells, including neurons, has been demonstrated; 3) their low cellular toxicity is unique among transgene delivery systems; 4) viral integration into the genome permits long term transgene expression; 5) their packaging capacity (6-14 kb) is much larger than other retroviral, or adeno-associated viral vectors. In a recent demonstration of the capabilities of this system, lentiviral vectors expressing GFP were used to infect murine stem cells resulting in live progeny, germline transmission, and promoter-, and tissue-specific expression of the reporter (Ailles, L. E. and Naldini, L., HIV-1-Derived Lentiviral Vectors. In: Trono, D. (Ed.), Lentiviral Vectors, Springer-Verlag, Berlin, Heidelberg, N.Y., 2002, pp. 31-52). An example of the current generation vectors is outlined in FIG. 2 of a review by Lois et al. (2002, Science, 295 868-872).

The chimeric construct can also be delivered without a vector. For example, the chimeric construct can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, (1991, Biochim. Biophys. Acta. 1097:1-17); and Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., 1987, Proc. Natl. Acad. Sci. USA 84:7413-7416); mRNA (Malone et al., 1989, Proc. Natl. Acad. Sci. USA 86:6077-6081); and purified transcription factors (Debs et al., 1990, J. Biol. Chem. 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., 1987, Proc. Natl. Acad. Sci. USA 84:7413-7416). Other commercially available lipids include (DDAB/DOPE) and DOTAP/DOPE (Boerhinger). Alternative cationic liposomes can be prepared from readily available materials using techniques well known in the art. See, e.g., Szoka et al., 1978, Proc. Natl. Acad. Sci. USA 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger al., in METHODS OF IMMUNOLOGY (1983), Vol. 101, pp. 512-527; Szoka et al., 1978, Proc. Natl. Acad. Sci. USA 75:4194-4198; Papahadjopoulos et al., 1975, Biochim. Biophys. Acta 394:483; Wilson et al., 1979, Cell 17:77); Deamer and Bangham, 1976, Biochim. Biophys. Acta 443:629; Ostro et al., 1977, Biochem. Biophys. Res. Commun. 76:836; Fraley et al., 1979, Proc. Natl. Acad. Sci. USA 76:3348); Enoch and Strittmatter, 1979, Proc. Natl. Acad. Sci. USA 76:145); Fraley et al., 1980, J. Biol. Chem. 255:10431; Szoka and Papahadjopoulos, 1978, Proc. Natl. Acad. Sci. USA 75:145; and Schaefer-Ridder et al., 1982, Science 215:166.

The chimeric construct can also be delivered in cochleate lipid compositions similar to those described by Papahadjopoulos et al., 1975, Biochem. Biophys. Acta. 394:483-491. See, also, U.S. Pat. Nos. 4,663,161 and 4,871,488.

The chimeric construct may also be encapsulated, adsorbed to, or associated with, particulate carriers. Such carriers present multiple copies-of a selected chimeric construct to the immune system. The particles can be taken up by professional antigen presenting cells such as macrophages and dendritic cells, and/or can enhance antigen presentation through other mechanisms such as stimulation of cytokine release. Examples of particulate carriers include those derived from polymethyl methacrylate polymers, as well as microparticles derived from poly(lactides) and poly (lactide-co-glycolides), known as PLG. See, e.g., Jeffery et al., 1993, Pharm. Res. 10:362-368; McGee J. P., et al., 1997, J. Microencapsul. 14(2):197-210; O'Hagan D. T., et al., 1993, Vaccine 11(2):149-54.

Furthermore, other particulate systems and polymers can be used for the in vivo delivery of the chimeric construct. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998) may also be used for delivery of a construct of the present invention.

Additionally, biolistic delivery systems employing particulate carriers such as gold and tungsten, are especially useful for delivering chimeric constructs of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefor, see, e.g., U.S. Pat. Nos. 4,945,050; 5,036,006; 5,100,792; 5,179,022; 5,371,015; and 5,478,744. In illustrative examples, gas-driven particle acceleration can be achieved with devices such as those manufactured by PowderMed Pharmaceuticals PLC (Oxford, UK) and PowderMed Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest. Other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

Alternatively, micro-cannula- and microneedle-based devices (such as those being developed by Becton Dickinson and others) can be used to administer the chimeric constructs of the invention. Illustrative devices of this type are described in EP 1 092 444 A1, and U.S. application Ser. No. 606,909, filed Jun. 29, 2000. Standard steel cannula can also be used for intra-dermal delivery using devices and methods as described in U.S. Ser. No. 417,671, filed Oct. 14, 1999. These methods and devices include the delivery of substances through narrow gauge (about 30 G) "micro-cannula" with limited depth of penetration, as defined by the total length of the cannula or the total length of the cannula that is exposed beyond a depth-limiting feature. It is within the scope of the present invention that targeted delivery of substances including chimeric constructs can be achieved either through a single microcannula or an array of microcannula (or "microneedles"), for example 3-6 microneedles mounted on an injection device that may include or be attached to a reservoir in which the substance to be administered is contained.

7. Compositions

The invention also provides compositions, particularly immunomodulating compositions, comprising one or more of the chimeric constructs described herein. The immunomodulating compositions may comprise a mixture of chimeric constructs, which in turn may be delivered, for example, using the same or different vectors or vehicles. Antigens may be administered individually or in combination, in e.g., prophylactic (i.e., to prevent infection or disease) or therapeutic (to treat infection or disease) immunomodulating compositions. The immunomodulating compositions may be given more than once (e.g., a "prime" administration followed by one or more "boosts") to achieve the desired effects. The same composition can be administered in one or more priming and one or more boosting steps. Alternatively, different compositions can be used for priming and boosting.

The immunomodulating compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Immunomodulating compositions will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Pharmaceutically compatible salts can also be used in compositions of the invention, for example, mineral salts such as hydrochlorides, hydrobromides, phosphates, or sulfates, as well as salts of organic acids such as acetates, proprionate, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art.

The chimeric constructs of the invention can also be adsorbed to, entrapped within or otherwise associated with liposomes and particulate carriers such as PLG.

The chimeric constructs of the present invention are formulated into compositions for delivery to a mammal. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

Once formulated, the compositions of the invention can be administered directly to the subject (e.g., as described above). Direct delivery of chimeric construct-containing compositions in vivo will generally be accomplished with or without vectors, as described above, by injection using either a conventional syringe, needless devices such as Bioject™ or a gene gun, such as the Accell™ gene delivery system (PowderMed Ltd, Oxford, England) or microneedle device. The constructs can be delivered (e.g., injected) either subcutaneously, epidermally, intradermally, intramuscularly, intravenous, intramucosally (such as nasally, rectally and vaginally), intraperitoneally or orally. Delivery of nucleic acid into cells of the epidermis is particularly preferred as this mode of administration provides access to skin-associated lymphoid cells and provides for a transient presence of nucleic acid (e.g., DNA) in the recipient. Other modes of administration include oral ingestion and pulmonary administration, suppositories, needle-less injection, transcutaneous, topical, and transdermal applications. Dosage treatment may be a single dose schedule or a multiple dose schedule.

In order that the invention may be readily understood and put into practical effect, particular preferred embodiments will now be described by way of the following non-limiting examples.

EXAMPLES

Example 1

Synthetic Construct System for Determining the Immune Response Preference of Codons in Mammals

Materials and Methods

Primer Design/Synthesis and Sequence Manipulation

Oligonucleotides for site-directed mutagenesis were designed according to the guidelines included in the mutagenesis kit manuals (QUIKCHANGE II Site-directed Mutagenesis kit or QUIKCHANGE Multi Site-directed Mutagenesis Kit; STRATAGENE, La Jolla Calif.). These primers were synthesized and PAGE purified by Sigma (formerly Proligo).

Oligonucleotides for whole gene synthesis were designed by eye and synthesized by Sigma (formerly Proligo). The primers were supplied as standard desalted oligos. No additional purification of the oligonucleotides was carried out.

Sequence manipulation and analysis was carried out using the suite of programs on Biomanager (ANGIS) and various other web-based programs including BLAST at NCBI (see web site at ncbi.nlm.nih.gov/blast/bl2seq/wblast2.cgi), NEBcutter V2.0 from New England Biolabs (see web site at tools.neb.com/NEBcutter2/index.php), the Translate Tool on ExPASy (see web site at au.expasy.org/tools/dna.html), and the SignalP 3.0 server (see web site at cbs.dtu.dk/services/SignalP/).

Standard Cloning Techniques

Restriction enzyme digests, alkaline phosphatase treatments and ligations were carried out according to the enzyme manufacturers' instructions (various manufacturers including New England Biolabs, Roche and Fermentas).

Purification of DNA from agarose gels and preparation of mini-prep DNA were carried out using commercial kits (Qiagen, Bio-Rad, Macherey-Nagel).

Agarose gel electrophoresis, phenol/chloroform extraction of contaminant protein from DNA, ethanol precipitation of DNA and other basic molecular biological procedures were carried out using standard protocols, similar to those described in Current Protocols in Molecular Biology (Ebook available via Wiley InterScience; edited by Ausubel et al.).

Sequencing was carried out by the Australian Genome Research Facility (AGRF, Brisbane).

Whole Gene Synthesis

Overlapping ~35-50mer oligonucleotides (Sigma-Proligo) were used to synthesize longer DNA sequences. Restriction enzyme sites were incorporated to facilitate cloning. The method used to synthesize the fragments is based on that given in Smith et al. (2003). First, oligonucleotides for the top or bottom strand were mixed and then phosphorylated using T4 polynucleotide kinase (PNK; New England Biolabs). The oligonucleotide mixes were then purified from the PNK by a standard phenol/chloroform extraction and sodium acetate/ethanol (NaAc/EtOH) precipitation. Equal volumes of oligonucleotide mixes for the top and bottom strands were then mixed and the oligonucleotides denatured by heating at 95° C. for 2 mins. The oligonucleotides were annealed by slowly cooling the sample to 55° C. and the annealed oligonucleotides ligated using Taq ligase (New England Biolabs). The resulting fragment was purified by phenol/$CHCl_3$ extraction and NaAc/EtOH precipitation.

The ends of the fragments were filled in and the fragments then amplified, using the outermost forward and reverse primers, with the Clontech Advantage HF 2 PCR kit (Clontech) according to the manufacturer's instructions. To fill in the ends the following PCR was used: 35 cycles of a denaturation step of 94° C. for 15 s, a slow annealing step where the temperature was ramped down to 55° C. over 7 minutes and then kept at 55° C. for 2 min, and an elongation step of 72° C. for 6 minutes. A final elongation step for 7 min at 72° C. was then carried out. The second PCR to amplify the fragment involved: an initial denaturation step at 94° C. for 30 s, followed by 25 cycles of 94° C. for 15 s, 55° C. 30 s and 68° C. for 1 min, and a final elongation step of 68° C. for 3 mins.

The fragments were then purified by gel electrophoresis, digested and ligated into the relevant vector. Following transformation of *E. coli* with the ligation mixture, minipreps were made for multiple colonies and the inserts sequenced. Sometimes it was not possible to isolate clones with entirely correct sequence. In those cases the errors were fixed by single or multi site-directed mutagenesis.

Site-Directed Mutagenesis

Mutagenesis was carried out using the QUIKCHANGE II Site-directed Mutagenesis kit or QUIKCHANGE Multi Site-directed Mutagenesis Kit (STRATAGENE, La Jolla Calif.), with appropriate PAGE (polyacrylamide gel electrophoresis)-purified primers (Sigma), according to the manufacturer's instructions.

Preparation of Constructs

The details of the constructs used to generate the codon preference table are summarized in TABLE 12. All constructs were made using pCDNA3 from INVITROGEN and were verified by sequencing prior to use, with the following redlined paragraph.

TABLE 12

SUMMARY OF SECRETORY E7 CONSTRUCT SERIES 1 AND 2

| Construct | AA & Codon | CU of Sec Seq | CU of E7 | E7 Protein |
|---|---|---|---|---|
| Control Constructs | | | | |
| IgkC1 | N/A | wt | wt | non-onc |
| IgkC2 | N/A | mc | mc | non-onc |
| IgkC3 | N/A | wt | wt | onc |
| IgkC4 | N/A | mc | mc | onc |
| Secretory E7 construct series 1 | | | | |
| IgkS1-1 | Ala GCG | wt | wt with all Ala gcg | non-onc |
| IgkS1-2 | Ala GCA | wt | wt with all Ala gca | non-onc |
| IgkS1-3 | Ala GCT | wt | wt with all Ala gct | non-onc |
| IgkS1-4 | Ala GCC | wt | wt with all Ala gcc | non-onc |
| IgkS1-5 | Arg AGG | wt | wt with all Arg agg | non-onc |
| IgkS1-6 | Arg AGA | wt | wt with all Arg aga | non-onc |
| IgkS1-7 | Arg CGG | wt | wt with all Arg cgg | non-onc |
| IgkS1-8 | Arg CGA | wt | wt with all Arg cga | non-onc |
| IgkS1-9 | Arg CGT | wt | wt with all Arg cgt | non-onc |
| IgkS1-10 | Arg CGC | wt | wt with all Arg cgc | non-onc |
| IgkS1-11 | Asn AAT | wt | wt with all Asn aat | non-onc |

TABLE 12-continued

SUMMARY OF SECRETORY E7 CONSTRUCT SERIES 1 AND 2

| Construct | AA & Codon | CU of Sec Seq | CU of E7 | E7 Protein |
|---|---|---|---|---|
| IgkS1-12 | Asn AAC | wt | wt with all Asn aac | non-onc |
| IgkS1-13 | Asp GAT | wt with all Asp gat | wt with all Asp gat | non-onc |
| IgkS1-14 | Asp GAC | wt with all Asp gac | wt with all Asp gac | non-onc |
| IgkS1-15 | Cys TGT | wt | wt with all Cys tgt | non-onc |
| IgkS1-16 | Cys TGC | wt | wt with all Cys tgc | non-onc |
| IgkS1-17 | Glu GAG | wt with all Glu gag | wt with all Glu gag | non-onc |
| IgkS1-18 | Glu GAA | wt with all Glu gaa | wt with all Glu gaa | non-onc |
| IgkS1-19 | Gln CAG | wt | wt with all Gln cag | non-onc |
| IgkS1-20 | Gln CAA | wt | wt with all Gln caa | non-onc |
| IgkS1-21 | Gly GGG | wt with all Gly ggg | wt with all Gly ggg | non-onc |
| IgkS1-22 | Gly GGA | wt with all Gly gga | wt with all Gly gga | non-onc |
| IgkS1-23 | Gly GGT | wt with all Gly ggt | wt with all Gly ggt | non-onc |
| IgkS1-24 | Gly GGC | wt with all Gly ggc | wt with all Gly ggc | non-onc |
| IgkS1-25 | His CAT | wt | wt with all His cat | non-onc |
| IgkS1-26 | His CAC | wt | wt with all His cac | non-onc |
| IgkS1-27 | Ile ATA | wt | wt with all Ile ata | non-onc |
| IgkS1-28 | Ile ATT | wt | wt with all Ile att | non-onc |
| IgkS1-29 | Ile ATC | wt | wt with all Ile atc | non-onc |
| IgkS1-30 | Lys AAG | wt | wt with all Lys aag | non-onc |
| IgkS1-31 | Lys AAA | wt | wt with all Lys aaa | non-onc |
| IgkS1-32 | Phe TTT | wt | wt with all Phe ttt | non-onc L15F, L22F |
| IgkS1-33 | Phe TTC | wt | wt with all Phe ttc | non-onc L15F, L22F |
| IgkS1-34 | Ser AGT | wt with all Ser agt | wt with all Ser agt | non-onc |
| IgkS1-35 | Ser AGC | wt with all Ser agc | wt with all Ser agc | non-onc |
| IgkS1-36 | Ser TCG | wt with all Ser tcg | wt with all Ser tcg | non-onc |
| IgkS1-37 | Ser TCA | wt with all Ser tca | wt with all Ser tca | non-onc |
| IgkS1-38 | Ser TCT | wt with all Ser tct | wt with all Ser tct | non-onc |
| IgkS1-39 | Ser TCC | wt | wt with all Ser tcc | non-onc |
| IgkS1-40 | Thr ACG | wt with all Thr acg | wt with all Thr acg | non-onc |
| IgkS1-41 | Thr ACA | wt with all Thr aca | wt with all Thr aca | non-onc |
| IgkS1-42 | Thr ACT | wt with all Thr act | wt with all Thr act | non-onc |
| IgkS1-43 | Thr ACC | wt with all Thr acc | wt with all Thr acc | non-onc |
| IgkS1-44 | Tyr TAT | wt | wt with all Tyr tat | non-onc |
| IgkS1-45 | Tyr TAC | wt | wt with all Tyr tac | non-onc |
| IgkS1-46 | Val GTG | wt with all Val gtg | wt with all Val gtg | non-onc |
| IgkS1-47 | Val GTA | wt with all Val gta | wt with all Val gta | non-onc |
| IgkS1-48 | Val GTT | wt with all Val gtt | wt with all Val gtt | non-onc |
| IgkS1-49 | Val GTC | wt with all Val gtc | wt with all Val gtc | non-onc |

TABLE 12-continued

| SUMMARY OF SECRETORY E7 CONSTRUCT SERIES 1 AND 2 | | | | |
|---|---|---|---|---|
| Construct | AA & Codon | CU of Sec Seq | CU of E7 | E7 Protein |
| IgkS1-50 | Leu CTG | altered with Leu ctg | altered with Leu ctg | onc |
| IgkS1-51 | Leu CTA | altered with Leu cta | altered with Leu cta | onc |
| IgkS1-52 | Leu CTT | altered with Leu ctt | altered with Leu ctt | onc |
| IgkS1-53 | Leu CTC | altered with Leu ctc | altered with Leu ctc | onc |
| IgkS1-54 | Leu TTG | altered with Leu ttg | altered with Leu ttg | onc |
| IgkS1-55 | Leu TTA | altered with Leu tta | altered with Leu tta | onc |
| IgkS1-56 | Pro CCG | altered with Pro ccg | altered with Pro ccg | onc |
| IgkS1-57 | Pro CCA | altered with Pro cca | altered with Pro cca | onc |
| IgkS1-58 | Pro CCT | altered with Pro cct | altered with Pro cct | onc |
| IgkS1-59 | Pro CCC | altered with Pro ccc | altered with Pro ccc | onc |
| Secretory E7 construct series 2 | | | | |
| IgkS2-1 | Ala GCG | mc | mc | linkerA-onc |
| IgkS2-2 | Ala GCA | mc | mc | linkerA-onc |
| IgkS2-3 | Ala GCT | mc | mc | linkerA-onc |
| IgkS2-4 | Ala GCC | mc | mc | linkerA-onc |
| IgkS2-5 | Arg AGG | mc | mc | linkerR-onc |
| IgkS2-6 | Arg AGA | mc | mc | linkerR-onc |
| IgkS2-7 | Arg CGG | mc | mc | linkerR-onc |
| IgkS2-8 | Arg CGA | mc | mc | linkerR-onc |
| IgkS2-9 | Arg CGT | mc | mc | linkerR-onc |
| IgkS2-10 | Arg CGC | mc | mc | linkerR-onc |
| IgkS2-11 | Asn AAT | mc | mc | linkerN-onc |
| IgkS2-12 | Asn AAC | mc | mc | linkerN-onc |
| IgkS2-13 | Asp GAT | wt with all Asp gat | wt with all Asp gat | onc |
| IgkS2-14 | Asp GAC | wt with all Asp gac | wt with all Asp gac | onc |
| IgkS2-15 | Cys TGT | wt | wt with all Cys tgt | onc |
| IgkS2-16 | Cys TGC | wt | wt with all Cys tgc | onc |
| IgkS2-17 | Glu GAG | wt with all Glu gag | wt with all Glu gag | onc |
| IgkS2-18 | Glu GAA | wt with all Glu gaa | wt with all Glu gaa | onc |
| IgkS2-19 | Gln CAG | wt | wt with all Gln cag | onc |
| IgkS2-20 | Gln CAA | wt | wt with all Gln caa | onc |
| IgkS2-21 | Gly GGG | wt with all Gly ggg | wt with all Gly ggg | onc |
| IgkS2-22 | Gly GGA | wt with all Gly gga | wt with all Gly gga | onc |
| IgkS2-23 | Gly GGT | wt with all Gly ggt | wt with all Gly ggt | onc |
| IgkS2-24 | Gly GGC | wt with all Gly ggc | wt with all Gly ggc | onc |
| IgkS2-25 | His CAT | mc | mc | linkerH-onc |
| IgkS2-26 | His CAC | mc | mc | linkerH-onc |
| IgkS2-27 | Ile ATA | wt | wt with all Ile ata | onc |
| IgkS2-28 | Ile ATT | wt | wt with all Ile att | onc |
| IgkS2-29 | Ile ATC | wt | wt with all Ile atc | onc |
| IgkS2-30 | Lys AAG | mc | mc | linkerK-onc |
| IgkS2-31 | Lys AAA | mc | mc | linkerK-onc |
| IgkS2-32 | Phe TTT | mc | mc | linkerF-onc |
| IgkS2-33 | Phe TTC | mc | mc | linkerF-onc |
| IgkS2-34 | Ser AGT | wt with all Ser agt | wt with all Ser agt | onc |
| IgkS2-35 | Ser AGC | wt with all Ser agc | wt with all Ser agc | onc |
| IgkS2-36 | Ser TCG | wt with all Ser tcg | wt with all Ser tcg | onc |

TABLE 12-continued

SUMMARY OF SECRETORY E7 CONSTRUCT SERIES 1 AND 2

| Construct | AA & Codon | CU of Sec Seq | CU of E7 | E7 Protein |
|---|---|---|---|---|
| IgkS2-37 | Ser TCA | wt with all Ser tca | wt with all Ser tca | onc |
| IgkS2-38 | Ser TCT | wt with all Ser tct | wt with all Ser tct | onc |
| IgkS2-39 | Ser TCC | wt | wt with all Ser tcc | onc |
| IgkS2-40 | Thr ACG | wt with all Thr acg | wt with all Thr acg | onc |
| IgkS2-41 | Thr ACA | wt with all Thr aca | wt with all Thr aca | onc |
| IgkS2-42 | Thr ACT | wt with all Thr act | wt with all Thr act | onc |
| IgkS2-43 | Thr ACC | wt with all Thr acc | wt with all Thr acc | onc |
| IgkS2-44 | Tyr TAT | mc | mc | linkerY-onc |
| IgkS2-45 | Tyr TAC | mc | mc | linkerY-onc |
| IgkS2-46 | Val GTG | wt with all Val gtg | wt with all Val gtg | onc |
| IgkS2-47 | Val GTA | wt with all Val gta | wt with all Val gta | onc |
| IgkS2-48 | Val GTT | wt with all Val gtt | wt with all Val gtt | onc |
| IgkS2-49 | Val GTC | wt with all Val gtc | wt with all Val gtc | onc |
| IgkS2-11b | Asn AAT | wt | wt with all Asn aat | linkerN-non-onc |
| IgkS2-12b | Asn AAC | wt | wt with all Asn aac | linkerN-non-onc |

AA = amino acid,
CU = codon usage,
mc = mammalian consensus,
wt = wild-type,
onc = oncogenic,
non-onc = non-oncogenic
Sec seq = secretory sequence,
N/A = not applicable Control Constructs Control E7 constructs were based on those from Liu et al. (2002). Both oncogenic (i.e. wild-type) and non-oncogenic E7 control constructs were made with wild-type or mammalian consensus codon usage. "Non-oncogenic" E7 is E7 with D21 G, C24G, E26G mutations, i.e. with mutations that have been reported to render E7 non-transforming (Edmonds and Vousden, 1989; Heck et al, 1992).

The secretory sequence was derived from *Mus musculus* IgK RNA for the anti-HLA-DR antibody light chain (GenBank accession number D84070). For some constructs the codon usage of this sequence was modified.

Wild-Type Codon Usage Control Constructs:

The wild-type (wt) codon usage E7 construct from Liu et al. was used as the template in a site-directed mutagenesis PCR to make the wt codon usage non-oncogenic E7 construct.

The non-oncogenic and oncogenic wild-type codon usage E7 sequences were amplified to incorporate a 5' BamHI site and a 3' EcoRI site. The resulting fragments were cloned into BamHI and EcoRI cut pcDNA3 and sequenced. The secretory fragment was made by whole gene synthesis using wild-type codon usage with flanking KpnI and BamHI sites. The Kozak-secretory fragments were then ligated into KpnI/BamHI cut pcDNA3-wtE7 (non-oncogenic or oncogenic) to make pcDNA3-Igk-nE7 and pcDNA3-Igk-E7 (named IgkC1 and IgkC3 respectively; see TABLE 12). The identity of the constructs was confirmed by sequencing.

Mammalian Consensus (mc) Codon Usage Control Constructs:

As there were errors in the original mammalian consensus (mc) E7 construct (L28F, Q70R and an E35 deletion; Liu et al., 2002) it was not used. A mc non-oncogenic E7 control construct was synthesized by whole gene synthesis. A mc oncogenic E7 (i.e., wild-type E7) control construct was subsequently made from the mc non-oncogenic E7 construct by single site-directed mutagenesis.

Secretory mc oncogenic and non-oncogenic constructs were made by amplifying the mc E7 sequence with a forward primer that introduced a BamHI site and a reverse primer that incorporated an EcoRI site. The resulting E7 fragment was cloned into the respective sites in pcDNA3 and sequenced. A mc secretory sequence flanked by KpnI and BamHI sites, 5' and 3' respectively, was synthesised and ligated into the KpnI and BamHI sites of pcDNA3-mcE7 (oncogenic or non-oncogenic) to make pcDNA3-mcIgk-mcnE7 and pcDNA3-mcIgk-mcE7 (named IgkC2 and IgkC4 respectively; see TABLE 12). The identity of the constructs was confirmed by sequencing.

Secreted Non-Oncogenic E7 Constructs with Predominantly Wild-Type Codon Usage, Modified for Individual Codons Plasmids encoding a non-oncogenic form of E7 were made for all of the codons, with the exception of the Pro and Leu codons, stop codons and codons for non-degenerate amino acids. As Phe occurs just once in the E7 sequence, the codons for two Leu residues, L15 and L22, were mutated to Phe codons. A combination of techniques was used to make these constructs. When few mutations were required single or multi site-directed mutagenesis of a control construct encoding non-oncogenic E7 was performed (details of the control construct are given above under "control constructs"). When more extensive modifications were required whole gene synthesis was employed. Regardless of the methods used these constructs all include an E7 encoding sequence with identical upstream and downstream sequence cloned into the KpnI and EcoRI sites of pcDNA3. These constructs were then modified to include a secretory sequence, as described below.

First, using the whole gene synthesis method, DNA fragments that included a secretory sequence flanked by KpnI and BamHI sites were synthesized. For some constructs the amino acid of interest occurred in the secretory sequence so individual modified secretory sequence fragments were made. For constructs for amino acids that did not occur in the secretory sequence, wild-type secretory sequence was used. These fragments were digested with KpnI and BamHI. Then, using the relevant nE7 construct as a template and a standard PCR protocol, a BamHI site was introduced at the 5' end of the E7 sequence. The 3' EcoRI site was retained. The resulting E7 fragments were cut with BamHI and EcoRI, purified, and ligated into pcDNA3. Following sequencing, the plasmids were cut with KpnI and BamHI and ligated with the relevant KpnI/BamHI secretory sequences. The sequences of the constructs were then confirmed. Constructs IgkS1-1 to IgkS1-49 were made in this way (see TABLE 12 and FIGS. 1 to 11, 13 and 15 to 17 for sequence comparisons).

Secreted E7 Constructs with Individual Pro or Leu Codons Modified

E7 DNA sequences in which the Pro or Leu codons were individually modified were designed. The rest of the codon usage for these E7 DNAs was the same for all of the Pro and Leu constructs but differed from the wild-type or mammalian consensus codon usage. [Note that this codon usage was based on our preliminary data from immunizing mice with the GFP constructs.]

The Pro/LeuE7 DNA fragments, flanked by HindIII and BamHI sites, were made by whole gene synthesis and cloned into the HindIII and BamHI sites of pcDNA3. Using these constructs as templates, a KpnI site was incorporated upstream and an EcoRI site downstream, of the Pro/Leu E7 sequences by standard PCR methods. The resulting fragments were cut with KpnI and EcoRI and cloned into pcDNA3. These constructs were then used to make the secreted E7 constructs with Pro or Leu codon modifications.

Firstly, using the whole gene synthesis method, DNA fragments that included a secretory sequence flanked by KpnI and BamHI sites were synthesized. As Pro and Leu occur in the secretory sequence, individually modified secretory sequence fragments were made for the different constructs. These fragments were digested with KpnI and BamHI. Then, using the relevant Pro or Leu E7 construct as a template and a standard PCR protocol, a BamHI site was introduced at the 5' end of the E7 sequence. The 3' EcoRI site was retained. The resulting fragments were cut with BamHI and EcoRI, purified, and ligated into pcDNA3. Following sequencing, the plasmids were cut with KpnI and BamHI and ligated with the relevant KpnI/BamHI secretory sequences. The resulting constructs were sequenced and are denoted IgkS1-50 to IgkS1-59 (see TABLE 12 and FIGS. 12 and 14 for sequence comparisons).

Secreted E7 Constructs with Predominantly Wild-Type Codon Usage, Modified for Individual Codons Constructs encoding a secreted form of oncogenic E7 (i.e. wild-type E7 protein) were made by site-directed mutagenesis of the plasmids encoding a secreted form of non-oncogenic E7. This was done for constructs for codons for the following amino acids: Asp, Cys, Glu, Gln, Gly, Ile, Ser, Thr and Val.

Site-directed mutagenesis was carried out using the QUIKCHANGE II Site-directed Mutagenesis kit (STRATAGENE, La Jolla Calif.) and appropriate PAGE (polyacrylamide gel electrophoresis)-purified primers (Sigma) according to the manufacturer's instructions. The pCDNA-kIgkX-nE7X series of constructs were used as templates for the mutagenesis (i.e. constructs IgkS1-13 to 24, IgkS1-27 to 29, IgkS1-34 to 43 and IgkS1-46 to 49). The primers introduced the desired G21D, G24C, G26E mutations.

The resulting constructs, IgkS2-13 to 24, IgkS2-27 to 29, IgkS2-34 to 43 and IgkS2-46 to 49 (see Table 8, SEQ ID NOs: 1 to 29), have wild-type codon usage for the Igk secretory sequence and E7 sequence with the exception that the codons for the relevant amino acid were changed, and they encode oncogenic E7.

Linker Constructs

Constructs encoding the N-terminal Igk secretory sequence followed by a linker sequence (XXGXGXX (SEQ ID NO:92), where X is the relevant amino acid for a particular construct and G is glycine) and the E7 protein were made for each of the following amino acids: Asn, Ala, Lys, Arg, Phe, His and Tyr.

Fragments consisting of the Igk secretory sequence (with mammalian consensus codon usage) and the linker sequences were made by PCR using Taq polymerase and standard cycling conditions, as recommended by the manufacturer.

The fragments were amplified from pcDNA3-kmcIgk-mcE7 using a common forward primer (5'TTGAATAGG-TACCGCCGCCACCATGGAGACCGACACCCTCC3'; SEQ ID NO: 90) that annealed to the KpnI site, the Kozak sequence and the beginning of the Igk secretory sequence. The reverse primers were different for each linker construct and annealed to the end of the Igk secretory sequence (with mammalian consensus codon usage), introduced new sequence that encoded the relevant linker sequence and a 3' BamHI site.

The fragments were digested with KpnI/BamHI and were ligated into KpnI/BamHI-cut pcDNA3-mcIgk-mcE7 (i.e. the Kozak sequence and secretory sequence had been removed from the plasmid by digestion) to make pcDNA3-mcIgk-linkerX-mcE7 (i.e., IgkS2-1 to 12, IgkS2-25 and 26, IgkS2-30 to 33 and IgkS2-44 and 45 as illustrated in Table 8, SEQ ID NOs: 30 to 49).

For Asn the fragments were also ligated into KpnI/BamHI-cut pcDNA3-Igk-nE7Asn1/2 (i.e. IgkS1-11 and 12) to make pcDNA3-mcIgk-linkerN1/2-nE7Asn1/2 (i.e., IgkS2-11b and IgkS2-12b, see Table 12).

E7 Protein Expression

Cell Culture

CHO cells were cultured in DMEM (GIBCO from INVITROGEN) containing 10% foetal bovine serum (FBS) (DKSH), penicillin, streptomycin and glutamine (GIBCO from INVITROGEN) at 37° C. and 5% $CO_2$. Cells were plated into 6-well plates at $3\times10^5$/well, 24 hours prior to transfection. For each transfection, 2 μg of DNA was mixed with 50 μL OptiMEM (GIBCO from INVITROGEN) and 4

μL Plus reagent (INVITROGEN) and incubated at room temperature (RT) for 30 min. Lipofectamine (INVITROGEN; 5 μL in 50 μL OptiMEM) was added and the complexes incubated at RT for 30 min. The cells were rinsed with OptiMEM, 2 mL OptiMEM were added to each well, and the complexes then added. The cells were incubated overnight at 37° C. and 5% $CO_2$. The following morning the complexes were removed and 2 ml of fresh DMEM containing 2% FBS added to each well.

Cell pellets and supernatants were collected about 40 h after transfection. The cell pellets were resuspended in lysis buffer (0.1% NP-40, 2 μg/mL Aprotinin, 1 μg/mL Leupeptin and 2 mM PMSF in PBS). Transfections were carried out in duplicate and repeated. Control transfections, with empty vector (pcDNA3), were also carried out.

Western Blotting

Western blots of the CHO cell supernatants or lysates were carried out according to standard protocols. Briefly, this involved firstly separating the samples by polyacrylamide gel electrophoresis (PAGE). For cell lysates, 30 μg of total protein were loaded for each sample. For supernatants, 30 μL of each was loaded. The protein samples were boiled with SDS-PAGE loading buffer for 10 mins before loading onto 12% SDS-PAGE gels and the gels were run at 150-200V for approximately 1 h.

The separated proteins were then transferred from the gels to PVDF membrane (100V for 1 h). The membranes were blocked with 5% skim milk (in PBS/0.05% Tween 20 (PBS-T)) for 1 h at room temperature and were then incubated with the primary antibody, HPV-16 E7 Mouse Monoclonal Antibody (Zymed Laboratories) at a concentration of 1:1000 in 5% skim milk (in PBS-T) overnight at 4° C. Following washing of the membrane in PBS-T (3×10 min), secondary antibody, anti-mouse IgG (Sigma) in 5% skim milk, was added and the membrane incubated at room temperature for 4 h. The membranes were washed as before, incubated in a mixture containing equal volumes of solution A (4.425 mL water, 50 luminol, 22 μL p-coumaric and 500 μL 1M Tris pH 8.5) and solution B (4.5 mL water, 3 μL1, 30% $H_2O_2$ and 500 μL 1M Tris pH8.5) for 1 min, and then dried and wrapped in plastic wrap. Film was exposed to the blots for various times (1 min, 3 min or 10 min) and the film then developed.

Gene Gun Immunization Protocols

Plasmid Purification

All plasmids used for vaccination were grown in the *Escherichia coli* strain DH5a and purified using the NUCLEOBOND Maxi Kit (Machery-Nagal). DNA concentration was quantitated spectrophotometrically at 260 nm.

Preparation of DNA/Gold Cartridges

Coating of gold particles with plasmid DNA was performed as described in the Biorad Helios Gene Gun System instruction manual using a microcarrier loading quantity (MLQ) of 0.5 mg gold/cartridge and a DNA loading ratio of 2 μg DNA/mg gold. This resulted in 1 μg of DNA per prepared cartridge. In brief 50 μL of 0.05M spermidine (Sigma) was added to 25 mg of 1.0 μm gold particles (Bio-Rad) and the spermidine/gold was sonicated for 3 seconds. 50 μg of plasmid DNA was then added, followed by the dropwise addition of 100 μM $CaCl_2$ while vortexing. The mixture was allowed to precipitate at room temperature for 10 min, then centrifuged to pellet the DNA/gold. The pellet was washed three times with HPLC grade ethanol (Scharlau), before resuspension in HPLC grade ethanol containing 0.5 mg/mL of polyvinylpyrrolidone (PVP) (Bio-Rad). The gold/plasmid suspension was then coated onto Tefzel tubing and 0.5 inch cartridges prepared.

Gene Gun Immunization of Mice

Groups of 8 female C57BL6/J (6-8 weeks old) (ARC, WA or Monash Animal Services, VIC) were immunized on Day 0, Day 21, Day 42 and Day 63 with the relevant DNA. The day before each immunization the abdomen of each mouse was shaved and depilatory cream (NAIR) applied for 1 minute. DNA was delivered with the HELIOS gene gun (Biorad) using a pressure of 400 psi. Mice were given 2 shots on either side of the abdomen, with 1 μg of DNA delivered per shot. Serum was collected via intra-ocular bleed 2 days prior to initial immunization and 2 weeks after each subsequent immunization (Day 2, Day 35, Day 56 and Day 77).

ELISA to Measure E7 Immune Response

Nine peptides spanning the full-length of HPV16E7 (Frazer et al., 1995) were used to measure the E7 antibody response. The peptides were synthesised and purified to >70% purity by Auspep (Melbourne). Peptides GF101 to 106 and GF108 to 109 described in Frazer et al. were made. Note that instead of GF107, GF107a was used: HYNIVTFCCKCDSTLRL (SEQ ID NO: 154).

GF102 D13G, GF103 D5G/C8G/E10 G and GF104E2G peptides, named GF102n, GF103n and GF104n respectively, were also synthesised. These peptides were used for the ELISA when measuring antibodies to non-oncogenic E7 i.e. these peptides incorporate the mutations that were made to make the E7 protein non-oncogenic.

Microtiter plates were coated overnight with 50 μL of 10 μg/mL E7 peptide per well. After coating, microtiter plates (Maxisorp, NUNC) were washed two times with PBS/0.05% Tween 20 (PBS-T) and then blocked for two hours at 37° C. with 100 μL of 5% skim milk powder in PBS-T. After blocking, plates were washed three times with PBS-T and 50 μL of mouse sera at a dilution of 1 in 100 was added for 2 hours at 37° C. All serum was assayed in duplicate wells. Plates were then washed three times with PBS-T and 50 μL of sheep anti-mouse IgG horseradish peroxidase conjugate (Sigma) was added at a 1 in 1000 dilution. After 1 hour plates were washed and 50 μL of OPD substrate was added. Absorbance was measured after 30 min and the addition of 25 μL of 2.5 M HCl at 490 nm in a MULTISKAN EX plate reader (Pathtech). Note controls were included: control primary antibody for a positive control, secondary antibody only, and day 0 serum/serum from unimmunized mice as negative controls.

The immune response preferences of codons determined from these experiments are tabulated in TABLE 1.

Example 2

Construction of Codon Modified Influenza A Virus (H5N1) HA DNA for Conferring an Enhanced Immune Response to H5N1 HA The wild-type nucleotide sequence of the influenza A virus, HA gene for hemagglutinin (A/Hong Kong/213/03 (H5N1), MDCK isolate, embryonated chicken egg isolate) is shown in SEQ ID NO: 50 and encodes the amino acid sequence shown in SEQ ID NO: 51. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 52.

Example 3

Construction of Codon Modified Influenza A Virus (H3N1) DNA for Conferring an Enhanced Immune Response to H3N1 HA The wild-type nucleotide sequence of the influenza A virus, HA gene for hemagglutinin (A/swine/Korea/PZ72-1/2006(H3N1)) is shown in SEQ ID NO: 53 and encodes the amino acid sequence shown in SEQ ID NO: 54. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 55.

Example 4

Construction of Codon Modified Influenza A Virus (H5N1) NA DNA for Conferring an Enhanced Immune Response to H5N1 NA The wild-type nucleotide sequence of the influenza A virus, NA gene for neuraminidase (A/Hong Kong/213/03 (H5N1), NA gene neuraminidase, MDCK isolate, embryonated chicken egg isolate) is shown in SEQ ID NO: 56 and encodes the amino acid sequence shown in SEQ ID NO: 57. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 58.

Example 5

Construction of Codon Modified Influenza A Virus (H1N1) NA DNA for Conferring an Enhanced Immune Response to H3N1 NA The wild-type nucleotide sequence of the influenza A virus, NA gene for neuraminidase (A/swine/MI/PU243/04 (H3N1)) is shown in SEQ ID NO: 59 and encodes the amino acid sequence shown in SEQ ID NO: 60. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 61.

Example 6

Construction of Codon Modified Hepatitis C Virus E1 (1AH77) DNA for Conferring an Enhanced Immune Response to HCV E1 (1AH77)

The wild-type nucleotide sequence of the hepatitis C Virus E1, (serotype 1A, isolate H77, from polyprotein nucleotide sequence AF009606) is shown in SEQ ID NO: 62 and encodes the amino acid sequence (NP 751920) shown in SEQ ID NO: 63. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 64.

Example 7

Construction of Codon Modified Hepatitis C Virus E2 (1AH77) DNA for Conferring an Enhanced Immune Response to HCV E2 (1AH77)

The wild-type nucleotide sequence of the hepatitis C Virus E2, (serotype 1A, isolate H77, from polyprotein nucleotide sequence AF009606) is shown in SEQ ID NO: 65 and encodes the amino acid sequence (NP 751921) shown in SEQ ID NO: 66. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in in SEQ ID NO: 67.

Example 8

Construction of Codon Modified Epstein-Barr Virus Type 1 gp350 DNA for Conferring an Enhanced Immune Response to EBV Type 1 gp350

The wild-type nucleotide sequence of the Epstein-Barr virus, EBV type 1 gp350 (Gene BLLF1, strand 77142-79865) is shown in SEQ ID NO: 68 and encodes amino acid sequence (CAD53417) shown in SEQ ID NO: 69. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 70.

Example 9

Construction of Codon Modified Epstein-Barr Virus Type 2 gp350 DNA for Conferring an Enhanced Immune Response to EBV Type 2 gp350

The wild-type nucleotide sequence of the Epstein-Barr virus, EBV type 2 gp350 (Gene BLLF1, strand 77267-29936) is shown in SEQ ID NO: 71 and encodes the amino acid sequence (YP 001129462) shown in SEQ ID NO: 72. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 73.

Example 10

Construction of Codon Modified Herpes Simplex Virus 2 Glycoprotein B DNA for Conferring an Enhanced Immune Response to HSV-2 Glycoprotein B The wild-type nucleotide sequence of the Herpes Simplex virus 2, glycoprotein B strain HG52 (genome strain NC 001798) is shown in SEQ ID NO: 74 and encodes the amino acid sequence (CAB06752) shown in SEQ ID NO: 75. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 76.

Example 11

Construction of Codon Modified Herpes Simplex Virus 2 Glycoprotein D DNA for Conferring an Enhanced Immune Response to HSV-2 Glycoprotein D The wild-type nucleotide sequence of the Herpes Simplex virus 2, glycoprotein D strain HG52 (genome strain NC 001798) is shown in SEQ ID NO: 77 and encodes the amino acid sequence (NP 044536) shown in SEQ ID NO: 78. Several codons within that sequence were mutated using the method described in Example 1. Specifically, the method involved replacing codons of the wild type nucleotide sequence with corresponding synonymous codons having higher immune response preferences than the codons they replaced, as represented in Table 1. An illustrative codon modified nucleotide sequence comprising high immune response preference codons is shown in SEQ ID NO: 79.

Example 12

Optimised E7 and HSV-2 Constructs

Design and Synthesis of Optimal and Least Optimal E7 Constructs

One de-optimized (W) and three optimized (O1-O3) E7 constructs were designed and made using the codon preferences summarized in Table 1 ("the Immune Coricode table"). The least favourable codons were used for construct W. For the first optimized construct, O1, whose sequence is shown in SEQ ID NO: 81, all of the codons were modified to those codons determined most optimal. O2, whose sequence is shown in SEQ ID NO: 82, is an alternative optimized construct which involved changing all Ala to GCT; Arg CGG and AGG to CGA and AGA, respectively; Glu to GAA; Gly to GGA; Ile to ATC; all Leu to CTG; Phe to TTT, Pro to CCT or CCC, Ser to TCG, Thr to ACG; and all Val except GTG to GTC. The O2 modifications avoided, with the exception of Leu and Ile, changing codons to mammalian consensus-preferred codons. For O3, whose sequence is shown in SEQ ID NO: 83, only certain amino acids for which particularly distinct differences were observed between codons, and for which the optimal codon(s) was not also a mammalian consensus preferred codon, were modified. In particular, in O3 all non-preferred Gly, Leu, Pro, Ser and Thr codons were changed to GGA, CTC, CCT, TCG and ACG, respectively, and where a preferred codon was already used it was not altered. Codons for other amino acids in O3 were not modified.

Humoral and Cellular Responses to Biolistic Immunization with the Optimal and Least Optimal E7 Constructs As may be seen in FIG. 18 (*a*) all three optimized constructs (O1 to O3) gave rise to significantly larger antibody responses than the wild-type construct as measured by both the peptide ELISA and a GST-E7 protein ELISA. The amplitudes of the response were not statistically different between the three optimized constructs. The de-optimized construct, W, whose sequence is shown in SEQ ID NO: 84, gave a very low antibody response, appearing slightly lower but not statistically different from the wild-type (wt) codon usage (CU) construct, whose sequence is shown in SEQ ID NO: 80. From the IFN-γ ELISPOT experiments, a representative example of which is shown in FIG. 18, it appears that the codon preferences for maximizing the antibody response are similar to those required for maximising the T cell response: the de-optimized construct W failed to give a measurable response in the IFN-γ ELISPOT assay and two of the optimized constructs (O2 and O3) gave statistically significantly larger responses than the wild-type CU construct. Over the three repeats the responses to O2 and O3 were not statistically different from each other. Unexpectedly, and in contrast to the antibody trend, in two of the three repeat experiments O1 gave a similar cellular response to the wt CU construct, which was less than that achieved by the O2 or O3 constructs.

Humoral and Cellular Responses to Immunization by Intradermal Injection with the Optimal and Least Optimal E7 Constructs The humoral and cellular responses of mice to the optimized, wild-type CU and de-optimized constructs delivered by intradermal injection were also measured and the results are summarized in FIG. 19. In general, similar trends were observed for intradermal injection as for biolistic delivery.

From the E7 protein ELISA, it is apparent that the three optimized constructs, O1-O3, were all significantly better at generating antibodies than the wild-type construct and that the de-optimized construct gave a very low antibody response similar to wild-type. The optimized constructs all gave rise to significantly more spots in the IFN-γELISPOT than the wild-type construct and the de-optimized construct failed to give rise to a measurable response.

The amplitudes of the antibody responses to gene gun immunization were larger than that for the intradermally (ID) delivered vaccines, despite the ID immunization delivering more than five times the dose.

Design and Synthesis of Optimal and Least Optimal HSV-2Constructs

Three optimized (O1-O3; whose sequences are shown in SEQ ID NO: 86-88, respectively) and a de-optimized construct (W; whose sequence is shown in SEQ ID NO: 88) encoding full-length glycoprotein D from Herpes Simplex Virus 2 (gD2) were prepared. A control construct pcDNA3- gD2 with wt CU was also made. Wild-type CU, whose sequence is shown in SEQ ID NO: 85, is close to MC CU.

Humoral Responses to Biolistic and Intradermal Immunization with the Optimal and Least Optimal gD2 Constructs C57Bl/6 mice were immunized in two groups (8 mice/construct; used intradermal injection (ID) and gene gun delivery) using the same immunization protocol as for the E7 constructs.

Group 1 included pcDNA3-gD2 and pcDNA3-gD2 O1. Group 2 included pcDNA3-gD2, pcDNA3-gD2 O2, pcDNA3-gD2 O3, and pcDNA3-gD2 W.

Antibody responses were measured by an ELISA using plates coated with CHO cell supernatant containing C-terminally His tagged and truncated gD2. The truncation is at amino acid residue 331 and removes the transmembrane region resulting in the protein being secreted into the medium. Control ELISA plates coated with supernatant from CHO cells transfected with empty vector were used as a control.

For both biolistic and intradermal injection delivery routes it was found that the three optimized constructs generated similar levels of antibodies as the wt CU gD2 construct (FIG. 20). The de-optimized construct, W gD2, was very poor at generating antibodies, particularly when delivered by intradermal injection. The two delivery methods resulted in similar levels of antibodies.

To date, there are no DNA vaccines on the market for the treatment or prevention of disease in humans. There is a need to maximize the immune responses generated by DNA vaccines and the present invention discloses ways of enhancing efficacy of DNA vaccines by using codons that have a higher preference for producing an immune response.

The study described in this Example has validated the Immune Coricode table by applying it to optimization or de-optimization of the HPV16 E7 and HSV-2 glycoprotein D (gD2) genes and demonstrating that this does enhance or reduce, respectively, the antibody or cellular response to biolistic delivery of these genes to mammals such as mice.

Material and Methods

ELISPOT Assay

For the IFN-γ ELISPOTs, mice were immunized twice, at days 0 and 21, and the spleens were collected 3 weeks after the second immunization.

Intradermal Injection Protocol

The timing and frequency of the immunizations by intradermal injection were the same as for gene gun immunization. At each immunization 5 μg of DNA was injected per ear i.e. a total of 10 μg was administered per immunization per mouse. Hair removal prior to immunization was not necessary. The timing of bleeds and spleen collection was the same as for the gene gun immunized mice.

GST-E7 ELISA

The GST-E7 ELISA was carried out in the same way as the peptide ELISA with the exception that the plates were coated overnight with 50 μL of 10 μg/mL GST-tagged E7 protein (kindly provided by the Frazer group from the Diamantina Institute, The University of Queensland, Brisbane).

HSV-2 gD ELISA

This ELISA was carried out in the same way as the E7 ELISAs with the exception that the plates were coated with supernatant from CHO cells transfected with a vector encoding C-terminally His-tagged and truncated gD2 protein. Control plates coated with supernatant from CHO cells transfected with empty vector were also used.

Detection of HPV-Specific Responses

For the detection of HPV-specific responses, 96-well filter ELISPOT plates (Millipore) were coated overnight with 10 μg/mL HPV GST-tagged E7 protein in 0.1 M $NaHCO_3$. For the detection of total IgG secreting cells, 96-well filter ELISPOT plates were coated overnight with 2 μg/mL goat anti-mouse Ig (Sigma) in PBS without $MgCl_2$ and $CaCl_2$. After coating, plates were washed once with complete DMEM without FCS and then blocked with complete DMEM supplemented with 10% FCS for one hour at 37° C. Cultured mouse spleen cells were washed and added to ELISPOT plates at $10^6$ cells/100 μL. For the detection of HPV-specific memory B cells, plates were incubated overnight at 37° C. and for measuring total IgG cells, plates were incubated for 1 hour at 37° C. For detection, we used biotinylated goat anti-mouse IgG (Sigma) in PBS-T/1% FCS, followed by 5 μg/mL HRP-conjugated avidin (Pierce) and developed using 3-amino-9-ethylcarbozole (Sigma). Developed plates were counted using an automated ELISPOT plate counter.

E7 IFN-γ ELISPOT 96-well filter plates (Millipore) were coated overnight with 4 μg/mL of monoclonal antibody (AN18; Mabtech). After coating, plates were washed once with complete RPMI and blocked for 2 hours with complete RPMI with 10% foetal calf serum (FCS; CSL Ltd). Mouse spleens were made into single cell suspensions and treated with ACK lysis buffer, washed and resuspended at a concentration of $10^7$ cells/mL. Spleen cells ($10^6$/well) were added to each well followed by the addition of complete RPMI supplemented with recombinant hIL-2 (ProSpec-Tany TechnoGene Ltd) and peptide to a final concentration of 10 IU/well and 1 μg/mL, respectively. Medium containing hIL-2 without peptide was added to control wells. Plates were incubated for approximately 18 hours at 37° C. in 5-8% $CO_2$.

After overnight incubation, cells were lysed by rinsing the plates in tap water and then washed six times in PBS/0.05% Tween 20 (PBS-T). For detection, biotinylated detection mAb (R4-6A2; Mabtech) in PBS-T/2% FCS was added, followed by horse radish peroxidase (HRP)-conjugated strepavidin and DAB (Sigma). Developed plates were counted using an automated ELISPOT plate counter.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Ausubel, F. M. (Ed.) 2007. Current Protocols in Molecular Biology. Ebook (http://www.nrw.interscience.wiley.com/emrw/9780471142720/cp/cpmb/toc).

Edmonds, C., and Vousden, K. H. (1989). A point mutational analysis of human papillomavirus type 16 E7 protein. Journal of Virology. 63: 2650-2656.

Frazer, I. H., Leippe, D. M., Dunn, L. A., Leim, A., Tindle, R. W., Fernando, G. J., Phelps, W. C., and Lambert, P. F. (1995). Immunological responses in human papillomavirus 16 E6/E7 transgenic mice to E7 protein correlate with the presence of skin disease. Cancer Research. 55: 2635-2639.

Heck, D. V., Yee, C. L., Howley, P. M., and Munger, K. (1992). Efficiency of binding the retinoblastoma protein correlates with the transforming capacity of the E7 oncoproteins of the human papillomaviruses. PNAS 89: 4442-4446.

Liu, W. J., Gao, F., Zhao, K N., Zhao, W., Fernando, G. J, Thomas, R. And Frazer, I. H. (2002). Codon modified human papillomavirus type 16 E7 DNA vaccine enhances cytotoxic T-lymphocyte induction and anti-tumour activity. Virology 301: 43-52.

Smith, H. O., Hutchison III, C. A., Pfannkoch, C. and Venter, J. C. (2003). Generating a synthetic genome by whole genome assembly: ϕX174 bacteriophage from synthetic oligonucleotides. PNAS. 100 (26): 15440-15445.

What is claimed is:

1. A method for constructing a synthetic polynucleotide from which a polypeptide is producible to confer a stronger or enhanced immune response to a target antigen in a mammal than that conferred by a parent polynucleotide that encodes the same polypeptide, wherein the immune response is selected from the group consisting of (1) a humoral immune response, (2) a cellular immune response and (3) a cellular immune response and a humoral immune response, wherein the polypeptide corresponds to at least a portion of the target antigen, the method comprising constructing the synthetic polynucleotide so that it is distinguished from the parent polynucleotide by replacement of at least 5% of codons which correspond to the target antigen in the parent polynucleotide with synonymous codons, wherein individual codon replacements are carried out by: (a) selecting a first codon of the parent polynucleotide for replacement with a synonymous codon according to TABLE 3:

TABLE 3

| First Codon | Synonymous Codon |
|---|---|
| Ala$^{GCG}$ | Ala$^{GCT}$ |
| Ala$^{GCA}$ | Ala$^{GCT}$ |
| Ala$^{GCC}$ | Ala$^{GCT}$ |
| Arg$^{CGG}$ | Arg$^{CGA}$ |
| Arg$^{CGG}$ | Arg$^{CGT}$ |
| Arg$^{CGG}$ | Arg$^{AGA}$ |
| Arg$^{AGG}$ | Arg$^{CGA}$ |
| Arg$^{AGG}$ | Arg$^{CGT}$ |
| Arg$^{AGG}$ | Arg$^{AGA}$ |
| Glu$^{GAG}$ | Glu$^{GAA}$ |
| Gly$^{GGC}$ | Gly$^{GGA}$ |
| Gly$^{GGT}$ | Gly$^{GGA}$ |
| Gly$^{GGG}$ | Gly$^{GGA}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTA}$ |
| Leu$^{TTG}$ | Leu$^{CTT}$ |
| Phe$^{TTC}$ | Phe$^{TTT}$ |
| Pro$^{CCG}$ | Pro$^{CCT}$ |
| Pro$^{CCA}$ | Pro$^{CCT}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACA}$ |
| Thr$^{ACA}$ | Thr$^{ACG}$ |
| Thr$^{ACC}$ | Thr$^{ACG}$ |
| Val$^{GTA}$ | Val$^{GTT}$ |

and (b) replacing the first codon with the synonymous codon.

2. The method according to claim 1, further comprising (i) selecting a second codon of the parent polynucleotide for replacement with a synonymous codon, wherein the synonymous codon is selected on the basis that it exhibits a higher immune response preference than the second codon in a comparison of immune response preferences; and (ii) replacing the second codon with the synonymous codon, wherein the comparison of immune response preferences of the codons is represented by TABLE 4:

| Second Codon | Synonymous Codon |
|---|---|
| Ala$^{GCG}$ | Ala$^{GCT}$ |
| Ala$^{GCG}$ | Ala$^{GCC}$ |
| Ala$^{GCA}$ | Ala$^{GCT}$ |
| Ala$^{GCA}$ | Ala$^{GCC}$ |
| Ala$^{GCC}$ | Ala$^{GCT}$ |
| Arg$^{CGG}$ | Arg$^{CGA}$ |
| Arg$^{CGG}$ | Arg$^{CGC}$ |
| Arg$^{CGG}$ | Arg$^{CGT}$ |
| Arg$^{CGG}$ | Arg$^{AGA}$ |
| Arg$^{AGG}$ | Arg$^{CGA}$ |
| Arg$^{AGG}$ | Arg$^{CGC}$ |
| Arg$^{AGG}$ | Arg$^{CGT}$ |
| Arg$^{AGG}$ | Arg$^{AGA}$ |
| Asn$^{AAT}$ | Asn$^{AAC}$ |
| Asp$^{GAT}$ | Asp$^{GAC}$ |
| Cys$^{TGT}$ | Cys$^{TGC}$ |
| Glu$^{GAG}$ | Glu$^{GAA}$ |
| Gly$^{GGC}$ | Gly$^{GGA}$ |
| Gly$^{GGT}$ | Gly$^{GGA}$ |
| Gly$^{GGG}$ | Gly$^{GGA}$ |
| Ile$^{ATA}$ | Ile$^{ATC}$ |
| Ile$^{ATA}$ | Ile$^{ATT}$ |
| Ile$^{ATT}$ | Ile$^{ATC}$ |
| Leu$^{TTA}$ | Leu$^{CTG}$ |
| Leu$^{TTA}$ | Leu$^{CTC}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTG}$ |
| Leu$^{TTG}$ | Leu$^{CTC}$ |
| Leu$^{TTG}$ | Leu$^{CTA}$ |
| Leu$^{TTG}$ | Leu$^{CTT}$ |
| Leu$^{CTT}$ | Leu$^{CTG}$ |
| Leu$^{CTT}$ | Leu$^{CTC}$ |
| Leu$^{CTA}$ | Leu$^{CTG}$ |
| Leu$^{CTA}$ | Leu$^{CTC}$ |
| Phe$^{TTC}$ | Phe$^{TTT}$ |
| Pro$^{CCG}$ | Pro$^{CCC}$ |
| Pro$^{CCG}$ | Pro$^{CCT}$ |
| Pro$^{CCA}$ | Pro$^{CCC}$ |
| Pro$^{CCA}$ | Pro$^{CCT}$ |
| Pro$^{CCT}$ | Pro$^{CCC}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGT}$ | Ser$^{TCC}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACC}$ |
| Thr$^{ACT}$ | Thr$^{ACA}$ |
| Thr$^{ACA}$ | Thr$^{ACG}$ |

-continued

| Second Codon | Synonymous Codon |
|---|---|
| $Thr^{ACA}$ | $Thr^{ACC}$ |
| $Thr^{ACC}$ | $Thr^{ACG}$ |
| $Tyr^{TAT}$ | $Tyr^{TAC}$ |
| $Val^{GTA}$ | $Val^{GTG}$ |
| $Val^{GTA}$ | $Val^{GTC}$ |
| $Val^{GTA}$ | $Val^{GTT}$ |
| $Val^{GTT}$ | $Val^{GTG}$ |
| $Val^{GTT}$ | $Val^{GTC}$. |

3. A method for constructing a synthetic polynucleotide from which a polypeptide is producible to confer a weaker or reduced immune response to a target antigen in a mammal than that conferred by a parent polynucleotide that encodes the same polypeptide, wherein the immune response is selected from the group consisting of (1) a humoral immune response; (2) a cellular immune response; and (3) a cellular immune response and a humoral immune response, wherein the polypeptide corresponds to at least a portion of the target antigen, the method comprising constructing the synthetic polynucleotide so that it is distinguished from the parent polynucleotide by replacement of at least 5% of codons, wherein individual codon replacements are carried out by: (a) selecting a first codon of the parent polynucleotide for replacement with a synonymous codon; and (b) replacing the first codon with the synonymous codon to construct the synthetic polynucleotide, wherein the first and synonymous codons are selected from the TABLE 5:

| First Codon | Synonymous Codon |
|---|---|
| $Ala^{GCT}$ | $Ala^{GCG}$ |
| $Ala^{GCT}$ | $Ala^{GCA}$ |
| $Ala^{GCT}$ | $Ala^{GCC}$ |
| $Ala^{GCC}$ | $Ala^{GCG}$ |
| $Ala^{GCC}$ | $Ala^{GCA}$ |
| $Arg^{CGA}$ | $Arg^{AGG}$ |
| $Arg^{CGA}$ | $Arg^{CGG}$ |
| $Arg^{CGC}$ | $Arg^{AGG}$ |
| $Arg^{CGC}$ | $Arg^{CGG}$ |
| $Arg^{CGT}$ | $Arg^{AGG}$ |
| $Arg^{CGT}$ | $Arg^{CGG}$ |
| $Arg^{AGA}$ | $Arg^{AGG}$ |
| $Arg^{AGA}$ | $Arg^{CGG}$ |
| $Asn^{AAC}$ | $Asn^{AAT}$ |
| $Asp^{GAC}$ | $Asp^{GAT}$ |
| $Cys^{TGC}$ | $Cys^{TGT}$ |
| $Glu^{GAA}$ | $Glu^{GAG}$ |
| $Gly^{GGA}$ | $Gly^{GGC}$ |
| $Gly^{GGA}$ | $Gly^{GGT}$ |
| $Gly^{GGA}$ | $Gly^{GGG}$ |
| $Ile^{ATC}$ | $Ile^{ATA}$ |
| $Ile^{ATC}$ | $Ile^{ATT}$ |
| $Ile^{ATT}$ | $Ile^{ATA}$ |
| $Leu^{CTG}$ | $Leu^{CTA}$ |
| $Leu^{CTG}$ | $Leu^{CTT}$ |
| $Leu^{CTG}$ | $Leu^{TTG}$ |
| $Leu^{CTG}$ | $Leu^{TTA}$ |
| $Leu^{CTC}$ | $Leu^{CTA}$ |
| $Leu^{CTC}$ | $Leu^{CTT}$ |
| $Leu^{CTC}$ | $Leu^{TTG}$ |
| $Leu^{CTC}$ | $Leu^{TTA}$ |
| $Leu^{CTA}$ | $Leu^{TTG}$ |
| $Leu^{CTA}$ | $Leu^{TTA}$ |
| $Leu^{CTT}$ | $Leu^{TTG}$ |
| $Leu^{CTT}$ | $Leu^{TTA}$ |
| $Leu^{TTG}$ | $Leu^{TTA}$ |
| $Phe^{TTT}$ | $Phe^{TTC}$ |
| $Pro^{CCC}$ | $Pro^{CCT}$ |
| $Pro^{CCC}$ | $Pro^{CCA}$ |
| $Pro^{CCC}$ | $Pro^{CCG}$ |
| $Pro^{CCT}$ | $Pro^{CCA}$ |

-continued

| First Codon | Synonymous Codon |
|---|---|
| $Pro^{CCT}$ | $Pro^{CCG}$ |
| $Ser^{TCG}$ | $Ser^{TCT}$ |
| $Ser^{TCG}$ | $Ser^{TCA}$ |
| $Ser^{TCG}$ | $Ser^{TCC}$ |
| $Ser^{TCG}$ | $Ser^{AGC}$ |
| $Ser^{TCG}$ | $Ser^{AGT}$ |
| $Ser^{TCT}$ | $Ser^{AGC}$ |
| $Ser^{TCT}$ | $Ser^{AGT}$ |
| $Ser^{TCA}$ | $Ser^{AGC}$ |
| $Ser^{TCA}$ | $Ser^{AGT}$ |
| $Ser^{TCC}$ | $Ser^{AGC}$ |
| $Ser^{TCC}$ | $Ser^{AGT}$ |
| $Thr^{ACG}$ | $Thr^{ACC}$ |
| $Thr^{ACG}$ | $Thr^{ACA}$ |
| $Thr^{ACG}$ | $Thr^{ACT}$ |
| $Thr^{ACC}$ | $Thr^{ACA}$ |
| $Thr^{ACC}$ | $Thr^{ACT}$ |
| $Thr^{ACA}$ | $Thr^{ACT}$ |
| $Tyr^{TAC}$ | $Tyr^{TAT}$ |
| $Val^{GTG}$ | $Val^{GTT}$ |
| $Val^{GTG}$ | $Val^{GTA}$ |
| $Val^{GTC}$ | $Val^{GTT}$ |
| $Val^{GTC}$ | $Val^{GTA}$ |
| $Val^{GTT}$ | $Val^{GTA}$. |

4. A method for constructing a synthetic polynucleotide from which a polypeptide is producible to confer a weaker or reduced immune response to a target antigen in a mammal than that conferred by a parent polynucleotide that encodes the same polypeptide, wherein the immune response is selected from the group consisting of (1) a humoral immune response; (2) a cellular immune response; and (3) a cellular immune response and a humoral immune response, wherein the polypeptide corresponds to at least a portion of the target antigen, the method comprising constructing the synthetic polynucleotide so that it is distinguished from the parent polynucleotide by replacement of at least 5% of codons, wherein individual codon replacements are carried out by: (a) selecting a first codon of the parent polynucleotide for replacement with a synonymous codon; and (b) replacing the first codon with the synonymous codon to construct the synthetic polynucleotide, wherein the first and synonymous codons are selected from TABLE 6:

| First Codon | Synonymous Codon |
|---|---|
| $Ala^{GCT}$ | $Ala^{GCG}$ |
| $Ala^{GCT}$ | $Ala^{GCA}$ |
| $Ala^{GCT}$ | $Ala^{GCC}$ |
| $Arg^{CGA}$ | $Arg^{AGG}$ |
| $Arg^{CGA}$ | $Arg^{CGG}$ |
| $Arg^{CGT}$ | $Arg^{AGG}$ |
| $Arg^{CGT}$ | $Arg^{CGG}$ |
| $Arg^{AGA}$ | $Arg^{AGG}$ |
| $Arg^{AGA}$ | $Arg^{CGG}$ |
| $Glu^{GAA}$ | $Glu^{GAG}$ |
| $Gly^{GGA}$ | $Gly^{GGC}$ |
| $Gly^{GGA}$ | $Gly^{GGT}$ |
| $Gly^{GGA}$ | $Gly^{GGG}$ |
| $Leu^{CTA}$ | $Leu^{TTG}$ |
| $Leu^{CTA}$ | $Leu^{TTA}$ |
| $Leu^{CTT}$ | $Leu^{TTG}$ |
| $Leu^{CTT}$ | $Leu^{TTA}$ |
| $Leu^{TTG}$ | $Leu^{TTA}$ |
| $Phe^{TTT}$ | $Phe^{TTC}$ |
| $Pro^{CCT}$ | $Pro^{CCA}$ |
| $Pro^{CCT}$ | $Pro^{CCG}$ |
| $Ser^{TCG}$ | $Ser^{TCT}$ |
| $Ser^{TCG}$ | $Ser^{TCA}$ |
| $Ser^{TCG}$ | $Ser^{TCC}$ |
| $Ser^{TCG}$ | $Ser^{AGC}$ |

-continued

| First Codon | Synonymous Codon |
|---|---|
| Ser$^{TCG}$ | Ser$^{AGT}$ |
| Ser$^{TCT}$ | Ser$^{AGC}$ |
| Ser$^{TCT}$ | Ser$^{AGT}$ |
| Ser$^{TCA}$ | Ser$^{AGC}$ |
| Ser$^{TCA}$ | Ser$^{AGT}$ |
| Ser$^{TCC}$ | Ser$^{AGC}$ |
| Thr$^{ACG}$ | Thr$^{ACC}$ |
| Thr$^{ACG}$ | Thr$^{ACA}$ |
| Thr$^{ACG}$ | Thr$^{ACT}$ |
| Thr$^{ACA}$ | Thr$^{ACT}$ |
| Val$^{GTT}$ | Val$^{GTA}$. |

5. The method according to claim 4, further comprising (i) selecting a second codon of the parent polynucleotide for replacement with a synonymous codon, wherein the synonymous codon is selected on the basis that it exhibits a lower immune response preference than the second codon in a comparison of immune response preferences; and; (ii) replacing the second codon with the synonymous codon, wherein the comparison of immune response preferences of the codons is represented by TABLE 7:

TABLE 7

| Second Codon | Synonymous Codon |
|---|---|
| Ala$^{GCT}$ | Ala$^{GCG}$ |
| Ala$^{GCT}$ | Ala$^{GCA}$ |
| Ala$^{GCT}$ | Ala$^{GCC}$ |
| Ala$^{GCC}$ | Ala$^{GCG}$ |
| Ala$^{GCC}$ | Ala$^{GCA}$ |
| Arg$^{CGA}$ | Arg$^{AGG}$ |
| Arg$^{CGA}$ | Arg$^{CGG}$ |
| Arg$^{CGC}$ | Arg$^{AGG}$ |
| Arg$^{CGC}$ | Arg$^{CGG}$ |
| Arg$^{CGT}$ | Arg$^{AGG}$ |
| Arg$^{CGT}$ | Arg$^{CGG}$ |
| Arg$^{AGA}$ | Arg$^{AGG}$ |
| Arg$^{AGA}$ | Arg$^{CGG}$ |
| Asn$^{AAC}$ | Asn$^{AAT}$ |
| Asp$^{GAC}$ | Asp$^{GAT}$ |
| Cys$^{TGC}$ | Cys$^{TGT}$ |
| Glu$^{GAA}$ | Glu$^{GAG}$ |
| Gly$^{GGA}$ | Gly$^{GGC}$ |
| Gly$^{GGA}$ | Gly$^{GGT}$ |
| Gly$^{GGA}$ | Gly$^{GGG}$ |
| Ile$^{ATC}$ | Ile$^{ATA}$ |
| Ile$^{ATC}$ | Ile$^{ATT}$ |
| Ile$^{ATT}$ | Ile$^{ATA}$ |
| Leu$^{CTG}$ | Leu$^{CTA}$ |
| Leu$^{CTG}$ | Leu$^{CTT}$ |
| Leu$^{CTG}$ | Leu$^{TTG}$ |
| Leu$^{CTG}$ | Leu$^{TTA}$ |
| Leu$^{CTC}$ | Leu$^{CTA}$ |
| Leu$^{CTC}$ | Leu$^{CTT}$ |
| Leu$^{CTC}$ | Leu$^{TTG}$ |
| Leu$^{CTC}$ | Leu$^{TTA}$ |
| Leu$^{CTA}$ | Leu$^{TTG}$ |
| Leu$^{CTA}$ | Leu$^{TTA}$ |
| Leu$^{CTT}$ | Leu$^{TTG}$ |
| Leu$^{CTT}$ | Leu$^{TTA}$ |
| Leu$^{TTG}$ | Leu$^{TTA}$ |
| Phe$^{TTT}$ | Phe$^{TTC}$ |
| Pro$^{CCC}$ | Pro$^{CCT}$ |
| Pro$^{CCC}$ | Pro$^{CCA}$ |
| Pro$^{CCC}$ | Pro$^{CCG}$ |
| Pro$^{CCT}$ | Pro$^{CCA}$ |
| Pro$^{CCT}$ | Pro$^{CCG}$ |
| Ser$^{TCG}$ | Ser$^{TCT}$ |
| Ser$^{TCG}$ | Ser$^{TCA}$ |
| Ser$^{TCG}$ | Ser$^{TCC}$ |
| Ser$^{TCG}$ | Ser$^{AGC}$ |
| Ser$^{TCG}$ | Ser$^{AGT}$ |
| Ser$^{TCT}$ | Ser$^{AGC}$ |
| Ser$^{TCT}$ | Ser$^{AGT}$ |
| Ser$^{TCA}$ | Ser$^{AGC}$ |
| Ser$^{TCA}$ | Ser$^{AGT}$ |
| Ser$^{TCC}$ | Ser$^{AGC}$ |
| Ser$^{TCC}$ | Ser$^{AGT}$ |
| Thr$^{ACG}$ | Thr$^{ACC}$ |
| Thr$^{ACG}$ | Thr$^{ACA}$ |
| Thr$^{ACG}$ | Thr$^{ACT}$ |
| Thr$^{ACC}$ | Thr$^{ACA}$ |
| Thr$^{ACC}$ | Thr$^{ACT}$ |
| Thr$^{ACA}$ | Thr$^{ACT}$ |
| Tyr$^{TAC}$ | Tyr$^{TAT}$ |
| Val$^{GTG}$ | Val$^{GTT}$ |
| Val$^{GTG}$ | Val$^{GTA}$ |
| Val$^{GTC}$ | Val$^{GTT}$ |
| Val$^{GTC}$ | Val$^{GTA}$ |
| Val$^{GTT}$ | Val$^{GTA}$. |

6. A method of making a chimeric construct, comprising constructing a synthetic polynucleotide according to the method of claim 1 and operably linking a regulatory polynucleotide to the synthetic polynucleotide.

7. The method according to claim 6, further comprising constructing the chimeric construct so that it includes the coding sequence of an adjuvant.

8. The method according to claim 7, wherein the adjuvant is selected from: detoxified mutants of bacterial ADP-ribosylating toxins, diphtheria toxin, pertussis toxin, cholera toxin, *Escherichia coli* heat-labile toxins, *Pseudomonas* endotoxin A, *Clostridium botulinum* C2 and C3 toxins, toxins from *C. perfringens, C. spiriforma* and *C. difficile*; and protein-destabilizing elements.

9. The method according to claim 7, wherein the adjuvant is a protein-destabilizing element selected from a destabilizing amino acid at the amino-terminus of the polypeptide, a PEST region or an ubiquitin.

10. The method according to claim 6, further comprising formulating the chimeric construct for transcutaneous administration, epidermal administration, dermal administration, intradermal administration, biolistic delivery, microneedle delivery or intradermal injection.

11. A synthetic polynucleotide comprising the nucleic acid sequence set forth in SEQ ID NO: 82.

12. A chimeric construct comprising the synthetic polynucleotide of claim 11 operably linked to a regulatory polynucleotide.

13. The method of claim 1, wherein the target antigen is a herpes simplex virus antigen.

14. The method of claim 13, wherein the herpes simplex virus antigen is a glycoprotein D.

15. The method of claim 13, wherein the herpes simplex virus antigen is gD2.

* * * * *

```
SEQUENCE LISTING

<160> NUMBER OF SEQ ID NOS: 154

<210> SEQ ID NO 1
<211> LENGTH: 387
<212> TYPE: DNA
<213> ORGANISM: Artificial sequence
<220> FEATURE:
<223> OTHER INFORMATION: Plasmid sequence

<400> SEQUENCE: 1

ggtaccgccg ccaccatgga gacagataca ctcctgctat gggtactgct gctctgggtt     60

ccaggttcca ctggtgatgg atccatgcat ggagatacac ctacattgca tgaatatatg    120

ttagatttgc aaccagagac aactgatctc tactgttatg agcaattaaa tgatagctca    180

gaggaggagg atgaaataga tggtccagct ggacaagcag aaccggatag agcccattac    240

aatattgtaa ccttttgttg caagtgtgat tctacgcttc ggttgtgcgt acaaagcaca    300

cacgtagata ttcgtacttt ggaagatctg ttaatgggca cactaggaat tgtgtgcccc    360

atctgctctc agaagcccta agaattc                                         387


<210> SEQ ID NO 2
<211> LENGTH: 387
<212> TYPE: DNA
<213> ORGANISM: Artificial sequence
<220> FEATURE:
<223> OTHER INFORMATION: Plasmid sequence

<400> SEQUENCE: 2

ggtaccgccg ccaccatgga gacagacaca ctcctgctat gggtactgct gctctgggtt     60

ccaggttcca ctggtgacgg atccatgcat ggagacacac ctacattgca tgaatatatg    120

ttagacttgc aaccagagac aactgacctc tactgttatg agcaattaaa tgacagctca    180

gaggaggagg acgaaataga cggtccagct ggacaagcag aaccggacag agcccattac    240

aatattgtaa ccttttgttg caagtgtgac tctacgcttc ggttgtgcgt acaaagcaca    300

cacgtagaca ttcgtacttt ggaagacctg ttaatgggca cactaggaat tgtgtgcccc    360

atctgctctc agaagcccta agaattc                                         387


<210> SEQ ID NO 3
<211> LENGTH: 387
<212> TYPE: DNA
<213> ORGANISM: Artificial sequence
<220> FEATURE:
<223> OTHER INFORMATION: Plasmid sequence

<400> SEQUENCE: 3

ggtaccgccg ccaccatgga gacagacaca ctcctgctat gggtactgct gctctgggtt     60

ccaggttcca ctggtgacgg atccatgcat ggagatacac ctacattgca tgaatatatg    120
```

ttagatttgc aaccagagac aactgatctc tactgttatg agcaattaaa tgacagctca 180
gaggaggagg atgaaataga tggtccagct ggacaagcag aaccggacag agcccattac 240
aatattgtaa ccttttgttg taagtgtgac tctacgcttc ggttgtgtgt acaaagcaca 300
cacgtagaca ttcgtacttt ggaagacctg ttaatgggca cactaggaat tgtgtgtccc 360
atctgttctc agaagcccta agaattc 387

<210> SEQ ID NO 4
<211> LENGTH: 387
<212> TYPE: DNA
<213> ORGANISM: Artificial sequence
<220> FEATURE:
<223> OTHER INFORMATION: Plasmid sequence

<400> SEQUENCE: 4
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactgatctc tactgctatg agcaattaaa tgacagctca 180
gaggaggagg atgaaataga tggtccagct ggacaagcag aaccggacag agcccattac 240
aatattgtaa ccttttgctg caagtgcgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 5
<211> LENGTH: 387
<212> TYPE: DNA
<213> ORGANISM: Artificial sequence
<220> FEATURE:
<223> OTHER INFORMATION: Plasmid sequence

<400> SEQUENCE: 5
ggtaccgccg ccaccatgga gacagacaca ctcctgctat gggtactgct gctctgggtt 60
ccaggttcca ctggtgacgg atccatgcat ggagatacac ctacattgca tgagtatatg 120
ttagatttgc aaccagagac aactgatctc tactgttatg agcaattaaa tgacagctca 180
gaggaggagg atgagataga tggtccagct ggacaagcag agccggacag agcccattac 240
aatattgtaa ccttttgttg caagtgtgac tctacgcttc ggttgtgcgt acaaagcaca 300
cacgtagaca ttcgtacttt ggaggacctg ttaatgggca cactaggaat tgtgtgcccc 360
atctgctctc agaagcccta agaattc 387

<210> SEQ ID NO 6
<211> LENGTH: 387
<212> TYPE: DNA
<213> ORGANISM: Artificial sequence
<220> FEATURE:
<223> OTHER INFORMATION: Plasmid sequence

<400> SEQUENCE: 6
ggtaccgccg ccaccatgga aacagacaca ctcctgctat gggtactgct gctctgggtt 60
ccaggttcca ctggtgacgg atccatgcat ggagatacac ctacattgca tgaatatatg 120
ttagatttgc aaccagaaac aactgatctc tactgttatg aacaattaaa tgacagctca 180
gaagaagaag atgaaataga tggtccagct ggacaagcag aaccggacag agcccattac 240
aatattgtaa ccttttgttg caagtgtgac tctacgcttc ggttgtgcgt acaaagcaca 300

```
cacgtagaca ttcgtacttt ggaagacctg ttaatgggca cactaggaat tgtgtgcccc    360

atctgctctc agaagcccta agaattc                                        387


<210> SEQ ID NO 7
<211> LENGTH: 387
<212> TYPE: DNA
<213> ORGANISM: Artificial sequence
<220> FEATURE:
<223> OTHER INFORMATION: Plasmid sequence

<400> SEQUENCE: 7

ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttgc agccagagac aactgatctc tactgttatg agcagttaaa tgacagctca    180

gaggaggagg atgaaataga tggtccagct ggacaggcag aaccggacag agcccattac    240

aatattgtaa ccttttgttg caagtgtgac tctacgcttc ggttgtgcgt acagagcaca    300

cacgtagaca ttcgtacttt ggaagacctg ttaatgggca cactaggaat tgtgtgcccc    360

atctgctctc agaagcccta agaattc                                        387


<210> SEQ ID NO 8
<211> LENGTH: 387
<212> TYPE: DNA
<213> ORGANISM: Artificial sequence
<220> FEATURE:
<223> OTHER INFORMATION: Plasmid sequence

<400> SEQUENCE: 8

ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttgc aaccagagac aactgatctc tactgttatg agcaattaaa tgacagctca    180

gaggaggagg atgaaataga tggtccagct ggacaagcag aaccggacag agcccattac    240

aatattgtaa ccttttgttg caagtgtgac tctacgcttc ggttgtgcgt acaaagcaca    300

cacgtagaca ttcgtacttt ggaagacctg ttaatgggca cactaggaat tgtgtgcccc    360

atctgctctc aaaagcccta agaattc                                        387


<210> SEQ ID NO 9
<211> LENGTH: 387
<212> TYPE: DNA
<213> ORGANISM: Artificial sequence
<220> FEATURE:
<223> OTHER INFORMATION: Plasmid sequence

<400> SEQUENCE: 9

ggtaccgccg ccaccatgga gacagacaca ctcctgctat gggtactgct gctctgggtt     60

ccagggtcca ctggggacgg atccatgcat ggggatacac ctacattgca tgaatatatg    120

ttagatttgc aaccagagac aactgatctc tactgttatg agcaattaaa tgacagctca    180

gaggaggagg atgaaataga tgggccagct gggcaagcag aaccggacag agcccattac    240

aatattgtaa ccttttgttg caagtgtgac tctacgcttc ggttgtgcgt acaaagcaca    300

cacgtagaca ttcgtacttt ggaagacctg ttaatgggga cactagggat tgtgtgcccc    360

atctgctctc agaagcccta agaattc                                        387


<210> SEQ ID NO 10
<211> LENGTH: 387
```

-continued

<212> TYPE: DNA
<213> ORGANISM: Artificial sequence
<220> FEATURE:
<223> OTHER INFORMATION: Plasmid sequence

<400> SEQUENCE: 10
ggtaccgccg ccaccatgga gacagacaca ctcctgctat gggtactgct gctctgggtt 60
ccaggatcca ctggagacgg atccatgcat ggagatacac ctacattgca tgaatatatg 120
ttagatttgc aaccagagac aactgatctc tactgttatg agcaattaaa tgacagctca 180
gaggaggagg atgaaataga tggaccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggaa cactaggaat tgtgtgcccc 360
atctgctctc agaagcccta agaattc 387

<210> SEQ ID NO 11
<211> LENGTH: 387
<212> TYPE: DNA
<213> ORGANISM: Artificial sequence
<220> FEATURE:
<223> OTHER INFORMATION: Plasmid sequence

<400> SEQUENCE: 11
ggtaccgccg ccaccatgga gacagacaca ctcctgctat gggtactgct gctctgggtt 60
ccaggttcca ctggtgacgg atccatgcat ggtgatacac ctacattgca tgaatatatg 120
ttagatttgc aaccagagac aactgatctc tactgttatg agcaattaaa tgacagctca 180
gaggaggagg atgaaataga tggtccagct ggtcaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggta cactaggtat tgtgtgcccc 360
atctgctctc agaagcccta agaattc 387

<210> SEQ ID NO 12
<211> LENGTH: 387
<212> TYPE: DNA
<213> ORGANISM: Artificial sequence
<220> FEATURE:
<223> OTHER INFORMATION: Plasmid sequence

<400> SEQUENCE: 12
ggtaccgccg ccaccatgga gacagacaca ctcctgctat gggtactgct gctctgggtt 60
ccaggctcca ctggcgacgg atccatgcat ggcgatacac ctacattgca tgaatatatg 120
ttagatttgc aaccagagac aactgatctc tactgttatg agcaattaaa tgacagctca 180
gaggaggagg atgaaataga tggcccagct ggccaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggcat tgtgtgcccc 360
atctgctctc agaagcccta agaattc 387

<210> SEQ ID NO 13
<211> LENGTH: 387
<212> TYPE: DNA
<213> ORGANISM: Artificial sequence
<220> FEATURE:
<223> OTHER INFORMATION: Plasmid sequence

<400> SEQUENCE: 13

-continued

```
ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttgc aaccagagac aactgatctc tactgttatg agcaattaaa tgacagctca    180

gaggaggagg atgaaataga tggtccagct ggacaagcag aaccggacag agcccattac    240

aatatagtaa ccttttgttg caagtgtgac tctacgcttc ggttgtgcgt acaaagcaca    300

cacgtagaca tacgtacttt ggaagacctg ttaatgggca cactaggaat agtgtgcccc    360

atatgctctc agaagcccta agaattc                                        387
```

<210> SEQ ID NO 14
<211> LENGTH: 387
<212> TYPE: DNA
<213> ORGANISM: Artificial sequence
<220> FEATURE:
<223> OTHER INFORMATION: Plasmid sequence

<400> SEQUENCE: 14

```
ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttgc aaccagagac aactgatctc tactgttatg agcaattaaa tgacagctca    180

gaggaggagg atgaaattga tggtccagct ggacaagcag aaccggacag agcccattac    240

aatattgtaa ccttttgttg caagtgtgac tctacgcttc ggttgtgcgt acaaagcaca    300

cacgtagaca ttcgtacttt ggaagacctg ttaatgggca cactaggaat tgtgtgcccc    360

atttgctctc agaagcccta agaattc                                        387
```

<210> SEQ ID NO 15
<211> LENGTH: 387
<212> TYPE: DNA
<213> ORGANISM: Artificial sequence
<220> FEATURE:
<223> OTHER INFORMATION: Plasmid sequence

<400> SEQUENCE: 15

```
ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttgc aaccagagac aactgatctc tactgttatg agcaattaaa tgacagctca    180

gaggaggagg atgaaatcga tggtccagct ggacaagcag aaccggacag agcccattac    240

aatatcgtaa ccttttgttg caagtgtgac tctacgcttc ggttgtgcgt acaaagcaca    300

cacgtagaca tccgtacttt ggaagacctg ttaatgggca cactaggaat cgtgtgcccc    360

atctgctctc agaagcccta agaattc                                        387
```

<210> SEQ ID NO 16
<211> LENGTH: 387
<212> TYPE: DNA
<213> ORGANISM: Artificial sequence
<220> FEATURE:
<223> OTHER INFORMATION: Plasmid sequence

<400> SEQUENCE: 16

```
ggtaccgccg ccaccatgga gacagacaca ctcctgctat gggtactgct gctctgggtt     60

ccaggtagta ctggtgacgg aagtatgcat ggagatacac ctacattgca tgaatatatg    120

ttagatttgc aaccagagac aactgatctc tactgttatg agcaattaaa tgacagtagt    180

gaggaggagg atgaaataga tggtccagct ggacaagcag aaccggacag agcccattac    240
```

aatattgtaa ccttttgttg caagtgtgac agtacgcttc ggttgtgcgt acaaagtaca 300
cacgtagaca ttcgtacttt ggaagacctg ttaatgggca cactaggaat tgtgtgcccc 360
atctgcagtc agaagcccta agaattc 387

<210> SEQ ID NO 17
<211> LENGTH: 387
<212> TYPE: DNA
<213> ORGANISM: Artificial sequence
<220> FEATURE:
<223> OTHER INFORMATION: Plasmid sequence

<400> SEQUENCE: 17
ggtaccgccg ccaccatgga gacagacaca ctcctgctat gggtactgct gctctgggtt 60
ccaggtagca ctggtgacgg aagcatgcat ggagatacac ctacattgca tgaatatatg 120
ttagatttgc aaccagagac aactgatctc tactgttatg agcaattaaa tgacagcagc 180
gaggaggagg atgaaataga tggtccagct ggacaagcag aaccggacag agcccattac 240
aatattgtaa ccttttgttg caagtgtgac agcacgcttc ggttgtgcgt acaaagcaca 300
cacgtagaca ttcgtacttt ggaagacctg ttaatgggca cactaggaat tgtgtgcccc 360
atctgcagcc agaagcccta agaattc 387

<210> SEQ ID NO 18
<211> LENGTH: 387
<212> TYPE: DNA
<213> ORGANISM: Artificial sequence
<220> FEATURE:
<223> OTHER INFORMATION: Plasmid sequence

<400> SEQUENCE: 18
ggtaccgccg ccaccatgga gacagacaca ctcctgctat gggtactgct gctctgggtt 60
ccaggttcga ctggtgacgg atcgatgcat ggagatacac ctacattgca tgaatatatg 120
ttagatttgc aaccagagac aactgatctc tactgttatg agcaattaaa tgactcgtcg 180
gaggaggagg atgaaataga tggtccagct ggacaagcag aaccggacag agcccattac 240
aatattgtaa ccttttgttg caagtgtgac tcgacgcttc ggttgtgcgt acaatcgaca 300
cacgtagaca ttcgtacttt ggaagacctg ttaatgggca cactaggaat tgtgtgcccc 360
atctgctcgc agaagcccta agaattc 387

<210> SEQ ID NO 19
<211> LENGTH: 387
<212> TYPE: DNA
<213> ORGANISM: Artificial sequence
<220> FEATURE:
<223> OTHER INFORMATION: Plasmid sequence

<400> SEQUENCE: 19
ggtaccgccg ccaccatgga gacagacaca ctcctgctat gggtactgct gctctgggtt 60
ccaggttcaa ctggtgacgg atcaatgcat ggagatacac ctacattgca tgaatatatg 120
ttagatttgc aaccagagac aactgatctc tactgttatg agcaattaaa tgactcatca 180
gaggaggagg atgaaataga tggtccagct ggacaagcag aaccggacag agcccattac 240
aatattgtaa ccttttgttg caagtgtgac tcaacgcttc ggttgtgcgt acaatcaaca 300
cacgtagaca ttcgtacttt ggaagacctg ttaatgggca cactaggaat tgtgtgcccc 360
atctgctcac agaagcccta agaattc 387

<210> SEQ ID NO 20
<211> LENGTH: 387
<212> TYPE: DNA
<213> ORGANISM: Artificial sequence
<220> FEATURE:
<223> OTHER INFORMATION: Plasmid sequence

<400> SEQUENCE: 20
ggtaccgccg ccaccatgga gacagacaca ctcctgctat gggtactgct gctctgggtt 60
ccaggttcta ctggtgacgg atctatgcat ggagatacac ctacattgca tgaatatatg 120
ttagatttgc aaccagagac aactgatctc tactgttatg agcaattaaa tgactcttct 180
gaggaggagg atgaaataga tggtccagct ggacaagcag aaccggacag agcccattac 240
aatattgtaa ccttttgttg caagtgtgac tctacgcttc ggttgtgcgt acaatctaca 300
cacgtagaca ttcgtacttt ggaagacctg ttaatgggca cactaggaat tgtgtgcccc 360
atctgctctc agaagcccta agaattc 387

<210> SEQ ID NO 21
<211> LENGTH: 387
<212> TYPE: DNA
<213> ORGANISM: Artificial sequence
<220> FEATURE:
<223> OTHER INFORMATION: Plasmid sequence

<400> SEQUENCE: 21
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactgatctc tactgttatg agcaattaaa tgactcctcc 180
gaggaggagg atgaaataga tggtccagct ggacaagcag aaccggacag agcccattac 240
aatattgtaa ccttttgttg caagtgtgac tccacgcttc ggttgtgcgt acaatccaca 300
cacgtagaca ttcgtacttt ggaagacctg ttaatgggca cactaggaat tgtgtgcccc 360
atctgctccc agaagcccta agaattc 387

<210> SEQ ID NO 22
<211> LENGTH: 387
<212> TYPE: DNA
<213> ORGANISM: Artificial sequence
<220> FEATURE:
<223> OTHER INFORMATION: Plasmid sequence

<400> SEQUENCE: 22
ggtaccgccg ccaccatgga gacggacacg ctcctgctat gggtactgct gctctgggtt 60
ccaggttcca cgggtgacgg atccatgcat ggagatacgc ctacgttgca tgaatatatg 120
ttagatttgc aaccagagac gacggatctc tactgttatg agcaattaaa tgacagctca 180
gaggaggagg atgaaataga tggtccagct ggacaagcag aaccggacag agcccattac 240
aatattgtaa cgttttgttg caagtgtgac tctacgcttc ggttgtgcgt acaaagcacg 300
cacgtagaca ttcgtacgtt ggaagacctg ttaatgggca cgctaggaat tgtgtgcccc 360
atctgctctc agaagcccta agaattc 387

<210> SEQ ID NO 23
<211> LENGTH: 387
<212> TYPE: DNA
<213> ORGANISM: Artificial sequence
<220> FEATURE:
<223> OTHER INFORMATION: Plasmid sequence

<400> SEQUENCE: 23
ggtaccgccg ccaccatgga gacagacaca ctcctgctat gggtactgct gctctgggtt 60
ccaggttcca caggtgacgg atccatgcat ggagatacac ctacattgca tgaatatatg 120
ttagatttgc aaccagagac aacagatctc tactgttatg agcaattaaa tgacagctca 180
gaggaggagg atgaaataga tggtccagct ggacaagcag aaccggacag agcccattac 240
aatattgtaa cattttgttg caagtgtgac tctacacttc ggttgtgcgt acaaagcaca 300
cacgtagaca ttcgtacatt ggaagacctg ttaatgggca cactaggaat tgtgtgcccc 360
atctgctctc agaagcccta agaattc 387

<210> SEQ ID NO 24
<211> LENGTH: 387
<212> TYPE: DNA
<213> ORGANISM: Artificial sequence
<220> FEATURE:
<223> OTHER INFORMATION: Plasmid sequence

<400> SEQUENCE: 24
ggtaccgccg ccaccatgga gactgacact ctcctgctat gggtactgct gctctgggtt 60
ccaggttcca ctggtgacgg atccatgcat ggagatactc ctactttgca tgaatatatg 120
ttagatttgc aaccagagac tactgatctc tactgttatg agcaattaaa tgacagctca 180
gaggaggagg atgaaataga tggtccagct ggacaagcag aaccggacag agcccattac 240
aatattgtaa ctttttgttg caagtgtgac tctactcttc ggttgtgcgt acaaagcact 300
cacgtagaca ttcgtacttt ggaagacctg ttaatgggca ctctaggaat tgtgtgcccc 360
atctgctctc agaagcccta agaattc 387

<210> SEQ ID NO 25
<211> LENGTH: 387
<212> TYPE: DNA
<213> ORGANISM: Artificial sequence
<220> FEATURE:
<223> OTHER INFORMATION: Plasmid sequence

<400> SEQUENCE: 25
ggtaccgccg ccaccatgga gaccgacacc ctcctgctat gggtactgct gctctgggtt 60
ccaggttcca ccggtgacgg atccatgcat ggagataccc ctaccttgca tgaatatatg 120
ttagatttgc aaccagagac caccgatctc tactgttatg agcaattaaa tgacagctca 180
gaggaggagg atgaaataga tggtccagct ggacaagcag aaccggacag agcccattac 240
aatattgtaa ccttttgttg caagtgtgac tctacccttc ggttgtgcgt acaaagcacc 300
cacgtagaca ttcgtacctt ggaagacctg ttaatgggca ccctaggaat tgtgtgcccc 360
atctgctctc agaagcccta agaattc 387

<210> SEQ ID NO 26
<211> LENGTH: 387
<212> TYPE: DNA
<213> ORGANISM: Artificial sequence
<220> FEATURE:
<223> OTHER INFORMATION: Plasmid sequence

<400> SEQUENCE: 26
ggtaccgccg ccaccatgga gacagacaca ctcctgctat gggtgctgct gctctgggtg 60
ccaggttcca ctggtgacgg atccatgcat ggagatacac ctacattgca tgaatatatg 120

-continued ttagatttgc aaccagagac aactgatctc tactgttatg agcaattaaa tgacagctca 180
gaggaggagg atgaaataga tggtccagct ggacaagcag aaccggacag agcccattac 240
aatattgtga ccttttgttg caagtgtgac tctacgcttc ggttgtgcgt gcaaagcaca 300
cacgtggaca ttcgtacttt ggaagacctg ttaatgggca cactaggaat tgtgtgcccc 360
atctgctctc agaagcccta agaattc 387

<210> SEQ ID NO 27
<211> LENGTH: 387
<212> TYPE: DNA
<213> ORGANISM: Artificial sequence
<220> FEATURE:
<223> OTHER INFORMATION: Plasmid sequence

<400> SEQUENCE: 27
ggtaccgccg ccaccatgga gacagacaca ctcctgctat gggtactgct gctctgggta 60
ccaggttcca ctggtgacgg atccatgcat ggagatacac ctacattgca tgaatatatg 120
ttagatttgc aaccagagac aactgatctc tactgttatg agcaattaaa tgacagctca 180
gaggaggagg atgaaataga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtatgcccc 360
atctgctctc agaagcccta agaattc 387

<210> SEQ ID NO 28
<211> LENGTH: 387
<212> TYPE: DNA
<213> ORGANISM: Artificial sequence
<220> FEATURE:
<223> OTHER INFORMATION: Plasmid sequence

<400> SEQUENCE: 28
ggtaccgccg ccaccatgga gacagacaca ctcctgctat gggttctgct gctctgggtt 60
ccaggttcca ctggtgacgg atccatgcat ggagatacac ctacattgca tgaatatatg 120
ttagatttgc aaccagagac aactgatctc tactgttatg agcaattaaa tgacagctca 180
gaggaggagg atgaaataga tggtccagct ggacaagcag aaccggacag agcccattac 240
aatattgtta ccttttgttg caagtgtgac tctacgcttc ggttgtgcgt tcaaagcaca 300
cacgttgaca ttcgtacttt ggaagacctg ttaatgggca cactaggaat tgtttgcccc 360
atctgctctc agaagcccta agaattc 387

<210> SEQ ID NO 29
<211> LENGTH: 387
<212> TYPE: DNA
<213> ORGANISM: Artificial sequence
<220> FEATURE:
<223> OTHER INFORMATION: Plasmid sequence

<400> SEQUENCE: 29
ggtaccgccg ccaccatgga gacagacaca ctcctgctat gggtcctgct gctctgggtc 60
ccaggttcca ctggtgacgg atccatgcat ggagatacac ctacattgca tgaatatatg 120
ttagatttgc aaccagagac aactgatctc tactgttatg agcaattaaa tgacagctca 180
gaggaggagg atgaaataga tggtccagct ggacaagcag aaccggacag agcccattac 240
aatattgtca ccttttgttg caagtgtgac tctacgcttc ggttgtgcgt ccaaagcaca 300
cacgtcgaca ttcgtacttt ggaagacctg ttaatgggca cactaggaat tgtctgcccc 360

-continued atctgctctc agaagcccta agaattc 387

<210> SEQ ID NO 30
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 30
ggtaccgccg ccaccatgga gaccgacacc ctcctgctgt gggtgctgct gctctgggtg 60
cccggctcca ccggcgacgc ggcgggcgcg ggcgcggcgg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 31
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 31
ggtaccgccg ccaccatgga gaccgacacc ctcctgctgt gggtgctgct gctctgggtg 60
cccggctcca ccggcgacgc agcaggcgca ggcgcagcag gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 32
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 32
ggtaccgccg ccaccatgga gaccgacacc ctcctgctgt gggtgctgct gctctgggtg 60
cccggctcca ccggcgacgc tgctggcgct ggcgctgctg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 33
<211> LENGTH: 408
<212> TYPE: DNA

<213> ORGANISM: Artificial sequence
<220> FEATURE:
<223> OTHER INFORMATION: Plasmid linker sequence

<400> SEQUENCE: 33
ggtaccgccg ccaccatgga gaccgacacc ctcctgctgt gggtgctgct gctctgggtg 60
cccggctcca ccggcgacgc cgccggcgcc ggcgccgccg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 34
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 34
ggtaccgccg ccaccatgga gaccgacacc ctcctgctgt gggtgctgct gctctgggtg 60
cccggctcca ccggcgacag gaggggcagg ggcaggaggg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 35
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 35
ggtaccgccg ccaccatgga gaccgacacc ctcctgctgt gggtgctgct gctctgggtg 60
cccggctcca ccggcgacag aagaggcaga ggcagaagag gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 36
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 36
ggtaccgccg ccaccatgga gaccgacacc ctcctgctgt gggtgctgct gctctgggtg 60
cccggctcca ccggcgaccg gcggggccgg ggccggcggg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 37
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 37
ggtaccgccg ccaccatgga gaccgacacc ctcctgctgt gggtgctgct gctctgggtg 60
cccggctcca ccggcgaccg acgaggccga ggccgacgag gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 38
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 38
ggtaccgccg ccaccatgga gaccgacacc ctcctgctgt gggtgctgct gctctgggtg 60
cccggctcca ccggcgaccg tcgtggccgt ggccgtcgtg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 39
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 39
ggtaccgccg ccaccatgga gaccgacacc ctcctgctgt gggtgctgct gctctgggtg 60
cccggctcca ccggcgaccg ccgcggccgc ggccgccgcg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240

-continued

```
gagcccgacc gcgcccacta caacatcgtg accttctgct gcaagtgcga cagcaccctg    300

cgcctctgcg tgcagagcac ccacgtggac atccgcaccc tggaggacct gctgatgggc    360

accctgggca tcgtgtgccc catctgctcc cagaagccct aagaattc                 408


<210> SEQ ID NO 40
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 40

ggtaccgccg ccaccatgga gaccgacacc ctcctgctgt gggtgctgct gctctgggtg     60

cccggctcca ccggcgacaa taatggcaat ggcaataatg gatccatgca cggcgacacc    120

cccaccctgc acgagtacat gctggacctg cagcccgaga ccaccgacct gtactgctac    180

gagcagctca acgacagcag cgaggaggag gacgagatcg acggccccgc cggccaggcc    240

gagcccgacc gcgcccacta caacatcgtg accttctgct gcaagtgcga cagcaccctg    300

cgcctctgcg tgcagagcac ccacgtggac atccgcaccc tggaggacct gctgatgggc    360

accctgggca tcgtgtgccc catctgctcc cagaagccct aagaattc                 408


<210> SEQ ID NO 41
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 41

ggtaccgccg ccaccatgga gaccgacacc ctcctgctgt gggtgctgct gctctgggtg     60

cccggctcca ccggcgacaa caacggcaac ggcaacaacg gatccatgca cggcgacacc    120

cccaccctgc acgagtacat gctggacctg cagcccgaga ccaccgacct gtactgctac    180

gagcagctca acgacagcag cgaggaggag gacgagatcg acggccccgc cggccaggcc    240

gagcccgacc gcgcccacta caacatcgtg accttctgct gcaagtgcga cagcaccctg    300

cgcctctgcg tgcagagcac ccacgtggac atccgcaccc tggaggacct gctgatgggc    360

accctgggca tcgtgtgccc catctgctcc cagaagccct aagaattc                 408


<210> SEQ ID NO 42
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 42

ggtaccgccg ccaccatgga gaccgacacc ctcctgctgt gggtgctgct gctctgggtg     60

cccggctcca ccggcgacca tcatggccat ggccatcatg gatccatgca cggcgacacc    120

cccaccctgc acgagtacat gctggacctg cagcccgaga ccaccgacct gtactgctac    180

gagcagctca acgacagcag cgaggaggag gacgagatcg acggccccgc cggccaggcc    240

gagcccgacc gcgcccacta caacatcgtg accttctgct gcaagtgcga cagcaccctg    300

cgcctctgcg tgcagagcac ccacgtggac atccgcaccc tggaggacct gctgatgggc    360

accctgggca tcgtgtgccc catctgctcc cagaagccct aagaattc                 408
```

-continued

<210> SEQ ID NO 43
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 43
ggtaccgccg ccaccatgga gaccgacacc ctcctgctgt gggtgctgct gctctgggtg 60
cccggctcca ccggcgacca ccacggccac ggccaccacg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 44
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 44
ggtaccgccg ccaccatgga gaccgacacc ctcctgctgt gggtgctgct gctctgggtg 60
cccggctcca ccggcgacaa gaagggcaag ggcaagaagg gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 45
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 45
ggtaccgccg ccaccatgga gaccgacacc ctcctgctgt gggtgctgct gctctgggtg 60
cccggctcca ccggcgacaa aaaaggcaaa ggcaaaaaag gatccatgca cggcgacacc 120
cccaccctgc acgagtacat gctggacctg cagcccgaga ccaccgacct gtactgctac 180
gagcagctca acgacagcag cgaggaggag gacgagatcg acggccccgc cggccaggcc 240
gagcccgacc gcgcccacta caacatcgtg accttctgct gcaagtgcga cagcaccctg 300
cgcctctgcg tgcagagcac ccacgtggac atccgcaccc tggaggacct gctgatgggc 360
accctgggca tcgtgtgccc catctgctcc cagaagccct aagaattc 408

<210> SEQ ID NO 46
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 46

```
ggtaccgccg ccaccatgga gaccgacacc ctcctgctgt gggtgctgct gctctgggtg     60
cccggctcca ccggcgactt ttttggcttt ggcttttttg gatccatgca cggcgacacc    120
cccaccctgc acgagtacat gctggacctg cagcccgaga ccaccgacct gtactgctac    180
gagcagctca acgacagcag cgaggaggag gacgagatcg acggccccgc cggccaggcc    240
gagcccgacc gcgcccacta caacatcgtg accttctgct gcaagtgcga cagcaccctg    300
cgcctctgcg tgcagagcac ccacgtggac atccgcaccc tggaggacct gctgatgggc    360
accctgggca tcgtgtgccc catctgctcc cagaagccct aagaattc                 408
```

<210> SEQ ID NO 47
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 47

```
ggtaccgccg ccaccatgga gaccgacacc ctcctgctgt gggtgctgct gctctgggtg     60
cccggctcca ccggcgactt cttcggcttc ggcttcttcg gatccatgca cggcgacacc    120
cccaccctgc acgagtacat gctggacctg cagcccgaga ccaccgacct gtactgctac    180
gagcagctca acgacagcag cgaggaggag gacgagatcg acggccccgc cggccaggcc    240
gagcccgacc gcgcccacta caacatcgtg accttctgct gcaagtgcga cagcaccctg    300
cgcctctgcg tgcagagcac ccacgtggac atccgcaccc tggaggacct gctgatgggc    360
accctgggca tcgtgtgccc catctgctcc cagaagccct aagaattc                 408
```

<210> SEQ ID NO 48
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 48

```
ggtaccgccg ccaccatgga gaccgacacc ctcctgctgt gggtgctgct gctctgggtg     60
cccggctcca ccggcgacta ttatggctat ggctattatg gatccatgca cggcgacacc    120
cccaccctgc acgagtacat gctggacctg cagcccgaga ccaccgacct gtactgctac    180
gagcagctca acgacagcag cgaggaggag gacgagatcg acggccccgc cggccaggcc    240
gagcccgacc gcgcccacta caacatcgtg accttctgct gcaagtgcga cagcaccctg    300
cgcctctgcg tgcagagcac ccacgtggac atccgcaccc tggaggacct gctgatgggc    360
accctgggca tcgtgtgccc catctgctcc cagaagccct aagaattc                 408
```

<210> SEQ ID NO 49
<211> LENGTH: 408
<212> TYPE: DNA
<213> ORGANISM: Artificial sequence
<220> FEATURE:
<223> OTHER INFORMATION: Plasmid linker sequence

<400> SEQUENCE: 49

```
ggtaccgccg ccaccatgga gaccgacacc ctcctgctgt gggtgctgct gctctgggtg     60
cccggctcca ccggcgacta ctacggctac ggctactacg gatccatgca cggcgacacc    120
cccaccctgc acgagtacat gctggacctg cagcccgaga ccaccgacct gtactgctac    180
```

```
gagcagctca acgacagcag cgaggaggag gacgagatcg acggccccgc cggccaggcc    240

gagcccgacc gcgcccacta caacatcgtg accttctgct gcaagtgcga cagcaccctg    300

cgcctctgcg tgcagagcac ccacgtggac atccgcaccc tggaggacct gctgatgggc    360

accctgggca tcgtgtgccc catctgctcc cagaagccct aagaattc                408
```

<210> SEQ ID NO 50
<211> LENGTH: 1707
<212> TYPE: DNA
<213> ORGANISM: Influenza A Virus

<400> SEQUENCE: 50

```
atggagaaaa tagtgcttct tttgcaata gtcagtcttg ttaaaagtga tcagatttgc      60

attggttacc atgcaaacaa ctcgacagag caggttgaca caataatgga aaagaacgtt    120

actgttacac atgcccaaga catactggaa aagacacaca acgggaagct ctgcgatcta    180

gatggagtga agcctctaat tttgagagat tgtagtgtag ctggatggct cctcggaaac    240

ccaatgtgtg acgaattcat caatgtgccg gaatggtctt acatagtgga gaaggccaat    300

ccagccaatg acctctgtta cccaggggat ttcaacgact atgaagaatt gaaacaccta    360

ttgagcagaa taaaccattt tgagaaaatt cagatcatcc ccaaaaattc ttggtccagt    420

catgaagcct cattaggggt gagctcagca tgtccatacc aaggaaagtc ctcctttttc    480

aggaatgtgg tatggcttat caaaaagaac aatgcatacc caacaataaa gaggagctac    540

aataatacca accaagaaga tcttttggta ttgtggggga ttcaccatcc taatgatgcg    600

gcagagcaga ctaggctcta tcaaaaccca accacctaca tttccgttgg gacatcaaca    660

ctaaaccaga gattggtacc aaaaatagct actagatcca aagtaaacgg gcaaaatgga    720

aggatggagt tcttctggac aattttaaaa ccgaatgatg caatcaactt cgagagcaat    780

ggaaatttca ttgctccaga atatgcatac aaaattgtca agaaagggga ctcagcaatt    840

atgaaaagtg aattggaata tggtaactgc aacaccaagt gtcaaactcc aatgggggcg    900

ataaactcta gtatgccatt ccacaatata caccctctca ccatcgggga atgccccaaa    960

tatgtgaaat caaacagatt agtccttgcg actgggctca gaaatagccc tcaaagagag   1020

agaagaagaa aaaagagagg attatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactcg   1200

atcattgaca aaatgaacac tcagtttgag gccgttggaa gggaatttaa taacttagaa   1260

aggagaatag agaatttaaa caagaagatg gaagacggat tcctagatgt ctggacttat   1320

aatgctgaac ttctggttct catggaaaat gagagaactc tagactttca tgactcaaat   1380

gtcaagaacc tttacgacaa ggtccgacta cagcttaggg ataatgcaaa ggagctgggt   1440

aacggttgtt tcgagttcta tcacaaatgt gataatgaat gtatggaaag tgtaagaaac   1500

ggaacgtatg actacccgca gtattcagaa gaagcaagac taaaaagaga ggaaataagt   1560

ggagtaaaat tggagtcaat aggaacttac caaatactgt caatttattc tacagtggcg   1620

agttccctag cactggcaat catggtagct ggtctatctt tatggatgtg ctccaatggg   1680

tcgttacaat gcagaatttg catttaa                                        1707
```

<210> SEQ ID NO 51
<211> LENGTH: 568
<212> TYPE: PRT

-continued

<213> ORGANISM: Influenza A Virus

<400> SEQUENCE: 51

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400
```

```
Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565


<210> SEQ ID NO 52
<211> LENGTH: 1707
<212> TYPE: DNA
<213> ORGANISM: Artificial sequence
<220> FEATURE:
<223> OTHER INFORMATION: Codon modified Influenza A Virus sequence

<400> SEQUENCE: 52

atggaaaaaa tcgtgctgct gttcgctatc gtctcgctgg tcaaatcgga tcagatctgc     60

atcggatacc atgctaacaa ctcgacggaa caggtcgaca cgatcatgga aaagaacgtc    120

acggtcacgc atgctcaaga catcctggaa aagacgcaca acggaaagct gtgcgatctg    180

gatggagtga agcctctgat cctgagagat tgttcggtcg ctggatggct gctgggaaac    240

cccatgtgtg acgaatttat caatgtgccc gaatggtcgt acatcgtgga aaaggctaat    300

cccgctaatg acctgtgtta ccccggagat tttaacgact atgaagaact gaaacacctg    360

ctgtcgagaa tcaaccattt cgaaaaaatc cagatcatcc ccaaaaattc gtggtcgtcg    420

catgaagctt cgctgggagt gtcgtcggct tgtccctacc aaggaaagtc gtcgttcttt    480

agaaatgtgg tctggctgat caaaaagaac aatgcttacc ccacgatcaa gagatcgtac    540

aataatacga accaagaaga tctgctggtc ctgtggggaa tccaccatcc taatgatgct    600

gctgaacaga cgagactgta tcaaaacccc acgacgtaca tctcggtcgg aacgtcgacg    660

ctgaaccaga gactggtccc caaaatcgct acgagatcga aagtcaacgg acaaaatgga    720

agaatggaat ttttttggac gatcctgaaa cccaatgatg ctatcaactt tgaatcgaat    780

ggaaatttta tcgctcccga atatgcttac aaaatcgtca agaaaggaga ctcggctatc    840

atgaaatcgg aactggaata tggaaactgc aacacgaagt gtcaaacgcc catgggagct    900

atcaactcgt cgatgccctt tcacaatatc caccctctga cgatcggaga atgcccccaaa    960

tatgtgaaat cgaacagact ggtcctggct acgggactga gaaattcgcc tcaaagagaa   1020

agaagaagaa aaaagagagg actgttcgga gctatcgctg gattcatcga aggaggatgg   1080
```

```
cagggaatgg tcgatggatg gtatggatac caccattcga atgaacaggg atcgggatac   1140

gctgctgaca aagaatcgac gcaaaaggct atcgatggag tcacgaataa ggtcaactcg   1200

atcatcgaca aaatgaacac gcagttcgaa gctgtcggaa gagaattcaa taacctggaa   1260

agaagaatcg aaaatctgaa caagaagatg gaagacggat ttctggatgt ctggacgtat   1320

aatgctgaac tgctggtcct gatggaaaat gaaagaacgc tggacttcca tgactcgaat   1380

gtcaagaacc tgtacgacaa ggtccgactg cagctgagag ataatgctaa ggaactggga   1440

aacggatgtt ttgaatttta tcacaaatgt gataatgaat gtatggaatc ggtcagaaac   1500

ggaacgtatg actaccccca gtattcggaa gaagctagac tgaaaagaga agaaatctcg   1560

ggagtcaaac tggaatcgat cggaacgtac caaatcctgt cgatctattc gacggtggct   1620

tcgtcgctgg ctctggctat catggtcgct ggactgtcgc tgtggatgtg ctcgaatgga   1680

tcgctgcaat gcagaatctg catctaa                                       1707
```

<210> SEQ ID NO 53
<211> LENGTH: 1701
<212> TYPE: DNA
<213> ORGANISM: Influenza A Virus

<400> SEQUENCE: 53

```
atgaagacta tcattgctct gagctacatt ttatgtctgg tcttcgctca aaaacttccc     60

cgaaatgaca acagcacggc aacgctgtgc ttgggacacc atgcagtgtc aaacggaaca    120

ctagtgaaaa caatcacgaa tgaccaaatt gaagtgacta atgctactga attggttcag    180

agttcctcaa caggtagaat atgtgaccga cctcatcgaa tccttgatgg ggaaaactgc    240

acactgatag atgctctctt gggagaccct cattgtgata gtttccaaaa caaggaatgg    300

gaccttttg tagaacgcag cacagcttac agcgactgtt acccttatga tgtgccggat    360

tatgcctccc ttaggtcact agttgcctca tccggcaccc tggagtttaa cgatgaaagt    420

ttcgattgga ctggagtctc tcaggatgga acaagcaatg cttgcaaaag gagatctgtt    480

aaaagttttt ttagtagatt aaattggttg tacaaattag aatacaaata tccagcactg    540

aacgtgacta tgccaaacaa tgaaaaattt gacaaattgt acatttgggg ggtgcaccac    600

ccgagcacgg acagtgacca aaccagtcta tatgttcaag catcagggag agtcacaatc    660

tctaccaaaa gaagccaaca aactgtaatc ccgaatatcg gatctagacc ctgggtaagg    720

ggtatctcca gcagaataag catctattgg acaatagtaa aacctggaga catacttatg    780

attaacagca cagggaatct aatcgcccct cggggttact tcaagatacg aagtggagaa    840

agctcaataa tgaggtcaga tgcacccatt gatagctgca attctgaatg catcactcca    900

aatggaagca ttcccaataa caaaccattt caaaatgtaa acaggatcac atatggggcc    960

tgtcctagat atgttaaaca aaaaactcta aaattggcaa cagggatgcg gaatgtacca   1020

gagaaacaag ctaggggcat attcggcgcc atcgcaggtt tcatagaaaa tggttgggag   1080

ggaatggtag acggttggta cggttttagg catctaaatt ctgagggctc aggacaagca   1140

gcagacctca aaagcactca ggcagcaatt aaccaaatca acgggaaact gaataggttg   1200

gtcgaaaaaa caaacgagaa attccatcaa attgaaaaag aattctcaga cgtggaaggg   1260

agaattcagg atctcgagaa atatgttgaa gacaccaaaa tagatctctg gtcatacaat   1320

gcggagcttc ttgttgccct ggagaaccaa cacacaattg atctaactga ctcagaaatg   1380

aacaaactgt tcgaaagaac aaggaaacaa ctgagggaaa atgctgagga catgggcaat   1440

ggttgcttca aaatatacca caaatgtgac aatgcctgca tagggtcgat cagaaatgga   1500
```

-continued

```
acttatgacc ataatgtata cagagacgaa gcattaaaca accgactcca tatcaaaggg   1560

gttgagctga agtcaggata caaagattgg atcttatgga tctcattttc catatcatgc   1620

tttttgtttt gtgttgtttt gctggggttc atcatgtggg cctgccaaaa aggcaacatt   1680

aggtgcaaca tttgcatttg a                                             1701
```

<210> SEQ ID NO 54
<211> LENGTH: 566
<212> TYPE: PRT
<213> ORGANISM: Influenza A Virus

<400> SEQUENCE: 54

```
Met Lys Thr Ile Ile Ala Leu Ser Tyr Ile Leu Cys Leu Val Phe Ala
1               5                   10                  15

Gln Lys Leu Pro Arg Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Arg Pro His Arg Ile Leu Asp Gly Glu Asn Cys
65                  70                  75                  80

Thr Leu Ile Asp Ala Leu Leu Gly Asp Pro His Cys Asp Ser Phe Gln
                85                  90                  95

Asn Lys Glu Trp Asp Leu Phe Val Glu Arg Ser Thr Ala Tyr Ser Asp
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asp Trp Thr
    130                 135                 140

Gly Val Ser Gln Asp Gly Thr Ser Asn Ala Cys Lys Arg Arg Ser Val
145                 150                 155                 160

Lys Ser Phe Phe Ser Arg Leu Asn Trp Leu Tyr Lys Leu Glu Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Thr
        195                 200                 205

Ser Leu Tyr Val Gln Ala Ser Gly Arg Val Thr Ile Ser Thr Lys Arg
    210                 215                 220

Ser Gln Gln Thr Val Ile Pro Asn Ile Gly Ser Arg Pro Trp Val Arg
225                 230                 235                 240

Gly Ile Ser Ser Arg Ile Ser Ile Tyr Trp Thr Ile Val Lys Pro Gly
                245                 250                 255

Asp Ile Leu Met Ile Asn Ser Thr Gly Asn Leu Ile Ala Pro Arg Gly
            260                 265                 270

Tyr Phe Lys Ile Arg Ser Gly Glu Ser Ser Ile Met Arg Ser Asp Ala
        275                 280                 285

Pro Ile Asp Ser Cys Asn Ser Glu Cys Ile Thr Pro Asn Gly Ser Ile
    290                 295                 300

Pro Asn Asn Lys Pro Phe Gln Asn Val Asn Arg Ile Thr Tyr Gly Ala
305                 310                 315                 320

Cys Pro Arg Tyr Val Lys Gln Lys Thr Leu Lys Leu Ala Thr Gly Met
                325                 330                 335
```

```
Arg Asn Val Pro Glu Lys Gln Ala Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Leu Asn Ser Glu Gly Ser Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Val Glu Lys Thr Asn Glu Lys Phe His Gln Ile Glu Lys Glu Phe Ser
                405                 410                 415

Asp Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asn Val Tyr Arg Asp Glu Ala Leu
            500                 505                 510

Asn Asn Arg Leu His Ile Lys Gly Val Glu Leu Lys Ser Gly Tyr Lys
        515                 520                 525

Asp Trp Ile Leu Trp Ile Ser Phe Ser Ile Ser Cys Phe Leu Phe Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 55
<211> LENGTH: 1701
<212> TYPE: DNA
<213> ORGANISM: Artificial sequence
<220> FEATURE:
<223> OTHER INFORMATION: Codon modified Influenza A Viral sequence

<400> SEQUENCE: 55

```
atgaagacga tcatcgctct gtcgtacatc ctgtgtctgg tctttgctca aaaactgccc     60

cgaaatgaca actcgacggc tacgctgtgc ctgggacacc atgctgtgtc gaacggaacg    120

ctggtgaaaa cgatcacgaa tgaccaaatc gaagtgacga atgctacgga actggtccag    180

tcgtcgtcga cgggaagaat ctgtgaccga cctcatcgaa tcctggatgg agaaaactgc    240

acgctgatcg atgctctgct gggagaccct cattgtgatt cgtttcaaaa caaggaatgg    300

gacctgttcg tcgaacgctc gacggcttac tcggactgtt acccttatga tgtgcccgat    360

tatgcttcgc tgagatcgct ggtcgcttcg tcgggaacgc tggaattcaa cgatgaatcg    420

tttgattgga cgggagtctc gcaggatgga acgtcgaatg cttgcaaaag aagatcggtc    480

aaatcgttct tctcgagact gaattggctg tacaaactgg aatacaaata tcccgctctg    540

aacgtgacga tgcccaacaa tgaaaaattc gacaaactgt acatctgggg agtgcaccac    600

ccctcgacgg actcggacca aacgtcgctg tatgtccaag cttcgggaag agtcacgatc    660

tcgacgaaaa gatcgcaaca aacggtcatc cccaatatcg gatcgagacc ctgggtcaga    720
```

```
ggaatctcgt cgagaatctc gatctattgg acgatcgtca aacctggaga catcctgatg    780

atcaactcga cgggaaatct gatcgctcct cgaggatact ttaagatccg atcgggagaa    840

tcgtcgatca tgagatcgga tgctcccatc gattcgtgca attcggaatg catcacgccc    900

aatggatcga tccccaataa caaacccttc caaaatgtca acagaatcac gtatggagct    960

tgtcctagat atgtcaaaca aaaaacgctg aaactggcta cgggaatgcg aaatgtcccc   1020

gaaaaacaag ctagaggaat ctttggagct atcgctggat ttatcgaaaa tggatgggaa   1080

ggaatggtcg acggatggta cggattcaga catctgaatt cggaaggatc gggacaagct   1140

gctgacctga aatcgacgca ggctgctatc aaccaaatca acggaaaact gaatagactg   1200

gtcgaaaaaa cgaacgaaaa atttcatcaa atcgaaaaag aattttcgga cgtggaagga   1260

agaatccagg atctggaaaa atatgtcgaa gacacgaaaa tcgatctgtg gtcgtacaat   1320

gctgaactgc tggtcgctct ggaaaaccaa cacacgatcg atctgacgga ctcggaaatg   1380

aacaaactgt ttgaaagaac gagaaaacaa ctgagagaaa atgctgaaga catgggaaat   1440

ggatgcttta aaatctacca caaatgtgac aatgcttgca tcggatcgat cagaaatgga   1500

acgtatgacc ataatgtcta cagagacgaa gctctgaaca accgactgca tatcaaagga   1560

gtcgaactga agtcgggata caaagattgg atcctgtgga tctcgttctc gatctcgtgc   1620

ttcctgttct gtgtcgtcct gctgggattt atcatgtggg cttgccaaaa aggaaacatc   1680

agatgcaaca tctgcatctg a                                              1701
```

<210> SEQ ID NO 56
<211> LENGTH: 1410
<212> TYPE: DNA
<213> ORGANISM: Influenza A Virus

<400> SEQUENCE: 56

```
atgaatccaa atcagaagat aacaaccatt ggatcaatct gtatggtaat tggaatagtt     60

agcttgatgt tacaaattgg gaacataatc tcaatatggg ttagtcattc aattcaaaca    120

gggaatcaac accaggctga accatgcaat caaagcatta ttacttatga aaacaacacc    180

tgggtaaacc agacatatgt caacatcagc aataccaatt ttcttactga gaaagctgtg    240

gcttcagtaa cattagcggg caattcatct ctttgcccca ttagtggatg ggctgtatac    300

agtaaggaca acggtataag aatcggttcc aagggggatg tgtttgttat aagagagccg    360

ttcatctcat gctcccactt ggaatgcaga actttctttt tgactcaggg agccttgctg    420

aatgacaagc attctaatgg gaccgtcaaa gacagaagcc ctcacagaac attaatgagt    480

tgtcccgtgg gtgaggctcc ttccccatac aactcgaggt ttgagtctgt tgcttggtcg    540

gcaagtgctt gtcatgatgg cactagttgg ttgacaattg gaatttctgg cccagacaat    600

ggggctgtgg ctgtattgaa atacaatggc ataataacag acactatcaa gagttggagg    660

aacaacataa tgagaactca agagtctgaa tgtgcatgtg taaatggctc ttgctttact    720

gttatgactg atggaccaag taatgggcag gcttcataca aaatcttcag aatagaaaaa    780

gggaaagtag ttaaatcagc cgaattaaat gcccctaatt atcactatga ggagtgctcc    840

tgttatcctg atgctggaga aatcacatgt gtgtgcaggg ataactggca tggctcaaat    900

cggccatggg tatctttcaa tcaaaatttg gagtatcgaa taggatatat atgcagtgga    960

gttttcggag acaatccacg ccccaatgat gggacaggca gttgtggtcc ggtgtcccct   1020

aaaggggcat atggaataaa agggttctca tttaaatacg gcaatggtgt ttggatcggg   1080
```

agaaccaaaa gcactaattc caggagcggc tttgaaatga tttgggatcc aaatggatgg 1140
actggtacgg acagtaattt ttcagtaaag caagatattg tagctataac cgattggtca 1200
ggatatagcg ggagttttgt ccagcatcca gaactgacag gattagattg cataagacct 1260
tgtttctggg ttgagctaat cagagggcgg cccaaagaga gcacaatttg gactagtggg 1320
agcagcatat ccttttgtgg tgtaaatagt gacactgtgg gttggtcttg gccagacggt 1380
gctgagttgc cattcaccat tgacaagtag 1410

<210> SEQ ID NO 57
<211> LENGTH: 469
<212> TYPE: PRT
<213> ORGANISM: Influenza A Virus

<400> SEQUENCE: 57

Met Asn Pro Asn Gln Lys Ile Thr Thr Ile Gly Ser Ile Cys Met Val
1 5 10 15

Ile Gly Ile Val Ser Leu Met Leu Gln Ile Gly Asn Ile Ile Ser Ile
20 25 30

Trp Val Ser His Ser Ile Gln Thr Gly Asn Gln His Gln Ala Glu Pro
35 40 45

Cys Asn Gln Ser Ile Ile Thr Tyr Glu Asn Asn Thr Trp Val Asn Gln
50 55 60

Thr Tyr Val Asn Ile Ser Asn Thr Asn Phe Leu Thr Glu Lys Ala Val
65 70 75 80

Ala Ser Val Thr Leu Ala Gly Asn Ser Ser Leu Cys Pro Ile Ser Gly
85 90 95

Trp Ala Val Tyr Ser Lys Asp Asn Gly Ile Arg Ile Gly Ser Lys Gly
100 105 110

Asp Val Phe Val Ile Arg Glu Pro Phe Ile Ser Cys Ser His Leu Glu
115 120 125

Cys Arg Thr Phe Phe Leu Thr Gln Gly Ala Leu Leu Asn Asp Lys His
130 135 140

Ser Asn Gly Thr Val Lys Asp Arg Ser Pro His Arg Thr Leu Met Ser
145 150 155 160

Cys Pro Val Gly Glu Ala Pro Ser Pro Tyr Asn Ser Arg Phe Glu Ser
165 170 175

Val Ala Trp Ser Ala Ser Ala Cys His Asp Gly Thr Ser Trp Leu Thr
180 185 190

Ile Gly Ile Ser Gly Pro Asp Asn Gly Ala Val Ala Val Leu Lys Tyr
195 200 205

Asn Gly Ile Ile Thr Asp Thr Ile Lys Ser Trp Arg Asn Asn Ile Met
210 215 220

Arg Thr Gln Glu Ser Glu Cys Ala Cys Val Asn Gly Ser Cys Phe Thr
225 230 235 240

Val Met Thr Asp Gly Pro Ser Asn Gly Gln Ala Ser Tyr Lys Ile Phe
245 250 255

Arg Ile Glu Lys Gly Lys Val Val Lys Ser Ala Glu Leu Asn Ala Pro
260 265 270

Asn Tyr His Tyr Glu Glu Cys Ser Cys Tyr Pro Asp Ala Gly Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Arg Ile Gly Tyr Ile Cys Ser Gly
305 310 315 320

-continued

```
Val Phe Gly Asp Asn Pro Arg Pro Asn Asp Gly Thr Gly Ser Cys Gly
                325                 330                 335

Pro Val Ser Pro Lys Gly Ala Tyr Gly Ile Lys Gly Phe Ser Phe Lys
            340                 345                 350

Tyr Gly Asn Gly Val Trp Ile Gly Arg Thr Lys Ser Thr Asn Ser Arg
        355                 360                 365

Ser Gly Phe Glu Met Ile Trp Asp Pro Asn Gly Trp Thr Gly Thr Asp
    370                 375                 380

Ser Asn Phe Ser Val Lys Gln Asp Ile Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Ser Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465
```

```
<210> SEQ ID NO 58
<211> LENGTH: 1410
<212> TYPE: DNA
<213> ORGANISM: Artificial sequence
<220> FEATURE:
<223> OTHER INFORMATION: Codon modified Influenza A Virus sequence

<400> SEQUENCE: 58

atgaatccca atcagaagat cacgacgatc ggatcgatct gtatggtcat cggaatcgtc      60

tcgctgatgc tgcaaatcgg aaacatcatc tcgatctggg tctcgcattc gatccaaacg     120

ggaaatcaac accaggctga accctgcaat caatcgatca tcacgtatga aaacaacacg     180

tgggtcaacc agacgtatgt caacatctcg aatacgaatt tcctgacgga aaaagctgtg     240

gcttcggtca cgctggctgg aaattcgtcg ctgtgcccca tctcgggatg ggctgtctac     300

tcgaaggaca acggaatcag aatcggatcg aagggagatg tgttcgtcat cagagaaccc     360

tttatctcgt gctcgcacct ggaatgcaga acgtttttcc tgacgcaggg agctctgctg     420

aatgacaagc attcgaatgg aacggtcaaa gacagatcgc ctcacagaac gctgatgtcg     480

tgtcccgtgg gagaagctcc ttcgccctac aactcgagat tcgaatcggt cgcttggtcg     540

gcttcggctt gtcatgatgg aacgtcgtgg ctgacgatcg gaatctcggg acccgacaat     600

ggagctgtgg ctgtcctgaa atacaatgga atcatcacgg acacgatcaa gtcgtggaga     660

aacaacatca tgagaacgca agaatcggaa tgtgcttgtg tcaatggatc gtgcttcacg     720

gtcatgacgg atggaccctc gaatggacag gcttcgtaca aaatctttag aatcgaaaaa     780

ggaaaagtcg tcaaatcggc tgaactgaat gctcctaatt atcactatga agaatgctcg     840

tgttatcctg atgctggaga aatcacgtgt gtgtgcagag ataactggca tggatcgaat     900

cgaccctggg tctcgtttaa tcaaaatctg gaatatcgaa tcggatatat ctgctcggga     960

gtctttggag acaatccccg ccccaatgat ggaacgggat cgtgtggacc cgtgtcgcct    1020

aaaggagctt atggaatcaa aggattttcg ttcaaatacg gaaatggagt ctggatcgga    1080

agaacgaaat cgacgaattc gagatcggga ttcgaaatga tctgggatcc caatggatgg    1140
```

-continued

```
acgggaacgg actcgaattt ctcggtcaag caagatatcg tcgctatcac ggattggtcg   1200

ggatattcgg gatcgttcgt ccagcatccc gaactgacgg gactggattg catcagacct   1260

tgtttttggg tcgaactgat cagaggacga cccaaagaat cgacgatctg gacgtcggga   1320

tcgtcgatct cgttctgtgg agtcaattcg gacacggtgg gatggtcgtg gcccgacgga   1380

gctgaactgc cctttacgat cgacaagtag                                    1410
```

<210> SEQ ID NO 59
<211> LENGTH: 1410
<212> TYPE: DNA
<213> ORGANISM: Influenza A Virus

<400> SEQUENCE: 59

```
atgaatacaa atcaaaaaat aataaccatt ggaacagcct gtctgatagt cggaataatt     60

agtctattat tgcagatagg agatatagtc tcgttatgga taagccattc aattcagact    120

ggagagaaaa accactctca gatatgcagt caaagtgtca ttacatatga aaacaacaca    180

tgggtgaacc aaacttatgt aaacattggc aataccaata ttgctgatgg acagggagta    240

aattcaataa tactagcggg caattcctct ctttgcccag taagtggatg ggccatatac    300

agcaaagaca atagcataag gatcggttcc aaaggagaca tttttgtcat aagagaacta    360

tttatctcat gctctcattt ggagtgcaga actttttatc tgacccaagg tgctttgctg    420

aatgacaagc attctaatgg aaccgtcaaa gacaggagtc cttatagaac cttaatgagc    480

tgcccgattg gtgaagctcc ttctccgtac aattcaaggt tcgaatcagt tgcttggtca    540

gcaagtgcat gccatgacgg aatgggatgg ctgacaatcg gaatttccgg cccagataat    600

ggagcagtgg ctgttttgaa atacaatggg ataataacag atacaataaa aagttggagg    660

aacaaaatac taagaacaca agaatcagaa tgtgtctgta taaacggttc gtgtttcact    720

ataatgactg atggcccaag caatgggcag gcctcataca aaatattcaa aatgaagaaa    780

gggaaaatta ttaaatcagt ggagatgaat gcacctaatt accactatga ggaatgctcc    840

tgttaccctg atacaggcaa agtggtgtgc gtgtgcagag acaattggca tgcttcgaat    900

agaccgtggg tctctttcga tcagaacctt aattatcaga tagggtacat atgtagtggg    960

gttttcggtg ataacccgcg ttctaatgat gggagaggcg attgtgggcc agtactttct   1020

aatggagcta atggagtgaa aggattctca tttaggtatg gcaatggcgt ttggatagga   1080

agaactaaaa gcatcagctc tagaagtgga tttgagatga tttgggatcc gaatggatgg   1140

acggaaaccg atagtagttt ctcgataaag caggatgtta tagcattaac tgattggtca   1200

ggatacagtg ggaactttgt ccaacatccc gaattaacag gaatgaactg cataaagcct   1260

tgtttctggg tagagttaat cagaggacag cccaaggaga gaacaatctg gactagtgga   1320

agcagcattt ctttctgtgg tgtagacagt gaaaccgcaa gctggtcatg gccagacgga   1380

gctgatctgc cattcactat tgacaagtag                                    1410
```

<210> SEQ ID NO 60
<211> LENGTH: 469
<212> TYPE: PRT
<213> ORGANISM: Influenza A Virus

<400> SEQUENCE: 60

```
Met Asn Thr Asn Gln Lys Ile Ile Thr Ile Gly Thr Ala Cys Leu Ile
1               5                   10                  15

Val Gly Ile Ile Ser Leu Leu Leu Gln Ile Gly Asp Ile Val Ser Leu
            20                  25                  30
```

-continued

```
Trp Ile Ser His Ser Ile Gln Thr Gly Glu Lys Asn His Ser Gln Ile
        35                  40                  45

Cys Ser Gln Ser Val Ile Thr Tyr Glu Asn Asn Thr Trp Val Asn Gln
    50                  55                  60

Thr Tyr Val Asn Ile Gly Asn Thr Asn Ile Ala Asp Gly Gln Gly Val
65                  70                  75                  80

Asn Ser Ile Ile Leu Ala Gly Asn Ser Ser Leu Cys Pro Val Ser Gly
                85                  90                  95

Trp Ala Ile Tyr Ser Lys Asp Asn Ser Ile Arg Ile Gly Ser Lys Gly
            100                 105                 110

Asp Ile Phe Val Ile Arg Glu Leu Phe Ile Ser Cys Ser His Leu Glu
        115                 120                 125

Cys Arg Thr Phe Tyr Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Val Cys Ile Asn Gly Ser Cys Phe Thr
225                 230                 235                 240

Ile Met Thr Asp Gly Pro Ser Asn Gly Gln Ala Ser Tyr Lys Ile Phe
                245                 250                 255

Lys Met Lys Lys Gly Lys Ile Ile Lys Ser Val Glu Met Asn Ala Pro
            260                 265                 270

Asn Tyr His Tyr Glu Glu Cys Ser Cys Tyr Pro Asp Thr Gly Lys Val
        275                 280                 285

Val Cys Val Cys Arg Asp Asn Trp His Ala Ser Asn Arg Pro Trp Val
    290                 295                 300

Ser Phe Asp Gln Asn Leu Asn Tyr Gln Ile Gly Tyr Ile Cys Ser Gly
305                 310                 315                 320

Val Phe Gly Asp Asn Pro Arg Ser Asn Asp Gly Arg Gly Asp Cys Gly
                325                 330                 335

Pro Val Leu Ser Asn Gly Ala Asn Gly Val Lys Gly Phe Ser Phe Arg
            340                 345                 350

Tyr Gly Asn Gly Val Trp Ile Gly Arg Thr Lys Ser Ile Ser Ser Arg
        355                 360                 365

Ser Gly Phe Glu Met Ile Trp Asp Pro Asn Gly Trp Thr Glu Thr Asp
    370                 375                 380

Ser Ser Phe Ser Ile Lys Gln Asp Val Ile Ala Leu Thr Asp Trp Ser
385                 390                 395                 400

Gly Tyr Ser Gly Asn Phe Val Gln His Pro Glu Leu Thr Gly Met Asn
                405                 410                 415

Cys Ile Lys Pro Cys Phe Trp Val Glu Leu Ile Arg Gly Gln Pro Lys
            420                 425                 430

Glu Arg Thr Ile Trp Thr Ser Gly Ser Ser Ile Ser Phe Cys Gly Val
        435                 440                 445
```

-continued

Asp Ser Glu Thr Ala Ser Trp Ser Trp Pro Asp Gly Ala Asp Leu Pro
450 455 460

Phe Thr Ile Asp Lys
465

<210> SEQ ID NO 61
<211> LENGTH: 1410
<212> TYPE: DNA
<213> ORGANISM: Artificial sequence
<220> FEATURE:
<223> OTHER INFORMATION: Codon modified Influenza A Virus sequence

<400> SEQUENCE: 61
atgaatacga atcaaaaaat catcacgatc ggaacggctt gtctgatcgt cggaatcatc 60
tcgctgctgc tgcagatcgg agatatcgtc tcgctgtgga tctcgcattc gatccagacg 120
ggagaaaaaa accactcgca gatctgctcg caatcggtca tcacgtatga aaacaacacg 180
tgggtgaacc aaacgtatgt caacatcgga aatacgaata tcgctgatgg acagggagtc 240
aattcgatca tcctggctgg aaattcgtcg ctgtgccccg tctcgggatg ggctatctac 300
tcgaaagaca attcgatcag aatcggatcg aaaggagaca tcttcgtcat cagagaactg 360
ttcatctcgt gctcgcatct ggaatgcaga acgttctatc tgacgcaagg agctctgctg 420
aatgacaagc attcgaatgg aacggtcaaa gacagatcgc cttatagaac gctgatgtcg 480
tgccccatcg gagaagctcc ttcgccctac aattcgagat ttgaatcggt cgcttggtcg 540
gcttcggctt gccatgacgg aatgggatgg ctgacgatcg gaatctcggg acccgataat 600
ggagctgtgg ctgtcctgaa atacaatgga atcatcacgg atacgatcaa atcgtggaga 660
aacaaaatcc tgagaacgca agaatcggaa tgtgtctgta tcaacggatc gtgttttacg 720
atcatgacgg atggaccctc gaatggacag gcttcgtaca aaatctttaa aatgaagaaa 780
ggaaaaatca tcaaatcggt ggaaatgaat gctcctaatt accactatga agaatgctcg 840
tgttaccctg atacgggaaa agtggtgtgc gtgtgcagag acaattggca tgcttcgaat 900
agaccctggg tctcgtttga tcagaacctg aattatcaga tcggatacat ctgttcggga 960
gtctttggag ataacccccg ttcgaatgat ggaagaggag attgtggacc cgtcctgtcg 1020
aatggagcta atggagtgaa aggattttcg ttcagatatg gaaatggagt ctggatcgga 1080
agaacgaaat cgatctcgtc gagatcggga ttcgaaatga tctgggatcc caatggatgg 1140
acggaaacgg attcgtcgtt ttcgatcaag caggatgtca tcgctctgac ggattggtcg 1200
ggatactcgg gaaacttcgt ccaacatccc gaactgacgg gaatgaactg catcaagcct 1260
tgtttttggg tcgaactgat cagaggacag cccaaggaaa gaacgatctg gacgtcggga 1320
tcgtcgatct cgttttgtgg agtcgactcg gaaacggctt cgtggtcgtg gcccgacgga 1380
gctgatctgc cctttacgat cgacaagtag 1410

<210> SEQ ID NO 62
<211> LENGTH: 576
<212> TYPE: DNA
<213> ORGANISM: Hepatitis C Virus E1

<400> SEQUENCE: 62
taccaagtgc gcaattcctc ggggctttac catgtcacca atgattgccc taactcgagt 60
attgtgtacg aggcggccga tgccatcctg cacactccgg ggtgtgtccc ttgcgttcgc 120
gagggtaacg cctcgaggtg ttgggtggcg gtgacccccca cggtggccac cagggacggc 180
aaactcccca caacgcagct tcgacgtcat atcgatctgc ttgtcgggag cgccaccctc 240

-continued

```
tgctcggccc tctacgtggg ggacctgtgc gggtctgtct ttcttgttgg tcaactgttt    300

accttctctc ccaggcgcca ctggacgacg caagactgca attgttctat ctatcccggc    360

catataacgg gtcatcgcat ggcatgggat atgatgatga actggtcccc tacggcagcg    420

ttggtggtag ctcagctgct ccggatccca caagccatca tggacatgat cgctggtgct    480

cactggggag tcctggcggg catagcgtat ttctccatgg tggggaactg ggcgaaggtc    540

ctggtagtgc tgctgctatt tgccggcgtc gacgcg                              576


<210> SEQ ID NO 63
<211> LENGTH: 192
<212> TYPE: PRT
<213> ORGANISM: Hepatitis C Virus E1

<400> SEQUENCE: 63

Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Val Ala
    130                 135                 140

Gln Leu Leu Arg Ile Pro Gln Ala Ile Met Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190


<210> SEQ ID NO 64
<211> LENGTH: 576
<212> TYPE: DNA
<213> ORGANISM: Artificial sequence
<220> FEATURE:
<223> OTHER INFORMATION: Codon modified Hepatitis C Virus E1 sequence

<400> SEQUENCE: 64

taccaagtgc gcaattcgtc gggactgtac catgtcacga atgattgccc taactcgtcg     60

atcgtgtacg aagctgctga tgctatcctg cacacgcccg gatgtgtccc ttgcgtccgc    120

gaaggaaacg cttcgagatg ttgggtggct gtgacgccca cggtggctac gagagacgga    180

aaactgccca cgacgcagct gcgacgtcat atcgatctgc tggtcggatc ggctacgctg    240

tgctcggctc tgtacgtggg agacctgtgc ggatcggtct tcctggtcgg acaactgttc    300

acgttttcgc ccagacgcca ctggacgacg caagactgca attgttcgat ctatcccgga    360
```

-continued

```
catatcacgg gacatcgcat ggcttgggat atgatgatga actggtcgcc tacggctgct    420
ctggtggtcg ctcagctgct gcgaatcccc caagctatca tggacatgat cgctggagct    480
cactggggag tcctggctgg aatcgcttat ttttcgatgg tgggaaactg ggctaaggtc    540
ctggtcgtgc tgctgctgtt cgctggagtc gacgct                              576
```

<210> SEQ ID NO 65
<211> LENGTH: 1089
<212> TYPE: DNA
<213> ORGANISM: Hepatitis C Virus E2

<400> SEQUENCE: 65

```
gaaacccacg tcaccggggg aagtgccggc cgcaccacgg ctgggcttgt tggtctcctt     60
acaccaggcg ccaagcagaa catccaactg atcaacacca acggcagttg gcacatcaat    120
agcacggcct tgaactgcaa tgaaagcctt aacaccggct ggttagcagg gctcttctat    180
cagcacaaat tcaactcttc aggctgtcct gagaggttgg ccagctgccg acgccttacc    240
gattttgccc agggctgggg tcctatcagt tatgccaacg gaagcggcct cgacgaacgc    300
ccctactgct ggcactaccc tccaagacct tgtggcattg tgcccgcaaa gagcgtgtgt    360
ggcccggtat attgcttcac tcccagcccc gtggtggtgg gaacgaccga caggtcgggc    420
gcgcctacct acagctgggg tgcaaatgat acggatgtct tcgtccttaa caacaccagg    480
ccaccgctgg gcaattggtt cggttgtacc tggatgaact caactggatt caccaaagtg    540
tgcggagcgc ccccttgtgt catcggaggg gtgggcaaca acaccttgct ctgccccact    600
gattgtttcc gcaagcatcc ggaagccaca tactctcggt gcggctccgg tccctggatt    660
acacccaggt gcatggtcga ctacccgtat aggctttggc actatccttg taccatcaat    720
tacaccatat tcaaagtcag gatgtacgtg ggaggggtcg agcacaggct ggaagcggcc    780
tgcaactgga cgcggggcga acgctgtgat ctggaagaca gggacaggtc cgagctcagc    840
ccattgctgc tgtccaccac acagtggcag gtccttccgt gttctttcac gaccctgcca    900
gccttgtcca ccggcctcat ccacctccac cagaacattg tggacgtgca gtacttgtac    960
ggggtagggt caagcatcgc gtcctgggcc attaagtggg agtacgtcgt tctcctgttc   1020
ctcctgcttg cagacgcgcg cgtctgctcc tgcttgtgga tgatgttact catatcccaa   1080
gcggaggcg                                                           1089
```

<210> SEQ ID NO 66
<211> LENGTH: 363
<212> TYPE: PRT
<213> ORGANISM: Hepatitis C Virus E2

<400> SEQUENCE: 66

```
Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95
```

```
Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
            340                 345                 350

Trp Met Met Leu Leu Ile Ser Gln Ala Glu Ala
        355                 360


<210> SEQ ID NO 67
<211> LENGTH: 1089
<212> TYPE: DNA
<213> ORGANISM: Artificial sequence
<220> FEATURE:
<223> OTHER INFORMATION: Codon modified Hepatitis C Virus E2 sequence

<400> SEQUENCE: 67

gaaacgcacg tcacgggagg atcggctgga cgcacgacgg ctggactggt cggactgctg      60

acgcccggag ctaagcagaa catccaactg atcaacacga acggatcgtg gcacatcaat     120

tcgacggctc tgaactgcaa tgaatcgctg aacacgggat ggctggctgg actgttttat     180

cagcacaaat ttaactcgtc gggatgtcct gaaagactgg cttcgtgccg acgcctgacg     240

gatttcgctc agggatgggg acctatctcg tatgctaacg gatcgggact ggacgaacgc     300

ccctactgct ggcactaccc tcccagacct tgtggaatcg tgcccgctaa gtcggtgtgt     360

ggacccgtct attgctttac gccctcgccc gtggtggtgg gaacgacgga cagatcggga     420

gctcctacgt actcgtgggg agctaatgat acggatgtct ttgtcctgaa caacacgaga     480

ccccccctgg gaaattggtt tggatgtacg tggatgaact cgacgggatt tacgaaagtg     540
```

```
tgcggagctc ccccttgtgt catcggagga gtgggaaaca acacgctgct gtgccccacg     600

gattgttttc gcaagcatcc cgaagctacg tactcgcgat gcggatcggg accctggatc     660

acgcccagat gcatggtcga ctacccctat agactgtggc actatccttg tacgatcaat     720

tacacgatct ttaaagtcag aatgtacgtg ggaggagtcg aacacagact ggaagctgct     780

tgcaactgga cgcgaggaga acgctgtgat ctggaagaca gagacagatc ggaactgtcg     840

cccctgctgc tgtcgacgac gcagtggcag gtcctgccct gttcgtttac gacgctgccc     900

gctctgtcga cgggactgat ccacctgcac cagaacatcg tggacgtgca gtacctgtac     960

ggagtcggat cgtcgatcgc ttcgtgggct atcaagtggg aatacgtcgt cctgctgttt    1020

ctgctgctgg ctgacgctcg cgtctgctcg tgcctgtgga tgatgctgct gatctcgcaa    1080

gctgaagct                                                            1089


<210> SEQ ID NO 68
<211> LENGTH: 2724
<212> TYPE: DNA
<213> ORGANISM: Epstein Barr Virus

<400> SEQUENCE: 68

atggaggcag ccttgcttgt gtgtcagtac accatccaga gcctgatcca tctcacgggt      60

gaagatcctg gtttttttcaa tgttgagatt ccggaattcc cattttaccc cacatgcaat     120

gtttgcacgg cagatgtcaa tgtaactatc aatttcgatg tcgggggcaa aaagcatcaa     180

cttgatcttg actttggcca gctgacaccc catacgaagg ctgtctacca acctcgaggt     240

gcatttggtg gctcagaaaa tgccaccaat ctctttctac tggagctcct tggtgcagga     300

gaattggctc taactatgcg gtctaagaag cttccaatta acgtcaccac cggagaggag     360

caacaagtaa gcctggaatc tgtagatgtc tactttcaag atgtgtttgg aaccatgtgg     420

tgccaccatg cagaaatgca aaaccccgtg tacctgatac cagaaacagt gccatacata     480

aagtgggata actgtaattc taccaatata acggcagtag tgagggcaca ggggctggat     540

gtcacgctac ccttaagttt gccaacgtca gctcaagact cgaatttcag cgtaaaaaca     600

gaaatgctcg gtaatgagat agatattgag tgtattatgg aggatggcga aatttcacaa     660

gttctgcccg gagacaacaa atttaacatc acctgcagtg gatacgagag ccatgttccc     720

agcggcggaa ttctcacatc aacgagtccc gtggccaccc caatacctgg tacagggtat     780

gcatacagcc tgcgtctgac accacgtcca gtgtcacgat ttcttggcaa taacagtatc     840

ctgtacgtgt tttactctgg gaatggaccg aaggcgagcg ggggagatta ctgcattcag     900

tccaacattg tgttctctga tgagattcca gcttcacagg acatgccgac aaacaccaca     960

gacatcacat atgtgggtga caatgctacc tattcagtgc caatggtcac ttctgaggac    1020

gcaaactcgc caaatgttac agtgactgcc ttttgggcct ggccaaacaa cactgaaact    1080

gactttaagt gcaaatggac tctcacctcg gggacacctt cgggttgtga aaatatttct    1140

ggtgcatttg cgagcaatcg gacatttgac attactgtct cgggtcttgg cacggccccc    1200

aagacactca ttatcacacg aacggctacc aatgccacca caacaaccca caaggttata    1260

ttctccaagg cacccgagag caccaccacc tcccctacct tgaatacaac tggatttgct    1320

gatcccaata caacgacagg tctacccagc tctactcacg tgcctaccaa cctcaccgca    1380

cctgcaagca caggccccac tgtatccacc gcggatgtca ccagcccaac accagccggc    1440

acaacgtcag gcgcatcacc ggtgacacca agtccatctc catgggacaa cggcacagaa    1500
```

-continued

```
agtaaggccc ccgacatgac cagctccacc tcaccagtga ctaccccaac cccaaatgcc   1560

accagcccca ccccagcagt gactacccca accccaaatg ccaccagccc caccccagca   1620

gtgactaccc caaccccaaa tgccaccagc cccaccttgg gaaaaacaag tcctacctca   1680

gcagtgacta ccccaacccc aaatgccacc agccccacct tgggaaaaac aagccccacc   1740

tcagcagtga ctaccccaac cccaaatgcc accagcccca ccttgggaaa aacaagcccc   1800

acctcagcag tgactacccc aaccccaaat gccaccggcc ctactgtggg agaaacaagt   1860

ccacaggcaa atgccaccaa ccacacctta ggaggaacaa gtcccacccc agtagttacc   1920

agccaaccaa aaaatgcaac cagtgctgtt accacaggcc aacataacat aacttcaagt   1980

tcaacctctt ccatgtcact gagacccagt tcaaacccag agacactcag cccctccacc   2040

agtgacaatt caacgtcaca tatgccttta ctaacctccg ctcacccaac aggtggtgaa   2100

aatataacac aggtgacacc agcctctatc agcacacatc atgtgtccac cagttcgcca   2160

gcaccccgcc caggcaccac cagccaagcg tcaggccctg gaaacagttc cacatccaca   2220

aaaccggggg aggttaatgt caccaaaggc acgccccccc aaaatgcaac gtcgccccag   2280

gcccccagtg gccaaaagac ggcggttccc acggtcacct caacaggtgg aaaggccaat   2340

tctaccaccg gtggaaagca caccacagga catggagccc ggacaagtac agagcccacc   2400

acagattacg gcggtgattc aactacgcca agaccgagat acaatgcgac cacctatcta   2460

cctcccagca cttctagcaa actgcggccc cgctggactt ttacgagccc accggttacc   2520

acagcccaag ccaccgtgcc agtcccgcca acgtcccagc ccagattctc aaacctctcc   2580

atgctagtac tgcagtgggc ctctctggct gtgctgaccc ttctgctgct gctggtcatg   2640

gcggactgcg cctttaggcg taacttgtct acatcccata cctacaccac cccaccatat   2700

gatgacgccg agacctatgt ataa                                          2724
```

<210> SEQ ID NO 69
<211> LENGTH: 907
<212> TYPE: PRT
<213> ORGANISM: Epstein Barr Virus

<400> SEQUENCE: 69

```
Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160
```

-continued

```
Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
            500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Pro Ala Val Thr Thr Pro
    530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575
```

-continued

```
Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
    610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                645                 650                 655

Ile Thr Ser Ser Ser Thr Ser Ser Met Ser Leu Arg Pro Ser Ser Asn
            660                 665                 670

Pro Glu Thr Leu Ser Pro Ser Thr Ser Asp Asn Ser Thr Ser His Met
        675                 680                 685

Pro Leu Leu Thr Ser Ala His Pro Thr Gly Gly Glu Asn Ile Thr Gln
    690                 695                 700

Val Thr Pro Ala Ser Ile Ser Thr His His Val Ser Thr Ser Ser Pro
705                 710                 715                 720

Ala Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
            740                 745                 750

Pro Gln Asn Ala Thr Ser Pro Gln Ala Pro Ser Gly Gln Lys Thr Ala
        755                 760                 765

Val Pro Thr Val Thr Ser Thr Gly Gly Lys Ala Asn Ser Thr Thr Gly
    770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                805                 810                 815

Thr Thr Tyr Leu Pro Pro Ser Thr Ser Ser Lys Leu Arg Pro Arg Trp
            820                 825                 830

Thr Phe Thr Ser Pro Pro Val Thr Thr Ala Gln Ala Thr Val Pro Val
        835                 840                 845

Pro Pro Thr Ser Gln Pro Arg Phe Ser Asn Leu Ser Met Leu Val Leu
    850                 855                 860

Gln Trp Ala Ser Leu Ala Val Leu Thr Leu Leu Leu Leu Leu Val Met
865                 870                 875                 880

Ala Asp Cys Ala Phe Arg Arg Asn Leu Ser Thr Ser His Thr Tyr Thr
                885                 890                 895

Thr Pro Pro Tyr Asp Asp Ala Glu Thr Tyr Val
            900                 905
```

<210> SEQ ID NO 70
<211> LENGTH: 2724
<212> TYPE: DNA
<213> ORGANISM: Artificial sequence
<220> FEATURE:
<223> OTHER INFORMATION: Codon modified Epstein Barr Virus sequence

<400> SEQUENCE: 70

```
atggaagctg ctctgctggt gtgtcagtac acgatccagt cgctgatcca tctgacggga      60

gaagatcctg gattctttaa tgtcgaaatc cccgaatttc ccttctaccc cacgtgcaat     120

gtctgcacgg ctgatgtcaa tgtcacgatc aattttgatg tcggaggaaa aaagcatcaa     180
```

-continued

```
ctggatctgg acttcggaca gctgacgccc catacgaagg ctgtctacca acctcgagga    240
gctttcggag gatcggaaaa tgctacgaat ctgttcctgc tggaactgct gggagctgga    300
gaactggctc tgacgatgcg atcgaagaag ctgcccatca acgtcacgac gggagaagaa    360
caacaagtct cgctggaatc ggtcgatgtc tacttccaag atgtgttcgg aacgatgtgg    420
tgccaccatg ctgaaatgca aaaccccgtg tacctgatcc ccgaaacggt gccctacatc    480
aagtgggata actgtaattc gacgaatatc acggctgtcg tgagagctca gggactggat    540
gtcacgctgc ccctgtcgct gcccacgtcg gctcaagact cgaatttttc ggtcaaaacg    600
gaaatgctgg gaaatgaaat cgatatcgaa tgtatcatgg aagatggaga aatctcgcaa    660
gtcctgcccg gagacaacaa attcaacatc acgtgctcgg gatacgaatc gcatgtcccc    720
tcgggaggaa tcctgacgtc gacgtcgccc gtggctacgc ccatccctgg aacgggatat    780
gcttactcgc tgcgtctgac gccccgtccc gtgtcgcgat tcctgggaaa taactcgatc    840
ctgtacgtgt tctactcggg aaatggaccc aaggcttcgg gaggagatta ctgcatccag    900
tcgaacatcg tgttttcgga tgaaatcccc gcttcgcagg acatgcccac gaacacgacg    960
gacatcacgt atgtgggaga caatgctacg tattcggtgc ccatggtcac gtcggaagac   1020
gctaactcgc ccaatgtcac ggtgacggct ttctgggctt ggcccaacaa cacggaaacg   1080
gacttcaagt gcaaatggac gctgacgtcg ggaacgcctt cgggatgtga aaatatctcg   1140
ggagctttcg cttcgaatcg aacgttcgac atcacggtct cgggactggg aacggctccc   1200
aagacgctga tcatcacgcg aacggctacg aatgctacga cgacgacgca caaggtcatc   1260
ttttcgaagg ctcccgaatc gacgacgacg tcgcctacgc tgaatacgac gggattcgct   1320
gatcccaata cgacgacggg actgccctcg tcgacgcacg tgcctacgaa cctgacggct   1380
cctgcttcga cgggacccac ggtctcgacg gctgatgtca cgtcgcccac gcccgctgga   1440
acgacgtcgg gagcttcgcc cgtgacgccc tcgccctcgc cctgggacaa cggaacggaa   1500
tcgaaggctc ccgacatgac gtcgtcgacg tcgcccgtga cgacgcccac gcccaatgct   1560
acgtcgccca cgcccgctgt gacgacgccc acgcccaatg ctacgtcgcc cacgcccgct   1620
gtgacgacgc ccacgcccaa tgctacgtcg cccacgctgg gaaaaacgtc gcctacgtcg   1680
gctgtgacga cgcccacgcc caatgctacg tcgcccacgc tgggaaaaac gtcgcccacg   1740
tcggctgtga cgacgcccac gcccaatgct acgtcgccca cgctgggaaa aacgtcgccc   1800
acgtcggctg tgacgacgcc cacgcccaat gctacgggac ctacggtggg agaaacgtcg   1860
ccccaggcta atgctacgaa ccacacgctg ggaggaacgt cgcccacgcc cgtcgtcacg   1920
tcgcaaccca aaaatgctac gtcggctgtc acgacgggac aacataacat cacgtcgtcg   1980
tcgacgtcgt cgatgtcgct gagaccctcg tcgaaccccg aaacgctgtc gccctcgacg   2040
tcggacaatt cgacgtcgca tatgcctctg ctgacgtcgg ctcaccccac gggaggagaa   2100
aatatcacgc aggtgacgcc cgcttcgatc tcgacgcatc atgtgtcgac gtcgtcgccc   2160
gctccccgcc ccggaacgac gtcgcaagct tcgggacctg gaaactcgtc gacgtcgacg   2220
aaacccggag aagtcaatgt cacgaaagga acgccccccc aaaatgctac gtcgccccag   2280
gctccctcgg gacaaaagac ggctgtcccc acggtcacgt cgacgggagg aaaggctaat   2340
tcgacgacgg gaggaaagca cacgacggga catggagctc gaacgtcgac ggaacccacg   2400
acggattacg gaggagattc gacgacgccc agacccagat acaatgctac gacgtatctg   2460
cctccctcga cgtcgtcgaa actgcgaccc cgctggacgt tcacgtcgcc ccccgtcacg   2520
acggctcaag ctacggtgcc cgtccccccc acgtcgcagc ccagattttc gaacctgtcg   2580
```

-continued

```
atgctggtcc tgcagtgggc ttcgctggct gtgctgacgc tgctgctgct gctggtcatg   2640

gctgactgcg ctttcagacg taacctgtcg acgtcgcata cgtacacgac gccccctat    2700

gatgacgctg aaacgtatgt ctaa                                          2724
```

<210> SEQ ID NO 71
<211> LENGTH: 2661
<212> TYPE: DNA
<213> ORGANISM: Epstein Barr Virus

<400> SEQUENCE: 71

```
atggaggcag ccttgcttgt gtgtcagtac accatccaga gccttatcca actcacgcgt     60

gatgatcctg gtttttcaa tgttgagatt ctggaattcc cattttaccc agcgtgcaat    120

gtttgcacgg cagatgtcaa tgcaactatc aatttcgatg tcgggggcaa aaagcataaa    180

cttaatcttg actttggcct gctgacaccc catacaaagg ctgtctacca acctcgaggt    240

gcatttggtg gctcagaaaa tgccaccaat ctctttctac tggagctcct tggtgcagga    300

gaattggctc taactatgcg gtctaagaag cttccaatta acatcaccac cggagaggag    360

caacaagtaa gcctggaatc tgtagatgtc tactttcaag atgtgtttgg caccatgtgg    420

tgccaccatg cagaaatgca aaacccagta tacctaatac cagaaacagt gccatacata    480

aagtgggata actgtaattc taccaatata acggcagtag taagggcaca ggggctggat    540

gtcacgctac ccttaagttt gccaacatca gctcaagact cgaatttcag cgtaaaaaca    600

gaaatgctcg gtaatgagat agatattgag tgtattatgg aggatggcga aatttcacaa    660

gttctgcccg gagacaacaa atttaacatc acctgcagtg gatacgagag ccatgttccc    720

agcggcggaa ttctcacatc aacgagtccc gtggccaccc caatacctgg tacagggtat    780

gcatacagcc tgcgtctgac accacgtcca gtgtcacgat ttcttggcaa taacagtata    840

ctgtacgtgt tttactctgg gaatggaccg aaggcgagcg gggagatta ctgcattcag     900

tccaacattg tgttctctga tgagattcca gcttcacagg acatgccgac aaacaccaca    960

gacatcacat atgtgggtga caatgctacc tattcagtgc caatggtcac ttctgaggac   1020

gcaaactcgc caaatgttac agtgactgcc ttttgggcct ggccaaacaa cactgaaact   1080

gactttaagt gcaaatggac tctcacctcg gggacacctt cgggttgtga aaatatttct   1140

ggtgcatttg cgagcaatcg gacatttgac attactgtct cgggtcttgg cacggccccc   1200

aagacactca ttatcacacg aacggctacc aatgccacca caacaaccca caaggttata   1260

ttctccaagg cacccgagag caccaccacc tcccctacct tgaatacaac tggatttgct   1320

gctcccaata caacgacagg tctacccagc tctactcacg tgcctaccaa cctcaccgca   1380

cctgcaagca caggccccac tgtatccacc gcggatgtca ccagcccaac accagccggc   1440

acaacgtcag gcgcatcacc ggtgacacca agtccatctc cacgggacaa cggcacagaa   1500

agtaaggccc ccgacatgac cagccccacc tcagcagtga ctaccccaac cccaaatgcc   1560

accagcccca ccccagcagt gactacccca accccaaatg ccaccagccc caccttggga   1620

aaaacaagtc ccacctcagc agtgactacc ccaaccccaa atgccaccag ccccacccca   1680

gcagtgacta ccccaacccc aaatgccacc atccccacct tgggaaaaac aagtcccacc   1740

tcagcagtga ctaccccaac cccaaatgcc accagcccta ccgtgggaga aacaagtcca   1800

caggcaaata ccaccaacca cacattagga ggaacaagtt ccaccccagt agttaccagc   1860

ccaccaaaaa atgcaaccag tgctgttacc acaggccaac ataacataac ttcaagttca   1920
```

```
acctcttcca tgtcactgag acccagttca atctcagaga cactcagccc ctccaccagt   1980

gacaattcaa cgtcacatat gcctttacta acctccgctc acccaacagg tggtgaaaat   2040

ataacacagg tgacaccagc ctctaccagc acacatcatg tgtccaccag ttcgccagcg   2100

ccccgcccag gcaccaccag ccaagcgtca ggccctggaa acagttccac atccacaaaa   2160

ccgggggagg ttaatgtcac caaaggcacg ccccccaaaa atgcaacgtc gccccaggcc   2220

cccagtggcc aaaagacggc ggttcccacg gtcacctcaa caggtggaaa ggccaattct   2280

accaccggtg gaaagcacac cacaggacat ggagcccgga caagtacaga gcccaccaca   2340

gattacggcg gtgattcaac tacgccaaga acgagataca atgcgaccac ctatctacct   2400

cccagcactt ctagcaaact gcggccccgc tggactttta cgagcccacc ggttaccaca   2460

gcccaagcca ccgtgcctgt cccgccaacg tcccagccca gattctcaaa cctctccatg   2520

ctagtactgc agtgggcctc tctggctgtg ctgacccttc tgctgctgct ggtcatggcg   2580

gactgcgcct tcaggcgtaa cttgtcgaca tcccatacct acaccacccc accatatgat   2640

gacgccgaga cctatgtata a                                             2661


<210> SEQ ID NO 72
<211> LENGTH: 886
<212> TYPE: PRT
<213> ORGANISM: Epstein Barr Virus

<400> SEQUENCE: 72

Met Glu Ala Ala Leu Leu Val Cys Gln Tyr Thr Ile Gln Ser Leu Ile
1               5                   10                  15

Gln Leu Thr Arg Asp Asp Pro Gly Phe Phe Asn Val Glu Ile Leu Glu
            20                  25                  30

Phe Pro Phe Tyr Pro Ala Cys Asn Val Cys Thr Ala Asp Val Asn Ala
        35                  40                  45

Thr Ile Asn Phe Asp Val Gly Gly Lys Lys His Lys Leu Asn Leu Asp
    50                  55                  60

Phe Gly Leu Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Ile Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240
```

-continued

```
Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Ala Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Arg Asp
                485                 490                 495

Asn Gly Thr Glu Ser Lys Ala Pro Asp Met Thr Ser Pro Thr Ser Ala
            500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Leu Gly Lys Thr Ser Pro
    530                 535                 540

Thr Ser Ala Val Thr Thr Pro Thr Pro Asn Ala Thr Ser Pro Thr Pro
545                 550                 555                 560

Ala Val Thr Thr Pro Thr Pro Asn Ala Thr Ile Pro Thr Leu Gly Lys
                565                 570                 575

Thr Ser Pro Thr Ser Ala Val Thr Thr Pro Thr Pro Asn Ala Thr Ser
            580                 585                 590

Pro Thr Val Gly Glu Thr Ser Pro Gln Ala Asn Thr Thr Asn His Thr
        595                 600                 605

Leu Gly Gly Thr Ser Ser Thr Pro Val Val Thr Ser Pro Pro Lys Asn
    610                 615                 620

Ala Thr Ser Ala Val Thr Thr Gly Gln His Asn Ile Thr Ser Ser Ser
625                 630                 635                 640

Thr Ser Ser Met Ser Leu Arg Pro Ser Ser Ile Ser Glu Thr Leu Ser
                645                 650                 655

Pro Ser Thr Ser Asp Asn Ser Thr Ser His Met Pro Leu Leu Thr Ser
```

```
            660                 665                 670

Ala His Pro Thr Gly Gly Glu Asn Ile Thr Gln Val Thr Pro Ala Ser
        675                 680                 685

Thr Ser Thr His His Val Ser Thr Ser Ser Pro Ala Pro Arg Pro Gly
    690                 695                 700

Thr Thr Ser Gln Ala Ser Gly Pro Gly Asn Ser Ser Thr Ser Thr Lys
705                 710                 715                 720

Pro Gly Glu Val Asn Val Thr Lys Gly Thr Pro Pro Lys Asn Ala Thr
                725                 730                 735

Ser Pro Gln Ala Pro Ser Gly Gln Lys Thr Ala Val Pro Thr Val Thr
            740                 745                 750

Ser Thr Gly Gly Lys Ala Asn Ser Thr Thr Gly Gly Lys His Thr Thr
        755                 760                 765

Gly His Gly Ala Arg Thr Ser Thr Glu Pro Thr Thr Asp Tyr Gly Gly
    770                 775                 780

Asp Ser Thr Thr Pro Arg Thr Arg Tyr Asn Ala Thr Thr Tyr Leu Pro
785                 790                 795                 800

Pro Ser Thr Ser Ser Lys Leu Arg Pro Arg Trp Thr Phe Thr Ser Pro
                805                 810                 815

Pro Val Thr Thr Ala Gln Ala Thr Val Pro Val Pro Pro Thr Ser Gln
            820                 825                 830

Pro Arg Phe Ser Asn Leu Ser Met Leu Val Leu Gln Trp Ala Ser Leu
        835                 840                 845

Ala Val Leu Thr Leu Leu Leu Leu Leu Val Met Ala Asp Cys Ala Phe
    850                 855                 860

Arg Arg Asn Leu Ser Thr Ser His Thr Tyr Thr Thr Pro Pro Tyr Asp
865                 870                 875                 880

Asp Ala Glu Thr Tyr Val
                885
```

```
<210> SEQ ID NO 73
<211> LENGTH: 2661
<212> TYPE: DNA
<213> ORGANISM: Artificial sequence
<220> FEATURE:
<223> OTHER INFORMATION: Codon modified Epstein Barr Virus sequence

<400> SEQUENCE: 73

atggaagctg ctctgctggt gtgtcagtac acgatccagt cgctgatcca actgacgcgt     60

gatgatcctg gattctttaa tgtcgaaatc ctggaatttc ccttctaccc cgcttgcaat    120

gtctgcacgg ctgatgtcaa tgctacgatc aattttgatg tcggaggaaa aaagcataaa    180

ctgaatctgg acttcggact gctgacgccc catacgaagg ctgtctacca acctcgagga    240

gctttcggag gatcggaaaa tgctacgaat ctgttcctgc tggaactgct gggagctgga    300

gaactggctc tgacgatgcg atcgaagaag ctgcccatca acatcacgac gggagaagaa    360

caacaagtct cgctggaatc ggtcgatgtc tacttccaag atgtgttcgg aacgatgtgg    420

tgccaccatg ctgaaatgca aaaccccgtc tacctgatcc ccgaaacggt gccctacatc    480

aagtgggata actgtaattc gacgaatatc acggctgtcg tcagagctca gggactggat    540

gtcacgctgc ccctgtcgct gcccacgtcg gctcaagact cgaatttttc ggtcaaaacg    600

gaaatgctgg gaaatgaaat cgatatcgaa tgtatcatgg aagatggaga aatctcgcaa    660

gtcctgcccg gagacaacaa attcaacatc acgtgctcgg gatacgaatc gcatgtcccc    720

tcgggaggaa tcctgacgtc gacgtcgccc gtggctacgc ccatccctgg aacgggatat    780
```

```
gcttactcgc tgcgtctgac gccccgtccc gtgtcgcgat tcctgggaaa taactcgatc    840

ctgtacgtgt tctactcggg aaatggaccc aaggcttcgg gaggagatta ctgcatccag    900

tcgaacatcg tgttttcgga tgaaatcccc gcttcgcagg acatgcccac gaacacgacg    960

gacatcacgt atgtgggaga caatgctacg tattcggtgc ccatggtcac gtcggaagac   1020

gctaactcgc ccaatgtcac ggtgacggct ttctgggctt ggcccaacaa cacggaaacg   1080

gacttcaagt gcaaatggac gctgacgtcg ggaacgcctt cgggatgtga aaatatctcg   1140

ggagctttcg cttcgaatcg aacgttcgac atcacggtct cgggactggg aacggctccc   1200

aagacgctga tcatcacgcg aacggctacg aatgctacga cgacgacgca caaggtcatc   1260

ttttcgaagg ctcccgaatc gacgacgacg tcgcctacgc tgaatacgac gggattcgct   1320

gctcccaata cgacgacggg actgccctcg tcgacgcacg tgcctacgaa cctgacggct   1380

cctgcttcga cgggacccac ggtctcgacg gctgatgtca cgtcgcccac gcccgctgga   1440

acgacgtcgg gagcttcgcc cgtgacgccc tcgccctcgc cccgagacaa cggaacggaa   1500

tcgaaggctc ccgacatgac gtcgcccacg tcggctgtga cgacgcccac gcccaatgct   1560

acgtcgccca cgcccgctgt gacgacgccc acgcccaatg ctacgtcgcc cacgctggga   1620

aaaacgtcgc ccacgtcggc tgtgacgacg cccacgccca atgctacgtc gcccacgccc   1680

gctgtgacga cgcccacgcc caatgctacg atccccacgc tgggaaaaac gtcgcccacg   1740

tcggctgtga cgacgcccac gcccaatgct acgtcgccta cggtgggaga aacgtcgccc   1800

caggctaata cgacgaacca cacgctggga ggaacgtcgt cgacgcccgt cgtcacgtcg   1860

ccccccaaaa atgctacgtc ggctgtcacg acgggacaac ataacatcac gtcgtcgtcg   1920

acgtcgtcga tgtcgctgag accctcgtcg atctcggaaa cgctgtcgcc ctcgacgtcg   1980

gacaattcga cgtcgcatat gcctctgctg acgtcggctc accccacggg aggagaaaat   2040

atcacgcagg tgacgcccgc ttcgacgtcg acgcatcatg tgtcgacgtc gtcgcccgct   2100

ccccgccccg gaacgacgtc gcaagcttcg ggacctggaa actcgtcgac gtcgacgaaa   2160

cccggagaag tcaatgtcac gaaaggaacg ccccccaaaa atgctacgtc gccccaggct   2220

ccctcgggac aaaagacggc tgtccccacg gtcacgtcga cgggaggaaa ggctaattcg   2280

acgacgggag gaaagcacac gacgggacat ggagctcgaa cgtcgacgga acccacgacg   2340

gattacggag gagattcgac gacgcccaga acgagataca atgctacgac gtatctgcct   2400

ccctcgacgt cgtcgaaact gcgaccccgc tggacgttca cgtcgccccc cgtcacgacg   2460

gctcaagcta cggtgcctgt cccccccacg tcgcagccca gattttcgaa cctgtcgatg   2520

ctggtcctgc agtgggcttc gctggctgtg ctgacgctgc tgctgctgct ggtcatggct   2580

gactgcgctt ttagacgtaa cctgtcgacg tcgcatacgt acacgacgcc cccctatgat   2640

gacgctgaaa cgtatgtcta a                                             2661
```

<210> SEQ ID NO 74
<211> LENGTH: 2715
<212> TYPE: DNA
<213> ORGANISM: Herpes Simplex Virus 2

<400> SEQUENCE: 74

```
atgcgcgggg ggggcttgat ttgcgcgctg gtcgtggggg cgctggtggc cgcggtggcg     60

tcggcggccc cggcggcccc ggcggccccc cgcgcctcgg gcggcgtggc cgcgaccgtc    120

gcggcgaacg gggtcccgc ctcccggccg ccccccgtcc cgagccccgc gaccaccaag     180
```

-continued

```
gcccggaagc ggaaaaccaa aaagccgccc aagcggcccg aggcgacccc gccccccgac    240
gccaacgcga ccgtcgccgc cggccacgcc acgctgcgcg cgcacctgcg ggaaatcaag    300
gtcgagaacg ccgatgccca gttttacgtg tgcccgcccc cgacgggcgc cacggtggtg    360
cagtttgagc agccgcgccg ctgcccgacg cgcccggagg ggcagaacta cacggagggc    420
atcgcggtgg tcttcaagga gaacatcgcc ccgtacaaat tcaaggccac catgtactac    480
aaagacgtga ccgtgtcgca ggtgtggttc ggccaccgct actcccagtt tatggggata    540
ttcgaggacc gcgcccccgt tcccttcgag gaggtgatcg acaagattaa caccaagggg    600
gtctgccgct ccacggccaa gtacgtgcgg aacaacatgg agaccaccgc gtttcaccgg    660
gacgaccacg agaccgacat ggagctcaag ccggcgaagg tcgccacgcg cacgagccgg    720
gggtggcaca ccaccgacct caagtacaac ccctcgcggg tggaggcgtt ccatcggtac    780
ggcacgacgg tcaactgcat cgtcgaggag gtggacgcgc ggtcggtgta cccgtacgat    840
gagtttgtgc tggcgacggg cgactttgtg tacatgtccc cgttttacgg ctaccgggag    900
gggtcgcaca ccgagcacac cagctacgcc gccgaccgct tcaagcaggt cgacggcttc    960
tacgcgcgcg acctcaccac gaaggcccgg gccacgtcgc cgacgacccg caacttgctg   1020
acgaccccca agtttaccgt ggcctgggac tgggtgccga agcgaccggc ggtctgcacc   1080
atgaccaagt ggcaggaggt ggacgagatg ctccgcgccg agtacggcgg ctccttccgc   1140
ttctcctccg acgccatctc gaccaccttc accaccaacc tgaccgagta ctcgctctcg   1200
cgcgtcgacc tgggcgactg catcggccgg gatgcccgcg aggccatcga ccgcatgttt   1260
gcgcgcaagt acaacgccac gcacatcaag gtgggccagc cgcagtacta cctggccacg   1320
gggggcttcc tcatcgcgta ccagcccctc ctcagcaaca cgctcgccga gctgtacgtg   1380
cgggagtaca tgcgggagca ggaccgcaag ccccggaatg ccacgcccgc gccactgcgg   1440
gaggcgccca gcgccaacgc gtccgtggag cgcatcaaga ccacctcctc gatcgagttc   1500
gcccggctgc agtttacgta taaccacata cagcgccacg tgaatgacat gctggggcgc   1560
atcgccgtcg cgtggtgcga gctgcagaac cacgagctga ctctctggaa cgaggcccgc   1620
aagctcaacc ccaacgccat cgcctccgcc accgtcggcc ggcgggtgag cgcgcgcatg   1680
ctcggagacg tcatggccgt ctccacgtgc gtgcccgtcg ccccggacaa cgtgatcgtg   1740
cagaactcga tgcgcgtcag ctcgcggccg gggacgtgct acagccgccc cctggtcagc   1800
tttcggtacg aagaccaggg cccgctgatc gaggggcagc tgggcgagaa caacgagctg   1860
cgcctcaccc gcgacgcgct cgagccgtgc accgtgggcc accggcgcta cttcatcttc   1920
ggcgggggct acgtgtactt cgaggagtac gcgtactctc accagctgag tcgcgccgac   1980
gtcaccaccg tcagcacctt catcgacctg aacatcacca tgctggagga ccacgagttt   2040
gtgcccctgg aggtctacac gcgccacgag atcaaggaca gcggcctgct ggactacacg   2100
gaggtccagc gccgcaacca gctgcacgac ctgcgctttg ccgacatcga cacggtcatc   2160
cgcgccgacg ccaacgccgc catgttcgcg gggctgtgcg cgttcttcga ggggatgggg   2220
gacttggggc gcgcggtcgg caaggtagtc atgggagtag tgggggcgt ggtgtcggcc   2280
gtctcgggcg tgtcctcctt tatgtccaac cccttcgggg cgcttgccgt ggggctgctg   2340
gtcctggccg gcctggtcgc ggccttcttc gccttccgct acgtcctgca actgcaacgc   2400
aatcccatga aggccctgta tccgctcacc accaaggaac tcaagacttc cgaccccggg   2460
ggcgtgggcg gggaggggga ggaaggcgcg gaggggggcg ggtttgacga ggccaagttg   2520
gccgaggccc gagaaatgat ccgatatatg gctttggtgt cggccatgga gcgcacggaa   2580
```

```
cacaaggcca gaaagaaggg cacgagcgcc ctgctcagct ccaaggtcac caacatggtt   2640

ctgcgcaagc gcaacaaagc caggtactct ccgctccaca acgaggacga ggccggagac   2700

gaagacgagc tctaa                                                     2715


<210> SEQ ID NO 75
<211> LENGTH: 904
<212> TYPE: PRT
<213> ORGANISM: Herpes Simplex Virus 2

<400> SEQUENCE: 75

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
            20                  25                  30

Ser Gly Gly Val Ala Ala Thr Val Ala Ala Asn Gly Gly Pro Ala Ser
        35                  40                  45

Arg Pro Pro Pro Val Pro Ser Pro Ala Thr Thr Lys Ala Arg Lys Arg
    50                  55                  60

Lys Thr Lys Lys Pro Pro Lys Arg Pro Glu Ala Thr Pro Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
    130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Thr Lys Gly Val Cys Arg Ser Thr Ala Lys Tyr
        195                 200                 205

Val Arg Asn Asn Met Glu Thr Thr Ala Phe His Arg Asp Asp His Glu
    210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Asn Cys Ile Val Glu Glu Val Asp
            260                 265                 270

Ala Arg Ser Val Tyr Pro Tyr Asp Glu Phe Val Leu Ala Thr Gly Asp
        275                 280                 285

Phe Val Tyr Met Ser Pro Phe Tyr Gly Tyr Arg Glu Gly Ser His Thr
    290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
```

-continued

```
            340                 345                 350

Pro Lys Arg Pro Ala Val Cys Thr Met Thr Lys Trp Gln Glu Val Asp
        355                 360                 365

Glu Met Leu Arg Ala Glu Tyr Gly Gly Ser Phe Arg Phe Ser Ser Asp
    370                 375                 380

Ala Ile Ser Thr Thr Phe Thr Thr Asn Leu Thr Glu Tyr Ser Leu Ser
385                 390                 395                 400

Arg Val Asp Leu Gly Asp Cys Ile Gly Arg Asp Ala Arg Glu Ala Ile
                405                 410                 415

Asp Arg Met Phe Ala Arg Lys Tyr Asn Ala Thr His Ile Lys Val Gly
            420                 425                 430

Gln Pro Gln Tyr Tyr Leu Ala Thr Gly Gly Phe Leu Ile Ala Tyr Gln
        435                 440                 445

Pro Leu Leu Ser Asn Thr Leu Ala Glu Leu Tyr Val Arg Glu Tyr Met
    450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495

Ser Ile Glu Phe Ala Arg Leu Gln Phe Thr Tyr Asn His Ile Gln Arg
            500                 505                 510

His Val Asn Asp Met Leu Gly Arg Ile Ala Val Ala Trp Cys Glu Leu
        515                 520                 525

Gln Asn His Glu Leu Thr Leu Trp Asn Glu Ala Arg Lys Leu Asn Pro
    530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
    610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
                645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
        675                 680                 685

His Glu Ile Lys Asp Ser Gly Leu Leu Asp Tyr Thr Glu Val Gln Arg
    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
        755                 760                 765
```

```
Ser Asn Pro Phe Gly Ala Leu Ala Val Gly Leu Leu Val Leu Ala Gly
    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Glu Gly Ala Glu Gly
            820                 825                 830

Gly Gly Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Arg
    850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu
            900
```

<210> SEQ ID NO 76
<211> LENGTH: 2715
<212> TYPE: DNA
<213> ORGANISM: Artificial sequence
<220> FEATURE:
<223> OTHER INFORMATION: Codon modified Herpes Simplex Virus 2 sequence

<400> SEQUENCE: 76

```
atgcgcggag gaggactgat ctgcgctctg gtcgtgggag ctctggtggc tgctgtggct     60
tcggctgctc ccgctgctcc cgctgctccc cgcgcttcgg gaggagtggc tgctacggtc    120
gctgctaacg gaggacccgc ttcgcgaccc ccccccgtcc cctcgcccgc tacgacgaag    180
gctcgaaagc gaaaaacgaa aaagcccccc aagcgacccg aagctacgcc cccccccgac    240
gctaacgcta cggtcgctgc tggacacgct acgctgcgcg ctcacctgcg agaaatcaag    300
gtcgaaaacg ctgatgctca gttctacgtg tgcccccccc ccacgggagc tacggtggtg    360
cagttcgaac agccccgccg ctgccccacg cgccccgaag gacagaacta cacggaagga    420
atcgctgtgg tctttaagga aaacatcgct ccctacaaat ttaaggctac gatgtactac    480
aaagacgtga cggtgtcgca ggtgtggttt ggacaccgct actcgcagtt catgggaatc    540
tttgaagacc gcgctcccgt cccctttgaa gaagtgatcg acaagatcaa cacgaaggga    600
gtctgccgct cgacggctaa gtacgtgcga aacaacatgg aaacgacggc tttccaccga    660
gacgaccacg aaacggacat ggaactgaag cccgctaagg tcgctacgcg cacgtcgcga    720
ggatggcaca cgacggacct gaagtacaac ccctcgcgag tggaagcttt tcatcgatac    780
ggaacgacgg tcaactgcat cgtcgaagaa gtggacgctc gatcggtgta cccctacgat    840
gaattcgtgc tggctacggg agacttcgtg tacatgtcgc ccttctacgg ataccgagaa    900
ggatcgcaca cggaacacac gtcgtacgct gctgaccgct ttaagcaggt cgacggattt    960
tacgctcgcg acctgacgac gaaggctcga gctacgtcgc ccacgacgcg caacctgctg   1020
acgacgccca agttcacggt ggcttgggac tgggtgccca agcgacccgc tgtctgcacg   1080
atgacgaagt ggcaggaagt ggacgaaatg ctgcgcgctg aatacggagg atcgtttcgc   1140
ttttcgtcgg acgctatctc gacgacgttt acgacgaacc tgacggaata ctcgctgtcg   1200
cgcgtcgacc tgggagactg catcggacga gatgctcgcg aagctatcga ccgcatgttc   1260
```

gctcgcaagt acaacgctac gcacatcaag gtgggacagc cccagtacta cctggctacg 1320
ggaggatttc tgatcgctta ccagcccctg ctgtcgaaca cgctggctga actgtacgtg 1380
cgagaataca tgcgagaaca ggaccgcaag ccccgaaatg ctacgcccgc tcccctgcga 1440
gaagctccct cggctaacgc ttcggtggaa cgcatcaaga cgacgtcgtc gatcgaattt 1500
gctcgactgc agttcacgta taaccacatc cagcgccacg tgaatgacat gctgggacgc 1560
atcgctgtcg cttggtgcga actgcagaac cacgaactga cgctgtggaa cgaagctcgc 1620
aagctgaacc ccaacgctat cgcttcggct acggtcggac gacgagtgtc ggctcgcatg 1680
ctgggagacg tcatggctgt ctcgacgtgc gtgcccgtcg ctcccgacaa cgtgatcgtg 1740
cagaactcga tgcgcgtctc gtcgcgaccc ggaacgtgct actcgcgccc cctggtctcg 1800
ttccgatacg aagaccaggg acccctgatc gaaggacagc tgggagaaaa caacgaactg 1860
cgcctgacgc gcgacgctct ggaaccctgc acggtgggac accgacgcta ctttatcttt 1920
ggaggaggat acgtgtactt tgaagaatac gcttactcgc accagctgtc gcgcgctgac 1980
gtcacgacgg tctcgacgtt tatcgacctg aacatcacga tgctggaaga ccacgaattc 2040
gtgcccctgg aagtctacac gcgccacgaa atcaaggact cgggactgct ggactacacg 2100
gaagtccagc gccgcaacca gctgcacgac ctgcgcttcg ctgacatcga cacggtcatc 2160
cgcgctgacg ctaacgctgc tatgtttgct ggactgtgcg ctttttttga aggaatggga 2220
gacctgggac gcgctgtcgg aaaggtcgtc atgggagtcg tgggaggagt ggtgtcggct 2280
gtctcgggag tgtcgtcgtt catgtcgaac ccctttggag ctctggctgt gggactgctg 2340
gtcctggctg gactggtcgc tgcttttttt gcttttcgct acgtcctgca actgcaacgc 2400
aatcccatga aggctctgta tcccctgacg acgaaggaac tgaagacgtc ggaccccgga 2460
ggagtgggag gagaaggaga agaaggagct gaaggaggag gattcgacga agctaagctg 2520
gctgaagctc gagaaatgat ccgatatatg gctctggtgt cggctatgga acgcacggaa 2580
cacaaggcta gaaagaaggg aacgtcggct ctgctgtcgt cgaaggtcac gaacatggtc 2640
ctgcgcaagc gcaacaaagc tagatactcg cccctgcaca acgaagacga agctggagac 2700
gaagacgaac tgtaa 2715

<210> SEQ ID NO 77
<211> LENGTH: 1182
<212> TYPE: DNA
<213> ORGANISM: Herpes Simplex Virus

<400> SEQUENCE: 77
atggggcgtt tgacctccgg cgtcgggacg gcggccctgc tagttgtcgc ggtgggactc 60
cgcgtcgtct gcgccaaata cgccttagca gacccctcgc ttaagatggc cgatcccaat 120
cgatttcgcg ggaagaacct tccggttttg gaccagctga ccgacccccc cggggtgaag 180
cgtgtttacc acattcagcc gagcctggag gacccgttcc agccccccag catcccgatc 240
actgtgtact acgcagtgct ggaacgtgcc tgccgcagcg tgctcctaca tgccccatcg 300
gaggcccccc agatcgtgcg cggggcttcg gacgaggccc gaaagcacac gtacaacctg 360
accatcgcct ggtatcgcat gggagacaat tgcgctatcc ccatcacggt tatggaatac 420
accgagtgcc cctacaacaa gtcgttgggg gtctgcccca tccgaacgca gccccgctgg 480
agctactatg acagctttag cgccgtcagc gaggataacc tgggattcct gatgcacgcc 540
cccgccttcg agaccgcggg tacgtacctg cggctagtga agataaacga ctggacggag 600

```
atcacacaat ttatcctgga gcaccgggcc cgcgcctcct gcaagtacgc tctccccctg    660

cgcatccccc cggcagcgtg cctcacctcg aaggcctacc aacagggcgt gacggtcgac    720

agcatcggga tgctaccccg ctttatcccc gaaaaccagc gcaccgtcgc cctatacagc    780

ttaaaaatcg ccgggtggca cggccccaag cccccgtaca ccagcaccct gctgccgccg    840

gagctgtccg acaccaccaa cgccacgcaa cccgaactcg ttccggaaga ccccgaggac    900

tcggccctct tagaggatcc cgccgggacg gtgtcttcgc agatcccccc aaactggcac    960

atcccgtcga tccaggacgt cgcgccgcac cacgcccccg ccgcccccag caacccgggc   1020

ctgatcatcg gcgcgctggc cggcagtacc ctggcggtgc tggtcatcgg cggtattgcg   1080

ttttgggtac gccgccgcgc tcagatggcc cccaagcgcc tacgtctccc ccacatccgg   1140

gatgacgacg cgccccccctc gcaccagcca ttgttttact ag                     1182
```

<210> SEQ ID NO 78
<211> LENGTH: 393
<212> TYPE: PRT
<213> ORGANISM: Herpes Simplex Virus

<400> SEQUENCE: 78

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270
```

```
Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390
```

<210> SEQ ID NO 79
<211> LENGTH: 1182
<212> TYPE: DNA
<213> ORGANISM: Artificial sequence
<220> FEATURE:
<223> OTHER INFORMATION: Codon modified Herpes Simplex Virus sequence

<400> SEQUENCE: 79

```
atgggacgtc tgacgtcggg agtcggaacg gctgctctgc tggtcgtcgc tgtgggactg     60

cgcgtcgtct gcgctaaata cgctctggct gacccctcgc tgaagatggc tgatcccaat    120

cgattccgcg gaaagaacct gcccgtcctg gaccagctga cggacccccc cggagtgaag    180

cgtgtctacc acatccagcc ctcgctggaa gacccctttc agcccccctc gatccccatc    240

acggtgtact acgctgtgct ggaacgtgct tgccgctcgg tgctgctgca tgctccctcg    300

gaagctcccc agatcgtgcg cggagcttcg gacgaagctc gaaagcacac gtacaacctg    360

acgatcgctt ggtatcgcat gggagacaat tgcgctatcc ccatcacggt catggaatac    420

acggaatgcc cctacaacaa gtcgctggga gtctgcccca tccgaacgca gccccgctgg    480

tcgtactatg actcgttctc ggctgtctcg gaagataacc tgggatttct gatgcacgct    540

cccgcttttg aaacggctgg aacgtacctg cgactggtga agatcaacga ctggacggaa    600

atcacgcaat tcatcctgga acaccgagct cgcgcttcgt gcaagtacgc tctgcccctg    660

cgcatccccc ccgctgcttg cctgacgtcg aaggcttacc aacagggagt gacggtcgac    720

tcgatcggaa tgctgccccg cttcatcccc gaaaaccagc gcacggtcgc tctgtactcg    780

ctgaaaatcg ctggatggca cggacccaag cccccctaca cgtcgacgct gctgcccccc    840

gaactgtcgg acacgacgaa cgctacgcaa cccgaactgg tccccgaaga ccccgaagac    900

tcggctctgc tggaagatcc cgctggaacg gtgtcgtcgc agatcccccc caactggcac    960

atcccctcga tccaggacgt cgctccccac cacgctcccg ctgctccctc gaaccccgga   1020

ctgatcatcg gagctctggc tggatcgacg ctggctgtgc tggtcatcgg aggaatcgct   1080

ttctgggtcc gccgccgcgc tcagatggct cccaagcgcc tgcgtctgcc ccacatccga   1140

gatgacgacg ctcccccctc gcaccagccc ctgttctact ag                      1182
```

<210> SEQ ID NO 80
<211> LENGTH: 387
<212> TYPE: DNA
<213> ORGANISM: Human papillomavirus type 16

<400> SEQUENCE: 80
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactgatctc tactgttatg agcaattaaa tgacagctca 180
gaggaggagg atgaaataga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 81
<211> LENGTH: 387
<212> TYPE: DNA
<213> ORGANISM: Artificial Sequence
<220> FEATURE:
<223> OTHER INFORMATION: HPV-16 E7 O1

<400> SEQUENCE: 81
ggtaccgccg ccaccatgga aacggacacg ctgctgctgt gggtcctgct gctgtgggtc 60
cccggatcga cgggagacgg atcgatgcat ggagacacgc ccacgctgca tgaatacatg 120
ctggacctgc aacccgaaac gacggacctg tactgctacg aacaactgaa cgactcgtcg 180
gaagaagaag acgaaatcga cggacccgct ggacaagctg aacccgacag agctcattac 240
aacatcgtca cgttctgctg caagtgcgac tcgacgctgc gactgtgcgt ccaatcgacg 300
cacgtcgaca tccgtacgct ggaagacctg ctgatgggaa cgctgggaat cgtgtgcccc 360
atctgctcgc agaagcccta agaattc 387

<210> SEQ ID NO 82
<211> LENGTH: 387
<212> TYPE: DNA
<213> ORGANISM: Artificial Sequence
<220> FEATURE:
<223> OTHER INFORMATION: HPV16 E7 O2

<400> SEQUENCE: 82
ggtaccgccg ccaccatgga aacggacacg ctgctgctgt gggtcctgct gctgtgggtc 60
cccggatcga cgggagacgg atcgatgcat ggagatacgc ctacgctgca tgaatatatg 120
ctggatctgc aacccgaaac gacggatctg tactgttatg aacaactgaa tgactcgtcg 180
gaagaagaag atgaaatcga tggacccgct ggacaagctg aacccgacag agctcattac 240
aatatcgtca cgttttgttg caagtgtgac tcgacgctgc gactgtgcgt ccaatcgacg 300
cacgtcgaca tccgtacgct ggaagacctg ctgatgggaa cgctgggaat cgtgtgcccc 360
atctgctcgc agaagcccta agaattc 387

<210> SEQ ID NO 83
<211> LENGTH: 417
<212> TYPE: DNA
<213> ORGANISM: Artificial Sequence
<220> FEATURE:
<223> OTHER INFORMATION: HPV-16 E7 O3

<400> SEQUENCE: 83
ggtaccgccg ccaccatgga gacggacacg ctcctgctct gggtactgct gctctgggtt 60
cctggatcga cgggattgtg gacggatcga tgcatggaga tacgcctacg ctccatgaat 120

```
atatgctcga tctccaacct ggttgagacg acggatctct actgttatga gcaactcaat    180

gactcgtcgg aggaggagga tgaattcata gatggacctg ctggacaagc agaacctgac    240

agagcccatt acaatattgt aacgtttgag aattgttgca agtgtgactc gacgctccgg    300

ctctgcgtac aatcgacgca cgtagacatt cgtccctcta cgctcgaaga cctgctcatg    360

ggaacgctcg gaattgtgtg ccccatctgc tcgcagaagt gtgcccccta agaattc       417


<210> SEQ ID NO 84
<211> LENGTH: 387
<212> TYPE: DNA
<213> ORGANISM: Artificial Sequence
<220> FEATURE:
<223> OTHER INFORMATION: HPV-16 E7 W

<400> SEQUENCE: 84

ggtaccgccg ccaccatgga gactgatact ttattattat gggtattatt attatgggtt     60

ccaggtagta ctggtgatgg cagtatgcat ggcgatactc caactttaca tgagtatatg    120

ttagatttac aaccagagac tactgattta tattgttatg agcaattaaa tgatagcagt    180

gaggaggagg atgagataga tggtccagcg ggccaagcag agccggatcg ggcgcattat    240

aatatagtaa ctttctgttg taagtgtgat agtactttac ggttatgtgt acaaagcact    300

cacgtagata tacggacttt agaggattta ttaatgggca ctttaggcat agtatgtcca    360

atatgtagtc agaagccata agaattc                                        387


<210> SEQ ID NO 85
<211> LENGTH: 1182
<212> TYPE: DNA
<213> ORGANISM: Herpes simplex virus type 2

<400> SEQUENCE: 85

atggggcgtt tgacctccgg cgtcgggacg gcggccctgc tagttgtcgc ggtgggactc     60

cgcgtcgtct gcgccaaata cgccttagca gacccctcgc ttaagatggc cgatcccaat    120

cgatttcgcg ggaagaacct tccggttttg gaccagctga ccgacccccc cggggtgaag    180

cgtgtttacc acattcagcc gagcctggag gacccgttcc agccccccag catcccgatc    240

actgtgtact acgcagtgct ggaacgtgcc tgccgcagcg tgctcctaca tgccccatcg    300

gaggcccccc agatcgtgcg cggggcttcg gacgaggccc gaaagcacac gtacaacctg    360

accatcgcct ggtatcgcat gggagacaat tgcgctatcc ccatcacggt tatggaatac    420

accgagtgcc cctacaacaa gtcgttgggg gtctgcccca tccgaacgca gccccgctgg    480

agctactatg acagctttag cgccgtcagc gaggataacc tgggattcct gatgcacgcc    540

cccgccttcg agaccgcggg tacgtacctg cggctagtga agataaacga ctggacggag    600

atcacacaat ttatcctgga gcaccgggcc cgcgcctcct gcaagtacgc tctcccccctg    660

cgcatccccc cggcagcgtg cctcacctcg aaggcctacc aacagggcgt gacggtcgac    720

agcatcggga tgctaccccg ctttatcccc gaaaaccagc gcaccgtcgc cctatacagc    780

ttaaaaatcg ccgggtggca cggccccaag cccccgtaca ccagcaccct gctgccgccg    840

gagctgtccg acaccaccaa cgccacgcaa cccgaactcg ttccggaaga ccccgaggac    900

tcggccctct tagaggatcc cgccgggacg gtgtcttcgc agatcccccc aaactggcac    960

atcccgtcga tccaggacgt cgcgccgcac cacgccccgg ccgcccccag caacccgggc   1020

ctgatcatcg gcgcgctggc cggcagtacc ctggcggtgc tggtcatcgg cggtattgcg   1080

ttttgggtac gccgccgcgc tcagatggcc cccaagcgcc tacgtctccc ccacatccgg   1140
```

gatgacgacg cgcccccctc gcaccagcca ttgttttact ag 1182

<210> SEQ ID NO 86
<211> LENGTH: 1182
<212> TYPE: DNA
<213> ORGANISM: Artificial Sequence
<220> FEATURE:
<223> OTHER INFORMATION: HSV-2 gD2 O1

<400> SEQUENCE: 86
atgggacgtc tgacgtcggg agtcggaacg gctgctctgc tggtcgtcgc tgtgggactc 60
cgcgtcgtct gcgctaaata cgctctggct gacccctcgc tgaagatggc tgaccccaac 120
cgatttcgcg gaaagaacct gcccgtcctg gaccagctga cggacccccc cggagtgaag 180
cgtgtctacc acatccagcc ctcgctggaa gacccctttc agcccccctc gatccccatc 240
acggtgtact acgctgtgct ggaacgtgct tgccgctcgg tgctcctcca tgctccctcg 300
gaagctcccc agatcgtgcg cggagcttcg gacgaagctc gaaagcacac gtacaacctg 360
acgatcgctt ggtaccgcat gggagacaac tgcgctatcc ccatcacggt catggaatac 420
acggaatgcc cctacaacaa gtcgctcgga gtctgcccca tccgaacgca gccccgctgg 480
tcgtactacg actcgttttc ggctgtctcg gaagacaacc tgggatttct gatgcacgct 540
cccgcttttg aaacggctgg aacgtacctg cgactcgtga agatcaacga ctggacggaa 600
atcacgcaat ttatcctgga acaccgagct cgcgcttcgt gcaagtacgc tctccccctg 660
cgcatccccc ccgctgcttg cctcacgtcg aaggcttacc aacagggagt gacggtcgac 720
tcgatcggaa tgctcccccg ctttatcccc gaaaaccagc gcacggtcgc tctctactcg 780
ctcaaaatcg ctggatggca cggacccaag cccccctaca cgtcgacgct gctgcccccc 840
gaactgtcgg acacgacgaa cgctacgcaa cccgaactcg tccccgaaga ccccgaagac 900
tcggctctcc tcgaagaccc cgctggaacg gtgtcgtcgc agatcccccc caactggcac 960
atcccctcga tccaggacgt cgctccccac cacgctcccg ctgctccctc gaaccccgga 1020
ctgatcatcg gagctctggc tggatcgacg ctggctgtgc tggtcatcgg aggaatcgct 1080
ttttgggtcc gccgccgcgc tcagatggct cccaagcgcc tccgtctccc ccacatccga 1140
gacgacgacg ctcccccctc gcaccagccc ctcttttact ag 1182

<210> SEQ ID NO 87
<211> LENGTH: 1182
<212> TYPE: DNA
<213> ORGANISM: Artificial Sequence
<220> FEATURE:
<223> OTHER INFORMATION: HSV-2 gD2 O2

<400> SEQUENCE: 87
atgggacgtc tgacgtcggg agtcggaacg gctgctctgc tggtcgtcgc tgtgggactg 60
cgcgtcgtct gcgctaaata cgctctggct gacccctcgc tgaagatggc tgatcccaat 120
cgatttcgcg gaaagaacct gcccgtcctg gaccagctga cggacccccc cggagtgaag 180
cgtgtctacc acatccagcc ctcgctggaa gacccctttc agcccccctc gatccccatc 240
acggtgtact acgctgtgct ggaacgtgct tgccgctcgg tgctgctgca tgctccctcg 300
gaagctcccc agatcgtgcg cggagcttcg gacgaagctc gaaagcacac gtacaacctg 360
acgatcgctt ggtatcgcat gggagacaat tgcgctatcc ccatcacggt catggaatac 420
acggaatgcc cctacaacaa gtcgctggga gtctgcccca tccgaacgca gccccgctgg 480

```
tcgtactatg actcgttttc ggctgtctcg gaagataacc tgggatttct gatgcacgct    540

cccgcttttg aaacggctgg aacgtacctg cgactggtga agatcaacga ctggacggaa    600

atcacgcaat ttatcctgga acaccgagct cgcgcttcgt gcaagtacgc tctgcccctg    660

cgcatccccc ccgctgcttg cctgacgtcg aaggcttacc aacagggagt gacggtcgac    720

tcgatcggaa tgctgccccg ctttatcccc gaaaaccagc gcacggtcgc tctgtactcg    780

ctgaaaatcg ctggatggca cggacccaag ccccccctaca cgtcgacgct gctgcccccc    840

gaactgtcgg acacgacgaa cgctacgcaa cccgaactgg tccccgaaga ccccgaagac    900

tcggctctgc tggaagatcc cgctggaacg gtgtcgtcgc agatcccccc caactggcac    960

atcccctcga tccaggacgt cgctccccac cacgctcccg ctgctccctc gaaccccgga   1020

ctgatcatcg gagctctggc tggatcgacg ctggctgtgc tggtcatcgg aggaatcgct   1080

ttttgggtcc gccgccgcgc tcagatggct cccaagcgcc tgcgtctgcc ccacatccga   1140

gatgacgacg ctccccccctc gcaccagccc ctgttttact ag                     1182
```

<210> SEQ ID NO 88
<211> LENGTH: 1182
<212> TYPE: DNA
<213> ORGANISM: Artificial Sequence
<220> FEATURE:
<223> OTHER INFORMATION: HSV-2 gD2 O3

<400> SEQUENCE: 88

```
atgggacgtc tcacgtcggg agtcggaacg gcggccctgc tcgttgtcgc ggtgggactc     60

cgcgtcgtct gcgccaaata cgccctcgca gacccctcgc tcaagatggc cgatcccaat    120

cgatttcgcg gaaagaacct ccctgttctc gaccagctga cggacccccc cggagtgaag    180

cgtgtttacc acattcagcc ttcgctggag gacccctttcc agcccccctc gatccctatc    240

acggtgtact acgcagtgct ggaacgtgcc tgccgctcgg tgctcctcca tgccccttcg    300

gaggcccccc agatcgtgcg cggagcttcg gacgaggccc gaaagcacac gtacaacctg    360

acgatcgcct ggtatcgcat gggagacaat tgcgctatcc ccatcacggt tatggaatac    420

acggagtgcc cctacaacaa gtcgctcgga gtctgcccca tccgaacgca gccccgctgg    480

tcgtactatg actcgttttc ggccgtctcg gaggataacc tgggattcct gatgcacgcc    540

cccgccttcg agacggcggg aacgtacctg cggctcgtga agataaacga ctggacggag    600

atcacgcaat ttatcctgga gcaccgggcc cgcgcctcgt gcaagtacgc tctccccctg    660

cgcatccccc ctgcagcgtg cctcacgtcg aaggcctacc aacagggagt gacggtcgac    720

tcgatcggaa tgctccccccg ctttatcccc gaaaaccagc gcacggtcgc cctctactcg    780

ctcaaaatcg ccggatggca cggacccaag ccccccttaca cgtcgacgct gctgcctcct    840

gagctgtcgg acacgacgaa cgccacgcaa cccgaactcg ttcctgaaga ccccgaggac    900

tcggccctcc tagaggatcc cgccggaacg gtgtcgtcgc agatcccccc taactggcac    960

atcccttcga tccaggacgt cgcgcctcac cacgcccccg ccgccccctc gaaccctgga   1020

ctgatcatcg gagcgctggc cggatcgacg ctggcggtgc tggtcatcgg aggaattgcg   1080

ttttgggtac gccgccgcgc tcagatggcc cccaagcgcc tccgtctccc ccacatccgg   1140

gatgacgacg cgccccccctc gcaccagcct ctcttttact ag                     1182
```

<210> SEQ ID NO 89
<211> LENGTH: 1182
<212> TYPE: DNA
<213> ORGANISM: Artificial Sequence
<220> FEATURE:
<223> OTHER INFORMATION: HSV-2 gD2 W

<400> SEQUENCE: 89
atggggcggt tgactagtgg cgtagggact gcggcgttat tagtagtagc ggtaggctta 60
cgggtagtat gtgcaaaata tgcgttagca gatccaagtt taaagatggc ggatccaaat 120
cggttccggg ggaagaattt accggtattg gatcagttaa ctgatccacc aggggtaaag 180
cgggtatatc acatacagcc gagcttagag gatccgttcc agccaccaag cataccgata 240
actgtatatt atgcagtatt agagcgggcg tgtcggagcg tattattaca tgcaccaagt 300
gaggcgccac agatagtacg gggggcaagt gatgaggcgc ggaagcacac ttataattta 360
actatagcat ggtatcggat gggcgataat tgtgcgatac caataactgt aatggagtat 420
actgagtgtc catataataa gagtttgggg gtatgtccaa tacggactca gccacggtgg 480
agctattatg atagcttcag cgcagtaagc gaggataatt taggcttctt aatgcacgcg 540
ccagcattcg agactgcggg tacttattta cggttagtaa agataaatga ttggactgag 600
ataactcaat tcatattaga gcaccgggca cgggcgagtt gtaagtatgc attaccatta 660
cggataccac cggcagcgtg tttaactagt aaggcatatc aacagggcgt aactgtagat 720
agcataggga tgttaccacg gttcatacca gagaatcagc ggactgtagc gttatatagc 780
ttaaaaatag cagggtggca cggcccaaag ccaccgtata ctagcacttt attaccgccg 840
gagttaagtg atactactaa tgcgactcaa ccagagttag taccggagga tccagaggat 900
agtgcattat tagaggatcc agcggggact gtaagtagtc agataccacc aaattggcac 960
ataccgagta tacaggatgt agcgccgcac cacgcaccag cggcaccaag caatccgggc 1020
ttaataatag gcgcgttagc aggcagtact ttagcggtat tagtaatagg cggtatagcg 1080
ttctgggtac ggcggcgggc gcagatggcg ccaaagcggt tacggttacc acacatacgg 1140
gatgatgatg cgccaccaag tcaccagcca ttgttctatt ag 1182

<210> SEQ ID NO 90
<211> LENGTH: 41
<212> TYPE: DNA
<213> ORGANISM: Artificial sequence
<220> FEATURE:
<223> OTHER INFORMATION: Common forward primer

<400> SEQUENCE: 90
ttgaataggt accgccgcca ccatggagac cgacaccctc c 41

<210> SEQ ID NO 91
<211> LENGTH: 24
<212> TYPE: DNA
<213> ORGANISM: Artificial Sequence
<220> FEATURE:
<223> OTHER INFORMATION: ODN-7909

<400> SEQUENCE: 91
tcgtcgtttt gtcgttttgt cgtt 24

<210> SEQ ID NO 92
<211> LENGTH: 7
<212> TYPE: PRT
<213> ORGANISM: Artificial Sequence
<220> FEATURE:
<223> OTHER INFORMATION: Secretory sequence
<220> FEATURE:
<221> NAME/KEY: MISC_FEATURE
<222> LOCATION: (1)..(1)

<223> OTHER INFORMATION: Any amino acid
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid

<400> SEQUENCE: 92

Xaa Xaa Gly Xaa Gly Xaa Xaa
1               5

<210> SEQ ID NO 93
<211> LENGTH: 387
<212> TYPE: DNA
<213> ORGANISM: Artificial Sequence
<220> FEATURE:
<223> OTHER INFORMATION: IgkC1

<400> SEQUENCE: 93
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 94
<211> LENGTH: 387
<212> TYPE: DNA
<213> ORGANISM: Artificial Sequence
<220> FEATURE:
<223> OTHER INFORMATION: IgkS1-1

<400> SEQUENCE: 94
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagcg ggacaagcgg aaccggacag agcgcattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 95
<211> LENGTH: 387
<212> TYPE: DNA
<213> ORGANISM: Artificial Sequence
<220> FEATURE:
<223> OTHER INFORMATION: IgKS1-2

<400> SEQUENCE: 95
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagca ggacaagcag aaccggacag agcacattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 96
<211> LENGTH: 387
<212> TYPE: DNA
<213> ORGANISM: Artificial Sequence
<220> FEATURE:
<223> OTHER INFORMATION: IgkS1-3

<400> SEQUENCE: 96
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagctg aaccggacag agctcattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 97
<211> LENGTH: 387
<212> TYPE: DNA
<213> ORGANISM: Artificial Sequence
<220> FEATURE:
<223> OTHER INFORMATION: IgkS1-4

<400> SEQUENCE: 97
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagcc ggacaagccg aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 98
<211> LENGTH: 387
<212> TYPE: DNA
<213> ORGANISM: Artificial Sequence
<220> FEATURE:
<223> OTHER INFORMATION: IgkC2

<400> SEQUENCE: 98
ggtaccgccg ccaccatgga gaccgacacc ctcctgctgt gggtgctgct gctctgggtg 60
cccggctcca ccggcgacgg atccatgcac ggcgacaccc ccaccctgca cgagtacatg 120
ctggacctgc agcccgagac caccggcctg tacggctacg gccagctcaa cgacagcagc 180

-continued gaggaggagg acgagatcga cggccccgcc ggccaggccg agcccgaccg cgcccactac 240
aacatcgtga ccttctgctg caagtgcgac agcaccctgc gcctctgcgt gcagagcacc 300
cacgtggaca tccgcaccct ggaggacctg ctgatgggca ccctgggcat cgtgtgcccc 360
atctgctccc agaagcccta agaattc 387

<210> SEQ ID NO 99
<211> LENGTH: 387
<212> TYPE: DNA
<213> ORGANISM: Artificial Sequence
<220> FEATURE:
<223> OTHER INFORMATION: IgkS1-5

<400> SEQUENCE: 99
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag ggcccattac 240
aatattgtaa ccttttgttg caagtgtgac tctacgctta ggttgtgcgt acaaagcaca 300
cacgtagaca ttaggacttt ggaagacctg ttaatgggca cactaggaat tgtgtgcccc 360
atctgctctc agaagcccta agaattc 387

<210> SEQ ID NO 100
<211> LENGTH: 387
<212> TYPE: DNA
<213> ORGANISM: Artificial Sequence
<220> FEATURE:
<223> OTHER INFORMATION: IgkS1-6

<400> SEQUENCE: 100
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgttg caagtgtgac tctacgctta gattgtgcgt acaaagcaca 300
cacgtagaca ttagaacttt ggaagacctg ttaatgggca cactaggaat tgtgtgcccc 360
atctgctctc agaagcccta agaattc 387

<210> SEQ ID NO 101
<211> LENGTH: 387
<212> TYPE: DNA
<213> ORGANISM: Artificial Sequence
<220> FEATURE:
<223> OTHER INFORMATION: IgkS1-7

<400> SEQUENCE: 101
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggaccg ggcccattac 240
aatattgtaa ccttttgttg caagtgtgac tctacgcttc ggttgtgcgt acaaagcaca 300
cacgtagaca ttcggacttt ggaagacctg ttaatgggca cactaggaat tgtgtgcccc 360
atctgctctc agaagcccta agaattc 387

<210> SEQ ID NO 102
<211> LENGTH: 387
<212> TYPE: DNA
<213> ORGANISM: Artificial Sequence
<220> FEATURE:
<223> OTHER INFORMATION: IgkS1-8

<400> SEQUENCE: 102
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggaccg agcccattac 240
aatattgtaa ccttttgttg caagtgtgac tctacgcttc gattgtgcgt acaaagcaca 300
cacgtagaca ttcgaacttt ggaagacctg ttaatgggca cactaggaat tgtgtgcccc 360
atctgctctc agaagcccta agaattc 387

<210> SEQ ID NO 103
<211> LENGTH: 387
<212> TYPE: DNA
<213> ORGANISM: Artificial Sequence
<220> FEATURE:
<223> OTHER INFORMATION: IgkS1-9

<400> SEQUENCE: 103
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggaccg tgcccattac 240
aatattgtaa ccttttgttg caagtgtgac tctacgcttc gtttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 104
<211> LENGTH: 387
<212> TYPE: DNA
<213> ORGANISM: Artificial Sequence
<220> FEATURE:
<223> OTHER INFORMATION: IgkS1-10

<400> SEQUENCE: 104
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggaccg cgcccattac 240
aatattgtaa ccttttgttg caagtgtgac tctacgcttc gcttgtgcgt acaaagcaca 300
cacgtagaca ttcgcacttt ggaagacctg ttaatgggca cactaggaat tgtgtgcccc 360
atctgctctc agaagcccta agaattc 387

<210> SEQ ID NO 105
<211> LENGTH: 387
<212> TYPE: DNA
<213> ORGANISM: Artificial Sequence -continued
<220> FEATURE:
<223> OTHER INFORMATION: IgkS1-12

<400> SEQUENCE: 105
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa cgacagctca 180
gaggaggagg atgaaataga tggtccagct ggacaagcag aaccggacag agcccattac 240
aacattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 106
<211> LENGTH: 387
<212> TYPE: DNA
<213> ORGANISM: Artificial Sequence
<220> FEATURE:
<223> OTHER INFORMATION: IgkS1-31

<400> SEQUENCE: 106
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgttg caaatgtgac tctacgcttc ggttgtgcgt acaaagcaca 300
cacgtagaca ttcgtacttt ggaagacctg ttaatgggca cactaggaat tgtgtgcccc 360
atctgctctc agaaacccta agaattc 387

<210> SEQ ID NO 107
<211> LENGTH: 387
<212> TYPE: DNA
<213> ORGANISM: Artificial Sequence
<220> FEATURE:
<223> OTHER INFORMATION: IgkS1-13

<400> SEQUENCE: 107
ggtaccgccg ccaccatgga gacagataca ctcctgctat gggtactgct gctctgggtt 60
ccaggttcca ctggtgatgg atccatgcat ggagatacac ctacattgca tgaatatatg 120
ttagatttgc aaccagagac aactggtctc tacggttatg ggcaattaaa tgatagctca 180
gaggaggagg atgaaataga tggtccagct ggacaagcag aaccggatag agcccattac 240
aatattgtaa ccttttgttg caagtgtgat tctacgcttc ggttgtgcgt acaaagcaca 300
cacgtagata ttcgtacttt ggaagatctg ttaatgggca cactaggaat tgtgtgcccc 360
atctgctctc agaagcccta agaattc 387

<210> SEQ ID NO 108
<211> LENGTH: 387
<212> TYPE: DNA
<213> ORGANISM: Artificial Sequence
<220> FEATURE:
<223> OTHER INFORMATION: IgkS1-14

<400> SEQUENCE: 108
ggtaccgccg ccaccatgga gacagacaca ctcctgctat gggtactgct gctctgggtt 60
ccaggttcca ctggtgacgg atccatgcat ggagacacac ctacattgca tgaatatatg 120
ttagacttgc aaccagagac aactggtctc tacggttatg ggcaattaaa tgacagctca 180
gaggaggagg acgaaataga cggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 109
<211> LENGTH: 387
<212> TYPE: DNA
<213> ORGANISM: Artificial Sequence
<220> FEATURE:
<223> OTHER INFORMATION: IgkS1-15

<400> SEQUENCE: 109
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgttg taagtgtgac tctacgcttc ggttgtgtgt acaaagcaca 300
cacgtagaca ttcgtacttt ggaagacctg ttaatgggca cactaggaat tgtgtgtccc 360
atctgttctc agaagcccta agaattc 387

<210> SEQ ID NO 110
<211> LENGTH: 387
<212> TYPE: DNA
<213> ORGANISM: Artificial Sequence
<220> FEATURE:
<223> OTHER INFORMATION: IgkS1-16

<400> SEQUENCE: 110
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgctg caagtgcgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 111
<211> LENGTH: 387
<212> TYPE: DNA
<213> ORGANISM: Artificial Sequence
<220> FEATURE:
<223> OTHER INFORMATION: IgkS1-17

<400> SEQUENCE: 111
ggtaccgccg ccaccatgga gacagacaca ctcctgctat gggtactgct gctctgggtt 60
ccaggttcca ctggtgacgg atccatgcat ggagatacac ctacattgca tgagtatatg 120
ttagatttgc aaccagagac aactggtctc tacggttatg ggcaattaaa tgacagctca 180
gaggaggagg atgagataga tggtccagct ggacaagcag agccggacag agcccattac 240
aatattgtaa ccttttgttg caagtgtgac tctacgcttc ggttgtgcgt acaaagcaca 300
cacgtagaca ttcgtacttt ggaggacctg ttaatgggca cactaggaat tgtgtgcccc 360
atctgctctc agaagcccta agaattc 387

<210> SEQ ID NO 112
<211> LENGTH: 387
<212> TYPE: DNA
<213> ORGANISM: Artificial Sequence
<220> FEATURE:
<223> OTHER INFORMATION: IgkS1-18

<400> SEQUENCE: 112
ggtaccgccg ccaccatgga aacagacaca ctcctgctat gggtactgct gctctgggtt 60
ccaggttcca ctggtgacgg atccatgcat ggagatacac ctacattgca tgaatatatg 120
ttagatttgc aaccagaaac aactggtctc tacggttatg ggcaattaaa tgacagctca 180
gaagaagaag atgaaataga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 113
<211> LENGTH: 387
<212> TYPE: DNA
<213> ORGANISM: Artificial Sequence
<220> FEATURE:
<223> OTHER INFORMATION: IgkS1-19

<400> SEQUENCE: 113
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc agccagagac aactggtctc tacggttatg ggcagttaaa tgacagctca 180
gaggaggagg atgaaataga tggtccagct ggacaggcag aaccggacag agcccattac 240
aatattgtaa ccttttgttg caagtgtgac tctacgcttc ggttgtgcgt acagagcaca 300
cacgtagaca ttcgtacttt ggaagacctg ttaatgggca cactaggaat tgtgtgcccc 360
atctgctctc agaagcccta agaattc 387

<210> SEQ ID NO 114
<211> LENGTH: 387
<212> TYPE: DNA
<213> ORGANISM: Artificial Sequence
<220> FEATURE:
<223> OTHER INFORMATION: IgkS1-20

<400> SEQUENCE: 114
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc aaaagcccta agaattc 387

<210> SEQ ID NO 115

<211> LENGTH: 387
<212> TYPE: DNA
<213> ORGANISM: Artificial Sequence
<220> FEATURE:
<223> OTHER INFORMATION: IgkS1-21

<400> SEQUENCE: 115
ggtaccgccg ccaccatgga gacagacaca ctcctgctat gggtactgct gctctgggtt 60
ccagggtcca ctggggacgg atccatgcat ggggatacac ctacattgca tgaatatatg 120
ttagatttgc aaccagagac aactgggctc tacgggtatg ggcaattaaa tgacagctca 180
gaggaggagg atgaaataga tgggccagct gggcaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggga cactagggat tgtgtgcccc 360
atctgctctc agaagcccta agaattc 387

<210> SEQ ID NO 116
<211> LENGTH: 387
<212> TYPE: DNA
<213> ORGANISM: Artificial Sequence
<220> FEATURE:
<223> OTHER INFORMATION: IgkS1-22

<400> SEQUENCE: 116
ggtaccgccg ccaccatgga gacagacaca ctcctgctat gggtactgct gctctgggtt 60
ccaggatcca ctggagacgg atccatgcat ggagatacac ctacattgca tgaatatatg 120
ttagatttgc aaccagagac aactggactc tacggatatg gacaattaaa tgacagctca 180
gaggaggagg atgaaataga tggaccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggaa cactaggaat tgtgtgcccc 360
atctgctctc agaagcccta agaattc 387

<210> SEQ ID NO 117
<211> LENGTH: 387
<212> TYPE: DNA
<213> ORGANISM: Artificial Sequence
<220> FEATURE:
<223> OTHER INFORMATION: IgkS1-23

<400> SEQUENCE: 117
ggtaccgccg ccaccatgga gacagacaca ctcctgctat gggtactgct gctctgggtt 60
ccaggttcca ctggtgacgg atccatgcat ggtgatacac ctacattgca tgaatatatg 120
ttagatttgc aaccagagac aactggtctc tacggttatg gtcaattaaa tgacagctca 180
gaggaggagg atgaaataga tggtccagct ggtcaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggta cactaggtat tgtgtgcccc 360
atctgctctc agaagcccta agaattc 387

<210> SEQ ID NO 118
<211> LENGTH: 387
<212> TYPE: DNA
<213> ORGANISM: Artificial Sequence
<220> FEATURE:
<223> OTHER INFORMATION: IgkS1-24

<400> SEQUENCE: 118
ggtaccgccg ccaccatgga gacagacaca ctcctgctat gggtactgct gctctgggtt 60
ccaggctcca ctggcgacgg atccatgcat ggcgatacac ctacattgca tgaatatatg 120
ttagatttgc aaccagagac aactggcctc tacggctatg gccaattaaa tgacagctca 180
gaggaggagg atgaaataga tggcccagct ggccaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggcat tgtgtgcccc 360
atctgctctc agaagcccta agaattc 387

<210> SEQ ID NO 119
<211> LENGTH: 387
<212> TYPE: DNA
<213> ORGANISM: Artificial Sequence
<220> FEATURE:
<223> OTHER INFORMATION: IgkS1-25

<400> SEQUENCE: 119
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtaa ccttttgttg caagtgtgac tctacgcttc ggttgtgcgt acaaagcaca 300
catgtagaca ttcgtacttt ggaagacctg ttaatgggca cactaggaat tgtgtgcccc 360
atctgctctc agaagcccta agaattc 387

<210> SEQ ID NO 120
<211> LENGTH: 387
<212> TYPE: DNA
<213> ORGANISM: Artificial Sequence
<220> FEATURE:
<223> OTHER INFORMATION: IgkS1-26

<400> SEQUENCE: 120
ggtaccgccg ccaccatgga gacagacaca ctcctgctat gggtactgct gctctgggtt 60
ccaggttcca ctggtgacgg atccatgcac ggagatacac ctacattgca cgaatatatg 120
ttagatttgc aaccagagac aactggtctc tacggttatg ggcaattaaa tgacagctca 180
gaggaggagg atgaaataga tggtccagct ggacaagcag aaccggacag agcccactac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 121
<211> LENGTH: 387
<212> TYPE: DNA
<213> ORGANISM: Artificial Sequence
<220> FEATURE:
<223> OTHER INFORMATION: IgkS1-27

<400> SEQUENCE: 121
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatatagtaa ccttttgttg caagtgtgac tctacgcttc ggttgtgcgt acaaagcaca 300
cacgtagaca tacgtacttt ggaagacctg ttaatgggca cactaggaat agtgtgcccc 360
atatgctctc agaagcccta agaattc 387

<210> SEQ ID NO 122
<211> LENGTH: 387
<212> TYPE: DNA
<213> ORGANISM: Artificial Sequence
<220> FEATURE:
<223> OTHER INFORMATION: IgkS1-28

<400> SEQUENCE: 122
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaattga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atttgctctc agaagcccta agaattc 387

<210> SEQ ID NO 123
<211> LENGTH: 387
<212> TYPE: DNA
<213> ORGANISM: Artificial Sequence
<220> FEATURE:
<223> OTHER INFORMATION: IgkS1-29

<400> SEQUENCE: 123
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaatcga tggtccagct ggacaagcag aaccggacag agcccattac 240
aatatcgtaa ccttttgttg caagtgtgac tctacgcttc ggttgtgcgt acaaagcaca 300
cacgtagaca tccgtacttt ggaagacctg ttaatgggca cactaggaat cgtgtgcccc 360
atctgctctc agaagcccta agaattc 387

<210> SEQ ID NO 124
<211> LENGTH: 387
<212> TYPE: DNA
<213> ORGANISM: Artificial Sequence
<220> FEATURE:
<223> OTHER INFORMATION: IgkS1-50

<400> SEQUENCE: 124
ggtaccgccg ccaccatgga aactgacact ctgctgctgt gggtactgct gctgtgggtt 60
ccaggatcga ctggagacgg atccatgcat ggagacactc caactctgca tgaatatatg 120
ctggacctgc aaccggaaac tactgacctg tactgctatg aacaactgaa tgacagctcg 180
gaagaagaag acgaaataga cggacctgca ggacaagcag aaccagaccg cgcacattac 240
aatattgtaa ctttttgctg caagtgcgac agtactctgc gcctgtgcgt acaaagcact 300
catgtagaca ttcgcactct ggaagacctg ctgatgggaa ctctgggaat tgtttgcccg 360
atctgctcgc aaaagcctta agaattc 387

-continued

<210> SEQ ID NO 125
<211> LENGTH: 387
<212> TYPE: DNA
<213> ORGANISM: Artificial Sequence
<220> FEATURE:
<223> OTHER INFORMATION: IgkS1-51

<400> SEQUENCE: 125
ggtaccgccg ccaccatgga aactgacact ctactactat gggtactact actatgggtt 60
ccaggatcga ctggagacgg atccatgcat ggagacactc caactctaca tgaatatatg 120
ctagacctac aaccggaaac tactgaccta tactgctatg aacaactaaa tgacagctcg 180
gaagaagaag acgaaataga cggacctgca ggacaagcag aaccagaccg cgcacattac 240
aatattgtaa ctttttgctg caagtgcgac agtactctac gcctatgcgt acaaagcact 300
catgtagaca ttcgcactct agaagaccta ctaatgggaa ctctaggaat tgtttgcccg 360
atctgctcgc aaaagcctta agaattc 387

<210> SEQ ID NO 126
<211> LENGTH: 387
<212> TYPE: DNA
<213> ORGANISM: Artificial Sequence
<220> FEATURE:
<223> OTHER INFORMATION: IgkS1-52

<400> SEQUENCE: 126
ggtaccgccg ccaccatgga aactgacact cttcttcttt gggtacttct tctttgggtt 60
ccaggatcga ctggagacgg atccatgcat ggagacactc caactcttca tgaatatatg 120
cttgaccttc aaccggaaac tactgacctt tactgctatg aacaacttaa tgacagctcg 180
gaagaagaag acgaaataga cggacctgca ggacaagcag aaccagaccg cgcacattac 240
aatattgtaa ctttttgctg caagtgcgac agtactcttc gcctttgcgt acaaagcact 300
catgtagaca ttcgcactct tgaagacctt cttatgggaa ctcttggaat tgtttgcccg 360
atctgctcgc aaaagcctta agaattc 387

<210> SEQ ID NO 127
<211> LENGTH: 387
<212> TYPE: DNA
<213> ORGANISM: Artificial Sequence
<220> FEATURE:
<223> OTHER INFORMATION: IgkS1-53

<400> SEQUENCE: 127
ggtaccgccg ccaccatgga aactgacact ctcctcctct gggtactcct cctctgggtt 60
ccaggatcga ctggagacgg atccatgcat ggagacactc caactctcca tgaatatatg 120
ctcgacctcc aaccggaaac tactgacctc tactgctatg aacaactcaa tgacagctcg 180
gaagaagaag acgaaataga cggacctgca ggacaagcag aaccagaccg cgcacattac 240
aatattgtaa ctttttgctg caagtgcgac agtactctcc gcctctgcgt acaaagcact 300
catgtagaca ttcgcactct cgaagacctc ctcatgggaa ctctcggaat tgtttgcccg 360
atctgctcgc aaaagcctta agaattc 387

<210> SEQ ID NO 128
<211> LENGTH: 387
<212> TYPE: DNA
<213> ORGANISM: Artificial Sequence
<220> FEATURE:

-continued

<223> OTHER INFORMATION: IgkS1-54

<400> SEQUENCE: 128
ggtaccgccg ccaccatgga aactgacact ttgttgttgt gggtattgtt gttgtgggtt 60
ccaggatcga ctggagacgg atccatgcat ggagacactc caactttgca tgaatatatg 120
ttggacttgc aaccggaaac tactgacttg tactgctatg aacaattgaa tgacagctcg 180
gaagaagaag acgaaataga cggacctgca ggacaagcag aaccagaccg cgcacattac 240
aatattgtaa ctttttgctg caagtgcgac agtactttgc gcttgtgcgt acaaagcact 300
catgtagaca ttcgcacttt ggaagacttg ttgatgggaa ctttgggaat tgtttgcccg 360
atctgctcgc aaaagcctta agaattc 387

<210> SEQ ID NO 129
<211> LENGTH: 387
<212> TYPE: DNA
<213> ORGANISM: Artificial Sequence
<220> FEATURE:
<223> OTHER INFORMATION: IgkS1-55

<400> SEQUENCE: 129
ggtaccgccg ccaccatgga aactgacact ttattattat gggtattatt attatgggtt 60
ccaggatcga ctggagacgg atccatgcat ggagacactc caactttaca tgaatatatg 120
ttagacttac aaccggaaac tactgactta tactgctatg aacaattaaa tgacagctcg 180
gaagaagaag acgaaataga cggacctgca ggacaagcag aaccagaccg cgcacattac 240
aatattgtaa ctttttgctg caagtgcgac agtactttac gcttatgcgt acaaagcact 300
catgtagaca ttcgcacttt agaagactta ttaatgggaa ctttaggaat tgtttgcccg 360
atctgctcgc aaaagcctta agaattc 387

<210> SEQ ID NO 130
<211> LENGTH: 387
<212> TYPE: DNA
<213> ORGANISM: Artificial Sequence
<220> FEATURE:
<223> OTHER INFORMATION: IgkC3

<400> SEQUENCE: 130
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactgatctc tactgttatg agcaattaaa tgacagctca 180
gaggaggagg atgaaataga tggtccagct ggacaagcag aaccggacag agcccattac 240
aatattgtaa cctttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 131
<211> LENGTH: 387
<212> TYPE: DNA
<213> ORGANISM: Artificial Sequence
<220> FEATURE:
<223> OTHER INFORMATION: IgkC4

<400> SEQUENCE: 131
ggtaccgccg ccaccatgga gaccgacacc ctcctgctgt gggtgctgct gctctgggtg 60
cccggctcca ccggcgacgg atccatgcac ggcgacaccc ccaccctgca cgagtacatg 120

```
ctggacctgc agcccgagac caccgacctg tactgctacg agcagctcaa cgacagcagc    180

gaggaggagg acgagatcga cggccccgcc ggccaggccg agcccgaccg cgcccactac    240

aacatcgtga ccttctgctg caagtgcgac agcaccctgc gcctctgcgt gcagagcacc    300

cacgtggaca tccgcaccct ggaggacctg ctgatgggca ccctgggcat cgtgtgcccc    360

atctgctccc agaagcccta agaattc                                        387
```

<210> SEQ ID NO 132
<211> LENGTH: 387
<212> TYPE: DNA
<213> ORGANISM: Artificial Sequence
<220> FEATURE:
<223> OTHER INFORMATION: IgKS1-32

<400> SEQUENCE: 132

```
ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagattttc aaccagagac aactggtttt tacggttatg ggcaattaaa tgacagctca    180

gaggaggagg atgaaataga tggtccagct ggacaagcag aaccggacag agcccattac    240

aatattgtaa ccttttgttg caagtgtgac tctacgcttc ggttgtgcgt acaaagcaca    300

cacgtagaca ttcgtacttt ggaagacctg ttaatgggca cactaggaat tgtgtgcccc    360

atctgctctc agaagcccta agaattc                                        387
```

<210> SEQ ID NO 133
<211> LENGTH: 387
<212> TYPE: DNA
<213> ORGANISM: Artificial Sequence
<220> FEATURE:
<223> OTHER INFORMATION: IgkS1-33

<400> SEQUENCE: 133

```
ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttcc aaccagagac aactggtttc tacggttatg ggcaattaaa tgacagctca    180

gaggaggagg atgaaataga tggtccagct ggacaagcag aaccggacag agcccattac    240

aatattgtaa ccttctgttg caagtgtgac tctacgcttc ggttgtgcgt acaaagcaca    300

cacgtagaca ttcgtacttt ggaagacctg ttaatgggca cactaggaat tgtgtgcccc    360

atctgctctc agaagcccta agaattc                                        387
```

<210> SEQ ID NO 134
<211> LENGTH: 387
<212> TYPE: DNA
<213> ORGANISM: Artificial Sequence
<220> FEATURE:
<223> OTHER INFORMATION: IgkS1-56

<400> SEQUENCE: 134

```
ggtaccgccg ccaccatgga aactgacact ctcctgctat gggtactgct gctctgggtt     60

ccgggatcga ctggagacgg atccatgcat ggagacactc cgactttgca tgaatatatg    120

ctcgacttgc aaccggaaac tactgacctc tactgctatg aacaattgaa tgacagctcg    180

gaagaagaag acgaaataga cggaccggca ggacaagcag aaccggaccg cgcacattac    240

aatattgtaa ctttttgctg caagtgcgac agtactctcc gcttgtgcgt acaaagcact    300
```

catgtagaca ttcgcacttt ggaagacctc ctcatgggaa ctttgggaat tgtttgcccg 360
atctgctcgc aaaagccgta agaattc 387

<210> SEQ ID NO 135
<211> LENGTH: 387
<212> TYPE: DNA
<213> ORGANISM: Artificial Sequence
<220> FEATURE:
<223> OTHER INFORMATION: IgkS1-57

<400> SEQUENCE: 135
ggtaccgccg ccaccatgga aactgacact ctcctgctat gggtactgct gctctgggtt 60
ccaggatcga ctggagacgg atccatgcat ggagacactc caactttgca tgaatatatg 120
ctcgacttgc aaccagaaac tactgacctc tactgctatg aacaattgaa tgacagctcg 180
gaagaagaag acgaaataga cggaccagca ggacaagcag aaccagaccg cgcacattac 240
aatattgtaa ctttttgctg caagtgcgac agtactctcc gcttgtgcgt acaaagcact 300
catgtagaca ttcgcacttt ggaagacctc ctcatgggaa ctttgggaat tgtttgccca 360
atctgctcgc aaaagccata agaattc 387

<210> SEQ ID NO 136
<211> LENGTH: 387
<212> TYPE: DNA
<213> ORGANISM: Artificial Sequence
<220> FEATURE:
<223> OTHER INFORMATION: IgkS1-58

<400> SEQUENCE: 136
ggtaccgccg ccaccatgga aactgacact ctcctgctat gggtactgct gctctgggtt 60
cctggatcga ctggagacgg atccatgcat ggagacactc ctactttgca tgaatatatg 120
ctcgacttgc aacctgaaac tactgacctc tactgctatg aacaattgaa tgacagctcg 180
gaagaagaag acgaaataga cggacctgca ggacaagcag aacctgaccg cgcacattac 240
aatattgtaa ctttttgctg caagtgcgac agtactctcc gcttgtgcgt acaaagcact 300
catgtagaca ttcgcacttt ggaagacctc ctcatgggaa ctttgggaat tgtttgccct 360
atctgctcgc aaaagcctta agaattc 387

<210> SEQ ID NO 137
<211> LENGTH: 387
<212> TYPE: DNA
<213> ORGANISM: Artificial Sequence
<220> FEATURE:
<223> OTHER INFORMATION: IgkS1-59

<400> SEQUENCE: 137
ggtaccgccg ccaccatgga aactgacact ctcctgctat gggtactgct gctctgggtt 60
cccggatcga ctggagacgg atccatgcat ggagacactc ccactttgca tgaatatatg 120
ctcgacttgc aacccgaaac tactgacctc tactgctatg aacaattgaa tgacagctcg 180
gaagaagaag acgaaataga cggacccgca ggacaagcag aacccgaccg cgcacattac 240
aatattgtaa ctttttgctg caagtgcgac agtactctcc gcttgtgcgt acaaagcact 300
catgtagaca ttcgcacttt ggaagacctc ctcatgggaa ctttgggaat tgtttgcccc 360
atctgctcgc aaaagcccta agaattc 387

<210> SEQ ID NO 138
<211> LENGTH: 387

<212> TYPE: DNA
<213> ORGANISM: Artificial Sequence
<220> FEATURE:
<223> OTHER INFORMATION: IgkS1-34

<400> SEQUENCE: 138
ggtaccgccg ccaccatgga gacagacaca ctcctgctat gggtactgct gctctgggtt 60
ccaggtagta ctggtgacgg aagtatgcat ggagatacac ctacattgca tgaatatatg 120
ttagatttgc aaccagagac aactggtctc tacggttatg ggcaattaaa tgacagtagt 180
gaggaggagg atgaaataga tggtccagct ggacaagcag aaccggacag agcccattac 240
aatattgtaa ccttttgttg caagtgtgac agtacgcttc ggttgtgcgt acaaagtaca 300
cacgtagaca ttcgtacttt ggaagacctg ttaatgggca cactaggaat tgtgtgcccc 360
atctgcagtc agaagcccta agaattc 387

<210> SEQ ID NO 139
<211> LENGTH: 387
<212> TYPE: DNA
<213> ORGANISM: Artificial Sequence
<220> FEATURE:
<223> OTHER INFORMATION: IgkS1-35

<400> SEQUENCE: 139
ggtaccgccg ccaccatgga gacagacaca ctcctgctat gggtactgct gctctgggtt 60
ccaggtagca ctggtgacgg aagcatgcat ggagatacac ctacattgca tgaatatatg 120
ttagatttgc aaccagagac aactggtctc tacggttatg ggcaattaaa tgacagcagc 180
gaggaggagg atgaaataga tggtccagct ggacaagcag aaccggacag agcccattac 240
aatattgtaa ccttttgttg caagtgtgac agcacgcttc ggttgtgcgt acaaagcaca 300
cacgtagaca ttcgtacttt ggaagacctg ttaatgggca cactaggaat tgtgtgcccc 360
atctgcagcc agaagcccta agaattc 387

<210> SEQ ID NO 140
<211> LENGTH: 387
<212> TYPE: DNA
<213> ORGANISM: Artificial Sequence
<220> FEATURE:
<223> OTHER INFORMATION: IgkS1-36

<400> SEQUENCE: 140
ggtaccgccg ccaccatgga gacagacaca ctcctgctat gggtactgct gctctgggtt 60
ccaggttcga ctggtgacgg atcgatgcat ggagatacac ctacattgca tgaatatatg 120
ttagatttgc aaccagagac aactggtctc tacggttatg ggcaattaaa tgactcgtcg 180
gaggaggagg atgaaataga tggtccagct ggacaagcag aaccggacag agcccattac 240
aatattgtaa ccttttgttg caagtgtgac tcgacgcttc ggttgtgcgt acaatcgaca 300
cacgtagaca ttcgtacttt ggaagacctg ttaatgggca cactaggaat tgtgtgcccc 360
atctgctcgc agaagcccta agaattc 387

<210> SEQ ID NO 141
<211> LENGTH: 387
<212> TYPE: DNA
<213> ORGANISM: Artificial Sequence
<220> FEATURE:
<223> OTHER INFORMATION: IgkS1-37

<400> SEQUENCE: 141

-continued

```
ggtaccgccg ccaccatgga gacagacaca ctcctgctat gggtactgct gctctgggtt     60

ccaggttcaa ctggtgacgg atcaatgcat ggagatacac ctacattgca tgaatatatg    120

ttagatttgc aaccagagac aactggtctc tacggttatg ggcaattaaa tgactcatca    180

gaggaggagg atgaaataga tggtccagct ggacaagcag aaccggacag agcccattac    240

aatattgtaa ccttttgttg caagtgtgac tcaacgcttc ggttgtgcgt acaatcaaca    300

cacgtagaca ttcgtacttt ggaagacctg ttaatgggca cactaggaat tgtgtgcccc    360

atctgctcac agaagcccta agaattc                                        387
```

```
<210> SEQ ID NO 142
<211> LENGTH: 387
<212> TYPE: DNA
<213> ORGANISM: Artificial Sequence
<220> FEATURE:
<223> OTHER INFORMATION: IgkS1-38

<400> SEQUENCE: 142

ggtaccgccg ccaccatgga gacagacaca ctcctgctat gggtactgct gctctgggtt     60

ccaggttcta ctggtgacgg atctatgcat ggagatacac ctacattgca tgaatatatg    120

ttagatttgc aaccagagac aactggtctc tacggttatg ggcaattaaa tgactcttct    180

gaggaggagg atgaaataga tggtccagct ggacaagcag aaccggacag agcccattac    240

aatattgtaa ccttttgttg caagtgtgac tctacgcttc ggttgtgcgt acaatctaca    300

cacgtagaca ttcgtacttt ggaagacctg ttaatgggca cactaggaat tgtgtgcccc    360

atctgctctc agaagcccta agaattc                                        387
```

```
<210> SEQ ID NO 143
<211> LENGTH: 387
<212> TYPE: DNA
<213> ORGANISM: Artificial Sequence
<220> FEATURE:
<223> OTHER INFORMATION: IgkS1-39

<400> SEQUENCE: 143

ggtaccgccg ccaccatgga gacagacaca ctcctgctat gggtactgct gctctgggtt     60

ccaggttcca ctggtgacgg atccatgcat ggagatacac ctacattgca tgaatatatg    120

ttagatttgc aaccagagac aactggtctc tacggttatg ggcaattaaa tgactcctcc    180

gaggaggagg atgaaataga tggtccagct ggacaagcag aaccggacag agcccattac    240

aatattgtaa ccttttgttg caagtgtgac tccacgcttc ggttgtgcgt acaatccaca    300

cacgtagaca ttcgtacttt ggaagacctg ttaatgggca cactaggaat tgtgtgcccc    360

atctgctccc agaagcccta agaattc                                        387
```

```
<210> SEQ ID NO 144
<211> LENGTH: 387
<212> TYPE: DNA
<213> ORGANISM: Artificial Sequence
<220> FEATURE:
<223> OTHER INFORMATION: IgkS1-40

<400> SEQUENCE: 144

ggtaccgccg ccaccatgga gacggacacg ctcctgctat gggtactgct gctctgggtt     60

ccaggttcca cgggtgacgg atccatgcat ggagatacgc ctacgttgca tgaatatatg    120

ttagatttgc aaccagagac gacgggtctc tacggttatg ggcaattaaa tgacagctca    180

gaggaggagg atgaaataga tggtccagct ggacaagcag aaccggacag agcccattac    240
```

-continued

```
aatattgtaa cgttttgttg caagtgtgac tctacgcttc ggttgtgcgt acaaagcacg    300

cacgtagaca ttcgtacgtt ggaagacctg ttaatgggca cgctaggaat tgtgtgcccc    360

atctgctctc agaagcccta agaattc                                        387
```

<210> SEQ ID NO 145
<211> LENGTH: 387
<212> TYPE: DNA
<213> ORGANISM: Artificial Sequence
<220> FEATURE:
<223> OTHER INFORMATION: IgkS1-41

<400> SEQUENCE: 145

```
ggtaccgccg ccaccatgga gacagacaca ctcctgctat gggtactgct gctctgggtt     60

ccaggttcca caggtgacgg atccatgcat ggagatacac ctacattgca tgaatatatg    120

ttagatttgc aaccagagac aacaggtctc tacggttatg ggcaattaaa tgacagctca    180

gaggaggagg atgaaataga tggtccagct ggacaagcag aaccggacag agcccattac    240

aatattgtaa cattttgttg caagtgtgac tctacacttc ggttgtgcgt acaaagcaca    300

cacgtagaca ttcgtacatt ggaagacctg ttaatgggca cactaggaat tgtgtgcccc    360

atctgctctc agaagcccta agaattc                                        387
```

<210> SEQ ID NO 146
<211> LENGTH: 387
<212> TYPE: DNA
<213> ORGANISM: Artificial Sequence
<220> FEATURE:
<223> OTHER INFORMATION: IgkS1-42

<400> SEQUENCE: 146

```
ggtaccgccg ccaccatgga gactgacact ctcctgctat gggtactgct gctctgggtt     60

ccaggttcca ctggtgacgg atccatgcat ggagatactc ctactttgca tgaatatatg    120

ttagatttgc aaccagagac tactggtctc tacggttatg ggcaattaaa tgacagctca    180

gaggaggagg atgaaataga tggtccagct ggacaagcag aaccggacag agcccattac    240

aatattgtaa ctttttgttg caagtgtgac tctactcttc ggttgtgcgt acaaagcact    300

cacgtagaca ttcgtacttt ggaagacctg ttaatgggca ctctaggaat tgtgtgcccc    360

atctgctctc agaagcccta agaattc                                        387
```

<210> SEQ ID NO 147
<211> LENGTH: 387
<212> TYPE: DNA
<213> ORGANISM: Artificial Sequence
<220> FEATURE:
<223> OTHER INFORMATION: IgkS1-43

<400> SEQUENCE: 147

```
ggtaccgccg ccaccatgga gaccgacacc ctcctgctat gggtactgct gctctgggtt     60

ccaggttcca ccggtgacgg atccatgcat ggagataccc ctaccttgca tgaatatatg    120

ttagatttgc aaccagagac caccggtctc tacggttatg ggcaattaaa tgacagctca    180

gaggaggagg atgaaataga tggtccagct ggacaagcag aaccggacag agcccattac    240

aatattgtaa ccttttgttg caagtgtgac tctacccttc ggttgtgcgt acaaagcacc    300

cacgtagaca ttcgtacctt ggaagacctg ttaatgggca ccctaggaat tgtgtgcccc    360

atctgctctc agaagcccta agaattc                                        387
```

<210> SEQ ID NO 148
<211> LENGTH: 387
<212> TYPE: DNA
<213> ORGANISM: Artificial Sequence
<220> FEATURE:
<223> OTHER INFORMATION: IgkS1-44

<400> SEQUENCE: 148
ggtaccgccg ccaccatgga gacagacaca ctcctgctat gggtactgct gctctgggtt 60
ccaggttcca ctggtgacgg atccatgcat ggagatacac ctacattgca tgaatatatg 120
ttagatttgc aaccagagac aactggtctc tatggttatg ggcaattaaa tgacagctca 180
gaggaggagg atgaaataga tggtccagct ggacaagcag aaccggacag agcccattat 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 149
<211> LENGTH: 387
<212> TYPE: DNA
<213> ORGANISM: Artificial Sequence
<220> FEATURE:
<223> OTHER INFORMATION: IgkS1-45

<400> SEQUENCE: 149
ggtaccgccg ccaccatgga gacagacaca ctcctgctat gggtactgct gctctgggtt 60
ccaggttcca ctggtgacgg atccatgcat ggagatacac ctacattgca tgaatacatg 120
ttagatttgc aaccagagac aactggtctc tacggttacg ggcaattaaa tgacagctca 180
gaggaggagg atgaaataga tggtccagct ggacaagcag aaccggacag agcccattac 240
aatattgtaa ccttttgttg caagtgtgac tctacgcttc ggttgtgcgt acaaagcaca 300
cacgtagaca ttcgtacttt ggaagacctg ttaatgggca cactaggaat tgtgtgcccc 360
atctgctctc agaagcccta agaattc 387

<210> SEQ ID NO 150
<211> LENGTH: 387
<212> TYPE: DNA
<213> ORGANISM: Artificial Sequence
<220> FEATURE:
<223> OTHER INFORMATION: IgkS1-46

<400> SEQUENCE: 150
ggtaccgccg ccaccatgga gacagacaca ctcctgctat gggtgctgct gctctgggtg 60
ccaggttcca ctggtgacgg atccatgcat ggagatacac ctacattgca tgaatatatg 120
ttagatttgc aaccagagac aactggtctc tacggttatg ggcaattaaa tgacagctca 180
gaggaggagg atgaaataga tggtccagct ggacaagcag aaccggacag agcccattac 240
aatattgtga ccttttgttg caagtgtgac tctacgcttc ggttgtgcgt gcaaagcaca 300
cacgtggaca ttcgtacttt ggaagacctg ttaatgggca cactaggaat tgtgtgcccc 360
atctgctctc agaagcccta agaattc 387

<210> SEQ ID NO 151
<211> LENGTH: 387
<212> TYPE: DNA
<213> ORGANISM: Artificial Sequence
<220> FEATURE:
<223> OTHER INFORMATION: IgkS1-47

<400> SEQUENCE: 151

```
ggtaccgccg ccaccatgga gacagacaca ctcctgctat gggtactgct gctctgggta    60
ccaggttcca ctggtgacgg atccatgcat ggagatacac ctacattgca tgaatatatg   120
ttagatttgc aaccagagac aactggtctc tacggttatg ggcaattaaa tgacagctca   180
gaggaggagg atgaaataga tggtccagct ggacaagcag aaccggacag agcccattac   240
aatattgtaa ccttttgttg caagtgtgac tctacgcttc ggttgtgcgt acaaagcaca   300
cacgtagaca ttcgtacttt ggaagacctg ttaatgggca cactaggaat tgtatgcccc   360
atctgctctc agaagcccta agaattc                                       387
```

<210> SEQ ID NO 152
<211> LENGTH: 387
<212> TYPE: DNA
<213> ORGANISM: Artificial Sequence
<220> FEATURE:
<223> OTHER INFORMATION: IgkS1-48

<400> SEQUENCE: 152

```
ggtaccgccg ccaccatgga gacagacaca ctcctgctat gggttctgct gctctgggtt    60
ccaggttcca ctggtgacgg atccatgcat ggagatacac ctacattgca tgaatatatg   120
ttagatttgc aaccagagac aactggtctc tacggttatg ggcaattaaa tgacagctca   180
gaggaggagg atgaaataga tggtccagct ggacaagcag aaccggacag agcccattac   240
aatattgtta ccttttgttg caagtgtgac tctacgcttc ggttgtgcgt tcaaagcaca   300
cacgttgaca ttcgtacttt ggaagacctg ttaatgggca cactaggaat tgtttgcccc   360
atctgctctc agaagcccta agaattc                                       387
```

<210> SEQ ID NO 153
<211> LENGTH: 387
<212> TYPE: DNA
<213> ORGANISM: Artificial Sequence
<220> FEATURE:
<223> OTHER INFORMATION: IgkS1-49

<400> SEQUENCE: 153

```
ggtaccgccg ccaccatgga gacagacaca ctcctgctat gggtcctgct gctctgggtc    60
ccaggttcca ctggtgacgg atccatgcat ggagatacac ctacattgca tgaatatatg   120
ttagatttgc aaccagagac aactggtctc tacggttatg ggcaattaaa tgacagctca   180
gaggaggagg atgaaataga tggtccagct ggacaagcag aaccggacag agcccattac   240
aatattgtca ccttttgttg caagtgtgac tctacgcttc ggttgtgcgt ccaaagcaca   300
cacgtcgaca ttcgtacttt ggaagacctg ttaatgggca cactaggaat tgtctgcccc   360
atctgctctc agaagcccta agaattc                                       387
```

<210> SEQ ID NO 154
<211> LENGTH: 17
<212> TYPE: PRT
<213> ORGANISM: Artificial Sequence
<220> FEATURE:
<223> OTHER INFORMATION: Synthetic peptide used to measure the E7
      antibody response -continued

```
<400> SEQUENCE: 154

His Tyr Asn Ile Val Thr Phe Cys Cys Lys Cys Asp Ser Thr Leu Arg
1               5                   10                  15

Leu
```